US007067626B2

(12) United States Patent
Benjamin et al.

(10) Patent No.: US 7,067,626 B2
(45) Date of Patent: Jun. 27, 2006

(54) HUMAN ION CHANNEL PROTEINS

(75) Inventors: Christopher W. Benjamin, Kalamazoo, MI (US); Steven L. Roberds, Mattawan, MI (US); Alla M. Karnovsky, Kalamazoo, MI (US); Cara L. Ruble, Paw Paw, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/899,495

(22) Filed: Jul. 5, 2001

(65) Prior Publication Data

US 2003/0088060 A1  May 8, 2003

Related U.S. Application Data

(60) Provisional application No. 60/217,096, filed on Jul. 10, 2000, provisional application No. 60/216,481, filed on Jul. 6, 2000, provisional application No. 60/216,479, filed on Jul. 6, 2000, provisional application No. 60/216,482, filed on Jul. 6, 2000, provisional application No. 60/215,815, filed on Jul. 5, 2000.

(51) Int. Cl.
*C07K 1/00* (2006.01)
(52) U.S. Cl. .................................................. 530/350
(58) Field of Classification Search ................. 530/350
See application file for complete search history.

(56) References Cited

U.S. PATENT DOCUMENTS

| 4,399,216 A | 8/1983 | Axel et al. ..................... 435/6 |
| 4,683,195 A | 7/1987 | Mullis et al. .................. 435/6 |
| 4,683,202 A | 7/1987 | Mullis .......................... 435/6 |
| 4,879,236 A | 11/1989 | Smith et al. ................ 435/235 |
| 5,202,231 A | 4/1993 | Drmanac et al. .............. 435/6 |
| 5,521,065 A | 5/1996 | Whiteley et al. .............. 435/6 |
| 5,585,277 A | 12/1996 | Bowie et al. ............... 436/518 |

FOREIGN PATENT DOCUMENTS

| EP | 0 367 566 A | 5/1990 |
| WO | WO 91/09955 | 7/1991 |
| WO | WO 91/18982 | 12/1991 |
| WO | WO 92/20808 | 11/1992 |
| WO | WO 93/11236 | 6/1993 |
| WO | WO 94/12650 | 6/1994 |
| WO | WO 95/20652 | 8/1995 |
| WO | WO 96/22976 | 8/1996 |
| WO | WO 97/09433 | 3/1997 |
| WO | WO 98/37177 | 8/1998 |
| WO | WO99/32615 | 7/1999 |
| WO | WO01/44283 | 6/2001 |
| WO | WO01/68849 | 9/2001 |

OTHER PUBLICATIONS

Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork et al. Trends in Genetics 12:425-427, 1996.*
Ayala FJ and Kiger JA. Multiple Alleles. In Modern Genetics. The Benjamin/Cummings Publishing Co., Inc. Reading, Massachusetts. pp. 45-48, 1980.*
Rieger R, et al. Glossary of Genetics:Classical and Molecular. 5th ed. Springer-Verlag. New York. pp. 16-17, 1991.*
Akane, A., et al., "direct dideoxy sequencing of genomic DNA by ligation-mediated PCR," *Biotechniques*, 1994, 16(2), 238-241 (p. 239—advertisement).
Altschul, S. F., et al., "Basic local alignment search tool," *J. Mol. Biol.*, 1990, 215, 403-410.
Altschul, S. F., et al., "Gapped BLAST and PSI-BLAST: a new generation of protein database search programs," *Nucleic Acids Research*, 1997, 25(17), 3389-3402.
American Veterinary Medical Association, *Report of the American Veterinary Medical Assoc.*, Panel on Euthanasia, *Journal of American Veterinary Medical Assoc.*, 1993, 202, 229-249.
Anderson, W. F., "Human gene therapy," *Science*, 1992, 256, 808-813.
Anderson, W.F., "Human gene therapy," *Nature*, Supplement to vol. 392(6679), 1998; 25-30.
Aukrust, P., et al., "Enhanced levels of soluble and membrane-bound CD40 ligand in patients with unstable angina; Possible Reflection of T lymphocyte and platelet involvement in the pathogenesis of acute coronary syndromes," *Circulation*, 1999, 100, 614-620.
Ausubel, et al. (Eds.), "Chapter 6, Screening of recombinant DNA libraries," *Current Protocols in Molecular Biology*, 1994, John Wiley & Sons, 6.0.1-6.4.10.
Ausubel, et al. (Eds.), *Current Protocols in Molecular Biology*, New York, 1987-1999, John Wiley & Sons, Inc.
Ausubel, F. M., et al., *Short Protocols in Molecular Biology*, 4th Ed., 1992, Greene & Wiley-Interscience, New York.
Baindur, N., et al., "Selective fluorescent ligands for pharmacological receptors," *Drug Dev. Res.*, 1994, 33, 373-398.

(Continued)

Primary Examiner—Robert S. Landsman
(74) Attorney, Agent, or Firm—Steve Zelson; E. Victor Donahue

(57) ABSTRACT

The present invention provides novel ion channel polypeptides and polynucleotides that identify and encode them. In addition, the invention provides expression vectors, host cells and methods for their production. The invention also provides methods for the identification of ion channel agonists/antagonists, useful for the treatment of human diseases and conditions.

1 Claim, No Drawings

OTHER PUBLICATIONS

Benoist C., et al., "In vivo sequence requirements of the SV40 early promoter region," *Nature*, 1981, 290, 304-310.

Berger, et al., *Guide to Molecular Cloning Techniques*, Methods in Enzymology 152, 1987, Academic Press, Inc., San Diego, CA.

Bossé, R., et al., "Development of nonseparation binding and functional assays for G protein-coupled receptors for high throughput screening: Pharmacological characterization of the immobilized CCR5 receptor on FlashPlate®," *J. Biomolecular Screening*, 1998, 3(4), 285-292.

Breeden, L., et al., "Regulation of the yeast HO gene," *Cold Spring Harb. Symp. Quant. Biol.*, 1985, vol. L, *Molecular Biology of Development*, 643-650.

Broeck, V., "G-protein-coupled receptors in insect cells," *Int. Rev. Cytology*, 1996, 164, 189-268.

Capecchi, M. R., "Altering the genome by homologous recombination," *Science*, 1989, 244, 1288-1292.

Chambers, R. C., et al., "Thrombin stimulates fibroblast procollagen production via proteolytic activation of protease-activated receptor 1," *Biochem J.*, 1998, 333, 121-127.

Choo, Y., et al., "Promoter-specific activation of gene expression directed by bacteriophage-selected zinc fingers," *J. Mol. Biol.*, 1997, 273, 525-532.

Cicala, C., et al., "Bronchoconstrictor effect of thrombin and thrombin receptor activating peptide in guinea-pigs in vivo," *Br. J. Pharmacol*, 1999, 126, 478-484.

Cirino, G., et al., "Thrombin functions as an inflammatory mediator through activation of its receptor," *J. Exp. Med.*, 1996, 183, 821-827.

Cobbold, et al., "Aequorin measurements of cytoplasmic free calcium," In: McCormack J.G., et al. (Eds.), *Cellular Calcium: A Practical Approach*, 1991, Oxford, IRL Press.

Colotta, F., et al., "Expression of monocyte chemotactic protein-1 by monocytes and endothelial cells exposed to thrombin," *Am. J. Pathol*, 1994, 144, 975-985.

Cosman, D., et al., "Cloning, sequence and expression of human interleukin-2 receptor," *Nature*, 1984, 312, 768-771.

Cosman, D., et al., "High Level Stable Expression of Human Interleukin-2 receptors in Mouse Cells Generates only Low Affinity Interleukin-2 Binding Sites," *Mol. Immunol.*, 1986, 23(9), 935-941.

*Current Protocols in Molecular Biology*, 1999, John Wiley & Sons, New York.

Cutting, G. R., "Cloning of the γ-aminobutyric acid (GABA) ρ1cDNA: A GABA receptor subunit highly expressed in the retina," *Proc. Natl. Acad. Sci. USA*, Apr. 1991, 88, 2673-2677.

Dayoff, in *Atlas of Protein Sequence and Structure*, 1972, National Biochemical Research Foundation, Washington, D.C., 5, 124.

DiCuccio, M. N., et al., "A functional tethered ligand thrombin receptor is present on human hematopoietic progenitor cells," *Exp. Hematol*, 1996, 24, 914-918.

Donovan, F. M., et al., "Thrombin induces apoptosis in cultured neurons and astrocytes via a pathway requiring tyrosin kinase and RhoA activities," *J. Neurosci*, 1997, 17(14), 5316-5326.

Douglas, A. M., et al., "Direct sequencing of double-stranded PCR products incorporating a chemiluminescent detection procedure," *Biotechniques*, 1993, 14, 824-828.

Drmanac, S., et al., "Accurate sequencing by hybridization for DNA diagnostics and individual genomics," *Nature Biotechnology*, 1998, 16, 54-58.

Dunlop, J., et al., "Characterization of 5-$HT_{1A}$ receptor functional coupling in cells expressing the human 5-$HT_{1A}$ receptor as assessed with the cytosensor microphysiometer," *J. Pharmacological and Toxicological Methods*, 1998, 40(1), 47-55.

Eisenthal, R., et al. (Eds.) In Enzyme Assays, *A Practical Approach*, 1992, Oxford University Press.

Fields, S., et al., "A novel genetic system to detect protein-protein interactions," *Nature*, 1989, 340, 245-246.

Fields, S., et al., "The two-hybrid system: an assay for protein-protein interactions," *Trends in Genetics*, 1994, 10(8), 286-292.

Fink, M. et al., "Cloning, functional expression and brain localization of a novel unconventional outward rectifier $K^+$channel," *The EMBO Journal*, 1996, 15(24), 6854-6862.

Fischer, S. G., et al., "DNA fragments differing by single base-pair substitutions are separated in denaturing gradient gels: Correspondence with melting theory," *Proc. Natl. Acad. Sci. USA*, 1983, 80, 1579-1583.

Friedmann, T., "Progress toward human gene therapy," *Science*, 1989, 244, 1275-1281.

Gerhardt, C. C., et al., "Functional characteristics of heterologously expressed 5-HT receptors," *Eur. J. Pharmacology*, 1997, 334, 1-23.

Gill, J. S., et al., "Thrombin induced inhibition of neurite outgrowth from dorsal root ganglion neurons," *Brain Res.*, 1998, 797, 321-327.

Greisman, H. A., et al., "A general strategy for selecting high-affinity zinc finger proteins for diverse DNA target sites," *Science*, 1997, 275, 657-661.

Harlow, et al. (Eds.), *Antibodies A Laboratory Manual*, 1988, Cold Spring Harbor Laboratory; Cold Spring Harbor, New York.

Hauck, R. W., et al., "α-thrombin stimulates contraction of human bronchial rings by activation of protease-activated receptors," *Am J. Physiol*, 1999, 277, L22-L29.

Haugland, *Handbook of Fluorescent probes and Research Chemicals*, 6th Ed., 1996, Eugene OR: Molecular Probes.

Henikoff, S., et al., "Amino acid substitution matrices from protein blocks," *Proc. Natl. Acad. Sci. USA*, 1992, 89, 10915-10919.

Hershey, A. D., (Ed.), *The Bacteriophage Lambda*, 1973, Cold Spring Harbor Press, Cold Spring Harbor, New York.

Hill, D. C., "Trends in development of high-throughput screening technologies for rapid discovery of novel drugs," *Cur. Opinion Drug Disc. Dev.*, 1998, 1(1), 92-97.

Hodgson, J., "Receptor screening and the search for new pharmacteuticals," *Bio/Technology*, 1992, 10, 973-980.

Hoffman, M., et al., "Thrombin enhances monocyte secretion of tumor necrosis factor and interleukin-1 beta by two distinct mechanisms," *Blood Cells Mol Dis*, 1995, 21, 156-167.

Jan, L. Y. et al., "Voltage-gated and inwardly rectifying potassium channels," *J. of Physiology*, 1997, 505(2), 267-282.

Jayawickreme, C. K., et al., Gene expression systems in the development of high-throughput screens, *Current Opinion in Biotechnology*, 1997, 8, 629-634.

Karlin, S., et al., "Applications and statistics for multiple high-scoring segments in molecular sequences," *Proc. Natl. Acad. Sci. USA*, 1993, 90, 5873-5877.

Kieleczawa, J., et al., "DNA sequencing by primer walking with strings of contiguous hexamers," *Science*, 1992, 258, 1787-1791.

Kim, J., et al., "Design of TATA box-binding protein/zinc finger fusions for targeted regulation of gene expression," *Proc. Natl. Acad. Sci. USA*, 1997, 94, 3616-3620.

Krogh, A. et al., "Hidden Markov Models in Computational Biology," *J. Mol. Biol.*, 1994, 253, 1501-1531.

Kruse et al. (eds.), in *Tissue Culture*, Academic Press, 1973.

Kuntzweiler, T. A., et al., "Rapid assessment of ligand actions with nicotinic acetylcholine receptors using calcium dynamics and FLIPR," *Drug Development Research*, 1998, 44(1), 14-20.

Lehninger, "Chapter 4, The amino acid building blocks of proteins," *Biochemistry*, 2nd Ed., 1975, Worth Publishers, Inc., New York, New York, 71-77.

Lesage et al., Potassium ion channels, molecular structure, function, and diseases, *Current topics in Membranes*, 1999, 46, pp. 199-222.

Levin, E. D. et al., "AR-R 17779, an α 7 nicotinic agonist, improves learning and memory in rats," *Behavioural Pharmacology*, 1999, 10 (6/7), 675-780.

Lin, A. H., et al., "The oxazolidinone eperezolid binds to the 50S ribosomal subunit and competes with binding of chloramphenicol and lincomycin," *Antimicrobial Agents and Chemotherapy*, 1997, 41(10), 2127-2131.

D.I. Wallis., Electrophysiology, A practical approach , IRL Press @ Oxford University Press, 1993.

Liu, Q., et al., "Design of polydactyl zinc-finger proteins for unique addressing within complex genomes," *Proc. Natl. Acad. Sci. USA*, 1997, 94, 5525-5530.

Lodish et al., *Molecular Cell Biology*, 1997, ISBN:0-7167-2380-8.

Luckow, V. A., et al., "High Level Expression of Nonfused Foreign Genes with *Autographa californica* Nuclear Polyhedrosis Virus Expression Vectors," *Virology*, 1989, 170, 31-39.

Luckow, V. A., et al., "Trends in the development of baculovirus expression vectors," *Bio/Technology*, 1988, 6, 47-55.

Mahajan, N. P. et al., "Bcl-2 and Bax interactions in mitochondria probed with green fluorescent protein and fluorescence resonance energy transfer," *Nature Biotechnology*, Jun. 1998, 16, 547-552.

Maxam, A. M., et al., "Sequencing end-labeled DNA with bse-secific chemical cleavages,", *Meth. Enzymol.*, 1977, vol. 65, 499-560.

McColl, D. J., et al., "Structure-based design of an RNA-binding zinc finger", *Proc. Natl. Acad. Sci. (USA)*, 1997, vol. 96, 9521-9526.

Miller, A. D., "Human gene therapy comes of age", *Nature*, 1992, vol. 357, pp. 455-460.

Mirzabekov, A. D., "DNA sequencing by hybridization—A megasequencing method and a diagnostic tool?", *TIBTECH*, 1994, vol. 12, 27-32.

Morris, R., et al., "Thrombin receptor expression in rheumatoid and osteoarthritic synovial tissue", *Ann. Rheum. Dis.*, 1996, vol. 55, 841-843.

Murphy, A. J., et al., "From DNA to drugs: the orphan G-protein coupled receptors," *Cur. Opinion Drug Disc. Dev.*, 1998, 1(2), 192-199.

Myers, R. M., et al., "Detection of single base substitutions by ribonuclease cleavage at mismatches in RNA: DNA duplexes", *Science*, 1985, vol. 230,1242-1246.

Myers, P., "Will combinatorial chemistry deliver real medicines," *Curr. Opin. Biotechnology*, 1997, 8, 701-707.

Nakayama, G. R., "Microplate assays for high-throughput screening," *Cur. Opinion Drug Disc. Dev.*, 1998, 1(1), 85-91.

Naldini, A., et al., "Thrombin modulation of natural killer activity in human peripheral lymphocytes," *Cell Immunol*, 1996, 172, 35-42.

Okayama, H., et al., "A cDNA cloning vector that permits expression of cDNA inserts in mammalian cells," *Mol. Cell. Biol.*, 1983, 3(2), 280-289.

Orita, M., et al., "Detection of polymorphisms of human DNA by gel electrophoresis as single-strand conformation polymorphisms," *Proc. Natl. Acad. Sci. USA*, 1989, 86, 2766-2770.

Osol, A. (Ed.), *Remington's Pharmaceutical Sciences*, 16th Ed., 1980.

Parodi, L. A., et al., "A consensus procedure for predicting the location of α-helical transmembrane segments in proteins," *Comput. Appl. Biosci.*, 1994, 10(5), 527-535.

Pastinen, T., et al., "Minisequencing: A specific tool for DNA analysis and diagnostics on oligonucleotide arrays," *Genome Res.*, 1997, 7, 606-614.

Patel, A. J. et al., "Inhalational anesthetic activate two-pore-domain background $K^+$ channels", *Nature Neuroscience*, 1999, 2, pp. 422-426.

Pausch, M. H., "G-protein-coupled receptors in saccharomyces cerevisiae: high-throughput screening assays for drug discovery," *Trends in Biotechnology*, 1997, 15, 487-494.

Pease, A. C., et al., "Light-generated oligonucleotide arrays for rapid DNA sequence analysis," *Proc. Natl. Acad. Sci. USA*, 1994, 91, 5022-5026.

Pindon, A., et al., "Thrombin-induced reversal if astricyte stellation is mediated by activation of protein kinase C β-1," *Eur. J. Biochem.*, 1998, 255, 766-774.

Ramsay, G., "DNA chips: state-of-the-art," *Nature Biotechnology*, 1999, 16, 40-48.

Riesner, D., et al., "Temperature-gradient gel electrophoresis of nucleic acids: Analysis of conformational transitions, sequence variations, and protein-nucleic acid interactions," *Electrophoresis*, 1989, 10, 377-389.

Roberts, E., et al., "Potassium permanganate and tetraethylammonium chloride are a safe and effective substitute for osmium tetroxide in solid-phase fluorescent chemical cleavage of mismatch," *Nucl. Acids Res.*, 1997, 25(16), 3377-3378.

Rogers, M. V., "Light on high-throughput screening: fluorescence-based assay technologies," *Drug Discovery Today*, 1997, 2(4), 156-160.

Rowley, G., et al., "Ultrarapid mutation detection by multiplex solid-phase chemical cleavage," *Genomics*, 1995, 30, 574-582.

Salkoff, L. et al., "Surfing the DNA Databases for $K^+$ Channels Nets Yet More Diversity," *Neuron*, Sep. 1995, 15, 489-492.

Sambrook, et al., (Eds.), *Molecular Cloning: A Laboratory Manual*, 1989, Cold Spring Harbor Laboratory Press: Cold Spring Harbor, New York, 9.47-9.51.

Sambrook, et al., *Antibodies A Laboratory Manual*, 1989, Cold Spring Harbor Laboratory; Cold Spring Harbor, New York.

Sanger, F., et al., "DNA sequencing with chain-terminating inhibitors," *Proc. Natl. Acad. Sci. USA*, 1977, 74(12), 5463-5467.

Drmanac, R., et al., "DNA Sequence Determination by Hybridization A Strategy for Efficient Large-Scale Sequencing," *Science*, 1993, 260, 1649-1652 (sequencing by hybridization).

Schaefer, A. J. et al., "DNA variation and the future of human genetics," *Nature Biotechnology*, Jan. 1998, 16, 33-39.

Schroeder, K. S., et al., "FLIPR: A new instrument for accurate, high throughput optical screening," *J. Biomolecular Screening*, 1996, 1(2), 75-80.

Segal, D. J., et al., "Toward controlling gene expression at will: Selection and design of zine finger domains recognizing each of the 5'-GNN-3' DNA target sequences," *Proc. Natl. Acad. Sci. USA*, 1999, 96, 2758-2763.

Shimada, S. et al., "γ-Aminobutyric Acid A or C Receptor? γ-Aminobutyric Acid $ρ_1$ Receptor RNA Induces Bicuculline-, Barbiturate-, and Benzodiazepine-Insensitive γ-Aminobutyric Acid Responses in *Xenopus* Oocytes," *Molecular Pharmacology*, 1992, 41, 683-687.

Shumaker, J. M., et al., "*Mutation detection by solid phase primer extension*," Hum. *Mutat.*, 1996, 7, 346-354.

Smith, T. F., et al., "Comparison of biosequences," *Adv. Appl. Math.*, 1981, 2, 482-489.

Smith et al., Voltage and patch clamping with microelectrodes, Waverly Press, Inc., for the American Physiology Society, (1985).

Smith-Swintosky, V. L., et al., "Protease-activated receptor-2 (PAR-2 is present in the rat hippocampus and is associated with neurodegeneration," *J. Neurocham*, 1997, 69, 1890-1896.

Stables, J., et al., "A bioluminescent assay for agonist activity at potentially any G-protein-coupled receptor," *Analytical Biochemistry*, 1997, 252, 115-126.

Strosberg, et al., "Functional expression of receptors in microorganisms," *Trends in Pharmacological Sciences*, 1992, 13, 95-98.

Suidan, H. A., et al., "The thrombin receptor in the nervous system," *Semin Thromb Hemost*, 1996, 22(2), 125-133.

Summers, et al., *A Manual of Methods for Baculovirus Vectors and Insect Cell Culture Procedures*, Texas Agricultural Experimental Station Bulletin No. 1555, 1987, 2-46.

Sweetnam, P. M., et al., "The role of receptor binding in drug discovery," *J. Natural Products*, 1993, 56(4), 441-455.

Trejo, J., et al., "The cloned thrombin receptor is necessary and sufficient for activation of mitogen-activated protein kinase and mitogenesis in mouse lung fibroblasts," *J. Biol. Chem.*, 1996, 271, 21536-21541.

Tsien R. Y., "The Green Fluorscent Protein," *Annu. Rev. Biochem.*, 1998, 67, 509-544.

Turgeon, V. L., et al., "Thrombin perturbs neurite outgrowth and induces apoptotic cell death in enriched chick spinal motoneuron cultures through caspase activation," *J. Neurosci*, 1998, 18(17), 6882-6891.

Ubl, J. J., et al., "Characteristics of thrombin-induced calcium signals in rat astrocytes," *Glia*, 1997, 21, 361-369.

Grabham, P., et al., Thrombin receptor activation stimulates astrocyte proliferation and reversal of stellation by distinct pathways: involvement of tyrosine phosphorylation, *J. Neurochem*, 1995, 64, 583-591.

Verma, I. M., "Gene therapy," *Scientific American*, 1990, 68-84 (pp. 73-80 and 83 are advertisements).

Wahlestedt, C. et al., "Potent and nontoxic antisense oligonucleotides containing locked nucleic acids," *PNAS*, May 9, 2000, 97(10), 5633-5638.

White, M. B., et al., "Detecting single base substitutions as heteroduplex polymorphisms," *Genomics*, 1992, 12, 301-306.

Wieboldt, R., et al., "Immunoaffinity ultrafiltration with ion spray HPLC/MS for screening small-molecule libraries," *Anal. Chem.*, 1997, 69(9), 1683-1691.

Williams, M., "Receptor binding in the drug discovery process," *Medicinal Research Reviews*, 1991, 11(2), 147-184.

Wu, H., et al., "Building zinc fingers by selection: toward a therapeutic application," *Proc. Natl. Acad. Sci. USA*, 1995, 92, 344-348.

Birren, et al., EMBL Acc. No. AC011116, Oct. 6, 1999.

Deneris, et al., "Beta3: A New Member of Nicotinic Acetylcholine Receptor gene Family Is Expressed in Brain," J. Biol. Chem. (1989) 264(11):6266-6272.

Cooper, et al., "Ion channel genes and human neurological disease: Recent progress, prospects and," Proc. Natl. Acad. Sci. USA (1999) 96:4759-4766.

Adams, et al., EMBL Acc. No. AQ315444, Dec. 23, 1998.

Miyake et al., "Molecular Cloning of Human 5-Hydroxytryptamine-3 Receptor: Heterogeneity in Distribution and Function Among Species," Mol. Pharmacol. (1995) 48(3):407-416.

John E. Macor et al., "The 5HT3 Antagonist Tropisetron NICS (205-930) is a Potent and Selective Alpha7 Nicotinic Receptor Partial Agonist", Bioorganic & Medicinal Chemistry Letters, Oxford, GB, 11, pp. 319-321 (2001), XP001120243.

\* cited by examiner

HUMAN ION CHANNEL PROTEINS

CROSS-REFERENCE TO RELATED APPLICATIONS

The present application claims priority of: Application Ser. No. 60/215,815, filed Jul. 5, 2000; Application Ser. No. 60/216,481, filed Jul. 6, 2000; Application Ser. No. 60/216,479, filed Jul. 6, 2000; Application Ser. No. 60/216,482, filed Jul. 6, 2000; and Application Ser. No. 60/217,096, filed Jul. 10, 2000; each of which is hereby incorporated by reference in its entirety.

FIELD OF THE INVENTION

The present invention is directed, in part, to nucleic acid molecules encoding ion channels, the novel polypeptides of these human ion channels, and assays for screening compounds that bind to these polypeptides and/or modulate their activities.

BACKGROUND OF THE INVENTION

Ion channels are "molecular gates" that regulate the flow of ions into and out of cells. Ion flow plays an important role in all brain cell communication necessary for learning and memory. Additionally, ion flow is important in many physiological processes including, but not limited to, heart rate and body movement. Aberrations in ion channels have been implicated in, amongst other disorders, epilepsy, schizophrenia, Alzheimer's disease, migraine, arrhythmia, diabetes, and stroke damage. Ions flow down their electrochemical gradient through the ion channels (passive transport). The core of the channel is hydrophilic, and contains a part of the protein, the selectivity filter, which recognizes only certain ions and allows them to pass through. Channels are named by the ion(s) they allow to pass. Examples of ion channels include, but are not limited to, calcium channels, potassium channels, sodium channels, chloride channels, etc. An additional component of the channel is the gate. Only when the gate is open can the ions recognized by the selectivity filter pass through the channel. Gates open in response to a variety of stimuli, including, but not limited to, changes in membrane potential or the presence of certain chemicals outside or inside the cell. Channel names often also include an indication of what controls the gate: e.g., "voltage-gated calcium channel." Presently, more than 50 different types of ion channels have been identified.

Communication between neurons is achieved by the release of neurotransmitters into the synapse. These neurotransmitters then activate receptors on the post-synaptic neuron. Many such receptors contain pores to rapidly conduct ions, such as sodium, calcium, potassium, and chloride, into the neuron. These pores, or channels, are made of protein subunits that are members of the family of proteins generally referred to as neurotransmitter-gated ion channel proteins. Included in this family are the serotonin 5-HT3 receptor, the gamma-aminobutyric-acid (GABA) receptor subunits, including gamma-1, rho-3, and beta-like, and the acetylcholine receptor protein subunits, including alpha-9 chain, epsilon chain, and beta-2 chain.

The neurotransmitter-gated ion channel superfamily includes 5-HT3, $GABA_A$, glutamate, glycine, and nicotinic acetylcholine receptor families. Within this superfamily, functional receptors are formed by homo- or heteropentamers of subunits having four transmembrane domains and an extracellular ligand-binding domain. The transmembrane domains of these receptors contribute to the formation of an ion pore.

Serotonin, also known as 5-hydroxytryptamine or 5-HT, is a biogenic amine that functions as a neurotransmitter, a mitogen and a hormone (Conley (1995) The Ion Channels FactsBook Vol. 1. Extracellular Ligand-Gated Channels, Academic Press, London and San Diego. pp. 426). Serotonin activates a large number of receptors, most of which are coupled to activation of G-proteins. However, 5-HT3 receptors are structurally distinct and belong to the neurotransmitter-gated ion channel superfamily. 5-HT3 receptors are expressed both pre- and post-synaptically on central and peripheral neurons. Post-synaptic 5-HT3 receptors achieve their effects by inducing excitatory potentials in the post-synaptic neuron, whereas pre-synaptic 5-HT3 receptors modulate the release of other neurotransmitters from the pre-synaptic neuron (Conley, 1995). 5-HT3 receptors have important roles in pain reception, cognition, cranial motor neuron activity, sensory processing and modulation of affect (Conley, 1995). Thus, ligands or drugs that modulate 5-HT3 receptors may be useful in treating pain, neuropathies, migraine, cognitive disorders, learning and memory deficits, Alzheimer's disease, Parkinson's disease, amyotrophic lateral sclerosis, emesis, cranial neuropathies, sensory deficits, anxiety, depression, schizophrenia, and other affective disorders.

Nicotinic acetylcholine receptors (AChR) are distinguished from other acetylcholine receptors by their affinity for nicotine and their structure—homo- or hetero-pentamers like all members of the neurotransmitter-gated ion channel superfamily. Nicotinic AChRs are found at the neuromuscular junction on skeletal muscle and on peripheral and central neurons. These receptors form nonselective cation channels and therefore induce excitatory currents when activated. Nicotinic AChRs are receptors for anesthetics, sedatives, and hallucinogens (Conley, 1995), and certain ligands have shown improvements in learning and memory in animals (Levin et al., Behavioral Pharmacology, 1999, 10:675–780). Thus, ligands or drugs that modulate nicotinic AChRs could be useful for anesthesia, sedation, improving learning and memory, improving cognition, schizophrenia, anxiety, depression, attention deficit hyperactivity disorder, and addiction or smoking cessation. Expression of AChR subunits is regulated during development enabling the design of ligands or drugs specifically targeted for particular developmental stages or diseases.

The neurotransmitter γ-aminobutyric acid (GABA) activates a family of neurotransmitter-gated ion channels ($GABA_A$) and a family of G protein-coupled receptors ($GABA_B$) (Conley, 1995). $GABA_A$ receptors form chloride channels that induce inhibitory or hyperpolarizing currents when stimulated by GABA or $GABA_A$ receptor agonists (Conley, 1995). $GABA_A$ receptors are modulated by benzodiazepines, barbiturates, picrotoxin, and bicucuilline (Conley, 1995). Thus, ligands or drugs that modulate $GABA_A$ receptors could be useful in sedation, anxiety, epilepsy, seizures, alcohol addiction or withdrawal, panic disorders, pre-menstrual syndrome, migraine, and other diseases characterized by hyper-excitability of central or peripheral neurons. The pharmacology of $GABA_A$ receptors is affected by changing the subunit composition of the receptor. GABA receptor rho subunits are relatively specifically expressed in the retina (Cutting et al., 1991, Proc. Natl. Acad. Sci. USA, 88:2673–7), and the pharmacology of rho receptor homomultimers resembles that of so-called GABAC receptors (Shimada et al., 1992, Mol. Pharmacol. 41:683–7). Therefore, GABA receptors consisting of rho subunits may be useful targets for discovering ligands or drugs to treat visual defects, macular degeneration, glaucoma, and other retinal disorders.

Potassium channels are proteins that form a pore allowing potassium ions to pass into or out of a cell. Potassium channels are comprised of an alpha- (or pore-forming) subunit, and are often associated with a beta- subunit. Three types of potassium ion pore-forming alpha-subunits have been described, exemplified by the Shaker channel (Jan, L Y and Jan, Y N. Voltage-gated and inwardly-rectifying potassium channels. J. Physiol. London 1997; 505:267–282), the inward-rectifier (ibid), and the two-pore (Fink M., Duprat, F., Lesage, F., Reyes, R., Romey, G., Heurteaux, C. and Lazdunski, M. Cloning, functional expression and brain localization of a novel outward rectifier K channel, EMBO J. 1996; 15:6854) channels. There are at least several members in each of these pore-forming families. These pores are comprised of a characteristic number of transmembrane-spanning domains; six transmembrane-spanning domains (Shaker), four transmembrane-spanning domains (two-pore) or two transmembrane-spanning domains (inward rectifier). Transmembrane-spanning domains are regions of the protein that traverse the plasma membrane of the cell. Hence, potassium channels with a Shaker-type alpha subunit are sometimes referred to as 6Tm-1P (for 6 transmembrane-spanning domains-i pore), inward-rectifier channels as 2Tm-1P and two-pore channels as 4Tm-2P.

The 4Tm-2P family of potassium channels was initially discovered in the nematode *C. elegans* (Salkoff, L. and Jegla, T. 1995, Neuron, 15: 489), but have also been found in yeast, *Drosophila melanogaster*, bacteria, plants and mammalian cells (Lesage F and Lazdunski M. (1999). "Potassium Ion Channels, Molecular Structure, Function, and Diseases" in Current Topics in Membranes 46; 199–222 ed. Kurachi, Y., Jan, LY., and Lazdunski, M.). In addition to the different biophysical characteristics described above the 4Tm-2P family of potassium channels have different physiological characteristics as well. For example they are regulated by $H^+$ ions, extracellular $K^+$ and $Na^+$ ions, and also by protein kinase c and protein kinase a activators. 4Tm-2P potassium channels are time and voltage-independent, and thus remain open at all membrane potentials. Because of this, these potassium channels are postulated to be responsible for the background potassium ion currents that are thought to set the resting membrane potential (Lesage et al., (1999), "Potassium Ion Channels, Molecular Structure, Function, and Diseases" in Current Topics in Membranes 46; 199–222 ed. Kurachi, Y., Jan, L Y., and Lazdunski, M.).

Potential uses for the channels described herein include the discovery of agents that modify the activity of the channels. Two previously described members of this family (TASK and TREK-1) are activated by volatile general anesthetics such as chloroform halothane and isoflurane (Patel et al., Nature Neuroscience, 1999, 2:422–426), implicating these channels as a site of activity for these anesthetics. In addition, compounds that modify the activity of these channels may also be useful for the control of neuromotor diseases including epilepsy and neurodegenerative diseases including Parkinson's and Alzheimer's. Also compounds that modulate the activity of these channels may treat diseases including but not limited to cardiovascular arrhythmias, stroke, and endocrine and muscular disorders.

Therefore, ion channels may be useful targets for discovering ligands or drugs to treat many diverse disorders and defects, including schizophrenia, depression, anxiety, attention deficit hyperactivity disorder, migraine, stroke, ischemia, and neurodegenerative disease such as Alzheimer's disease, Parkinson's disease, glaucoma and macular degeneration. In addition compounds which modulate ion channels can be used for the treatment of cardiovascular diseases including ischemia, congestive heart failure, arrhythmia, high blood pressure and restenosis. Also, compounds which modulate ion channels can be used to treat diseases and disorders including inflammatory bowel disease, irritable bowel syndrome, diverticulitis, polyps, and the like.

SUMMARY OF THE INVENTION

The present invention relates to an isolated nucleic acid molecule that comprises a nucleotide sequence that encodes a polypeptide comprising an amino acid sequence homologous to a sequence selected from the group consisting of SEQ ID NO:58 to SEQ ID NO:114, SEQ ID NO:116, and SEQ ID NO:118, or a fragment thereof. The nucleic acid molecule encodes at least a portion of ion-x (where x is 42 to 55, 103 to 118, 129 to 155, 5HT-3C and 5HT-3D). In some embodiments, the nucleic acid molecule comprises a sequence that encodes a polypeptide comprising a sequence selected from the group consisting of SEQ ID NO:58 to SEQ ID NO:114, SEQ ID NO:116, and SEQ ID NO:118, or a fragment thereof. In some embodiments, the nucleic acid molecule comprises a sequence homologous to a sequence selected from the group consisting of SEQ ID NO:1 to SEQ ID NO:57, SEQ ID NO:115, SEQ ID NO:117, and SEQ ID NO:119, or a fragment thereof. In some embodiments, the nucleic acid molecule comprises a sequence selected from the group consisting of SEQ ID NO:1 to SEQ ID NO:57, SEQ ID NO:115, SEQ ID NO:117, and SEQ ID NO:119, and fragments thereof.

According to some embodiments, the present invention provides vectors which comprise the nucleic acid molecule of the invention. In some embodiments, the vector is an expression vector.

According to some embodiments, the present invention provides host cells which comprise the vectors of the invention. In some embodiments, the host cells comprise expression vectors.

The present invention provides an isolated nucleic acid molecule comprising a nucleotide sequence complementary to at least a portion of a sequence selected from the group consisting of SEQ ID NO:1 to SEQ ID NO:57, SEQ ID NO:115, SEQ ID NO:117, and SEQ ID NO:119, said portion comprising at least 10 nucleotides.

The present invention provides a method of producing a polypeptide comprising a sequence selected from the group consisting of SEQ ID NO:58 to SEQ ID NO:114, SEQ ID NO:116, and SEQ ID NO:118, or a homolog or fragment thereof. The method comprising the steps of introducing a recombinant expression vector that includes a nucleotide sequence that encodes the polypeptide into a compatible host cell, growing the host cell under conditions for expression of the polypeptide and recovering the polypeptide.

The present invention provides an isolated antibody which binds to an epitope on a polypeptide comprising a sequence selected from the group consisting of SEQ ID NO:58 to SEQ ID NO:114, SEQ ID NO:116, and SEQ ID NO:118, or a homolog or fragment thereof.

The present invention provides an method of inducing an immune response in a mammal against a polypeptide comprising a sequence selected from the group consisting of SEQ ID NO:58 to SEQ ID NO:114, SEQ ID NO:116, and SEQ ID NO:118, or a homolog or fragment thereof. The method comprises administering to a mammal an amount of the polypeptide sufficient to induce said immune response.

The present invention provides a method for identifying a compound which binds ion-x. The method comprises the steps of: contacting ion-x with a compound and determining whether the compound binds ion-x. Compounds identified as binding ion-x may be further tested in other assays including, but not limited to, in vivo models, in order to confirm or quantitate their activity.

The present invention provides a method for identifying a compound which binds a nucleic acid molecule encoding ion-x. The method comprises the steps of contacting said nucleic acid molecule encoding ion-x with a compound and determining whether said compound binds said nucleic acid molecule.

The present invention provides a method for identifying a compound that modulates the activity of ion-x. The method comprises the steps of contacting ion-x with a compound and determining whether ion-x activity has been modulated. Compounds identified as modulating ion-x activity may be further tested in other assays including, but not limited to, in vivo models, in order to confirm or quantitate their activity.

The present invention provides a method of identifying an animal homolog of ion-x. The method comprises the steps screening a nucleic acid database of the animal with a sequence selected from the group consisting of SEQ ID NO:1 to SEQ ID NO:57, SEQ ID NO:115, SEQ ID NO:117, and SEQ ID NO:119, or a portion thereof and determining whether a portion of said library or database is homologous to said sequence selected from the group consisting of SEQ ID NO:1 to SEQ ID NO:57, SEQ ID NO:115, SEQ ID NO:117, and SEQ ID NO:119, or portion thereof.

The present invention provides a method of identifying an animal homolog of ion-x. The methods comprises the steps screening a nucleic acid library of the animal with a nucleic acid molecule having a sequence selected from the group consisting of SEQID NO:1 to SEQ ID NO:57, SEQ ID NO:115, SEQ ID NO:117, and SEQ ID NO:119, or a portion thereof; and determining whether a portion of said library or database is homologous to said sequence selected from the group consisting of SEQ ID NO:1 to SEQ ID NO:57, SEQ ID NO:115, SEQ ID NO:117, and SEQ ID NO:119, or a portion thereof.

Another aspect of the present invention relates to methods of screening a human subject to diagnose a disorder affecting the brain or genetic predisposition therefor. The methods comprise the steps of assaying nucleic acid of a human subject to determine a presence or an absence of a mutation altering an amino acid sequence, expression, or biological activity of at least one ion channel that is expressed in the brain. The ion channels comprise an amino acid sequence selected from the group consisting of: SEQ ID NO:58 to SEQ ID NO:114, SEQ ID NO:116, and SEQ ID NO:118, and allelic variants thereof. A diagnosis of the disorder or predisposition is made from the presence or absence of the mutation. The presence of a mutation altering the amino acid sequence, expression, or biological activity of the ion channel in the nucleic acid correlates with an increased risk of developing the disorder.

The present invention further relates to methods of screening for an ion-x mental disorder genotype in a human patient. The methods comprise the steps of providing a biological sample comprising nucleic acid from the patient, in which the nucleic acid includes sequences corresponding to alleles of ion-x. The presence of one or more mutations in the ion-x allele is detected indicative of a mental disorder genotype. In some embodiments, the mental disorder includes, but is not limited to, schizophrenia, affective disorders, ADHD/ADD (i.e., Attention Deficit-Hyperactivity Disorder/Attention Deficit Disorder), and neural disorders such as Alzheimer's disease, Parkinson's disease, migraine, and senile dementia as well as depression, anxiety, bipolar disease, epilepsy, neuritis, neurasthenia, neuropathy, neuroses, and the like.

The present invention provides kits for screening a human subject to diagnose a mental disorder or a genetic predisposition therefor. The kits include an oligonucleotide useful as a probe for identifying polymorphisms in a human ion-x gene. The oligonucleotide comprises 6–50 nucleotides in a sequence that is identical or complementary to a sequence of a wild type human ion-x gene sequence or coding sequence, except for one sequence difference selected from the group consisting of a nucleotide addition, a nucleotide deletion, or nucleotide substitution. The kit also includes a media packaged with the oligonucleotide. The media contains information for identifying polymorphisms that correlate with a mental disorder or a genetic predisposition therefor, the polymorphisms being identifiable using the oligonucleotide as a probe.

The present invention further relates to methods of identifying ion channel allelic variants that correlates with mental disorders. The methods comprise the steps of providing biological samples that comprise nucleic acid from a human patient diagnosed with a mental disorder, or from the patient's genetic progenitors or progeny, and detecting in the nucleic acid the presence of one or more mutations in an ion channel that is expressed in the brain. The ion channel comprises an amino acid sequence selected from the group consisting of SEQ ID NO:58 to SEQ ID NO:114, SEQ ID NO:116, and SEQ ID NO:118, and allelic variants thereof. The nucleic acid includes sequences corresponding to the gene or genes encoding ion-x. The one or more mutations detected indicate an allelic variant that correlates with a mental disorder.

The present invention further relates to purified polynucleotides comprising nucleotide sequences encoding alleles of ion-x from a human with a mental disorder. The polynucleotide hybridizes to the complement of SEQ ID NO:1 to SEQ ID NO:57, SEQ ID NO:115, SEQ ID NO:117, and SEQ ID NO:119, under the following hybridization conditions: (a) hybridization for 16 hours at 42° C. in a hybridization solution comprising 50% formamide, 1% SDS, 1 M NaCl, 10% dextran sulfate and (b) washing 2 times for 30 minutes at 60° C. in a wash solution comprising 0.1×SSC and 1% SDS. The polynucleotide encodes an ion-x amino acid sequence of the human that differs from SEQ ID NO:58 to SEQ ID NO:114, SEQ ID NO:116, and SEQ ID NO:118, by at least one residue.

The present invention also provides methods for identifying a modulator of biological activity of ion-x comprising the steps of contacting a cell that expresses ion-x in the presence and in the absence of a putative modulator compound and measuring ion-x biological activity in the cell. The decreased or increased ion-x biological activity in the presence versus absence of the putative modulator is indicative of a modulator of biological activity. Compounds identified as modulating ion-x activity may be further tested in other assays including, but not limited to, in vivo models, in order to confirm or quantitate their activity.

As used herein, the term "biological activity" of an ion channel refers to the native activity of the ion channel. Activities of ion channels include, but are not limited to, the ability to bind or be affected by certain compounds, and the ability to transport ions from one side of the membrane to the other side.

The present invention further provides methods to identify compounds useful for the treatment of mental disorders. The methods comprise the steps of contacting a composition comprising ion-x with a compound suspected of binding ion-x. The binding between ion-x and the compound suspected of binding ion-x is detected. Compounds identified as binding ion-x are candidate compounds useful for the treatment of mental disorders.

The present invention further provides methods for identifying a compound useful as a modulator of binding between ion-x and a binding partner of ion-x. The methods comprise the steps of contacting the binding partner and a composition comprising ion-x in the presence and in the absence of a putative modulator compound and detecting binding between the binding partner and ion-x. Decreased or increased binding between the binding partner and ion-x in the presence of the putative modulator, as compared to binding in the absence of the putative modulator is indicative a modulator compound useful for the treatment of mental disorders.

The present invention further provides chimeric receptors comprising at least a portion of a sequence selected from the group consisting of SEQ ID NO:1 to SEQ ID NO:57, SEQ ID NO:115, SEQ ID NO:117, and SEQ ID NO:119, said portion comprising at least 10 nucleotides.

These and other aspects of the invention are described in greater detail below.

DETAILED DESCRIPTION OF PREFERRED EMBODIMENTS

The present invention provides, inter alia, isolated and purified polynucleotides that encode human ion channels or a portion thereof, vectors containing these polynucleotides, host cells transformed with these vectors, processes of making ion channels and subunits, methods of using the above polynucleotides and vectors, isolated and purified ion channels and subunits, methods of screening compounds which modulate ion channel activity, and compounds that modulate ion channel activity.

Definitions

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used herein, the phrase "ion channel" refers to an entire channel that allows the movement of ions across a membrane, as well as to subunit polypeptide chains that comprise such a channel. As the ion channels of the present inventions are ligand-gated, the ion channels are also referred to as "receptors." Those of skill in the art will recognize that ion channels are made of subunits. As used herein, the term "subunit" refers to any component portion of an ion channel, including but not limited to the beta subunit and other associated subunits.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

By the term "region" is meant a physically contiguous portion of the primary structure of a biomolecule. In the case of proteins, a region is defined by a contiguous portion of the amino acid sequence of that protein.

The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of ion channel domains include, but are not limited to, the extracellular (i.e., N-terminal), transmembrane and cytoplasmic (i.e., C-terminal) domains, which are co-extensive with like-named regions of ion channels; and each of the loop segments (both extracellular and intracellular loops) connecting adjacent transmembrane segments.

As used herein, the term "activity" refers to a variety of measurable indicia suggesting or revealing binding, either direct or indirect; affecting a response, i.e., having a measurable affect in response to some exposure or stimulus, including, for example, the affinity of a compound for directly binding a polypeptide or polynucleotide of the invention. Activity can also be determined by measurement of downstream enzyme activities, and downstream messengers such as $K^+$ ions, $Ca^{2+}$ ions, $Na^+$ ions, $Cl^-$ ions, cyclic AMP, and phospholipids after some stimulus or event. For example, activity can be determined by measuring ion flux. As used herein, the term "ion flux" includes ion current. Activity can also be measured by measuring changes in membrane potential using electrodes or voltage-sensitive dyes, or by measuring neuronal or cellular activity such as action potential duration or frequency, the threshold for stimulating action potentials, long-term potentiation, or long-term inhibition.

As used herein, the term "protein" is intended to include full length and partial fragments of proteins. The term "protein" may be used, herein, interchangeably with "polypeptide." Thus, as used herein, the term "protein" includes polypeptide, peptide, oligopeptide, or amino acid sequence.

As used herein, the term "chimeric receptor" is intended to refer to a receptor comprising portions of more than one type of receptor. As a non-limiting example, a chimeric receptor may comprise the transmembrane domain of the neuronal potassium channel and the extracellular domain of the outward rectifier potassium channel. Chimeric receptors of the present invention are not limited to hybrids of related receptors; chimeric receptors may also include, for example, the pore-forming transmembrane domain of an alpha7 nicotinic acetylcholine receptor and the extracellular domain of the glutamate receptor. Chimeric receptors may also include portions of known wild-type receptors and portions of artificial receptors.

As used herein, the term "antibody" is meant to refer to complete, intact antibodies, Fab fragments, and $F(ab)_2$ fragments thereof. Complete, intact antibodies include monoclonal antibodies such as murine monoclonal antibodies, polyclonal antibodies, chimeric antibodies, humanized antibodies, and recombinant antibodies identified using phage display.

As used herein, the term "binding" means the physical or chemical interaction between two proteins, compounds or molecules (including nucleic acids, such as DNA or RNA), or combinations thereof. Binding includes ionic, non-ionic, hydrogen bonds, Van der Waals, hydrophobic interactions, etc. The physical interaction, the binding, can be either direct or indirect, indirect being through or due to the effects of another protein, compound or molecule. Direct binding refers to interactions that do not take place through or due to the effect of another protein, compound or molecule, but instead are without other substantial chemical intermediates. Binding may be detected in many different manners. As a non-limiting example, the physical binding interaction between an ion channel of the invention and a compound can be detected using a labeled compound. Alternatively, functional evidence of binding can be detected using, for example, a cell transfected with and expressing an ion channel of the invention. Binding of the transfected cell to a ligand of the ion channel that was transfected into the cell provides functional evidence of binding. Other methods of detecting binding are well known to those of skill in the art.

As used herein, the term "compound" means any identifiable chemical or molecule, including, but not limited to a small molecule, peptide, protein, sugar, nucleotide, or nucleic acid. Such compound can be natural or synthetic.

As used herein, the term "complementary" refers to Watson-Crick base-pairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be present in any number of buffers, salts, solutions, etc. Contacting includes, for example, placing the compound into a beaker, microtiter plate, cell culture flask, or a microarray, such as a gene chip, or the like, which contains either the ion channel polypeptide or fragment thereof, or nucleic acid molecule encoding an ion channel or fragment thereof.

As used herein, the phrase "homologous nucleotide sequence," or "homologous amino acid sequence," or variations thereof, refers to sequences characterized by a homology, at the nucleotide level or amino acid level, of at least about 60%, more preferably at least about 70%, more preferably at least about 80%, more preferably at least about 90%, and most preferably at least about 95% to the entirety of SEQ ID NO:1 to SEQ ID NO:57, SEQ ID NO:115, SEQ ID NO:117, and SEQ ID NO:119, or to at least a portion of SEQ ID NO:1 to SEQ ID NO:57, SEQ ID NO:115, SEQ ID NO:117, and SEQ ID NO:119, which portion encodes a functional domain of the encoded polypeptide, or to SEQ ID NO:58 to SEQ ID NO:114, SEQ ID NO:116, and SEQ ID NO:118. Homologous nucleotide sequences include those sequences coding for isoforms of ion channel proteins. Such isoforms can be expressed in different tissues of the same organism as a result of, for example, alternative splicing of RNA. Alternatively, isoforms can be encoded by different genes. Homologous nucleotide sequences include nucleotide sequences encoding for an ion channel protein of a species other than human, including, but not limited to, mammals. Homologous nucleotide sequences also include, but are not limited to, naturally occurring allelic variations and mutations of the nucleotide sequences set forth herein. Although the present invention provides particular sequences, it is understood that the invention is intended to include within its scope other human allelic variants and non-human forms of the ion channels described herein.

Homologous amino acid sequences include those amino acid sequences which contain conservative amino acid substitutions in SEQ ID NO:58 to SEQ ID NO:114, SEQ ID NO:116, and SEQ ID NO:118, as well as polypeptides having ion channel activity. A homologous amino acid sequence does not, however, include the sequence of known polypeptides having ion channel activity. Percent homology can be determined by, for example, the Gap program (Wisconsin Sequence Analysis Package, Version 8 for Unix, Genetics Computer Group, University Research Park, Madison Wis.), which uses the algorithm of Smith and Waterman (*Adv. Appl. Math.*, 1981, 2, 482–489, which is incorporated herein by reference in its entirety) using the default settings.

As used herein, the term "percent homology" and its variants are used interchangeably with "percent identity" and "percent similarity."

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, cell signaling, or cell survival. An abnormal condition may also include obesity, diabetic complications such as retinal degeneration, and irregularities in glucose uptake and metabolism, and fatty acid uptake and metabolism.

Abnormal cell proliferative conditions include cancers such as fibrotic and mesangial disorders, abnormal angiogenesis and vasculogenesis, wound healing, psoriasis, diabetes mellitus, and inflammation.

Abnormal differentiation conditions include, but are not limited to, neurodegenerative disorders, slow wound healing rates, and slow tissue grafting healing rates. Abnormal cell signaling conditions include, but are not limited to, psychiatric disorders involving excess neurotransmitter activity.

Abnormal cell survival conditions may also relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The abnormal condition can also be prevented or treated by administering a compound to a group of cells having an aberration in ion channel in an organism. The effect of administering a compound on organism function can then be monitored. The organism is preferably a mouse, rat, rabbit, guinea pig or goat, more preferably a monkey or ape, and most preferably a human.

By "amplification" it is meant increased numbers of DNA or RNA in a cell compared with normal cells. "Amplification" as it refers to RNA can be the detectable presence of RNA in cells, since in some normal cells there is no basal expression of a particular RNA. In other normal cells, a basal level of expression exists, therefore, in these cases amplification is the detection of at least 1 to 2-fold, and preferably more, compared to the basal level.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and are carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

The amino acid sequences are presented in the amino (N) to carboxy (C) direction, from left to right. The N-terminal α-amino group and the C-terminal β-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commision, or amino acids are represented by their three letters code designations.

Polynucleotides

The present invention provides purified and isolated polynucleotides (e.g., DNA sequences and RNA transcripts, both sense and complementary antisense strands, both single- and double-stranded, including splice variants thereof) that encode previously unknown ion channels. These genes are described herein and designated herein collectively as ion-x (where x is 42 to 55, 103 to 118, 129 to 155, 5HT-3C, and 5HT-3D). That is, these genes and gene products are described herein and designated herein as ion-42, ion-43, ion-44, ion-45, ion-46, ion-47, ion-48, ion-49, ion-50, ion-51, ion-52, ion-53, ion-54, ion-55, ion-103, ion-104, ion-105, ion-106, ion-107, ion-108, ion-109, ion-110, ion-111, ion-112, ion-113, ion-114, ion-115, ion-116, ion-117, ion-118, ion-129, ion-130, ion-131, ion-132, ion-133, ion-134, ion-135, ion-136, ion-137, ion-138, ion-139, ion-140, ion-141, ion-142, ion-143, ion-144, ion-145, ion-146, ion-147, ion-148, ion-149, ion-150, ion-151, ion-152, ion-153, ion-154, ion-155, ion-5HT-3C, and ion-5HT-3D. Table 1 below identifies the novel gene sequence ion-x designation, the SEQ ID NO: of the gene sequence, and the SEQ ID NO: of the polypeptide encoded thereby.

TABLE 1

| ion-x | Nucleotide Sequence (SEQ ID NO:) | Amino acid Sequence (SEQ ID NO:) | Originally filed in: |
|---|---|---|---|
| 42 | 1 | 58 | A |
| 43 | 2 | 59 | A |
| 44 | 3 | 60 | A |
| 45 | 4 | 61 | A |
| 46 | 5 | 62 | A |
| 47 | 6 | 63 | A |
| 48 | 7 | 64 | A |
| 49 | 8 | 65 | A |
| 50 | 9 | 66 | A |
| 51 | 10 | 67 | A |
| 52 | 11 | 68 | A |
| 53 | 12 | 69 | A |
| 54 | 13 | 70 | A |
| 55 | 14 | 71 | A |
| 103 | 15 | 72 | B |
| 104 | 16 | 73 | B |
| 105 | 17 | 74 | B |
| 106 | 18 | 75 | B |
| 107 | 19 | 76 | B |
| 108 | 20 | 77 | B |
| 109 | 21 | 78 | B |
| 110 | 22 | 79 | B |
| 111 | 23 | 80 | B |
| 112 | 24 | 81 | B |
| 113 | 25 | 82 | B |
| 114 | 26 | 83 | B |
| 115 | 27 | 84 | B |

TABLE 1-continued

| ion-x | Nucleotide Sequence (SEQ ID NO:) | Amino acid Sequence (SEQ ID NO:) | Originally filed in: |
|---|---|---|---|
| 116 | 28 | 85 | B |
| 117 | 29 | 86 | B |
| 118 | 30 | 87 | B |
| 129 | 31 | 88 | C |
| 130 | 32 | 89 | C |
| 131 | 33 | 90 | C |
| 132 | 34 | 91 | C |
| 133 | 35 | 92 | C |
| 134 | 36 | 93 | C |
| 135 | 37 | 94 | C |
| 136 | 38 | 95 | C |
| 137 | 39 | 96 | D |
| 138 | 40 | 97 | D |
| 139 | 41 | 98 | D |
| 140 | 42 | 99 | D |
| 141 | 43 | 100 | D |
| 142 | 44 | 101 | D |
| 143 | 45 | 102 | D |
| 144 | 46 | 103 | D |
| 145 | 47 | 104 | D |
| 146 | 48 | 105 | D |
| 147 | 49 | 106 | E |
| 148 | 50 | 107 | E |
| 149 | 51 | 108 | E |
| 150 | 52 | 109 | E |
| 151 | 53 | 110 | E |
| 152 | 54 | 111 | E |
| 153 | 55 | 112 | E |
| 154 | 56 | 113 | E |
| 155 | 57 | 114 | E |
| 5HT-3C | 115 | 116 | F |
| 5HT-3D | 117, 119 | 118 | F |

Legend
A = Ser. No. 60/215,815
B = Ser. No. 60/216,481
C = Ser. No. 60/216,479
D = Ser. No. 60/216,482
E = Ser. No. 60/217,096
F = herein When a specific ion-x is identified (for example ion-5HT-3D), it is understood that only that specific ion channel is being referred to.

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression of the expression of ion-x in a cultured cell, a tissue, or an animal; for therapeutic purposes; or to provide a model for disease or conditions characterized by aberrant ion-x expression. Specifically excluded from the definition of polynucleotides of the invention are entire isolated, non-recombinant native chromosomes of host cells. A preferred polynucleotide has a sequence selected from the group consisting of SEQ ID NO:1 to SEQ ID NO:57, SEQ ID NO:115, SEQ ID NO:117, and SEQ ID NO:119, which correspond to naturally occurring ion-x sequences. It will be appreciated that numerous other polynucleotide sequences exist that also encode ion-x having sequence selected from the group consisting of SEQ ID NO:58 to SEQ ID NO:114, SEQ ID NO:116, and SEQ ID NO:118, due to the well-known degeneracy of the universal genetic The invention also provides a purified and isolated polynucleotide comprising a nucleotide sequence that encodes a mammalian polypeptide, wherein the polynucleotide hybridizes to a polynucleotide having a sequence selected from the group consisting of SEQ ID NO:1 to SEQ ID NO:57, SEQ ID NO:115, SEQ ID NO:117, and SEQ ID NO:119, or the non-coding strand complementary thereto, under the following hybridization conditions:

(a) hybridization for 16 hours at 42° C. in a hybridization solution comprising 50% formamide, 1% SDS, 1 M NaCl, 10% dextran sulfate; and (b) washing 2 times for 30 minutes each at 60° C. in a wash solution comprising 0.1% SSC, 1% SDS. Polynucleotides that encode a human allelic variant are highly preferred.

The present invention relates to molecules which comprise the gene sequences that encode the ion channels; constructs and recombinant host cells incorporating the gene sequences; the novel ion-x polypeptides encoded by the gene sequences; antibodies to the polypeptides and homologs; kits employing the polynucleotides and polypeptides, and methods of making and using all of the foregoing. In addition, the present invention relates to homologs of the gene sequences and of the polypeptides and methods of making and using the same.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode an ion-x polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding ion-x (conventionally followed by second strand synthesis of a complementary strand to provide a double-stranded DNA).

Preferred DNA sequences encoding human ion-x polypeptides are set out in sequences selected from the group consisting of SEQ ID NO:1 to SEQ ID NO:57, SEQ ID NO:115, SEQ ID NO:117, and SEQ ID NO:119. A preferred DNA of the invention comprises a double stranded molecule along with the complementary molecule (the "non-coding strand" or "complement") having a sequence unambiguously deducible from the coding strand according to Watson-Crick base-pairing rules for DNA. Also preferred are other polynucleotides encoding the ion-x polypeptide of sequences selected from the group consisting of SEQ ID NO:58 to SEQ ID NO:114, SEQ ID NO:116, and SEQ ID NO:118, which differ in sequence from the polynucleotides of sequences selected from the group consisting of SEQ ID NO:1 to SEQ ID NO:57, SEQ ID NO:115, SEQ ID NO:117, and SEQ ID NO:119, by virtue of the well-known degeneracy of the universal nuclear genetic code.

The invention further embraces other species, preferably mammalian, homologs of the human ion-x DNA. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Generally, percent sequence "homology" with respect to polynucleotides of the invention may be calculated as the percentage of nucleotide bases in the candidate sequence that are identical to nucleotides in the ion-x sequence selected from the group consisting of SEQ ID NO:1 to SEQ ID NO:57, SEQ ID NO:115, SEQ ID NO:117, and SEQ ID NO:119, after aligning the sequences and introducing gaps, if necessary, to achieve the maximum percent sequence identity.

Polynucleotides of the invention permit identification and isolation of polynucleotides encoding related ion-x polypeptides, such as human allelic variants and species homologs, by well-known techniques including Southern and/or Northern hybridization, and polymerase chain reaction (PCR). Examples of related polynucleotides include human and non-human genomic sequences, including allelic variants, as well as polynucleotides encoding polypeptides homologous to ion-x and structurally related polypeptides sharing one or more biological, immunological, and/or physical properties of ion-x. Non-human species genes encoding proteins homologous to ion-x can also be identified by Southern and/or PCR analysis and are useful in animal models for ion-x disorders. Knowledge of the sequence of a human ion-x DNA also makes possible through use of Southern hybridization or polymerase chain reaction (PCR) the identification of genomic DNA sequences encoding ion-x expression control regulatory sequences such as promoters, operators, enhancers, repressors, and the like. Polynucleotides of the invention are also useful in hybridization assays to detect the capacity of cells to express ion-x. Polynucleotides of the invention may also provide a basis for diagnostic methods useful for identifying a genetic alteration(s) in an ion-x locus that underlies a disease state or states, which information is useful both for diagnosis and for selection of therapeutic strategies.

According to the present invention, the ion-x nucleotide sequences disclosed herein may be used to identify homologs of the ion-x, in other animals, including but not limited to humans and other mammals, and invertebrates. Any of the nucleotide sequences disclosed herein, or any portion thereof, can be used, for example, as probes to screen databases or nucleic acid libraries, such as, for example, genomic or cDNA libraries, to identify homologs, using screening procedures well known to those skilled in the art. Accordingly, homologs having at least 50%, more preferably at least 60%, more preferably at least 70%, more preferably at least 80%, more preferably at least 90%, more preferably at least 95%, and most preferably at least 100% homology with ion-x sequences can be identified.

The disclosure herein of polynucleotides encoding ion-x polypeptides makes readily available to the worker of ordinary skill in the art many possible fragments of the ion channel polynucleotide. Polynucleotide sequences provided herein may encode, as non-limiting examples, a native channel, a constitutive active channel, or a dominant-negative channel.

One preferred embodiment of the present invention provides an isolated nucleic acid molecule comprising a sequence homologous to a sequence selected from the group consisting of SEQ ID NO:1 to SEQ ID NO:57, SEQ ID NO:115, SEQ ID NO:117, and SEQ ID NO:119, and fragments thereof. Another preferred embodiment provides an isolated nucleic acid molecule comprising a sequence selected from the group consisting of SEQ ID NO:1 to SEQ ID NO:57, SEQ ID NO:115, SEQ ID NO:117, and SEQ ID NO:119, and fragments thereof.

As used in the present invention, fragments of ion-x-encoding polynucleotides comprise at least 10, and preferably at least 12, 14, 16, 18, 20, 25, 50, or 75 consecutive nucleotides of a polynucleotide encoding ion-x. Preferably, fragment polynucleotides of the invention comprise sequences unique to the ion-x-encoding polynucleotide sequence, and therefore hybridize under highly stringent or moderately stringent conditions only (i.e., "specifically") to polynucleotides encoding ion-x (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragments of ion-x polynucleotides. One or more polynucleotides can be included in kits that are used to detect the presence of a polynucleotide encoding ion-x, or used to detect variations in a polynucleotide sequence encoding ion-x.

The invention also embraces DNAs encoding ion-x polypeptides that hybridize under moderately stringent or high stringency conditions to the non-coding strand, or complement, of the polynucleotides set forth in a sequence selected from the group consisting of SEQ ID NO:1 to SEQ ID NO:57, SEQ ID NO:115, SEQ ID NO:117, and SEQ ID NO:119.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described Ausubel et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook et al., (Eds.), *Molecular Cloning: A Laboratory Manual*, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode ion-x from different sources (i.e., different tissues or different organisms) through a variety of means well known to the skilled artisan and as disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, DNA that encodes ion-x may be obtained by screening mRNA, cDNA, or genomic DNA with oligonucleotide probes generated from the ion-x gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the ion-x nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, Methods in Enzymology 152, Academic Press, Inc., San Diego, Calif. (Berger), which is incorporated herein by reference in its entirety.

Automated sequencing methods can be used to obtain or verify the nucleotide sequence of ion-x. The ion-x nucleotide sequences of the present invention are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphism (RFLP) associated with certain disorders, as well as for genetic mapping.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding ion-x and/or to express DNA which encodes ion-x. Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxyiruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), PQE™ vectors (Qiagen), pSE420™ (Invitrogen), and pYES2™ (Invitrogen).

Expression constructs preferably comprise ion-x-encoding polynucleotides operatively linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but may also be utilized simply to amplify an ion-x-encoding polynucleotide sequence. In preferred embodiments, the vector is an expression vector wherein the polynucleotide of the invention is operatively linked to a polynucleotide comprising an expression control sequence. Autonomously replicating recombinant expression constructs such as plasmid and viral DNA vectors incorporating polynucleotides of the invention are also provided. Preferred expression vectors are replicable DNA constructs in which a DNA sequence encoding ion-x is operably linked or connected to suitable control sequences capable of effecting the expression of the ion-x in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences which control the termination of transcription and translation.

Preferred vectors preferably contain a promoter that is recognized by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist et al. *Nature,* 1981, 290, 304–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by DNA encoding ion-x and result in the expression of the mature ion-x protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and ion-x DNA. An example of a suitable marker is dihydrofolate reductase (DHFR) or thymidine kinase (see, U.S. Pat. No. 4,399,216).

Nucleotide sequences encoding ion-x may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.,* 1983, 3, 280, Cosman et al., *Mol. Immunol.,* 1986, 23, 935, Cosman et al., *Nature,* 1984, 312, 768, EP-A-0367566, and WO 91/18982, each of which is incorporated herein by reference in its entirety.

Host Cells

According to another aspect of the invention, host cells are provided, including prokaryotic and eukaryotic cells, comprising a polynucleotide of the invention (or vector of the invention) in a manner that permits expression of the encoded ion-x polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts.

Expression systems of the invention include bacterial, yeast, fungal, plant, insect, invertebrate, vertebrate, and mammalian cells systems.

The invention provides host cells that are transformed or transfected (stably or transiently) with polynucleotides of the invention or vectors of the invention. As stated above, such host cells are useful for amplifying the polynucleotides and also for expressing the ion-x polypeptide or fragment thereof encoded by the polynucleotide.

In still another related embodiment, the invention provides a method for producing an ion-x polypeptide (or fragment thereof) comprising the steps of growing a host cell of the invention in a nutrient medium and isolating the polypeptide or variant thereof from the cell or the medium. Because ion-x is a membrane spanning channel, it will be appreciated that, for some applications, such as certain activity assays, the preferable isolation may involve isolation of cell membranes containing the polypeptide embedded therein, whereas for other applications a more complete isolation may be preferable.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces,* and *Staphylococcus.*

If an eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human HEK-293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera *Saccharomyces, Pichia,* and *Kluveromyces.* Preferred yeast hosts are *S. cerevisiae* and *P. pastoris.* Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology,* 1988, 6, 47, Baculovirus Expression Vectors: A Laboratory Manual, O'Rielly et al. (Eds.), W.H. Freeman and Company, New York, 1992, and U.S. Pat. No. 4,879,236, each of which is incorporated herein by reference in its entirety). In addition, the MAXBAC™ complete baculovirus expression system (Invitrogen) can, for example, be used for production in insect cells.

Host cells of the invention are a valuable source of immunogen for development of antibodies specifically immunoreactive with ion-x. Host cells of the invention are also useful in methods for the large-scale production of ion-x polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of ion-x DNA sequences allows for modification of cells to permit, or increase, expression of endogenous ion-x. Cells can be modified (e.g., by homologous recombination) to provide increased expression by replacing, in whole or in part, the naturally occurring ion-x promoter with all or part of a heterologous promoter so that the cells express ion-x at higher levels. The heterologous promoter is inserted in such a manner that it is operatively linked to endogenous ion-x encoding sequences. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the ion-x coding sequence, amplification of the marker DNA by standard selection methods results in co-amplification of the ion-x coding sequences in the cells.

Knock-outs

The DNA sequence information provided by the present invention also makes possible the development (e.g., by homologous recombination or "knock-out" strategies; see Capecchi, *Science* 244:1288–1292 (1989), which is incorporated herein by reference) of animals that fail to express functional ion-x or that express a variant of ion-x. Such animals (especially small laboratory animals such as rats, rabbits, and mice) are useful as models for studying the in vivo activities of ion-x and modulators of ion-x.

Antisense

Also made available by the invention are anti-sense polynucleotides that recognize and hybridize to polynucleotides encoding ion-x. Full-length and fragment anti-sense polynucleotides are provided. Fragment antisense molecules of the invention include (i) those that specifically recognize and hybridize to ion-x RNA (as determined by sequence comparison of DNA encoding ion-x to DNA encoding other known molecules). Identification of sequences unique to ion-x encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Anti-sense polynucleotides are particularly relevant to regulating expression of ion-x by those cells expressing ion-x mRNA.

Antisense nucleic acids (preferably 10 to 30 base-pair oligonucleotides) capable of specifically binding to ion-x expression control sequences or ion-x RNA are introduced into cells (e.g., by a viral vector or colloidal dispersion system such as a liposome). The antisense nucleic acid binds to the ion-x target nucleotide sequence in the cell and prevents transcription and/or translation of the target sequence. Phosphorothioate and methylphosphonate antisense oligonucleotides are specifically contemplated for therapeutic use by the invention. Locked nucleic acids are also specifically contemplated for therapeutic use by the present invention. (See, for example, Wahlestedt et al., Proc. Natl. Acad. Sci. USA, Vol. 97, Issue 10, 5633–5638, May 9, 2000, which is incorporated by reference in its entirety) The antisense oligonucleotides may be further modified by adding poly-L-lysine, transferrin polylysine, or cholesterol moieties at their 5' end. Suppression of ion-x expression at either the transcriptional or translational level is useful to generate cellular or animal models for diseases/conditions characterized by aberrant ion-x expression.

Antisense oligonucleotides, or fragments of nucleotide sequences selected from the group consisting of SEQ ID NO:1 to SEQ ID NO:57, SEQ ID NO:115, SEQ ID NO:117, and SEQ ID NO:119, or sequences complementary or homologous thereto, derived from the nucleotide sequences of the present invention encoding ion-x are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of sequences selected from the group consisting of SEQ ID NO:1 to SEQ ID NO:57, SEQ ID NO:115, SEQ ID NO:117, and SEQ ID NO:119, or mRNA corresponding thereto, including, but not limited to, the initiation codon, TATA box, enhancer sequences, and the like.

Transcription Factors

The ion-x sequences taught in the present invention facilitate the design of novel transcription factors for modulating ion-x expression in native cells and animals, and cells transformed or transfected with ion-x polynucleotides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular ion-x target sequence of the present invention facilitates the engineering of zinc finger proteins specific for the target sequence using known methods such as a combination of structure-based modeling and screening of phage display libraries (Segal et al., Proc. Natl. Acad. Sci. (USA) 96:2758–2763 (1999); Liu et al., Proc. Natl. Acad. Sci. (USA) 94:5525–5530 (1997); Greisman et al., Science 275: 657–661 (1997); Choo et al., J. Mol. Biol. 273:525–532 (1997)). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al.) The artificial zinc finger repeats, designed based on ion-x sequences, are fused to activation or repression domains to promote or suppress ion-x expression (Liu et al.) Alternatively, the zinc finger domains can be fused to the TATA box-binding factor (TBP) with varying lengths of linker region between the zinc finger peptide and the TBP to create either transcriptional activators or repressors (Kim et al., Proc. Natl. Acad. Sci. (USA) 94:3616–3620 (1997). Such proteins and polynucleotides that encode them, have utility for modulating ion-x expression in vivo in both native cells, animals and humans; and/or cells transfected with ion-x— encoding sequences. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., Proc. Natl. Acad. Sci. (USA) 96:9521–9526 (1997); Wu et al., Proc. Natl. Acad. Sci. (USA) 92:344–348 (1995)). The present invention contemplates methods of designing such transcription factors based on the gene sequence of the invention, as well as customized zinc finger proteins, that are useful to modulate ion-x expression in cells (native or transformed) whose genetic complement includes these sequences.

Polypeptides

The invention also provides purified and isolated mammalian ion-x polypeptides encoded by a polynucleotide of the invention. Presently preferred is a human ion-x polypeptide comprising the amino acid sequence set out in sequences selected from the group consisting of SEQ ID NO:58 to SEQ ID NO:114, SEQ ID NO:116, and SEQ ID NO:118, or fragments thereof comprising an epitope specific to the polypeptide. By "epitope specific to" is meant a portion of the ion-x receptor that is recognizable by an antibody that is specific for the ion-x, as defined in detail below.

Although the sequences provided are particular human sequences, the invention is intended to include within its scope other human allelic variants; non-human mammalian forms of ion-x, and other vertebrate forms of ion-x.

It will be appreciated that extracellular epitopes are particularly useful for generating and screening for antibodies and other binding compounds that bind to receptors such as ion-x. Thus, in another preferred embodiment, the invention provides a purified and isolated polypeptide comprising at least one extracellular domain of ion-x. Purified and isolated polypeptides comprising the extracellular domain of ion-x are highly preferred. Also preferred is a purified and isolated polypeptide comprising an ion-x fragment selected from the group consisting of the extracellular domain of ion-x, a transmembrane domain of ion-x, the cytoplasmic region of ion-x, and fusions thereof. Such fragments may be continuous portions of the native receptor. However, it will also be appreciated that knowledge of the ion-x gene and protein sequences as provided herein permits recombining of various domains that are not contiguous in the native protein.

Using a FORTRAN computer program called "tmtrest.all" [Parodi et al., Comput. Appl. Biosci. 5:527–535 (1994)], ion-x was shown to contain transmembrane-spanning domains.

The invention also embraces polypeptides that have at least 99%, at least 95%, at least 90%, at least 85%, at least 80%, at least 75%, at least 70%, at least 65%, at least 60%, at least 55% or at least 50% identity and/or homology to the preferred polypeptide of the invention. Percent amino acid sequence "identity" with respect to the preferred polypeptide of the invention is defined herein as the percentage of amino acid residues in the candidate sequence that are identical with the residues in the ion-x sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the ion-x sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment [Dayhoff, in *Atlas of Protein Sequence and Structure,* Vol. 5, p. 124, National Biochemical Research Foundation, Washington, D.C. (1972), incorporated herein by reference].

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of ion-x polypeptides are embraced by the invention.

The invention also embraces variant (or analog) ion-x polypeptides. In one example, insertion variants are provided wherein one or more amino acid residues supplement an ion-x amino acid sequence. Insertions may be located at either or both termini of the protein, or may be positioned within internal regions of the ion-x amino acid sequence. Insertional variants with additional residues at either or both termini can include, for example, fusion proteins and proteins including amino acid tags or labels.

Insertion variants include ion-x polypeptides wherein one or more amino acid residues are added to an ion-x acid sequence or to a biologically active fragment thereof.

Variant products of the invention also include mature ion-x products, i.e., ion-x products wherein leader or signal sequences are removed, with additional amino terminal residues. The additional amino terminal residues may be derived from another protein, or may include one or more residues that are not identifiable as being derived from specific proteins. Ion-x products with an additional methionine residue at position -1 ($Met^{-1}$-ion-x) are contemplated, as are variants with additional methionine and lysine residues at positions -2 and -1 ($Met^{-2}$-$Lys^{-1}$-ion-x). Variants of ion-x with additional Met, Met-Lys, Lys residues (or one or more basic residues in general) are particularly useful for enhanced recombinant protein production in bacterial host cells.

The invention also embraces ion-x variants having additional amino acid residues that result from use of specific expression systems. For example, use of commercially available vectors that express a desired polypeptide as part of a glutathione-S-transferase (GST) fusion product provides the desired polypeptide having an additional glycine residue at position -1 after cleavage of the GST component from the desired polypeptide. Variants that result from expression in other vector systems are also contemplated.

Insertional variants also include fusion proteins wherein the amino terminus and/or the carboxy terminus of ion-x is/are fused to another polypeptide.

In another aspect, the invention provides deletion variants wherein one or more amino acid residues in an ion-x polypeptide are removed. Deletions can be effected at one or both termini of the ion-x polypeptide, or with removal of one or more non-terminal amino acid residues of ion-x. Deletion variants, therefore, include all fragments of an ion-x polypeptide.

The invention also embraces polypeptide fragments of sequences selected from the group consisting of SEQ ID NO:58 to SEQ ID NO:114, SEQ ID NO:116, and SEQ ID NO:118, wherein the fragments maintain biological (e.g., ligand binding and/or ion trafficking) and/or immunological properties of a ion-x polypeptide.

In one preferred embodiment of the invention, an isolated nucleic acid molecule comprises a nucleotide sequence that encodes a polypeptide comprising an amino acid sequence homologous to a sequence selected from the group consisting of SEQ ID NO:58 to SEQ ID NO:114, SEQ ID NO:116, and SEQ ID NO:118, and fragments thereof, wherein the nucleic acid molecule encodes at least a portion of ion-x. In a more preferred embodiment, the isolated nucleic acid molecule comprises a sequence selected from the group consisting of SEQ ID NO:1 to SEQ ID NO:57, SEQ ID NO:115, SEQ ID NO:117, and SEQ ID NO:119, and fragments thereof.

As used in the present invention, polypeptide fragments comprise at least 5, 10, 15, 20, 25, 30, 35, or 40 consecutive amino acids of a sequence selected from the group consisting of SEQ ID NO:58 to SEQ ID NO:114, SEQ ID NO:116, and SEQ ID NO:118. Preferred polypeptide fragments display antigenic properties unique to, or specific for, human ion-x and its allelic and species homologs. Fragments of the invention having the desired biological and immunological properties can be prepared by any of the methods well known and routinely practiced in the art.

In one embodiment of the invention, the nucleic acid molecule comprises SEQ ID NO:1. Alternatively, the nucleic acid molecule comprises a fragment of SEQ ID NO:1. Preferably, the invention provides fragments of SEQ ID NO:1 which comprise at least 14 and preferably at least 16, 18, 20, 25, 50, or 75 consecutive nucleotides. The fragment can be located within any portion of SEQ ID NO:1, may include more than one portion of SEQ ID NO:1, or may include repeated portions of SEQ ID NO:1. In a preferred embodiment, the nucleic acid molecule comprises a sequence related to the neuronal acetylcholine receptor, beta-3 chain precursor.

In another embodiment of the invention, the nucleic acid molecule comprises SEQ ID NO:2. Alternatively, the nucleic acid molecule comprises a fragment of SEQ ID NO:2. Preferably, the invention provides fragments of SEQ ID NO:2 which comprise at least 14 and preferably at least 16, 18, 20, 25, 50, or 75 consecutive nucleotides. The fragment can be located within any portion of SEQ ID NO:2, may include more than one portion of SEQ ID NO:2, or may include repeated portions of SEQ ID NO:2. In a preferred embodiment, the nucleic acid molecule comprises a sequence related the neuronal acetylcholine receptor, beta-4 chain precursor.

In yet another embodiment of the invention, the nucleic acid molecule comprises SEQ ID NO:3. Alternatively, the nucleic acid molecule comprises a fragment of SEQ ID NO:3. Preferably, the invention provides fragments of SEQ ID NO:3 which comprise at least 14 and preferably at least 16, 18, 20, 25, 50, or 75 consecutive nucleotides. The fragment can be located within any portion of SEQ ID NO:3, may include more than one portion of SEQ ID NO:3, or may include repeated portions of SEQ ID NO:3. In a preferred embodiment, the nucleic acid molecule comprises a sequence related the neuronal acetylcholine receptor, alpha-6 chain precursor.

In still another embodiment of the invention, the nucleic acid molecule comprises SEQ ID NO:4. Alternatively, the nucleic acid molecule comprises a fragment of SEQ ID NO:4. Preferably, the invention provides fragments of SEQ ID NO:4 which comprise at least 14 and preferably at least 16, 18, 20, 25, 50, or 75 consecutive nucleotides. The fragment can be located within any portion of SEQ ID NO:4, may include more than one portion of SEQ ID NO:4, or may include repeated portions of SEQ ID NO:4. In a preferred embodiment, the nucleic acid molecule comprises a sequence related to the serotonin-gated ion channel receptor.

In another embodiment of the invention, the nucleic acid molecule comprises SEQ ID NO:5. Alternatively, the nucleic acid molecule comprises a fragment of SEQ ID NO:5. Preferably, the invention provides fragments of SEQ ID NO:5 which comprise at least 14 and preferably at least 16, 18, 20, 25, 50, or 75 consecutive nucleotides. The fragment can be located within any portion of SEQ ID NO:5, may include more than one portion of SEQ ID NO:5, or may include repeated portions of SEQ ID NO:5. In a preferred embodiment, the nucleic acid molecule comprises a sequence related to the acetylcholine receptor, alpha chain precursor.

In yet another embodiment of the invention, the nucleic acid molecule comprises SEQ ID NO:6. Alternatively, the nucleic acid molecule comprises a fragment of SEQ ID NO:6. Preferably, the invention provides fragments of SEQ ID NO:6 which comprise at least 14 and preferably at least 16, 18, 20, 25, 50, or 75 consecutive nucleotides. The fragment can be located within any portion of SEQ ID NO:6, may include more than one portion of SEQ ID NO:6, or may include repeated portions of SEQ ID NO:6. In a preferred embodiment, the nucleic acid molecule comprises a sequence related to the acetylcholine receptor, alpha chain precursor.

In still another embodiment of the invention, the nucleic acid molecule comprises SEQ ID NO:7. Alternatively, the nucleic acid molecule comprises a fragment of SEQ ID NO:7. Preferably, the invention provides fragments of SEQ ID NO:7 which comprise at least 14 and preferably at least 16, 18, 20, 25, 50, or 75 consecutive nucleotides. The fragment can be located within any portion of SEQ ID NO:7, may include more than one portion of SEQ ID NO:7, or may include repeated portions of SEQ ID NO:7. In a preferred embodiment, the nucleic acid molecule comprises a sequence related to the acetylcholine receptor, alpha-9 chain precursor.

In yet another embodiment of the invention, the nucleic acid molecule comprises SEQ ID NO:8. Alternatively, the nucleic acid molecule comprises a fragment of SEQ ID NO:8. Preferably, the invention provides fragments of SEQ ID NO:8 which comprise at least 14 and preferably at least 16, 18, 20, 25, 50, or 75 consecutive nucleotides. The fragment can be located within any portion of SEQ ID NO:8, may include more than one portion of SEQ ID NO:8, or may include repeated portions of SEQ ID NO:8. In a preferred embodiment, the nucleic acid molecule comprises a sequence related to the neuronal acetylcholine receptor, alpha-7 chain precursor.

In another embodiment of the invention, the nucleic acid molecule comprises SEQ ID NO:9. Alternatively, the nucleic acid molecule comprises a fragment of SEQ ID NO:9. Preferably, the invention provides fragments of SEQ ID NO:9 which comprise at least 14 and preferably at least 16, 18, 20, 25, 50, or 75 consecutive nucleotides. The fragment can be located within any portion of SEQ ID NO:9, may include more than one portion of SEQ ID NO:9, or may include repeated portions of SEQ ID NO:9. In a preferred embodiment, the nucleic acid molecule comprises a sequence related to the neuronal acetylcholine receptor, beta-3 chain precursor.

In yet another embodiment of the invention, the nucleic acid molecule comprises SEQ ID NO:10. Alternatively, the nucleic acid molecule comprises a fragment of SEQ ID NO:10. Preferably, the invention provides fragments of SEQ ID NO:10 which comprise at least 14 and preferably at least 16, 18, 20, 25, 50, or 75 consecutive nucleotides. The fragment can be located within any portion of SEQ ID NO:10, may include more than one portion of SEQ ID NO:10, or may include repeated portions of SEQ ID NO:10. In a preferred embodiment, the nucleic acid molecule comprises a sequence related to the neuronal acetylcholine receptor, beta-3 chain precursor.

In still another embodiment of the invention, the nucleic acid molecule comprises SEQ ID NO:11. Alternatively, the nucleic acid molecule comprises a fragment of SEQ ID NO:11. Preferably, the invention provides fragments of SEQ ID NO:11 which comprise at least 14 and preferably at least 16, 18, 20, 25, 50, or 75 consecutive nucleotides. The fragment can be located within any portion of SEQ ID NO:1, may include more than one portion of SEQ ID NO:11, or may include repeated portions of SEQ ID NO:11. In a preferred embodiment, the nucleic acid molecule comprises a sequence related to the serotonin receptor.

In another embodiment of the invention, the nucleic acid molecule comprises SEQ ID NO:12. Alternatively, the nucleic acid molecule comprises a fragment of SEQ ID NO:12. Preferably, the invention provides fragments of SEQ ID NO:12 which comprise at least 14 and preferably at least 16, 18, 20, 25, 50, or 75 consecutive nucleotides. The fragment can be located within any portion of SEQ ID NO:12, may include more than one portion of SEQ ID NO:12, or may include repeated portions of SEQ ID NO:12. In a preferred embodiment, the nucleic acid molecule comprises a sequence related to the acetylcholine receptor, epsilon chain precursor.

In yet another embodiment of the invention, the nucleic acid molecule comprises SEQ ID NO:13. Alternatively, the nucleic acid molecule comprises a fragment of SEQ ID NO:13. Preferably, the invention provides fragments of SEQ ID NO:13 which comprise at least 14 and preferably at least 16, 18, 20, 25, 50, or 75 consecutive nucleotides. The fragment can be located within any portion of SEQ ID NO:13, may include more than one portion of SEQ ID NO:13, or may include repeated portions of SEQ ID NO:13. In a preferred embodiment, the nucleic acid molecule comprises a sequence related to the GABA receptor, rho-3 subunit.

In still another embodiment of the invention, the nucleic acid molecule comprises SEQ ID NO:14. Alternatively, the nucleic acid molecule comprises a fragment of SEQ ID NO:14. Preferably, the invention provides fragments of SEQ ID NO:14 which comprise at least 14 and preferably at least 16, 18, 20, 25, 50, or 75 consecutive nucleotides. The fragment can be located within any portion of SEQ ID NO:14, may include more than one portion of SEQ ID NO:14, or may include repeated portions of SEQ ID NO:14. In a preferred embodiment, the nucleic acid molecule comprises a sequence related to the acetylcholine receptor, alpha-4 chain precursor.

In one embodiment of the invention, the nucleic acid molecule comprises SEQ ID NO:15. Alternatively, the nucleic acid molecule comprises a fragment of SEQ ID NO:15. Preferably, the invention provides fragments of SEQ ID NO:15 which comprise at least 14 and preferably at least 16, 18, 20, 25, 50, or 75 consecutive nucleotides. The fragment can be located within any portion of SEQ ID NO:15, may include more than one portion of SEQ ID NO:15, or may include repeated portions of SEQ ID NO:15. In a preferred embodiment, the nucleic acid molecule comprises a sequence related to the neuronal acetylcholine receptor, beta-4 chain precursor.

In another embodiment of the invention, the nucleic acid molecule comprises SEQ ID NO:16. Alternatively, the nucleic acid molecule comprises a fragment of SEQ ID NO:16. Preferably, the invention provides fragments of SEQ ID NO:16 which comprise at least 14 and preferably at least 16, 18, 20, 25, 50, or 75 consecutive nucleotides. The fragment can be located within any portion of SEQ ID NO:16, may include more than one portion of SEQ ID NO:16, or may include repeated portions of SEQ ID NO:16. In a preferred embodiment, the nucleic acid molecule comprises a sequence related the neuronal acetylcholine receptor, beta-4 chain precursor.

In yet another embodiment of the invention, the nucleic acid molecule comprises SEQ ID NO:17. Alternatively, the nucleic acid molecule comprises a fragment of SEQ ID NO:17. Preferably, the invention provides fragments of SEQ ID NO:17 which comprise at least 14 and preferably at least 16, 18, 20, 25, 50, or 75 consecutive nucleotides. The fragment can be located within any portion of SEQ ID NO:17, may include more than one portion of SEQ ID NO:17, or may include repeated portions of SEQ ID NO:17. In a preferred embodiment, the nucleic acid molecule comprises a sequence related the neuronal acetylcholine receptor, beta-4 chain precursor.

In still another embodiment of the invention, the nucleic acid molecule comprises SEQ ID NO:18. Alternatively, the nucleic acid molecule comprises a fragment of SEQ ID NO:18. Preferably, the invention provides fragments of SEQ ID NO:18 which comprise at least 14 and preferably at least 16, 18, 20, 25, 50, or 75 consecutive nucleotides. The fragment can be located within any portion of SEQ ID NO:18, may include more than one portion of SEQ ID NO:18, or may include repeated portions of SEQ ID NO:18. In a preferred embodiment, the nucleic acid molecule comprises a sequence related to the glycine receptor, alpha-2 chain precursor.

In another embodiment of the invention, the nucleic acid molecule comprises SEQ ID NO:19. Alternatively, the nucleic acid molecule comprises a fragment of SEQ ID NO:19. Preferably, the invention provides fragments of SEQ ID NO:19 which comprise at least 14 and preferably at least 16, 18, 20, 25, 50, or 75 consecutive nucleotides. The fragment can be located within any portion of SEQ ID NO:19, may include more than one portion of SEQ ID NO:19, or may include repeated portions of SEQ ID NO:19.

In a preferred embodiment, the nucleic acid molecule comprises a sequence related to the glycine receptor, alpha-2 chain precursor.

In yet another embodiment of the invention, the nucleic acid molecule comprises SEQ ID NO:20. Alternatively, the nucleic acid molecule comprises a fragment of SEQ ID NO:20. Preferably, the invention provides fragments of SEQ ID NO:20 which comprise at least 14 and preferably at least 16, 18, 20, 25, 50, or 75 consecutive nucleotides. The fragment can be located within any portion of SEQ ID NO:20, may include more than one portion of SEQ ID NO:20, or may include repeated portions of SEQ ID NO:20. In a preferred embodiment, the nucleic acid molecule comprises a sequence related to the glycine receptor, alpha-2 chain precursor.

In still another embodiment of the invention, the nucleic acid molecule comprises SEQ ID NO:21. Alternatively, the nucleic acid molecule comprises a fragment of SEQ ID NO:21. Preferably, the invention provides fragments of SEQ ID NO:21 which comprise at least 14 and preferably at least 16, 18, 20, 25, 50, or 75 consecutive nucleotides. The fragment can be located within any portion of SEQ ID NO:21, may include more than one portion of SEQ ID NO:21, or may include repeated portions of SEQ ID NO:21. In a preferred embodiment, the nucleic acid molecule comprises a sequence related to the GABA receptor, rho-3 subunit.

In yet another embodiment of the invention, the nucleic acid molecule comprises SEQ ID NO:22. Alternatively, the nucleic acid molecule comprises a fragment of SEQ ID NO:22. Preferably, the invention provides fragments of SEQ ID NO:22 which comprise at least 14 and preferably at least 16, 18, 20, 25, 50, or 75 consecutive nucleotides. The fragment can be located within any portion of SEQ ID NO:22, may include more than one portion of SEQ ID NO:22, or may include repeated portions of SEQ ID NO:22. In a preferred embodiment, the nucleic acid molecule comprises a sequence related to the serotonin receptor.

In another embodiment of the invention, the nucleic acid molecule comprises SEQ ID NO:23. Alternatively, the nucleic acid molecule comprises a fragment of SEQ ID NO:23. Preferably, the invention provides fragments of SEQ ID NO:23 which comprise at least 14 and preferably at least 16, 18, 20, 25, 50, or 75 consecutive nucleotides. The fragment can be located within any portion of SEQ ID NO:23, may include more than one portion of SEQ ID NO:23, or may include repeated portions of SEQ ID NO:23. In a preferred embodiment, the nucleic acid molecule comprises a sequence related to the serotonin receptor.

In yet another embodiment of the invention, the nucleic acid molecule comprises SEQ ID NO:24. Alternatively, the nucleic acid molecule comprises a fragment of SEQ ID NO:24. Preferably, the invention provides fragments of SEQ ID NO:24 which comprise at least 14 and preferably at least 16, 18, 20, 25, 50, or 75 consecutive nucleotides. The fragment can be located within any portion of SEQ ID NO:24, may include more than one portion of SEQ ID NO:24, or may include repeated portions of SEQ ID NO:24. In a preferred embodiment, the nucleic acid molecule comprises a sequence related to the neuronal nicotinic cholinergic receptor, alpha polypeptide 2.

In still another embodiment of the invention, the nucleic acid molecule comprises SEQ ID NO:25. Alternatively, the nucleic acid molecule comprises a fragment of SEQ ID NO:25. Preferably, the invention provides fragments of SEQ ID NO:25 which comprise at least 14 and preferably at least 16, 18, 20, 25, 50, or 75 consecutive nucleotides. The fragment can be located within any portion of SEQ ID NO:25, may include more than one portion of SEQ ID NO:25, or may include repeated portions of SEQ ID NO:25. In a preferred embodiment, the nucleic acid molecule comprises a sequence related to the nicotinic acetylcholine receptor, epsilon polypeptide precursor.

In another embodiment of the invention, the nucleic acid molecule comprises SEQ ID NO:26. Alternatively, the nucleic acid molecule comprises a fragment of SEQ ID NO:26. Preferably, the invention provides fragments of SEQ ID NO:26 which comprise at least 14 and preferably at least 16, 18, 20, 25, 50, or 75 consecutive nucleotides. The fragment can be located within any portion of SEQ ID NO:26, may include more than one portion of SEQ ID NO:26, or may include repeated portions of SEQ ID NO:26. In a preferred embodiment, the nucleic acid molecule comprises a sequence related to the nicotinic acetylcholine receptor, epsilon polypeptide precursor.

In yet another embodiment of the invention, the nucleic acid molecule comprises SEQ ID NO:27. Alternatively, the nucleic acid molecule comprises a fragment of SEQ ID NO:27. Preferably, the invention provides fragments of SEQ ID NO:27 which comprise at least 14 and preferably at least 16, 18, 20, 25, 50, or 75 consecutive nucleotides. The fragment can be located within any portion of SEQ ID NO:27, may include more than one portion of SEQ ID NO:27, or may include repeated portions of SEQ ID NO:27. In a preferred embodiment, the nucleic acid molecule comprises a sequence related to the GABA A receptor, alpha-6 precursor.

In still another embodiment of the invention, the nucleic acid molecule comprises SEQ ID NO:28. Alternatively, the nucleic acid molecule comprises a fragment of SEQ ID NO:28. Preferably, the invention provides fragments of SEQ ID NO:28 which comprise at least 14 and preferably at least 16, 18, 20, 25, 50, or 75 consecutive nucleotides. The fragment can be located within any portion of SEQ ID NO:28, may include more than one portion of SEQ ID NO:28, or may include repeated portions of SEQ ID NO:28. In a preferred embodiment, the nucleic acid molecule comprises a sequence related to the GABA A receptor, delta polypeptide precursor.

In still another embodiment of the invention, the nucleic acid molecule comprises SEQ ID NO:29. Alternatively, the nucleic acid molecule comprises a fragment of SEQ ID NO:29. Preferably, the invention provides fragments of SEQ ID NO:29 which comprise at least 14 and preferably at least 16, 18, 20, 25, 50, or 75 consecutive nucleotides. The fragment can be located within any portion of SEQ ID NO:29, may include more than one portion of SEQ ID NO:29, or may include repeated portions of SEQ ID NO:29. In a preferred embodiment, the nucleic acid molecule comprises a sequence related to the acetylcholine receptor, alpha-6 chain precursor.

In another embodiment of the invention, the nucleic acid molecule comprises SEQ ID NO:30. Alternatively, the nucleic acid molecule comprises a fragment of SEQ ID NO:30. Preferably, the invention provides fragments of SEQ ID NO:30 which comprise at least 14 and preferably at least 16, 18, 20, 25, 50, or 75 consecutive nucleotides. The fragment can be located within any portion of SEQ ID NO:30, may include more than one portion of SEQ ID NO:30, or may include repeated portions of SEQ ID NO:30. In a preferred embodiment, the nucleic acid molecule comprises a sequence related to the acetylcholine receptor, alpha-7 chain precursor.

In yet another embodiment of the invention, the nucleic acid molecule comprises SEQID NO:31. Alternatively, the nucleic acid molecule comprises a fragment of SEQ ID NO:31. Preferably, the invention provides fragments of SEQ ID NO:31 which comprise at least 14 and preferably at least 16, 18, 20, 25, 50, or 75 consecutive nucleotides. The fragment can be located within any portion of SEQ ID NO:31, may include more than one portion of SEQ ID NO:31, or may include repeated portions of SEQ ID NO:31. In a preferred embodiment, the nucleic acid molecule comprises a sequence related to the serotonin 3 receptor In still another embodiment of the invention, the nucleic acid molecule comprises SEQ ID NO:32. Alternatively, the nucleic acid molecule comprises a fragment of SEQ ID NO:32. Preferably, the invention provides fragments of SEQ ID NO:32 which comprise at least 14 and preferably at least 16, 18, 20, 25, 50, or 75 consecutive nucleotides. The fragment can be located within any portion of SEQ ID NO:32, may include more than one portion of SEQ ID NO:32, or may include repeated portions of SEQ ID NO:32. In a preferred embodiment, the nucleic acid molecule comprises a sequence related to the nicotinic acetylcholine receptor, alpha-4 chain.

In another embodiment of the invention, the nucleic acid molecule comprises SEQ ID NO:33. Alternatively, the nucleic acid molecule comprises a fragment of SEQ ID NO:33. Preferably, the invention provides fragments of SEQ ID NO:33 which comprise at least 14 and preferably at least 16, 18, 20, 25, 50, or 75 consecutive nucleotides. The fragment can be located within any portion of SEQ ID NO:33, may include more than one portion of SEQ ID NO:33, or may include repeated portions of SEQ ID NO:33. In a preferred embodiment, the nucleic acid molecule comprises a sequence related to the glutamate receptor, kainate-binding protein.

In yet another embodiment of the invention, the nucleic acid molecule comprises SEQ ID NO:34. Alternatively, the nucleic acid molecule comprises a fragment of SEQ ID NO:34. Preferably, the invention provides fragments of SEQ ID NO:34 which comprise at least 14 and preferably at least 16, 18, 20, 25, 50, or 75 consecutive nucleotides. The fragment can be located within any portion of SEQ ID NO:34, may include more than one portion of SEQ ID NO:34, or may include repeated portions of SEQ ID NO:34. In a preferred embodiment, the nucleic acid molecule comprises a sequence related to the glutamate receptor, ionotropic kainate 4 precursor.

In still another embodiment of the invention, the nucleic acid molecule comprises SEQ ID NO:35. Alternatively, the nucleic acid molecule comprises a fragment of SEQ ID NO:35. Preferably, the invention provides fragments of SEQ ID NO:35 which comprise at least 14 and preferably at least 16, 18, 20, 25, 50, or 75 consecutive nucleotides. The fragment can be located within any portion of SEQ ID NO:35, may include more than one portion of SEQ ID NO:35, or may include repeated portions of SEQ ID NO:35. In a preferred embodiment, the nucleic acid molecule comprises a sequence related to the acetylcholine receptor, delta chain precursor.

In yet another embodiment of the invention, the nucleic acid molecule comprises SEQ ID NO:36. Alternatively, the nucleic acid molecule comprises a fragment of SEQ ID NO:36. Preferably, the invention provides fragments of SEQ ID NO:36 which comprise at least 14 and preferably at least 16, 18, 20, 25, 50, or 75 consecutive nucleotides. The fragment can be located within any portion of SEQ ID NO:36, may include more than one portion of SEQ ID NO:36, or may include repeated portions of SEQ ID NO:36.

In one embodiment of the invention, the nucleic acid molecule comprises SEQ ID NO:37. Alternatively, the nucleic acid molecule comprises a fragment of SEQ ID NO:37. Preferably, the invention provides fragments of SEQ ID NO:37 which comprise at least 14 and preferably at least 16, 18, 20, 25, 50, or 75 consecutive nucleotides. The fragment can be located within any portion of SEQ ID NO:37, may include more than one portion of SEQ ID NO:37, or may include repeated portions of SEQ ID NO:37. In a preferred embodiment, the nucleic acid molecule comprises a sequence related to the nicotinic acetylcholine receptor, alpha-5 subunit precursor.

In another embodiment of the invention, the nucleic acid molecule comprises SEQ ID NO:38. Alternatively, the nucleic acid molecule comprises a fragment of SEQ ID NO:38. Preferably, the invention provides fragments of SEQ ID NO:38 which comprise at least 14 and preferably at least 16, 18, 20, 25, 50, or 75 consecutive nucleotides. The fragment can be located within any portion of SEQ ID NO:38, may include more than one portion of SEQ ID NO:38, or may include repeated portions of SEQ ID NO:38. In a preferred embodiment, the nucleic acid molecule comprises a sequence related to the nicotinic acetylcholine receptor, alpha-chain subunit precursor.

In yet another embodiment of the invention, the nucleic acid molecule comprises SEQ ID NO:39. Alternatively, the nucleic acid molecule comprises a fragment of SEQ ID NO:39. Preferably, the invention provides fragments of SEQ ID NO:39 which comprise at least 14 and preferably at least 16, 18, 20, 25, 50, or 75 consecutive nucleotides. The fragment can be located within any portion of SEQ ID NO:39, may include more than one portion of SEQ ID NO:39, or may include repeated portions of SEQ ID NO:39. In a preferred embodiment, the nucleic acid molecule comprises a sequence related to the nicotinic acetylcholine receptor beta-1 chain precursor.

In still another embodiment of the invention, the nucleic acid molecule comprises SEQ ID NO:40. Alternatively, the nucleic acid molecule comprises a fragment of SEQ ID NO:40. Preferably, the invention provides fragments of SEQ ID NO:40 which comprise at least 14 and preferably at least 16, 18, 20, 25, 50, or 75 consecutive nucleotides. The fragment can be located within any portion of SEQ ID NO:40, may include more than one portion of SEQ ID NO:4, or may include repeated portions of SEQ ID NO:40. In a preferred embodiment, the nucleic acid molecule comprises a sequence related to the nicotinic acetylcholine receptor, delta chain precursor.

In another embodiment of the invention, the nucleic acid molecule comprises SEQ ID NO:41. Alternatively, the nucleic acid molecule comprises a fragment of SEQ ID NO:41. Preferably, the invention provides fragments of SEQ ID NO:41 which comprise at least 14 and preferably at least 16, 18, 20, 25, 50, or 75 consecutive nucleotides. The fragment can be located within any portion of SEQ ID NO:41, may include more than one portion of SEQ ID NO:41, or may include repeated portions of SEQ ID NO:41. In a preferred embodiment, the nucleic acid molecule comprises a sequence related to the NMDA receptor.

In yet another embodiment of the invention, the nucleic acid molecule comprises SEQ ID NO:42. Alternatively, the nucleic acid molecule comprises a fragment of SEQ ID NO:42. Preferably, the invention provides fragments of SEQ ID NO:42 which comprise at least 14 and preferably at least 16, 18, 20, 25, 50, or 75 consecutive nucleotides. The fragment can be located within any portion of SEQ ID NO:42, may include more than one portion of SEQ ID NO:42, or may include repeated portions of SEQ ID NO:42. In a preferred embodiment, the nucleic acid molecule comprises a sequence related to the NMDA receptor, subunit 2C precursor.

In still another embodiment of the invention, the nucleic acid molecule comprises SEQ ID NO:43. Alternatively, the nucleic acid molecule comprises a fragment of SEQ ID NO:43. Preferably, the invention provides fragments of SEQ ID NO:43 which comprise at least 14 and preferably at least 16, 18, 20, 25, 50, or 75 consecutive nucleotides. The fragment can be located within any portion of SEQ ID NO:43, may include more than one portion of SEQ ID NO:43, or may include repeated portions of SEQ ID NO:43. In a preferred embodiment, the nucleic acid molecule comprises a sequence related to the acetylcholine receptor, alpha chain precursor.

In yet another embodiment of the invention, the nucleic acid molecule comprises SEQ ID NO:44. Alternatively, the nucleic acid molecule comprises a fragment of SEQ ID NO:44. Preferably, the invention provides fragments of SEQ ID NO:44 which comprise at least 14 and preferably at least 16, 18, 20, 25, 50, or 75 consecutive nucleotides. The fragment can be located within any portion of SEQ ID NO:44, may include more than one portion of SEQ ID NO:44, or may include repeated portions of SEQ ID NO:44. In a preferred embodiment, the nucleic acid molecule comprises a sequence related to the glutamate receptor, kainate binding protein.

In yet another embodiment of the invention, the nucleic acid molecule comprises SEQ ID NO:45. Alternatively, the nucleic acid molecule comprises a fragment of SEQ ID NO:45. Preferably, the invention provides fragments of SEQ ID NO:45 which comprise at least 14 and preferably at least 16, 18, 20, 25, 50, or 75 consecutive nucleotides. The fragment can be located within any portion of SEQ ID NO:45, may include more than one portion of SEQ ID NO:45, or may include repeated portions of SEQ ID NO:45. In a preferred embodiment, the nucleic acid molecule comprises a sequence related to the NMDA receptor, subunit 2D precursor.

In still another embodiment of the invention, the nucleic acid molecule comprises SEQ ID NO:46. Alternatively, the nucleic acid molecule comprises a fragment of SEQ ID NO:46. Preferably, the invention provides fragments of SEQ ID NO:46 which comprise at least 14 and preferably at least 16, 18, 20, 25, 50, or 75 consecutive nucleotides. The fragment can be located within any portion of SEQ ID NO:46, may include more than one portion of SEQ ID NO:46, or may include repeated portions of SEQ ID NO:46. In a preferred embodiment, the nucleic acid molecule comprises a sequence related to the nicotinic acetylcholine receptor, beta-chain precursor.

In one embodiment of the invention, the nucleic acid molecule comprises SEQ ID NO:47. Alternatively, the nucleic acid molecule comprises a fragment of SEQ ID NO:47. Preferably, the invention provides fragments of SEQ ID NO:47 which comprise at least 14 and preferably at least 16, 18, 20, 25, 50, or 75 consecutive nucleotides. The fragment can be located within any portion of SEQ ID NO:47, may include more than one portion of SEQ ID NO:47, or may include repeated portions of SEQ ID NO:47. In a preferred embodiment, the nucleic acid molecule comprises a sequence related to the nicotinic cholinergic receptor, alpha polypeptide 1 precursor.

In another embodiment of the invention, the nucleic acid molecule comprises SEQ ID NO:48. Alternatively, the nucleic acid molecule comprises a fragment of SEQ ID NO:48. Preferably, the invention provides fragments of SEQ ID NO:48 which comprise at least 14 and preferably at least 16, 18, 20, 25, 50, or 75 consecutive nucleotides. The fragment can be located within any portion of SEQ ID NO:48, may include more than one portion of SEQ ID NO:48, or may include repeated portions of SEQ ID NO:48.

In yet another embodiment of the invention, the nucleic acid molecule comprises SEQ ID NO:49. Alternatively, the nucleic acid molecule comprises a fragment of SEQ ID NO:49. Preferably, the invention provides fragments of SEQ ID NO:49 which comprise at least 14 and preferably at least 16, 18, 20, 25, 50, or 75 consecutive nucleotides. The fragment can be located within any portion of SEQ ID NO:49, may include more than one portion of SEQ ID NO:49, or may include repeated portions of SEQ ID NO:49. In a preferred embodiment, the nucleic acid molecule comprises a sequence related to the nicotinic acetylcholine receptor, alpha chain.

In still another embodiment of the invention, the nucleic acid molecule comprises SEQ ID NO:50. Alternatively, the nucleic acid molecule comprises a fragment of SEQ ID NO:50. Preferably, the invention provides fragments of SEQ ID NO:50 which comprise at least 14 and preferably at least 16, 18, 20, 25, 50, or 75 consecutive nucleotides. The fragment can be located within any portion of SEQ ID NO:50, may include more than one portion of SEQ ID NO:50, or may include repeated portions of SEQ ID NO:50. In a preferred embodiment, the nucleic acid molecule comprises a sequence related to the N-methyl-D-aspartate receptor subunit 2D precursor.

In another embodiment of the invention, the nucleic acid molecule comprises SEQ ID NO:51. Alternatively, the nucleic acid molecule comprises a fragment of SEQ ID NO:51. Preferably, the invention provides fragments of SEQ ID NO:51 which comprise at least 14 and preferably at least 16, 18, 20, 25, 50, or 75 consecutive nucleotides. The fragment can be located within any portion of SEQ ID NO:51, may include more than one portion of SEQ ID NO:51, or may include repeated portions of SEQ ID NO:51. In a preferred embodiment, the nucleic acid molecule comprises a sequence related to the 5-HT3 receptor, subunit A.

In yet another embodiment of the invention, the nucleic acid molecule comprises SEQ ID NO:52. Alternatively, the nucleic acid molecule comprises a fragment of SEQ ID NO:52. Preferably, the invention provides fragments of SEQ ID NO:52 which comprise at least 14 and preferably at least 16, 18, 20, 25, 50, or 75 consecutive nucleotides. The fragment can be located within any portion of SEQ ID NO:52, may include more than one portion of SEQ ID NO:52, or may include repeated portions of SEQ ID NO:52. In a preferred embodiment, the nucleic acid molecule comprises a sequence related to the glutamate receptor subunit kainate subtype.

In still another embodiment of the invention, the nucleic acid molecule comprises SEQ ID NO:53. Alternatively, the nucleic acid molecule comprises a fragment of SEQ ID NO:53. Preferably, the invention provides fragments of SEQ ID NO:53 which comprise at least 14 and preferably at least 16, 18, 20, 25, 50, or 75 consecutive nucleotides. The fragment can be located within any portion of SEQ ID NO:53, may include more than one portion of SEQ ID NO:53, or may include repeated portions of SEQ ID NO:53.

In a preferred embodiment, the nucleic acid molecule comprises a sequence related to the nicotinic acetylcholine receptor, subunit ACR-3.

In yet another embodiment of the invention, the nucleic acid molecule comprises SEQ ID NO:54. Alternatively, the nucleic acid molecule comprises a fragment of SEQ ID NO:54. Preferably, the invention provides fragments of SEQ ID NO:54 which comprise at least 14 and preferably at least 16, 18, 20, 25, 50, or 75 consecutive nucleotides. The fragment can be located within any portion of SEQ ID NO:54, may include more than one portion of SEQ ID NO:54, or may include repeated portions of SEQ ID NO:54. In a preferred embodiment, the nucleic acid molecule comprises a sequence related to the glutamate receptor 6 kainate-preferring precursor.

In yet another embodiment of the invention, the nucleic acid molecule comprises SEQ ID NO:55. Alternatively, the nucleic acid molecule comprises a fragment of SEQ ID NO:55. Preferably, the invention provides fragments of SEQ ID NO:55 which comprise at least 14 and preferably at least 16, 18, 20, 25, 50, or 75 consecutive nucleotides. The fragment can be located within any portion of SEQ ID NO:55, may include more than one portion of SEQ ID NO:55, or may include repeated portions of SEQ ID NO:55. In a preferred embodiment, the nucleic acid molecule comprises a sequence related to the 5-HT3-Al receptor precursor.

In yet another embodiment of the invention, the nucleic acid molecule comprises SEQ ID NO:56. Alternatively, the nucleic acid molecule comprises a fragment of SEQ ID NO:56. Preferably, the invention provides fragments of SEQ ID NO:56 which comprise at least 14 and preferably at least 16, 18, 20, 25, 50, or 75 consecutive nucleotides. The fragment can be located within any portion of SEQ ID NO:56, may include more than one portion of SEQ ID NO:56, or may include repeated portions of SEQ ID NO:56.

In yet another embodiment of the invention, the nucleic acid molecule comprises SEQ ID NO:57. Alternatively, the nucleic acid molecule comprises a fragment of SEQ ID NO:57. Preferably, the invention provides fragments of SEQ ID NO:57 which comprise at least 14 and preferably at least 16, 18, 20, 25, 50, or 75 consecutive nucleotides. The fragment can be located within any portion of SEQ ID NO:57, may include more than one portion of SEQ ID NO:57, or may include repeated portions of SEQ ID NO:57. In a preferred embodiment, the nucleic acid molecule comprises a sequence related to the hypothetical acetylcholine receptor like protein.

In yet another embodiment of the invention, the nucleic acid molecule comprises SEQ ID NO:115. Alternatively, the nucleic acid molecule comprises a fragment of SEQ ID NO:115. Preferably, the invention provides fragments of SEQ ID NO:115 which comprise at least 14 and preferably at least 16, 18, 20, 25, 50, or 75 consecutive nucleotides. The fragment can be located within any portion of SEQ ID NO:115, may include more than one portion of SEQ ID NO:115, or may include repeated portions of SEQ ID NO:115.

In yet another embodiment of the invention, the nucleic acid molecule comprises SEQ ID NO:117. Alternatively, the nucleic acid molecule comprises a fragment of SEQ ID NO:117. Preferably, the invention provides fragments of SEQ ID NO:117 which comprise at least 14 and preferably at least 16, 18, 20, 25, 50, or 75 consecutive nucleotides. The fragment can be located within any portion of SEQ ID NO:117, may include more than one portion of SEQ ID NO:117, or may include repeated portions of SEQ ID NO:117.

In still another aspect, the invention provides substitution variants of ion-x polypeptides. Substitution variants include those polypeptides wherein one or more amino acid residues of an ion-x polypeptide are removed and replaced with alternative residues. In one aspect, the substitutions are conservative in nature; however, the invention embraces substitutions that are also non-conservative. Conservative substitutions for this purpose may be defined as set out in Tables 2, 3, or 4 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2 (from WO 97/09433, page 10, published Mar. 13, 1997 (PCT/GB96/02197, filed Sep. 6, 1996), immediately below.

TABLE 2

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [*Biochemistry*, Second Edition; Worth Publishers, Inc. New York, N.Y. (1975), pp. 71–77] as set out in Table 3, below.

TABLE 3

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 4, below.

TABLE 4

Conservative Substitutions III

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces ion-x polypeptides that have been covalently modified to include one or more water-soluble polymer attachments such as polyethylene glycol, polyoxyethylene glycol, or polypropylene glycol. Variants that display ligand binding properties of native ion-x and are expressed at higher levels, as well as variants that provide for constitutively active receptors, are particularly useful in assays of the invention; the variants are also useful in providing cellular, tissue and animal models of diseases/conditions characterized by aberrant ion-x activity.

In a related embodiment, the present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Variants that display ligand binding properties of native ion-x and are expressed at higher levels, as well as variants that provide for constitutively active receptors, are particularly useful in assays of the invention; the variants are also useful in assays of the invention and in providing cellular, tissue and animal models of diseases/conditions characterized by aberrant ion-x activity.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for ion-x or fragments thereof. Preferred antibodies of the invention are human antibodies that are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind ion-x polypeptides exclusively (i.e., are able to distinguish ion-x polypeptides from other known ion channel polypeptides by virtue of measurable differences in binding affinity, despite the possible existence of localized sequence identity, homology, or similarity between ion-x and such polypeptides). It will be understood that specific antibodies may also interact with other proteins (for example, S. aureus protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), *Antibodies A Laboratory Manual;* Cold Spring Harbor Laboratory; Cold Spring Harbor, N.Y. (1988), Chapter 6. Antibodies that recognize and bind fragments of the ion-x polypeptides of the invention are also contemplated, provided that the antibodies are specific for ion-x polypeptides. Antibodies of the invention can be produced using any method well known and routinely practiced in the art.

The invention provides an antibody that is specific for the ion-x of the invention. Antibody specificity is described in greater detail below. However, it should be emphasized that antibodies that can be generated from polypeptides that have previously been described in the literature and that are capable of fortuitously cross-reacting with ion-x (e.g., due to the fortuitous existence of a similar epitope in both polypeptides) are considered "cross-reactive" antibodies. Such cross-reactive antibodies are not antibodies that are "specific" for ion-x. The determination of whether an antibody is specific for ion-x or is cross-reactive with another known receptor is made using any of several assays, such as Western blotting assays, that are well known in the art. For identifying cells that express ion-x and also for modulating ion-x -ligand binding activity, antibodies that specifically bind to an extracellular epitope of the ion-x are preferred.

In one preferred variation, the invention provides monoclonal antibodies. Hybridomas that produce such antibodies also are intended as aspects of the invention. In yet another variation, the invention provides a humanized antibody. Humanized antibodies are useful for in vivo therapeutic indications.

In another variation, the invention provides a cell-free composition comprising polyclonal antibodies, wherein at least one of the antibodies is an antibody of the invention specific for ion-x. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for ion-x.

It is well known that antibodies contain relatively small antigen binding domains that can be isolated chemically or by recombinant techniques. Such domains are useful ion-x binding molecules themselves, and also may be reintroduced into human antibodies, or fused to toxins or other polypeptides. Thus, in still another embodiment, the invention provides a polypeptide comprising a fragment of an ion-x-specific antibody, wherein the fragment and the polypeptide bind to the ion-x. By way of non-limiting example, the invention provides polypeptides that are single chain antibodies and CDR-grafted antibodies.

Non-human antibodies may be humanized by any of the methods known in the art. In one method, the non-humans CDRs are inserted into a human antibody or consensus antibody framework sequence. Further changes can then be introduced into the antibody framework to modulate affinity or immunogenicity.

Antibodies of the invention are useful for, e.g., therapeutic purposes (by modulating activity of ion-x), diagnostic purposes to detect or quantitate ion-x, and purification of ion-x. Kits comprising an antibody of the invention for any of the purposes described herein are also comprehended. In general, a kit of the invention also includes a control antigen for which the antibody is immunospecific.

Compositions

Mutations in the ion-x gene that result in loss of normal function of the ion-x gene product underlie ion-x-related human disease states. The invention comprehends gene therapy to restore ion-x activity to treat those disease states. Delivery of a functional ion-x gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature,* supplement to vol. 392, No. 6679, pp. 25–20 (1998). For additional reviews of gene therapy technology see Friedmann, *Science,* 244: 1275–1281 (1989); Verma, *Scientific American:* 68–84 (1990); and Miller, *Nature,* 357: 455–460 (1992). Alternatively, it is contemplated that in other human disease states, preventing the expression of, or inhibiting the activity of, ion-x will be useful in treating disease states. It is contemplated that antisense therapy or gene therapy could be applied to negatively regulate the expression of ion-x.

Another aspect of the present invention is directed to compositions, including pharmaceutical compositions, comprising any of the nucleic acid molecules or recombinant expression vectors described above and an acceptable carrier or diluent. Preferably, the carrier or diluent is pharmaceutically acceptable. Suitable carriers are described in the most recent edition of *Remington's Pharmaceutical Sciences,* A. Osol, a standard reference text in this field, which is incorporated herein by reference in its entirety. Preferred examples of such carriers or diluents include, but are not limited to, water, saline, Ringer's solution, dextrose solution, and 5% human serum albumin. Liposomes and non-aqueous vehicles such as fixed oils may also be used. The formulations are sterilized by commonly used techniques.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating ligand binding of an ion-x comprising the step of contacting the ion-x with an antibody specific for the ion-x, under conditions wherein the antibody binds the receptor.

It is well known to those skilled in the art that many ion channels are expressed in the brain. Ion channels that may be expressed in the brain, such as ion-x, provide an indication that aberrant ion-x signaling activity may correlate with one or more neurological or psychological disorders. The invention also provides a method for treating a neurological or psychiatric disorder comprising the step of administering to a mammal in need of such treatment an amount of an antibody-like polypeptide of the invention that is sufficient to modulate ligand binding to an ion-x in neurons of the mammal. Ion-x may also be expressed in many tissues, including but not limited to, kidney, colon, small intestine, stomach, testis, placenta, adrenal gland, peripheral blood leukocytes, bone marrow, retina, ovary, fetal brain, fetal liver, heart, spleen, liver, lung, muscle, thyroid gland, uterus, prostate, skin, salivary gland, and pancreas. Specific localization of the expression of ion-x may be determined, inter alia, using the methodology set forth in Example 12, below.

Kits

The present invention is also directed to kits, including pharmaceutical kits. The kits can comprise any of the nucleic acid molecules described above, any of the polypeptides described above, or any antibody which binds to a polypeptide of the invention as described above, as well as a negative control. The kit preferably comprises additional components, such as, for example, instructions, solid support, reagents helpful for quantification, and the like.

In another aspect, the invention features methods for detection of a polypeptide in a sample as a diagnostic tool for diseases or disorders, wherein the method comprises the steps of: (a) contacting the sample with a nucleic acid probe which hybridizes under hybridization assay conditions to a nucleic acid target region of a polypeptide having a sequence selected from the group consisting of SEQ ID NO:58 to SEQ ID NO:114, SEQ ID NO:116, and SEQ ID NO:118, said probe comprising the nucleic acid sequence encoding the polypeptide, fragments thereof, and the complements of the sequences and fragments; and (b) detecting the presence or amount of the probe:target region hybrid as an indication of the disease.

In preferred embodiments of the invention, the disease is selected from the group consisting of thyroid disorders (e.g. thyreotoxicosis, myxoedema); renal failure; inflammatory conditions (e.g., Crohn's disease); diseases related to cell differentiation and homeostasis; rheumatoid arthritis; autoimmune disorders; movement disorders; CNS disorders (e.g., pain including neuropathic pain, migraine, and other headaches; stroke; psychotic and neurological disorders, including anxiety, schizophrenia, manic depression, anxiety, generalized anxiety disorder, post-traumatic-stress disorder, depression, bipolar disorder, delirium, dementia, severe mental retardation; dyskinesias, such as Huntington's disease or Tourette's Syndrome; attention disorders including ADD and ADHD, and degenerative disorders such as Parkinson's, Alzheimer's; movement disorders, including ataxias, supranuclear palsy, etc.); infections, such as viral infections caused by HIV-1 or HIV-2; metabolic and cardiovascular diseases and disorders (e.g., type 2 diabetes, obesity, anorexia, hypotension, hypertension, thrombosis, myocardial infarction, cardiomyopathies, atherosclerosis, etc.); proliferative diseases and cancers (e.g., different cancers such as breast, colon, lung, etc., and hyperproliferative disorders such as psoriasis, prostate hyperplasia, etc.); hormonal disorders (e.g., male/female hormonal replacement, polycystic ovarian syndrome, alopecia, etc.); and sexual dysfunction, and other diseases including inflammatory bowel disease, irritable bowel syndrome, diverticulitis, and polyps, among others.

Kits may be designed to detect either expression of polynucleotides encoding these proteins or the proteins themselves in order to identify tissue as being neurological. For example, oligonucleotide hybridization kits can be provided which include a container having an oligonucleotide probe specific for the ion-x-specific DNA and optionally, containers with positive and negative controls and/or instructions. Similarly, PCR kits can be provided which include a container having primers specific for the ion-x-specific sequences, DNA and optionally, containers with size markers, positive and negative controls and/or instructions.

Hybridization conditions should be such that hybridization occurs only with the genes in the presence of other nucleic acid molecules. Under stringent hybridization conditions only highly complementary nucleic acid sequences hybridize. Preferably, such conditions prevent hybridization of nucleic acids having 1 or 2 mismatches out of 20 contiguous nucleotides. Such conditions are defined supra.

The diseases for which detection of genes in a sample could be diagnostic include diseases in which nucleic acid (DNA and/or RNA) is amplified in comparison to normal cells. By "amplification" is meant increased numbers of DNA or RNA in a cell compared with normal cells.

The diseases that could be diagnosed by detection of nucleic acid in a sample preferably include central nervous system and metabolic diseases. The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

Alternatively, immunoassay kits can be provided which have containers container having antibodies specific for the ion-x protein and optionally, containers with positive and negative controls and/or instructions.

Kits may also be provided useful in the identification of ion-x binding partners such as natural ligands, neurotransmitters, or modulators (agonists or antagonists). Substances useful for treatment of disorders or diseases preferably show positive results in one or more in vitro assays for an activity corresponding to treatment of the disease or disorder in question. Substances that modulate the activity of the polypeptides preferably include, but are not limited to, antisense oligonucleotides, agonists and antagonists, and inhibitors of protein kinases.

Methods of Inducing Immune Response

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Methods of Identifying Ligands

The invention also provides assays to identify compounds that bind ion-x. One such assay comprises the steps of: (a) contacting a composition comprising an ion-x with a compound suspected of binding ion-x; and (b) measuring binding between the compound and ion-x. In one variation, the composition comprises a cell expressing ion-x on its surface. In another variation, isolated ion-x or cell membranes comprising ion-x are employed. The binding may be measured directly, e.g., by using a labeled compound, or may be measured indirectly by several techniques, including measuring ion trafficking of ion-x induced by the compound. Compounds identified as binding ion-x may be further tested in other assays including, but not limited to, in vivo models, in order to confirm or quantitate their activity.

Specific binding molecules, including natural ligands and synthetic compounds, can be identified or developed using isolated or recombinant ion-x products, ion-x variants, or preferably, cells expressing such products. Binding partners are useful for purifying ion-x products and detection or quantification of ion-x products in fluid and tissue samples using known immunological procedures. Binding molecules are also manifestly useful in modulating (i.e., blocking, inhibiting or stimulating) biological activities of ion-x, especially those activities involved in signal transduction.

The DNA and amino acid sequence information provided by the present invention also makes possible identification of binding partner compounds with which an ion-x polypeptide or polynucleotide will interact. Methods to identify binding partner compounds include solution assays, in vitro assays wherein ion-x polypeptides are immobilized, and cell-based assays. Identification of binding partner compounds of ion-x polypeptides provides candidates for therapeutic or prophylactic intervention in pathologies associated with ion-x normal and aberrant biological activity.

The invention includes several assay systems for identifying ion-x-binding partners. In solution assays, methods of the invention comprise the steps of (a) contacting an ion-x polypeptide with one or more candidate binding partner compounds and (b) identifying the compounds that bind to the ion-x polypeptide. Identification of the compounds that bind the ion-x polypeptide can be achieved by isolating the ion-x polypeptide/binding partner complex, and separating the binding partner compound from the ion-x polypeptide. An additional step of characterizing the physical, biological, and/or biochemical properties of the binding partner compound is also comprehended in another embodiment of the invention. In one aspect, the ion-x polypeptide/binding partner complex is isolated using an antibody immunospecific for either the ion-x polypeptide or the candidate binding partner compound.

In still other embodiments, either the ion-x polypeptide or the candidate binding partner compound comprises a label or tag that facilitates its isolation, and methods of the invention to identify binding partner compounds include a step of isolating the ion-x polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized ion-x polypeptide with a candidate binding partner compound and (b) detecting binding of the candidate compound to the ion-x polypeptide. In an alternative embodiment, the candidate binding partner compound is immobilized and binding of ion-x is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. Detection of binding can be accomplished (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

The invention also provides cell-based assays to identify binding partner compounds of an ion-x polypeptide. In one embodiment, the invention provides a method comprising the steps of contacting an ion-x polypeptide expressed on the surface of a cell with a candidate binding partner compound and detecting binding of the candidate binding partner compound to the ion-x polypeptide. In a preferred embodiment, the detection comprises detecting a calcium flux or other physiological event in the cell caused by the binding of the molecule.

Another aspect of the present invention is directed to methods of identifying compounds that bind to either ion-x or nucleic acid molecules encoding ion-x, comprising contacting ion-x, or a nucleic acid molecule encoding the same, with a compound, and determining whether the compound binds ion-x or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology*, 1999, John Wiley & Sons, NY, which is incorporated herein by reference in its entirety. The compounds to be screened include (which may include compounds which are suspected to bind ion-x, or a nucleic acid molecule encoding the same), but are not limited to, extracellular, intracellular, biologic or chemical origin. The methods of the invention also embrace ligands, especially neuropeptides, that are attached to a label, such as a radiolabel (e.g., $^{125}$I, $^{35}$S, $^{32}$P, $^{33}$P, $^{3}$H), a fluorescence label, a chemiluminescent label, an enzymic label and an immunogenic label. Modulators falling within the scope of the invention include, but are not limited to, non-peptide molecules such as non-peptide mimetics, non-peptide allosteric effectors, and peptides. The ion-x polypeptide or polynucleotide employed in such a test may either be free in solution, attached to a solid support, borne on a cell surface or located intracellularly or associated with a portion of a cell. One skilled in the art can, for example, measure the formation of complexes between ion-x and the compound being tested. Alternatively, one skilled in the art can examine the diminution in complex formation between ion-x and its substrate caused by the compound being tested.

In another embodiment of the invention, high throughput screening for compounds having suitable binding affinity to ion-x is employed. Briefly, large numbers of different small peptide test compounds are synthesized on a solid substrate. The peptide test compounds are contacted with ion-x and washed. Bound ion-x is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed ion-x can be used for HTS binding assays in conjunction with its defined ligand, in this case the corresponding neuropeptide that activates it. The identified peptide is labeled with a suitable radioisotope, including, but not limited to, $^{125}$I, $^{3}$H, $^{35}$S or $^{32}$P, by methods that are well known to those skilled in the art. Alternatively, the peptides may be labeled by well-known methods with a suitable fluorescent derivative (Baindur et al., *Drug Dev. Res.*, 1994, 33, 373–398; Rogers, *Drug Discovery Today*, 1997, 2, 156–160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147–184; Sweetnam et al., *J. Natural Products*, 1993, 56, 441–455). Alternative methods include a scintillation proximity assay (SPA) or a FlashPlate format in which such separation is unnecessary (Nakayama, *Cur. Opinion Drug Disc. Dev.*, 1998, 1, 85–91 Bossé et al., *J. Biomolecular Screening*, 1998, 3, 285–292.). Binding of fluorescent ligands can be detected in various ways, including fluorescence energy transfer (FRET), direct spectrophotofluorometric analysis of bound ligand, or fluorescence polarization (Rogers, *Drug Discovery Today*, 1997, 2, 156–160; Hill, *Cur. Opinion Drug Disc. Dev.*, 1998, 1, 92–97).

Other assays may be used to identify specific ligands of a ion-x receptor, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., Nature, 340:245–246 (1989), and Fields et al., Trends in Genetics, 10:286–292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is an ion channel gene product, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to an ion-x receptor, or fragment thereof, a fusion polynucleotide encoding both an ion-x receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683–1691 (1997), incorporated herein by reference. This technique screens combinatorial libraries of 20–30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with ion-x. Radiolabeled competitive binding studies are described in A. H. Lin et al. *Antimicrobial Agents and Chemotherapy,* 1997, vol. 41, no. 10. pp. 2127–2131, the disclosure of which is incorporated herein by reference in its entirety.

Identification of Modulating Agents

The invention also provides methods for identifying a modulator of binding between a ion-x and an ion-x binding partner, comprising the steps of: (a) contacting an ion-x binding partner and a composition comprising an ion-x in the presence and in the absence of a putative modulator compound; (b) detecting binding between the binding partner and the ion-x; and (c) identifying a putative modulator compound or a modulator compound in view of decreased or increased binding between the binding partner and the ion-x in the presence of the putative modulator, as compared to binding in the absence of the putative modulator. Compounds identified as modulating binding between ion-x and an ion-x binding partner may be further tested in other assays including, but not limited to, in vivo models, in order to confirm or quantitate their activity.

Ion-x binding partners that stimulate ion-x activity are useful as agonists in disease states or conditions characterized by insufficient ion-x signaling (e.g., as a result of insufficient activity of an ion-x ligand). Ion-x binding partners that block ligand-mediated ion-x signaling are useful as ion-x antagonists to treat disease states or conditions characterized by excessive ion-x signaling. In addition ion-x modulators in general, as well as ion-x polynucleotides and polypeptides, are useful in diagnostic assays for such diseases or conditions.

In another aspect, the invention provides methods for treating a disease or abnormal condition by administering to a patient in need of such treatment a substance that modulates the activity or expression of a polypeptide having a sequence selected from the group consisting of SEQ ID NO:58 to SEQ ID NO:114, SEQ ID NO:116, and SEQ ID NO:118.

Agents that modulate (i.e., increase, decrease, or block) ion-x activity or expression may be identified by incubating a putative modulator with a cell containing an ion-x polypeptide or polynucleotide and determining the effect of the putative modulator on ion-x activity or expression. The selectivity of a compound that modulates the activity of ion-x can be evaluated by comparing its effects on ion-x to its effect on other ion channel compounds. Selective modulators may include, for example, antibodies and other proteins, peptides, or organic molecules that specifically bind to an ion-x polypeptide or an ion-x encoding nucleic acid. Modulators of ion-x activity will be therapeutically useful in treatment of diseases and physiological conditions in which normal or aberrant ion-x activity is involved. Compounds identified as modulating ion-x activity may be further tested in other assays including, but not limited to, in vivo models, in order to confirm or quantitate their activity.

Ion-x polynucleotides, polypeptides, and modulators may be used in the treatment of such diseases and conditions as infections, such as viral infections caused by HIV-1 or HIV-2; thyroid disorders (e.g. thyreotoxicosis, myxoedema); renal failure; inflammatory conditions (e.g., Crohn's disease); diseases related to cell differentiation and homeostasis; rheumatoid arthritis; autoimmune disorders; movement disorders; CNS disorders (e.g., pain including neuropathic pain, migraine, and other headaches; stroke; psychotic and neurological disorders, including anxiety, schizophrenia, manic depression, anxiety, generalized anxiety disorder, post-traumatic-stress disorder, depression, bipolar disorder, delirium, dementia, severe mental retardation; dyskinesias, such as Huntington's disease or Tourette's Syndrome; attention disorders including ADD and ADHD, and degenerative disorders such as Parkinson's, Alzheimer's; movement disorders, including ataxias, supranuclear palsy, etc.); infections, such as viral infections caused by HIV-1 or HIV-2; metabolic and cardiovascular diseases and disorders (e.g., type 2 diabetes, obesity, anorexia, hypotension, hypertension, thrombosis, myocardial infarction, cardiomyopathies, atherosclerosis, etc.); proliferative diseases and cancers (e.g., different cancers such as breast, colon, lung, etc., and hyperproliferative disorders such as psoriasis, prostate hyperplasia, etc.); hormonal disorders (e.g., male/female hormonal replacement, polycystic ovarian syndrome, alopecia, etc.); and sexual dysfunction, and other diseases including inflammatory bowel disease, irritable bowel syndrome, diverticulitis, and polyps, among others.

Ion-x polynucleotides and polypeptides, as well as ion-x modulators may also be used in diagnostic assays for such diseases or conditions.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between the ion-x polypeptide and the binding partner compound changes in the presence of the candidate modulator compared to binding in the absence of the candidate modulator compound. A modulator that increases binding between the ion-x polypeptide and the binding partner compound is described as an enhancer or activator, and a modulator that decreases binding between the ion-x polypeptide and the binding partner compound is described as an inhibitor.

The invention also comprehends high-throughput screening (HTS) assays to identify compounds that interact with or inhibit biological activity (i.e., affect enzymatic activity, binding activity, etc.) of an ion-x polypeptide. HTS assays permit screening of large numbers of compounds in an efficient manner. Cell-based HTS systems are contemplated to investigate ion-x receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the ion-x polypeptide.

Another aspect of the present invention is directed to methods of identifying compounds which modulate (i.e., increase or decrease) activity of ion-x comprising contacting ion-x with a compound, and determining whether the compound modifies activity of ion-x. The activity in the presence of the test compared is measured to the activity in the absence of the test compound. One of skill in the art can, for example, measure the activity of the ion channel polypeptide using electrophysiological methods, described infra. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The activity of the polypeptides of the invention can also be determined by, as non-limiting examples, the ability to bind or be activated by certain ligands, including, but not limited to, known neurotransmitters, agonists and antagonists, including but not limited to serotonin, acetylcholine, nicotine, and GABA. Alternatively, the activity of the ion channels can be assayed by examining activity such as ability to bind or be affected by calcium ions, hormones, chemokines, neuropeptides, neurotransmitters, nucleotides, lipids, odorants, and photons. In various embodiments of the method, the assay may take the form of an ion flux assay, a membrane potential assay, a yeast growth assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^3$H]-arachidonic acid), and an assay for extracellular acidification rates, as well as other binding or function-based assays of activity that are generally known in the art Another potentially useful assay to examine the activity of ion channels is electrophysiology, the measurement of ion permeability across the cell membrane. This technique is described in, for example, Electrophysiology, A Practical Approach, D I Wallis editor, IRL Press at Oxford University Press, (1993), and Voltage and patch Clamping with Microelectrodes, Smith et al., eds., Waverly Press, Inc for the American Physiology Society (1985), each of which is incorporated by reference in its entirety.

Another assay to examine the activity of ion channels is through the use of the Fluorometric Imaging Plate Reader (FLIPR) system, developed by Dr. Vince Groppi of the Pharmacia Corporation to perform cell-based, high-throughput screening (HTS) assays measuring, for example, membrane potential. Changes in plasma membrane potential correlate with the modulation of ion channels as ions move into or out of the cell. The FLIPR system measures such changes in membrane potential. This is accomplished by loading cells expressing an ion channel gene with a cell-membrane permeant fluorescent indicator dye suitable for measuring changes in membrane potential such as diBAC (bis-(1,3-dibutylbarbituric acid)pentamethine oxonol, Molecular Probes). Thus the modulation of ion channel activity can be assessed with FLIPR and detected as changes in the emission spectrum of the diBAC dye.

The present invention is particularly useful for screening compounds by using ion-x in any of a variety of drug screening techniques. The compounds to be screened include (which may include compounds which are suspected to modulate ion-x activity), but are not limited to, extracellular, intracellular, biologic or chemical origin. The ion-x polypeptide employed in such a test may be in any form, preferably, free in solution, attached to a solid support, borne on a cell surface or located intracellularly. One skilled in the art can, for example, measure the formation of complexes between ion-x and the compound being tested. Alternatively, one skilled in the art can examine the diminution in complex formation between ion-x and its substrate caused by the compound being tested.

The activity of ion-x polypeptides of the invention can be determined by, for example, examining the ability to bind or be activated by chemically synthesized peptide ligands. Alternatively, the activity of ion-x polypeptides can be assayed by examining their ability to bind calcium ions, hormones, chemokines, neuropeptides, neurotransmitters, nucleotides, lipids, odorants, and photons. Alternatively, the activity of the ion-x polypeptides can be determined by examining the activity of effector molecules including, but not limited to, adenylate cyclase, phospholipases and ion channels. Thus, modulators of ion-x polypeptide activity may alter ion channel function, such as a binding property of a channel or an activity such as ion selectivity. In various embodiments of the method, the assay may take the form of an ion flux assay, a yeast growth assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^3$H]-arachidonic acid), and an assay for extracellular acidification rates, as well as other binding or function-based assays of ion-x activity that are generally known in the art. Ion-x activity can be determined by methodologies that are used to assay for FaRP activity, which is well known to those skilled in the art. Biological activities of ion-x receptors according to the invention include, but are not limited to, the binding of a natural or an unnatural ligand, as well as any one of the functional activities of ion channels known in the art.

The modulators of the invention exhibit a variety of chemical structures, which can be generally grouped into non-peptide mimetics of natural ion channel ligands, peptide and non-peptide allosteric effectors of ion channels, and peptides that may function as activators or inhibitors (competitive, uncompetitive and non-competitive) (e.g., antibody products) of ion channels. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Examples of organic modulators of ion channels are GABA, serotonin, acetylcholine, nicotine, glutamate, glycine, NMDA, and kainic acid.

Other assays can be used to examine enzymatic activity including, but not limited to, photometric, radiometric, HPLC, electrochemical, and the like, which are described in, for example, *Enzyme Assays: A Practical Approach*, eds., R. Eisenthal and M. J. Danson, 1992, Oxford University Press, which is incorporated herein by reference in its entirety.

The use of cDNAs encoding ion channels in drug discovery programs is well known; assays capable of testing thousands of unknown compounds per day in high-throughput screens (HTSs) are thoroughly documented. The literature is replete with examples of the use of radiolabeled ligands in HTS binding assays for drug discovery (see Williams, *Medicinal Research Reviews*, 1991, 11, 147–184; Sweetnam, et al., *J. Natural Products*, 1993, 56, 441–455 for review). Recombinant receptors are preferred for binding assay HTS because they allow for better specificity (higher relative purity), provide the ability to generate large amounts of receptor material, and can be used in a broad variety of formats (see Hodgson, *Bio/Technology*, 1992, 10, 973–980; each of which is incorporated herein by reference in its entirety).

A variety of heterologous systems are available for functional expression of recombinant receptors that are well known to those skilled in the art. Such systems include bacteria (Strosberg, et al., *Trends in Pharmacological Sciences*, 1992, 13, 95–98), yeast (Pausch, *Trends in Biotechnology*, 1997, 15, 487–494), several kinds of insect cells (Vanden Broeck, *Int. Rev. Cytology*, 1996, 164, 189–268), amphibian cells (Jayawickreme et al., *Current Opinion in Biotechnology*, 1997, 8, 629–634) and several mammalian cell lines (CHO, HEK-293, COS, etc.; see Gerhardt, et al., *Eur. J. Pharmacology*, 1997, 334, 1–23). These examples do not preclude the use of other possible cell expression systems, including cell lines obtained from nematodes (PCT application WO 98/37177).

In preferred embodiments of the invention, methods of screening for compounds that modulate ion-x activity comprise contacting test compounds with ion-x and assaying for the presence of a complex between the compound and ion-x. In such assays, the ligand is typically labeled. After suitable incubation, free ligand is separated from that present in bound form, and the amount of free or uncomplexed label is a measure of the ability of the particular compound to bind to ion-x.

Examples of such biological responses include, but are not limited to, the following: the ability to survive in the absence of a limiting nutrient in specifically engineered yeast cells (Pausch, *Trends in Biotechnology*, 1997, 15, 487–494); changes in intracellular $Ca^{2+}$ concentration as measured by fluorescent dyes (Murphy, et al., *Cur. Opinion Drug Disc. Dev.*, 1998, 1, 192–199). Fluorescence changes can also be used to monitor ligand-induced changes in membrane potential or intracellular pH; an automated system suitable for HTS has been described for these purposes (Schroeder, et al., *J. Biomolecular Screening*, 1996, 1, 75–80). Melanophores prepared from *Xenopus laevis* show a ligand-dependent change in pigment organization in response to heterologous ion channel activation; this response is adaptable to HTS formats (Jayawickreme et al., *Cur. Opinion Biotechnology*, 1997, 8, 629–634). Assays are also available for the measurement of common second messengers, including cAMP, phosphoinositides and arachidonic acid, but these are not generally preferred for HTS.

In another embodiment of the invention, permanently transfected CHO cells could be used for the preparation of membranes which contain significant amounts of the recombinant receptor proteins; these membrane preparations would then be used in receptor binding assays, employing the radiolabeled ligand specific for the particular receptor. Alternatively, a functional assay, such as fluorescent monitoring of ligand-induced changes in internal $Ca^{2+}$ concentration or membrane potential in permanently transfected CHO cells containing each of these receptors individually or in combination would be preferred for HTS. Equally preferred would be an alternative type of mammalian cell, such as HEK-293 or COS cells, in similar formats. More preferred would be permanently transfected insect cell lines, such as *Drosophila* S2 cells. Even more preferred would be recombinant yeast cells expressing the *Drosophila melanogaster* receptors in HTS formats well known to those skilled in the art (e.g., Pausch, *Trends in Biotechnology*, 1997, 15, 487–494).

The invention contemplates a multitude of assays to screen and identify inhibitors of ligand binding to ion-x. In one example, the ion-x is immobilized and interaction with a binding partner is assessed in the presence and absence of a candidate modulator such as an inhibitor compound. In another example, interaction between the ion-x and its binding partner is assessed in a solution assay, both in the presence and absence of a candidate inhibitor compound. In either assay, an inhibitor is identified as a compound that decreases binding between the ion-x and its binding partner. Another contemplated assay involves a variation of the dihybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits"

or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63–68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as such peptide modulators as neuropeptides other than natural ligands, antibodies, antibody fragments, and modified compounds comprising antibody domains that are immunospecific for the expression product of the identified ion-x gene.

The polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for the ion-x of the invention, but which are smaller and exhibit a longer half time than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequences of the present invention with the sequences present in all the available databases showed a significant homology with the transmembrane domains, including the pore domain, of ion channel proteins. Accordingly, computer modeling can be used to develop a putative tertiary structure of the proteins of the invention based on the available information of the transmembrane domain of other proteins. Thus, novel ligands based on the predicted structure of ion-x can be designed.

In a particular embodiment, the novel molecules identified by the screening methods according to the invention are low molecular weight organic molecules, in which case a composition or pharmaceutical composition can be prepared thereof for oral intake, such as in tablets. The compositions, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in Remington's Pharmaceutical Sciences, $16^{th}$ edition, Osol, A (ed.), 1980, which is incorporated herein by reference in its entirety.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth. In a particular embodiment, the present molecules are used in gene therapy. For a review of gene therapy procedures, see e.g. Anderson, *Science,* 1992, 256, 808–813, which is incorporated herein by reference in its entirety.

The present invention also encompasses a method of agonizing (stimulating) or antagonizing an ion-x natural binding partner associated activity in a mammal comprising administering to said mammal an agonist or antagonist to one of the above disclosed polypeptides in an amount sufficient to effect said agonism or antagonism. One embodiment of the present invention, then, is a method of treating diseases in a mammal with an agonist or antagonist of the protein of the present invention comprises administering the agonist or antagonist to a mammal in an amount sufficient to agonize or antagonize ion-x-associated functions.

Exemplary diseases and conditions amenable to treatment based on the present invention include, but are not limited to, thyroid disorders (e.g. thyreotoxicosis, myxoedema); renal failure; inflammatory conditions (e.g., Crohn's disease); diseases related to cell differentiation and homeostasis; rheumatoid arthritis; autoimmune disorders; movement disorders; CNS disorders (e.g., pain including neuropathic pain, migraine, and other headaches); stroke; epilepsy or seizures; psychotic and neurological disorders, including anxiety, schizophrenia, manic depression, anxiety, generalized anxiety disorder, post-traumatic-stress disorder, depression, bipolar disorder, delirium, dementia, severe mental retardation; dyskinesias, such as Huntington's disease or Tourette's Syndrome; attention disorders including ADD and ADHD, and degenerative disorders such as Parkinson's, Alzheimer's; movement disorders, including ataxias, supranuclear palsy, etc.); infections, such as viral infections caused by HIV-1 or HIV-2; metabolic and cardiovascular diseases and disorders (e.g., type 2 diabetes, obesity, anorexia, hypotension, hypertension, thrombosis, myocardial infarction, cardiomyopathies, atherosclerosis, etc.); proliferative diseases and cancers (e.g., different cancers such as breast, colon, lung, etc., and hyperproliferative disorders such as psoriasis, prostate hyperplasia, etc.); hormonal disorders (e.g., male/female hormonal replacement, polycystic ovarian syndrome, alopecia, etc.); and sexual dysfunction, and other diseases including inflammatory bowel disease, irritable bowel syndrome, diverticulitis, and polyps, among others.

Compounds that can traverse cell membranes and are resistant to acid hydrolysis are potentially advantageous as therapeutics as they can become highly bioavailable after being administered orally to patients. However, many of these protein inhibitors only weakly inhibit function. In addition, many inhibit a variety of protein kinases and will therefore cause multiple side effects as therapeutics for diseases.

Methods of determining the dosages of compounds to be administered to a patient and modes of administering compounds to an organism are disclosed in International patent publication number WO 96/22976, published Aug. 1, 1996, which is incorporated herein by reference in its entirety, including any drawings, figures or tables. Those skilled in the art will appreciate that such descriptions are applicable to the present invention and can be adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, Journal of American Veterinary Medical Assoc., 202:229–249, 1993). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness. Plasma levels should reflect the potency of the drug. Generally, the more potent the compound the lower the plasma levels necessary to achieve efficacy.

Sequences selected from the group consisting of SEQ ID NO:1 to SEQ ID NO:57, SEQ ID NO:115, SEQ ID NO:117, and SEQ ID NO:119, and fragments thereof, will, as detailed above, enable screening the endogenous neurotransmitters/hormones/ligands which activate, agonize, or antagonize ion-x and for compounds with potential utility in treating disorders including, but not limited to, thyroid disorders (e.g. thyreotoxicosis, myxoedema); renal failure; inflammatory conditions (e.g., Crohn's disease); diseases related to cell differentiation and homeostasis; rheumatoid arthritis; autoimmune disorders; movement disorders; CNS disorders (e.g., pain including neuropathic pain, migraine, and other headaches); stroke; epilepsy or seizures; psychotic and neurological disorders, including anxiety, schizophrenia, manic depression, anxiety, generalized anxiety disorder, post-traumatic-stress disorder, depression, bipolar disorder, delirium, dementia, severe mental retardation; dyskinesias, such as Huntington's disease or Tourette's Syndrome; attention disorders including ADD and ADHD, and degenerative disorders such as Parkinson's, Alzheimer's; movement disorders, including ataxias, supranuclear palsy, etc.); infections, such as viral infections caused by HIV-1 or HIV-2; metabolic and cardiovascular diseases and disorders (e.g., type 2 diabetes, obesity, anorexia, hypotension, hypertension, thrombosis, myocardial infarction, cardiomyopathies, atherosclerosis, etc.); proliferative diseases and cancers (e.g., different cancers such as breast, colon, lung, etc., and hyperproliferative disorders such as psoriasis, prostate hyperplasia, etc.); hormonal disorders (e.g., male/female hormonal replacement, polycystic ovarian syndrome, alopecia, etc.); and sexual dysfunction, and other diseases including inflammatory bowel disease, irritable bowel syndrome, diverticulitis, and polyps, among others.

For example, ion-x may be useful in the treatment of respiratory ailments such as asthma, where T cells are implicated by the disease. Contraction of airway smooth muscle is stimulated by thrombin. Cicala et al (1999) Br J Pharmacol 126:478–484. Additionally, in bronchiolitis obliterans, it has been noted that activation of thrombin receptors may be deleterious. Hauck et al.(1999) Am J Physiol 277: L22–L29. Furthermore, mast cells have also been shown to have thrombin receptors. Cirino et al (1996) J Exp Med 183:821–827. Ion-x may also be useful in remodeling of airway structures in chronic pulmonary inflammation via stimulation of fibroblast procollagen synthesis. See, e.g., Chambers et al. (1998) Biochem J 333:121–127; Trejo et al. (1996) J Biol Chem 271:21536–21541.

In another example, increased release of sCD40L and expression of CD40L by T cells after activation of thrombin receptors suggests that ion-x may be useful in the treatment of unstable angina due to the role of T cells and inflammation. See Aukrust et al. (1999) Circulation 100:614–620.

A further example is the treatment of inflammatory diseases, such as psoriasis, inflammatory bowel disease, multiple sclerosis, rheumatoid arthritis, and thyroiditis. Due to the tissue expression profile of ion-x, inhibition of thrombin receptors may be beneficial for these diseases. See, e.g., Morris et al. (1996) Ann Rheum Dis 55:841–843. In addition to T cells, NK cells and monocytes are also critical cell types which contribute to the pathogenesis of these diseases. See, e.g., Naldini & Carney (1996) Cell Immunol 172:35–42; Hoffman & Cooper (1995) Blood Cells Mol Dis 21:156–167; Colotta et al. (1994) Am J Pathol 144:975–985.

Expression of ion-x in spleen may suggest that it may play a role in the proliferation of hematopoietic progenitor cells. See DiCuccio et al. (1996) Exp Hematol 24:914–918.

Expression of 5HT-3C in the small intestine, colon, placenta, and peripheral blood leukocytes suggests that 5HT-3C may be useful in such diseases and disorders as inflammatory bowel disease, irritable bowel syndrome, diverticulitis, and polyps, among others.

Expression of 5HT-3D in the fetal brain and whole brain suggests that 5HT-3D may play a role in, among others, CNS disorders (e.g., pain including neuropathic pain, migraine, and other headaches); stroke; epilepsy or seizures; psychotic and neurological disorders, including anxiety, schizophrenia, manic depression, anxiety, generalized anxiety disorder, post-traumatic-stress disorder, depression, bipolar disorder, delirium, dementia, severe mental retardation; dyskinesias, such as Huntington's disease or Tourette's Syndrome; attention disorders including ADD and ADHD, and degenerative disorders such as Parkinson's, Alzheimer's; movement disorders, including ataxias, supranuclear palsy, etc.).

Expression of 5HT-3D in testis suggests that 5HT-3D may play a role in hormonal disorders and sexual dysfunction, among others.

As another example, ion-x may be useful in the treatment of acute and/or traumatic brain injury. Astrocytes have been demonstrated to express thrombin receptors. Activation of thrombin receptors may be involved in astrogliosis following brain injury. Therefore, inhibition of receptor activity may be beneficial for limiting neuroinflammation. Scar formation mediated by astrocytes may also be limited by inhibiting thrombin receptors. See, e.g, Pindon et al. (1998) Eur J Biochem 255:766–774; Ubl & Reiser. (1997) Glia 21:361–369; Grabham & Cunningham (1995) J Neurochem 64:583–591.

Ion-x receptor activation may mediate neuronal and astrocyte apoptosis and prevention of neurite outgrowth. Inhibition would be beneficial in both chronic and acute brain injury. See, e.g., Donovan et al. (1997) J Neurosci 17:5316–5326; Turgeon et al (1998) J Neurosci 18:6882–6891; Smith-Swintosky et al. (1997) J Neurochem 69:1890–1896; Gill et al. (1998) Brain Res 797:321–327; Suidan et al. (1996) Semin Thromb Hemost 22:125–133.

The attached Sequence Listing contains the sequences of the polynucleotides and polypeptides of the invention and is incorporated herein by reference in its entirety.

The identification of modulators such as agonists and antagonists is therefore useful for the identification of compounds useful to treat neurological diseases and disorders. Such neurological diseases and disorders, include, but are not limited to, schizophrenia, affective disorders, ADHD/ADD (i.e., Attention Deficit-Hyperactivity Disorder/Attention Deficit Disorder), and neural disorders such as Alzheimer's disease, Parkinson's disease, migraine, and senile dementia as well as depression, anxiety, bipolar disease, epilepsy, neuritis, neurasthenia, neuropathy, neuroses, and the like. Other diseases and disorders that may be treated by such agonists and antagonists include, but are not limited to, inflammatory bowel disease, irritable bowel syndrome, diverticulitis, and polyps.

Methods of Screening Human Subjects

Thus in yet another embodiment, the invention provides genetic screening procedures that entail analyzing a person's genome—in particular their alleles for ion channels of the invention—to determine whether the individual possesses a genetic characteristic found in other individuals that are considered to be afflicted with, or at risk for, developing a mental disorder or disease of the brain that is suspected of having a hereditary component. For example, in one embodiment, the invention provides a method for determining a potential for developing a disorder affecting the brain in a human subject comprising the steps of analyzing the coding sequence of one or more ion channel genes from the human subject; and determining development potential for the disorder in said human subject from the analyzing step.

More particularly, the invention provides a method of screening a human subject to diagnose a disorder affecting the brain or genetic predisposition therefor, comprising the steps of: (a) assaying nucleic acid of a human subject to determine a presence or an absence of a mutation altering the amino acid sequence, expression, or biological activity of at least one ion channel that may be expressed in the brain, wherein the ion channel comprises an amino acid sequence selected from the group consisting of SEQ ID NO:58 to SEQ ID NO:114, SEQ ID NO:116, and SEQ ID NO:118, or an allelic variant thereof, and wherein the nucleic acid corresponds to the gene encoding the ion channel; and (b) diagnosing the disorder or predisposition from the presence or absence of said mutation, wherein the presence of a mutation altering the amino acid sequence, expression, or biological activity of allele in the nucleic acid correlates with an increased risk of developing the disorder.

By "human subject" is meant any human being, human embryo, or human fetus. It will be apparent that methods of the present invention will be of particular interest to individuals that have themselves been diagnosed with a disorder affecting the brain or have relatives that have been diagnosed with a disorder affecting the brain.

By "screening for an increased risk" is meant determination of whether a genetic variation exists in the human subject that correlates with a greater likelihood of developing a disorder affecting the brain than exists for the human population as a whole, or for a relevant racial or ethnic human sub-population to which the individual belongs. Both positive and negative determinations (i.e., determinations that a genetic predisposition marker is present or is absent)

are intended to fall within the scope of screening methods of the invention. In preferred embodiments, the presence of a mutation altering the sequence or expression of at least one ion-x ion channel allele in the nucleic acid is correlated with an increased risk of developing the disorder, whereas the absence of such a mutation is reported as a negative determination.

The "assaying" step of the invention may involve any techniques available for analyzing nucleic acid to determine its characteristics, including but not limited to well-known techniques such as single-strand conformation polymorphism analysis (SSCP) [Orita et al., *Proc Natl. Acad. Sci. USA*, 86: 2766–2770 (1989)]; heteroduplex analysis [White et al., *Genomics*, 12: 301–306 (1992)]; denaturing gradient gel electrophoresis analysis [Fischer et al., *Proc. Natl. Acad. Sci. USA*, 80: 1579–1583 (1983); and Riesner et al., *Electrophoresis*, 10: 377–389 (1989)]; DNA sequencing; RNase cleavage [Myers et al., *Science*, 230: 1242–1246 (1985)]; chemical cleavage of mismatch techniques [Rowley et al., *Genomics*, 30: 574–582 (1995); and Roberts et al., *Nucl. Acids Res.*, 25: 3377–3378 (1997)]; restriction fragment length polymorphism analysis; single nucleotide primer extension analysis [Shumaker et al., *Hum. Mutat.*, 7: 346–354 (1996); and Pastinen et al., *Genome Res.*, 7: 606–614 (1997)]; 5' nuclease assays [Pease et al., *Proc. Natl. Acad. Sci. USA*, 91:5022–5026 (1994)]; DNA Microchip analysis [Ramsay, G., *Nature Biotechnology*, 16: 40–48 (1999); and Chee et al., U.S. Pat. No. 5,837,832]; and ligase chain reaction [Whiteley et al., U.S. Pat. No. 5,521,065]. [See generally, Schafer and Hawkins, *Nature Biotechnology*, 16: 33–39 (1998).] All of the foregoing documents are hereby incorporated by reference in their entirety.

Thus, in one preferred embodiment involving screening ion-x sequences, for example, the assaying step comprises at least one procedure selected from the group consisting of: (a) determining a nucleotide sequence of at least one codon of at least one ion-x allele of the human subject; (b) performing a hybridization assay to determine whether nucleic acid from the human subject has a nucleotide sequence identical to or different from one or more reference sequences; (c) performing a polynucleotide migration assay to determine whether nucleic acid from the human subject has a nucleotide sequence identical to or different from one or more reference sequences; and (d) performing a restriction endonuclease digestion to determine whether nucleic acid from the human subject has a nucleotide sequence identical to or different from one or more reference sequences.

In a highly preferred embodiment, the assaying involves sequencing of nucleic acid to determine nucleotide sequence thereof, using any available sequencing technique. [See, e.g., Sanger et al., *Proc. Natl. Acad. Sci. (USA)*, 74: 5463–5467 (1977) (dideoxy chain termination method); Mirzabekov, *TIBTECH*, 12: 27–32 (1994) (sequencing by hybridization); Drmanac et al., *Nature Biotechnology*, 16: 54–58 (1998); U.S. Pat. No. 5,202,231; and *Science*, 260: 1649–1652 (1993) (sequencing by hybridization); Kieleczawa et al., *Science*, 258: 1787–1791 (1992) (sequencing by primer walking); (Douglas et al., *Biotechniques*, 14: 824–828 (1993) (Direct sequencing of PCR products); and Akane et al., *Biotechniques* 16: 238–241 (1994); Maxam and Gilbert, *Meth. Enzymol.*, 65: 499–560 (1977) (chemical termination sequencing), all incorporated herein by reference.] The analysis may entail sequencing of the entire ion-x gene genomic DNA sequence, or portions thereof; or sequencing of the entire receptor coding sequence or portions thereof. In some circumstances, the analysis may involve a determination of whether an individual possesses a particular allelic variant, in which case sequencing of only a small portion of nucleic acid—enough to determine the sequence of a particular codon characterizing the allelic variant—is sufficient. This approach is appropriate, for example, when assaying to determine whether one family member inherited the same allelic variant that has been previously characterized for another family member, or, more generally, whether a person's genome contains an allelic variant that has been previously characterized and correlated with a mental disorder having a heritable component.

In another highly preferred embodiment, the assaying step comprises performing a hybridization assay to determine whether nucleic acid from the human subject has a nucleotide sequence identical to or different from one or more reference sequences. In a preferred embodiment, the hybridization involves a determination of whether nucleic acid derived from the human subject will hybridize with one or more oligonucleotides, wherein the oligonucleotides have nucleotide sequences that correspond identically to a portion of the ion-x gene sequence taught herein, or that correspond identically except for one mismatch. The hybridization conditions are selected to differentiate between perfect sequence complementarity and imperfect matches differing by one or more bases. Such hybridization experiments thereby can provide single nucleotide polymorphism sequence information about the nucleic acid from the human subject, by virtue of knowing the sequences of the oligonucleotides used in the experiments.

Several of the techniques outlined above involve an analysis wherein one performs a polynucleotide migration assay, e.g., on a polyacrylamide electrophoresis gel (or in a capillary electrophoresis system), under denaturing or non-denaturing conditions. Nucleic acid derived from the human subject is subjected to gel electrophoresis, usually adjacent to (or co-loaded with) one or more reference nucleic acids, such as reference ion channel-encoding sequences having a coding sequence identical to all or a portion of a sequence selected from the group consisting of SEQ ID NO:1 to SEQ ID NO:57, SEQ ID NO:115, SEQ ID NO:117, and SEQ ID NO:119, (or identical except for one known polymorphism). The nucleic acid from the human subject and the reference sequence(s) are subjected to similar chemical or enzymatic treatments and then electrophoresed under conditions whereby the polynucleotides will show a differential migration pattern, unless they contain identical sequences. [See generally Ausubel et al. (eds.), *Current Protocols in Molecular Biology*, New York: John Wiley & Sons, Inc. (1987–1999); and Sambrook et al., (eds.), *Molecular Cloning, A Laboratory Manual*, Cold Spring Harbor, N.Y.: Cold Spring Harbor Laboratory Press (1989), both incorporated herein by reference in their entirety.]

In the context of assaying, the term "nucleic acid of a human subject" is intended to include nucleic acid obtained directly from the human subject (e.g., DNA or RNA obtained from a biological sample such as a blood, tissue, or other cell or fluid sample); and also nucleic acid derived from nucleic acid obtained directly from the human subject. By way of non-limiting examples, well known procedures exist for creating cDNA that is complementary to RNA derived from a biological sample from a human subject, and for amplifying DNA or RNA derived from a biological sample obtained from a human subject. Any such derived polynucleotide which retains relevant nucleotide sequence information of the human subject's own DNA/RNA is intended to fall within the definition of "nucleic acid of a human subject" for the purposes of the present invention.

In the context of assaying, the term "mutation" includes addition, deletion, and/or substitution of one or more nucleotides in the ion-x gene sequence (e.g., as compared to the ion channel-encoding sequences set forth of SEQ ID NO:1 to SEQ ID NO:57, SEQ ID NO:115, SEQ ID NO:117, and SEQ ID NO:119) and other polymorphisms that occur in introns (where introns exist) and that are identifiable via sequencing, restriction fragment length polymorphism, or other techniques. The various activity examples provided herein permit determination of whether a mutation modulates activity of the relevant receptor in the presence or absence of various test substances.

In a related embodiment, the invention provides methods of screening a person's genotype with respect to ion channels of the invention, and correlating such genotypes with diagnoses for disease or with predisposition for disease (for genetic counseling). For example, the invention provides a method of screening for an ion-x mental disorder genotype in a human patient, comprising the steps of: (a) providing a biological sample comprising nucleic acid from the patient, the nucleic acid including sequences corresponding to said patient's ion-x alleles; (b) analyzing the nucleic acid for the presence of a mutation or mutations; (c) determining an ion-x genotype from the analyzing step; and (d) correlating the presence of a mutation in an ion-x allele with a mental disorder genotype. In a preferred embodiment, the biological sample is a cell sample containing human cells that contain genomic DNA of the human subject. The analyzing can be performed analogously to the assaying described in preceding paragraphs. For example, the analyzing comprises sequencing a portion of the nucleic acid (e.g., DNA or RNA), the portion comprising at least one codon of the ion-x alleles.

Although more time consuming and expensive than methods involving nucleic acid analysis, the invention also may be practiced by assaying protein of a human subject to determine the presence or absence of an amino acid sequence variation in ion channel protein from the human subject. Such protein analyses may be performed, e.g., by fragmenting ion channel protein via chemical or enzymatic methods and sequencing the resultant peptides; or by Western analyses using an antibody having specificity for a particular allelic variant of the ion channel.

The invention also provides materials that are useful for performing methods of the invention. For example, the present invention provides oligonucleotides useful as probes in the many analyzing techniques described above. In general, such oligonucleotide probes comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides that have a sequence that is identical, or exactly complementary, to a portion of a human ion channel gene sequence taught herein (or allelic variant thereof), or that is identical or exactly complementary except for one nucleotide substitution. In a preferred embodiment, the oligonucleotides have a sequence that corresponds in the foregoing manner to a human ion channel coding sequence taught herein, and in particular, the coding sequences set forth in SEQ ID NO:1 to SEQ ID NO:57, SEQ ID NO:115, SEQ ID NO:117, and SEQ ID NO:119. In one variation, an oligonucleotide probe of the invention is purified and isolated. In another variation, the oligonucleotide probe is labeled, e.g., with a radioisotope, chromophore, or fluorophore. In yet another variation, the probe is covalently attached to a solid support. [See generally Ausubel et al. and Sambrook et al., supra.]

In a related embodiment, the invention provides kits comprising reagents that are useful for practicing methods of the invention. For example, the invention provides a kit for screening a human subject to diagnose a mental disorder or a genetic predisposition therefor, comprising, in association: (a) an oligonucleotide useful as a probe for identifying polymorphisms in a human ion-x ion channel gene, the oligonucleotide comprising 6–50 nucleotides that have a sequence that is identical or exactly complementary to a portion of a human ion-x gene sequence or ion-x coding sequence, except for one sequence difference selected from the group consisting of a nucleotide addition, a nucleotide deletion, or nucleotide substitution; and (b) a media packaged with the oligonucleotide containing information identifying polymorphisms identifiable with the probe that correlate with a mental disorder or a genetic predisposition therefor. Exemplary information-containing media include printed paper package inserts or packaging labels; and magnetic and optical storage media that are readable by computers or machines used by practitioners who perform genetic screening and counseling services. The practitioner uses the information provided in the media to correlate the results of the analysis with the oligonucleotide with a diagnosis. In a preferred variation, the oligonucleotide is labeled.

In still another embodiment, the invention provides methods of identifying those allelic variants of ion channels of the invention that correlate with mental disorders. It is well known that ion channels, including ion-x, are expressed in many different tissues, including the brain. Accordingly, the ion-x of the present invention may be useful, inter alia, for treating and/or diagnosing mental disorders. For example, the invention provides a method of identifying an ion channel allelic variant that correlates with a mental disorder, comprising steps of: (a) providing a biological sample comprising nucleic acid from a human patient diagnosed with a mental disorder, or from the patient's genetic progenitors or progeny; (b) analyzing the nucleic acid for the presence of a mutation or mutations in at least ion channel that is expressed in the brain, wherein the ion channel comprises an amino acid sequence selected from the group consisting of SEQ ID NO:1 to SEQ ID NO:57, SEQ ID NO:115, SEQ ID NO:117, and SEQ ID NO:119, or an allelic variant thereof, and wherein the nucleic acid includes sequence corresponding to the gene or genes encoding the ion channel; (c) determining a genotype for the patient for the ion channel from said analyzing step; and (d) identifying an allelic variant that correlates with the mental disorder from the determining step. To expedite this process, it may be desirable to perform linkage studies in the patients (and possibly their families) to correlate chromosomal markers with disease states. The chromosomal localization data provided herein facilitates identifying an involved ion channel with a chromosomal marker.

The foregoing method can be performed to correlate ion channels of the invention to a number of disorders having hereditary components that are causative or that predispose persons to the disorder. For example, in one preferred variation, the ion channel comprises ion-5HT-3D having an amino acid sequence set forth in SEQ ID NO:118, or an allelic variant thereof.

Also contemplated as part of the invention are polynucleotides that comprise the allelic variant sequences identified by such methods, and polypeptides encoded by the allelic variant sequences, and oligonucleotide and oligopeptide fragments thereof that embody the mutations that have been identified. Such materials are useful in in vitro cell-free and cell-based assays for identifying lead compounds and therapeutics for treatment of the disorders. For example, the variants are used in activity assays, binding assays, and assays to screen for activity modulators described herein. In one preferred embodiment, the invention provides a purified and isolated polynucleotide comprising a nucleotide sequence encoding an ion channel allelic variant identified according to the methods described above; and an oligonucleotide that comprises the sequences that differentiate the ion-x allelic variant from the sequences set forth in SEQ ID NO:1 to SEQ ID NO:57, SEQ ID NO:115, SEQ ID NO:117, and SEQ ID NO:119. The invention also provides a vector comprising the polynucleotide (preferably an expression vector); and a host cell transformed or transfected with the polynucleotide or vector. The invention also provides an isolated cell line that is expressing the allelic variant ion channel polypeptide; purified cell membranes from such cells; purified polypeptide; and synthetic peptides that embody the allelic variation amino acid sequence. In one particular embodiment, the invention provides a purified polynucleotide comprising a nucleotide sequence encoding a ion-5HT-3D protein of a human that is affected with a mental disorder; wherein said polynucleotide hybridizes to the complement of SEQ ID NO:117 under the following hybridization conditions: (a) hybridization for 16 hours at 42° C. in a hybridization solution comprising 50% formamide, 1% SDS, 1 M NaCl, 10% dextran sulfate and (b) washing 2 times for 30 minutes at 60° C. in a wash solution comprising 0.1×SSC and 1% SDS; and wherein the polynucleotide encodes an ion-5HT-3D amino acid sequence that differs from SEQ ID NO:118 by at least one residue.

An exemplary assay for using the allelic variants is a method for identifying a modulator of ion-x biological activity, comprising the steps of: (a) contacting a cell expressing the allelic variant in the presence and in the absence of a putative modulator compound; (b) measuring ion-x biological activity in the cell; and (c) identifying a putative modulator compound in view of decreased or increased ion-x biological activity in the presence versus absence of the putative modulator.

Additional features of the invention will be apparent from the following Examples. Examples 1, 2, and portions of Example 12 are actual, while the remaining Examples are prophetic. Additional features and variations of the invention will be apparent to those skilled in the art from the entirety of this application, including the detailed description, and all such features are intended as aspects of the invention. Likewise, features of the invention described herein can be recombined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. Table 5 contains the sequences of the polynucleotides and polypeptides of the invention, in addition to exemplary primers useful for cloning said sequences. "X" indicates an unknown amino acid or gap (absence of amino acid(s)).

TABLE 5

```
The following DNA sequence Ion42 <SEQ ID NO.1> was identified in H.
sapiens:
TTCCTGCCTAGTGTTCTGGCTGCTCTCGAGGCCTCCTGCTTGACTGTTAGCCTGGGGCTTACCTTCTTTCC

TCTCCTGCTTTCCGAATCGCATGTTTCCCTCTTTCTTGATTTATTCGCTTATTTTGGTGGAACACATCTCC

AGTATCTTCCTAGGAAAAGGAACATGGTAGATCAATTTTTCAAATTCTTGCATGTCTGATTTATTCTCTCT

TCATACTTGATTGGTAGTTTTGATACCAAATTCTAGGTTGAAAATAATTTTCACTTGGAATTTTAAAGGCA

TTTATTCCTCCATTGTCTTCTAGGTTCCAGCATTGCTATTGAGGACTCTGATGACATTTTCTTTTTCTTTT

TTTCTTTAGGCTCTGGAAACTTTTAGGATCTTCTCCTTAATAACAGTGTCCTGAATTTCACACTGATGTGC

CTTAGGACGGGTCTTTT

The following amino acid sequence <SEQ ID NOS.58> is a predicted amino
acid sequence derived from the DNA sequence of SEQ ID NO.1:
WNLEDNGGINAFKIPSENYFQPRI The following DNA sequence Ion43 <SEQ ID NO.2> was identified in H.
sapiens:
CTTTGTAGCTGTCATCTGCAGTGTGGGACAGCTGCACAAGGGCCCAGCATGTCTGTGTGTTTACCCAG

GGGACTGCCGCATGGCTCATGCTGAGCAGAAGCTGATGGACGACCTTCTGAACAAAACCCGTTACAAC

AACCTGATCTGCCCAGCCACCAGCTCCTCACAGCTCATCTCCATCGAGACAGAGCTCTCCCTGGCGCA

GTGCATCAGTGTGGTAAGTGCAGAGGGCACCTGTGGCTCAGGCTCAGATGAAGAGGCAGCTCATGCCC

AAGCCTCAAGCAATCAATGTCCAGAGGAATGAAATGACCAGAGTTGACTTAGACTCACCAATACGTGG

CGGGGAGGCTGGAGGAAGGTCCCTGAGGTTTATAGGTGTCCAATATTTAATGAGGTCATGGTTTTCTT

AACAAAGAAGAAATGAGGGTGGGAGCGGGATCACCACTGGCTAGGCAGCCAATGGGCCTGCATAGACT

CTGCTCAGCTGAGTCTCCAGCACGACTATAAGC
```

TABLE 5-continued

The following amino acid sequence <SEQ ID NO.59> is a predicted amino acid sequence derived from the DNA sequence of SEQ ID NO.2:
PATSSSQLISIETELSLAQCISVVSAE The following DNA sequence Ion44 <SEQ ID NO.3> was identified in *H. sapiens*:
GAAAAGGAATGTTATTGATGAATTTTGAGATAATTTTTGTATATAGCATAGGGTAAGGAAAAGAGAGG

TGTAAAGGATTAGAGATCAGTCTTAGAATGTACCTGGTGGACACAACTCTCCCAAAGGGCTATGTTCC

CATTGCTGTGTGCCAATTGATTGATCATGAAGTTTGATGGTTGCAGCTGAGCTAGGTACGACCTGTGG

GGACAAAGCAGGGACTGGCATGAGTGGCTTCCAGATCTCACCCATTACAAGATCAATCTCACATTCCA

TTCCCCCAAGCCTCCAAAATTAGACAGAACTTGCATCTTTCTCCCAGTTCTAAAACTCAACCATTTGT

TTGTGCTCATCTTTGTCTCTTTGTCCCCATGCCCCCAGCCTGTGGCAACTACCATTCTACTGTCTGTT

TCTATGAATTTAACTACTCTACATACTTCATATAAATGGAGACATACAGTATTTTATGGTTTTCTTGA

GGCTGGCATATTTCAATTAGCATAAAATCATCACGATCCATCCATTCGGTACCATGCA

The following amino acid sequence <SEQ ID NO.60> is a predicted amino acid sequence derived from the DNA sequence of SEQ ID NO.3:
TCIFLPVLKLNHLFVLIFVSLSPCPQPVATTILLSVSMNLTTLHTSYKWRHTVFYGFLEAGIF The following DNA sequence Ion45 <SEQ ID NO.4> was identified in *H. sapiens*:
AAGGGGATCTGTGCTGAGACCGGGAGTCTGAAGTTCAGGTTCCTGCCCTGCCACTAACCAACCATTGG

AGGGACACTTCTGGGCCTCAGTTTCCTCATCTGTAAAGCCCTGGTGATTCTCGAGAGTTCTTCACACT

TCTTTGTAGACAGACGCCGGGGCTCAGGCAAGAAAGCCTACGCTAATAAGCAGCCCCAGGGGAAGCCA

GCAGCAGGGGCCCTTCCCTCCTGGCTAAGAAAACTGCCACTGGGGAGAAGAGGAGGAGAGCCCAGGCC

TAGCTCTGAACGTACCTGATGTCACTTCCCCTCCCTGGTCCACAGTTCCAGCAGATTCACTCCAGCAT

TTTAGGATTCTGCGAGATTTGTCTGAGGGGCCTGATTTATAGGAGAGAGGAGGCCAGACTTGCCCCTC

CCTTACCCGACTTAGGATGGTAAAGCAACTTGGGAAAAGCATTTACTCTCAGCTCCCGGAATTACCCT

TCACTTTCCTGGCAGATAAATGGGGCAAAACAGAAGATGCAGTTACATTTAAATGGAGCGAGGCAGGT

GGAAGTTTATAAGATTTGAATACACTTTTTGGCTGCTTTTGAATATTCATT

The following amino acid sequence <SEQ ID NO.61> is a predicted amino acid sequence derived from the DNA sequence of SEQ ID NO.4:
TIGGTLLGLSFLICKALVILESSSHFFVDRRRGSGKKAYANKQPQGKPAAGALPSWLRKLPLGR The following DNA sequence Ion46 <SEQ ID NO.5> was identified in *H. sapiens*:
CTTCTTCCTGTAGGAAAATGCACATCATTTTTTAGGTGCTGAGACAGAGGACTAAGAAATCAATGACATAA

AAATGCATACTTTAATATTTTTTCTTTAAAACTATTATCCTAAGGTGTCCTACATACTATAATTTATAAGT

ATCTGGAAGAGTGAAAACAATTTTATTGAGGCCTTGTAAAATATGGCAGGTGCCTAGGACCTCATGGAACT

CAGGTATCTTCAGTAGGATGTGAAACATCACATCATGGGGCGTGGTGCAGTGTAAGCAGGTAAAGAAAAGC

CAGTTCTTCCACATGTAAACTACTTGAACTCCATTTCATCTTTTTTCATACCATCTC

The following amino acid sequence <SEQ ID NO.62> is a predicted amino acid sequence derived from the DNA sequence of SEQ ID NO.5:
WKNWLFFTCLHCTTPHDVMFHILLKIPEFHEVLGTCHILQGLNKIVFTLP The following DNA sequence Ion47 <SEQ ID NO.6> was identified in *H. sapiens*:
CAGACGGGGAGTCAGTACTTGAGAAGACCCGGAAGGCGGGGAGCACTTGGACTCCAGACGGGGAGTCA

GTACTGAGAGACCCGGAAGGCTGGGAGCACTGGACTCCAGACGGGGAGTCAGTACTGAGAGACCCGGA

AGGCTGGGAGCACTGGACTCCAGACGGGGAGTCAGTACTTGAGAGACCCAGAAGGCGGGGAGCACCCG

AAGACTCCACACCGGGGAGTCAGTACTGAGAGACCCG

The following amino acid sequence <SEQ ID NO.63> is a predicted amino acid sequence derived from the DNA sequence of SEQ ID NO.6:
TWTPDGESVLRDPEGWEHWTPDGESVLRDPEGWEHW

TABLE 5-continued

The following DNA sequence Ion48 <SEQ ID NO.7> was identified in *H. sapiens*:
GGACACCTGGCACGGGGCCTGTGCGTGCGGGAAAGAGGGGAGCCCTGTGGGCAGTCCAGGCCACCTGA

GTTATCTCCTAGCCCCCAGTCGCCTGAAGGAGGGGCTGGCCCCCCAGCGGGCCCTTGCCACGAGCCAC

GATGTCTGTGCCGCCAGGAAGCCCTACTGCACCACGTAGCCACCATTGCCAATACCTTCCGCAGCCAC

CGAGCTGCCCAGCGCTGCCATGAGGACTGGAAGCGCCTGGCCCGTGTGATGGACCGCTTCTTCCTGGC

CATCTTCTTCTCCATGGCCCTGGTCATGAGCCTCCTGGTGCTGGTGCAGGCCCTGTGAGGGCTGGGAC

TAAGTCACAGGGATCTGCTGCAGCCACAGCTCCTCCAGAAAGGGACAGCCACGGCCAAGTGGTTGCTG

GTCTTTGGGCCAGCCAGTCTCTCCCCACTGCTCCTAAGATCCTGAGACACTTGACTTCACAATCCACA

AGGGAGCACTCATTGTCTACACACCCTAACTAAAGGAAGTCCAGA

The following amino acid sequence <SEQ ID NO.64> is a predicted amino acid sequence derived from the DNA sequence of SEQ ID NO.7:
RQEALLHHVATIANTFRSHRAAQRCHEDWKRLARVMDRFFLAIFF The following DNA sequence Ion49 <SEQ ID NO.8> was identified in *H. sapiens*:
TTTTGTTCCGTTACACTTCCAATTTTGGACTTCTTTGTGTAGTTTTACAAGAGGGATATCTCTTTTAA

AAAAAAAAGCACAACAAATTCCACACACAAAATATAAGTACAAATCAGCTCTCTGCATGAGTGGGTC

TCCATCTCTTGCTTAACCAACAGCTGATGGAAAATATTCCGGGGGGCAGTGGGGAGAGCTGACAATGC

AAAAATAAAAATAATATAAATAAAAACCAATATAGTATAACAACTATTCGCATAGCATTACACTGTAT

TATGTATATAAGTAATCTAAAGATGATTTCAAGTATACGGGAGCATGCGCATACTTTCTCATTTTATA

TAAGGAACTTGAGCATCACTTTTTGGTATTGGGGGTAGGTCCTAGAACCTATTCCCCCCTGTTTCCAA

GGCAAGACTTTGTATAAATTGCGTGACATATTAAATGTAATTTTAAAAACCTGGTAACATTTTCCGAG

TTCCACAATGGCAGCATTTTCAGGATTTTAGCCTAACCTTTAACCTAACAAAATACTATGATACTTCT

TGGAGGTAGTTTTATTTTTAAATAATTTCCTTTTTCCATTTGGTAAGAAACATCTTGGTGTTTATGAA

TAAACTTAATGC

The following amino acid sequence <SEQ ID NO.65> is a predicted amino acid sequence derived from the DNA sequence of SEQ ID NO.8:
HCQLSPLPPGIFSISCWLSKRWRP The following DNA sequence Ion50 <SEQ ID NO.9> was identified in *H. sapiens*:
CCTCTAGGCCAGGGCCCCAAGTGCTGAGCTGGGCAGGGAACAGGACTCAGCCCTGGATAGTGCTGGGG

TCTCCTGCTGCGTTCTTTCAACACAGCGCTCACCCTGAGGTGATGCATTGCCCTTCCCCCAGGACATC

CTGCGATACACAATGTCCTCCATGCTGCTGCTTAGGCTGGTGAGCTCCTATGCCTGGGGAGGTGGGAT

GGGAAAGCCCAGCTGAGTCCAGCTCAGAACTACCAGCCTTCATCAACATGCTGAGCTTAGGGGCATGG

ATATGTGGAGAGCAGGAGCCTCAGTGGTGCCCTTGTGTCCCCAGTCCTGGCTGGACACTCGCCTGGCC

TGGAACACTAGTGCACACCCGCGGCACGCCATCACGCTGCCCTGGGAGTCTCTCTGGACACCAAGGCT

CACCATCCTGGAGGCGTAAGTGAGACAGTTCCTGC

The following amino acid sequence <SEQ ID NO.66> is a predicted amino acid sequence derived from the DNA sequence of SEQ ID NO.9:
QSWLDTRLAWNTSAHPRHAITLPWESLWTPRLTILE The following DNA sequence Ion51 <SEQ ID NO.10> was identified in *H. sapiens*:
AATTGAAGGATTAGAAAATAATGTTAGAGAAAAACCTACCAGAACAACAAAAAAGAAATGAAACATAG

GAGAGAAATATCAGAAAACTAGAGGATCAATGCACAAAGGCCGACAGTGGATTGGAATATTAAGAGTT

CCAAAAAGAGAACAGAGGAAAAGATGAGGAAGAAATTAAGGATGAACTAACCGTAAGAAAATTTGCCA

AAACAGAGAATGAGTCTTCAATGCTAAAAGGTTGACTGAGTTCCCAAAAAAGACCCGTCCTAAGGCAC

TABLE 5-continued

ATCAGTGTGAAATTCAGGACACTGTTATTAAGGAGAAGATCCTAAAAGTTTCCAGAGCCTAAAGAAAA

AAAGAAAAAGAAAATGTCATCAGAGTCCTCAATAGCAATGCTGGAACCTAGAAGACAATGGAGGAATA

AATGCCTTTAAAATTCCAAGTGAAAATTATTTTCAACCTAGAATTTGGTATCAAAACTACCAATCAAG

TATGAAGAGAGAATAAATCAGACATGCAAGAATTTGAAAAATTGATCTACCATGTTCCTTTTCCTAGG

AAGATACTGGAGATGTGTT

The following amino acid sequence <SEQ ID NO.67> is a predicted amino
acid sequence derived from the DNA sequence of SEQ ID NO.10:
WNLEDNGGINAFKIPSENYFQPRI The following DNA sequence Ion52 <SEQ ID NO.11> was identified in *H. sapiens*:
CTGGAAAGGTCCATCGCGTGGCTGAACTGCAACCACAGCTCCACTGAGTGCTGCTTCTGGGCCTCGTG

TTCCCGCTGGGCCCTTGTCCATTCTGAGCCCCCTGTCAGCTCTGCCTCCGCAGGGCCCGGCATCTGCC

CTGCTGATACCTCTGGCTCCTTCACACCTACAGAAAGACAGAGACTCAGCCATGGGCTGCAAATGTCA

CCTGTGGAGGGAGGGAGACAGGGAAGGAGGCAGGAGCAGAGAAGTGGAGGTGGGGGAAGAGGAATGTG

ACTTCCCTCACCGGGCAGGTGGGTGGGGGGTGAGACCCGGGCCCTTATTTTCCTTCTGGGGCGCAGTG

GGACAGCATCTCCCCGGGCTGTTGCAGTGGAGCAGCAGGGAGTGGAGCCACCGAGGCAGGGGTGGGGG

CTGGGTGGTGGCCACGTGCAGCAGGTGGGTGATGAAGATGGTCTCCAGCAGGCTGCCCACCATCAGGG

ACAGGCACA

The following amino acid sequence <SEQ ID NO.68> is a predicted amino
acid sequence derived from the DNA sequence of SEQ ID NO.11
CLSLMVGSLLETIFITHLLHVATTQPPPLPRWLHSLLL The following DNA sequence Ion53 <SEQ ID NO.12> was identified in *H. sapiens*:
TAGATGATAATTACGGCTTTTTTTTTTGTGGTTTTTATTTGAAAACTCGTATGATCTATAACCTTCG

CCGGGAGTGATCTGCCGCCACTAGGGCGCAGCAGATAGCTCAGGGGAGACTGACGTCATCTACTTACT

CATCATCTGCCGGAAATCACAAACATCATGGTTCCCTGCGTGCTCATCTCAGGCTTGGTGCTGCTAGC

CTACTTCCTGCCGGCTGCCTCACCAGAGCCTGGGCACTGCCGCCCCGGAGATACGCTGCTGTGGGGAT

GCCGTGAACTTCGTGGCCAAGAACATGAGAGGGCAGGACACGAGAGGCCAGGACGCCATCGGCGAGGT

TGGACAGGAGCCAGAGGCGGATGGAGCGCGGCAGAGGCGCCCCCACTGTCTCCCGTGCCACTGGCTCC

TGCAGCTGCCCCTTTAAGGACTGTTTGTGCCGACCCTTCCCCAGGAAGTGACGGCATCTGCTTCTGGG

TCGCTCGGGTGCTCTTCAGCCTGGGCTCCAACCTTATCTCATCGTGGCCTA

The following amino acid sequence <SEQ ID NO.69> is a predicted amino
acid sequence derived from the DNA sequence of SEQ ID NO.12:
GETDVIYLLIICRKITNIMVPCVLISGLVLLAYFLPASLGTAAPEIRCCGDAVNFVAKNMRGQDTRGQDDG

ICFWVARVLFSLGSNLI

The following DNA sequence Ion54 <SEQ ID NO.13> was identified in *H. sapiens*:
ATGACAGTACCAAAGCGCGGCCTCAGAAATATGAGCAACTTCTCCATATAGAGGACAACGATTTCGCA

ATGAGACCTGGATTTGGAGGTGAGTATTATCCTCTCAAAATTCATTTCAAAACCCATTGCACTGTCAA

AATGGAGGTGAAAATTTAAAACAAGACCAAAATGCAAGTAAAGTCCATCAGTTTAAAACAAAAAAAGA

AGGCTTTTACAATCACCTTCTCTTTAATGAGAACAATTGATGAGTTATCCATTTTAAATTGACCAAAA

AAACTCATTTTCCTACTATGCACACTGTAGTAAATAGTATGTGTTCCATAAATACGAGAATGGATATA

TGTTGCCTATACACCAACTTATTTTCTAACTAAAAATCCTTAAATTGGATACATGGTTATTTATAAAA

TCTTATTGAATATTCTTATGAGCTAGAAATGCCATGCTTTGGG

The following amino acid sequence <SEQ ID NO.70> is a predicted amino
acid sequence derived from the DNA sequence of SEQ ID NO.13:
DSTKARPQKYEQLLHIEDNDFAMRPGFGG TABLE 5-continued The following DNA sequence Ion55 <SEQ ID NO.14> was identified in *H. sapiens*:
CCCACAAGGGTCTGTTGTCCACCCCGCGTGGACCGCCCAGGCCGGTGGGAGTCAAAAAAGGGGAGGG

GCGGGGGATCTTCCACTTTCTCACCCCGAGTTTCTTTGCTTGCTTGCCCCGAGTATCTGTCAAGAGGC

AGCCCTCTCCCCTAAAGGCCCCTTCATCCTGAACGTGCATGATGCCCCTGCAGTGACAAATACAGAAT

CTTAGGGGCCTGGATTCGAGGCCGAGCTAATCACTGGGTTGCTGCGGGTGGGTAGGTTATTTAAACC

ACCTGGAAATCAGTTTCTCTGGGTTATGGGGATTGTACCTGGCTCACTGGATTTGAGGAGTAACCAGA

TTTTAGGACAGACTCTTTCTCTGTCCGTCCTACTCAGATCCCAGTAGGAAACTTACCCTTCCCCTGCG

CCACGGAGTGCAAAGAAAACAGCCCAAAGACTTCTTTAACGACTCTGGATCCCTCAGCCAGATCACGG

ATATGGAAAAAGCTTAAATTAGAAAGAGGAGGTCGTGAAGGGACCTCC

The following amino acid sequence <SEQ ID NO.71> is a predicted amino acid sequence derived from the DNA sequence of SEQ ID NO.14:
PDFRTDSFSVRPTQIPVGNLPFPCATECKENSPKTSLTTL The following DNA sequence Ion103 <SEQ ID NO.15> was identified in *H. sapiens*:
AGACTCAGCTGAGCAGAGTCTCTGCAGGCCCATTGGCTGCCTAGCCAGTGGTGATCTCGCTCCCACCC

TCATTTCTTCTTTGTTAACAAAACCATGACCTCATTAAATACTGGACACCTATAAACCTCATGGACCC

TCCTCCAGCCTCCCCACCGTGTACCGGTGAGTCTAAGTCAACTCTAGTCATTTCATTCCTCTGGACAT

TGACTGCTTAGGGCTTGGGCATGAGCTGCCTCTTCACCTGAGCCTGAGCCACAGGTACCCTCTGCACC

TACCACGCTGATGCACTGGGCCAGGGAGAGCGCCGTCTGGATGGAGATGAGCTGTGAGGAGCTGGTGG

CTGGGCGGATCAGGTTGTTGTAACAGGTTTTGTTCAAAAGGTCGTCCATCAATTTCTGCTCGGCATGG

GCCATGCGGCAGTCCCCTGGGTAAACACACAGACATGCTGGGCCCTTGTGCAGCTGGCTCCCACTGCA

GCTGACAGCTATGAAGCAGGAGCTG

The following amino acid sequence <SEQ ID NG72> is a predicted amino acid sequence derived from the DNA sequence of SEQ ID NO.15:
GDCRMAHAEQKLMDDLLNKTCYNNLIRPATSSSQLISIQTALSLAQCISV The following DNA sequence Ion 104 <SEQ ID NO.16> was identified in *H. sapiens*:
GTGGGCAGGGCGGGGAGGCAGGGACATGGCTGTAGCCGTGGAGATGGGAGGACAGACAGGACTTGGT

GGCCACTTGGGTGAACCAAGGGAGGGGTCAGGAAGAGACACCCAGTTTTGTATCAGATGTGTAGAGCG

TGGGATGCTGTTCATTGATTGAGGGAGGAGGAGGAGGAAGAGGTATGGCATGGGAGGAGGTAGCTGAG

CTCTGTCATGAATGTCATTTGAAGTCCCCAGGGAGAGCCAGGCCGGCCAGCCCCTTCACTGCTTTAGC

CAGCTCTCAGGGTGTCTGTGCTCCCTGGCCCTCTCAGCTCCTGCTTCATAGCTGTCAACTGCAGTGGG

GGACAGCTGCACAAGGACCAAGCAGGTCTGTGTGTTTACGCAGGGTTCTGCCGCATGGCCCTGCCGAG

CAGAAGCTGATGGACGACCTTCTGAACAAAACCCGTTACCACAACCTGATCCGCCCAGCCGCCAGCTC

CTCACAGCTCATCTCCATCGAGATGGAGCTCTCCCTGGCCCAGTGCATCAGTGTGGTAGGTGCAGAGG

GCACCTGTGGCTCAGGCTCAGGCGAAGAGGCAGCTCATGCCCAAGCCCAAAGCAATCAATGTCCAGAG

GAATGAAATGACTAGAGTTGACTTAGACTCACCAATACATTGGCGGGAGGC

The following amino acid sequence <SEQ ID NO.73> is a predicted amino acid sequence derived from the DNA sequence of SEQ ID NO.16:
AEQKLMDDLLNKTRYHNLIRPAASSSQLISIEMELSLAQCISV The following DNA sequence Ion 105 <SEQ ID NO.17 > was identified in *H. sapiens*:
GTCCTGCGCCTACACCTGGGCCTCTGTACCCGTCAGTTCCCCCAGTCTGGTTCTTATTCCCTGCAAAG

AGTAGGGAGCCTGTAAGGTCACCTGTTGAGCAAGCTGGGGGAGAAAAGTAGGGTGGGGATGGGAGGAT

CAGGATGAGAAGCTCATGGTCGTGCTGGAGACTCAGCTGAGCAGAGTCTCTGCAGGCCCATTGGCTGC

TABLE 5-continued

CTAGCCAGTGGTGATCTCGCTCCCACCCTCATTTCTTCTTTGTTAACAAAACCATGACCTCATTAAAT

ACTGGACACCTATAAACCTCATGGACCCTCCTCCAGCCTCCCCACCGTGTACCGGTGAGTCTAAGTCA

ACTCTAGTCATTTCATTCCTCTGGACATTGACTGCTTAGGGCTTGGGCATGAGCTGCCTCTTCACCTG

AGCCTGAGCCACAGGTACCCTCTGCACCTACCACGCTGATGCACTGGGCCAGGGAGAGCGCCGTCTGG

ATGGAGATGAGCTGTGAGGAGCTGGTGGCTGGGCGGATCAGGTTGTTGTAACAGGTTTTGTTCAGAAG

GTCGTCCATCAGTTTTCTGCTCGGCATGGGCCATGCGGCAGTTCCCCTGGGTAAACACACAGACATGC

TGGGCCCTTGTGCAGC

The following amino acid sequence <SEQ ID NO.74 > is a predicted amino
acid sequence derived from the DNA sequence of SEQ ID NO.17:
RGTAAWPMPSRKLMDDLLNKTCYNNLIRPATSSSQLISIQTALSLAQCISV The following DNA sequence Ion 106 <SEQ ID NO.18> was identified in *H.
sapiens*:
GGCTGCATCCATATTTATCCAAAGGGAAACCCAGGACAAAATTACTATAAGCAGGCTTGGGATGTACA

TCTGGATCAAATAATATCCCATTTGGCGTTCCAGATGAAACTTGACCTCAATGCAGGTAAACTTTCCT

AGAAGGAGGAGGGGGTCATTTAAAGTCCAGCCTGAATTTATATTTCCAATTCCATTATCCCACGTTGT

TTAAAAAAAAAAAAAAAAAGACTACTGCAGATGGATTTGGAAGATTGCACAAAATGTTCACCCTACGT

AACCAATTCAACTCTTCTCCAACTGAACCAGTAATAGAAATAATTACTGGGGAATAATAGTGATAATA

ATAGTGTG

The following amino acid sequence <SEQ ID NO.75> is a predicted amino
acid sequence derived from the DNA sequence of SEQ ID NO.18:
GKFTCIEVKFHLERQMGYYLIQMYIPSLLIVILSWVSLWINMDAA The following DNA sequence Ion 107 <SEQ ID NO.19 > was identified in *H.
sapiens*:
ATTGCCTATCTAGTCCTTGCAGCCCTGGGGTGGGTCTTGGTTTGTGGGGAGGCGGAGTAGGGAGGAAG

GAGTCCAAAGGAGAAAGGCAGTGGGCCGCTCCCTAGTTGTACTCACCAAGCGTTGGCGCCTCTGCCTT

CTTCGAAGTCGTATGAATTCTTTATGCTGACGAGAAACAAAATTTATGGCAGCATACTCCAGCAAGGC

AGCGAACACAAAGAGCAGACACACAGCCATCCAGATGTCGATTGCCTTCACGTAGGACACCTACAACA

TCCAGCGACAGAACGATCAACCTTCTTGAAGTCCTTCCGTGGCCTACTGAGTGGATTTTCAACCCCTA

TCGATTGCCTGCTCTTTTTGAGCTTTATCCTGAATTTCTTCTGGTGTTTAAAGAAGCCTTCCATGACA

TATCCCATTGTCTGAAAGCCCAGATGGAAAAGATCGGACTGCCCATCATACTCCACCTCTTCGCACTC

TCCACCCTCTACTTCTACAAGTTTTTCCTTCCTACAATTCTTTCCCTTTCTTTCTTTATTCTTCTTGT

ACTTCTGCTTCTGCTTTTTATTATT

The following amino acid sequence <SEQ ID NO.76 > is a predicted amino
acid sequence derived from the DNA sequence of SEQ ID NO.19:
VSYVKAIDIWMAVCLLFVFAALLEYAAINFVSRQHKEFIRLRRRQRRQRL The following DNA sequence Ion 108<SEQ ID NO.20 > was identified in *H.
sapiens*:
CATTTTTATAGGCATCTTCAATGTCTTAATTCAAGAGAGGTAAAGGTGGAACTACTTCAGGCACTGTG

AGAGGGGACATACGTTTGGGCAGAGAAGATGTCGCTCAAATCGCCCCCCAAAACAGCACAAACACATT

TGTGCGTAAGGCTGATGCCTTCCCGTTCCCCAGCCCCATGGAACAGCCAGATCAGCAAATAACGTGGG

GATGAAAAACACACTGGGCTAGGGGTTAGGGACCCCTGGTTTCTAGTCTCATCTGTGCCAAGAATTGG

CTGGGTGTGCTTGAGTAAGTTCCTCCCAACTCTGAGTGGCCCTTTTCCTGTCTGTGATGTCATGAGGT

CGGGTTAACTGGCTGTTATTCCAGGCTCTCTGTGACTCTATATAGACACTTACAGCTCTCAAGCTGCA

TCGTGCAGGTCTGGATGTCCATGGGGAAGTTCTTGAGGTCCATCAGGCAGGACAAAATGAGGGTCAGC

CTAGTGGGGACAGTAAGAAAGAAGTGACATCGGCTTACTGGGGCCCATCACAGTGCAA

TABLE 5-continued

The following amino acid sequence <SEQ ID NO.77> is a predicted amino acid sequence derived from the DNA sequence of SEQ ID NO.20:
RLTLILSCLMDLKNFPMDIQTCTMQLES The following DNA sequence Ion 109<SEQ ID NO.21> was identified in *H. sapiens*:
GTTGAACAAATGTTGATGGAGTGCCAGGCCCAACTAAATGGAGATGAGTTTGTCAAATTCCGTGTCCC

CAAGAGCTTGGAGTCTAAAGAAGCAGGTCATTTCACTAAGTGCAGTGTTTCTAAGGGGAAGCTTGCTC

TAATGAAAACTTTGGCTTTTTTCCACAGGTTGGTACAATAGGCTTTTCATCAACTTTGTGCTAAGGAG

GCATGTTTTCTTCTTTGTGCTGCAAACCTATTTCCCAGCCATATTGATGGTGATGCTTTCATGGGTTT

CATTTTGGATTGACCGAAGAGCTGTTCCTGCAAGAGTTTCCCTGGGTAAATCTTTCCCCATCTTTATA

AAATGTTAACAATGGGAGAAAGTTCAAGGGAGGTAAATAAAATGGGTCATACATGGAGAGGAAAAGAG

AGTGGTGGTTTAGTAGGGATAGTCAGAGATG

The following amino acid sequence <SEQ ID NO.78> is a predicted amino acid sequence derived from the DNA sequence of SEQ ID NO.21:
ISLSAVFLRGSLLKLWLFSTGWYNRLFINFVLRRHVFFFVLQTYFPAILMVMLSWVSFWIDRRAVPA

RVSLG

The following DNA sequence Ion 110<SEQ ID NO.22> was identified in *H. sapiens*:
TACCTGTCTTGACAGCCTCCCAGCCTACTTGCTCACTTGCCCCTCCTTCTCCTCCCACCAGGTGGCC

ATCAGGCACAGGTGCAGGCCCAGCCCCTACGTGGTAAACTTTCTGGTGCCCAGTGGCATTCTGATTGC

CATCGATGCCCTCAGTTTCTACCTGCCACTGGAAAGTGGGAATTGTGCCCCATTCAAGATGACTGTTC

TGCTGGGCTACAGCGTCTTCCTGCTCATGATGAATGACTTGCTCCCAGCCACTAGCACTTCATCACAT

GCTTCACTAGTACGTCCTCATCCATCAAGAGACCAAAAGCGAGGTGTGTGTTGGATGGGGAGAGGGAT

GGGCAGAACCAGGCGAAGTGAAAAGGGATCCTGGAAAAAGATCCTCTGGGAAAGAAACAAGAAATTCT

AGGTGGCGCCTCTGGCCCTCATGCAGACCCCCTTGCCTGCAGGTGTCTACTTCGCCCTGTGCCTGTCC

CTGATGGTGGGCAGCCTGCTGGAGACCATCTTCATCACCCACCTGCTTGCACGTGGCCACCACCCAGC

CCCTACCTCTGCCTCGGTGGCTCCACTCCCTGCTGCTGCACTGCACCGGCCAAGGGAGATGCTGTCCC

ACTGCGCCCC

The following amino acid sequence <SEQ ID NO.79> is a predicted amino acid sequence derived from the DNA sequence of SEQ ID NO.22:
RCRPSPYVVNFLVPSGILIAIDALSFYLPLESGNCAPFKMTVLLGYSVFLLMMNDLLPATSTSSHASLVRP

HPSRDQKRGVCWMGRGMGRTRRSEKGSWKKILWERNKKFVAPLALMQTPLPAGVYFALCLSLMVGSLLETI

FITHLLARGHHPAPTSA

The following DNA sequence Ion 111<SEQ ID NO.23> was identified in *H. sapiens*:
CCCAGCACTTTGGGAGGCCAAGGTGGGTGGATCACTTCAGTTCAGGAGTTTGAGACCAGCCTGGGCAA

CATGGTGAAACCTCATCTCTTAAAAAAAAAAAAAAAAAAAAAAATTAGCCAGGCCTGGTGGTGCGCCTG

TAGTCCCAGCTACTTGGGAGGCTGAGGCTGAGACAGGAGGATCATTTGAGCCCAGGACATGGAAGTTG

CAGTGAGCTGAGAGCATGCCACTCTACTCCAGCCTGGGTGACAGAGCAAGATCCTGTCTCAAAAAAAA

AAAAAAAAAAAAGGAGAGAGAGAAACTGCGGCCCCTGCCTCTTGCGTTATCTCTCCTCCAGCATGGA

TGTGGATAAAACCCCAAAAGGCCTCACAGCATATGTAAGTAATGAAGGTCGCATCAGGTATAAAAAAC

CCATGAAGGGGACAGTATCTGTAACCTGGACATCTTCTACTTCCCCTTCGACCAGCAAAACTGCACA

CTCACCTTCAGCTCATTCCTCTACACAGGTAAGTTGCAGTGAGGTCTCAGGGATGGGGTGAATGAGAG

CAACCAACAAATTTAAAGAAACTATGAGTAAATGGTGACC

The following amino acid sequence <SEQ ID NO.80> is a predicted amino acid sequence derived from the DNA sequence of SEQ ID NO.23:
LSSSMDVDKTPKGLTAYVSNEGRIRYKKPMKGDSICNLDIFYFPFDQQNCTLTFSSFLYT TABLE 5-continued The following DNA sequence Ion 112<SEQ ID NO.24> was identified in *H. sapiens*:
TCCCTACACTATTCTGGGCTGGGTGGGGAGCCCTGGCTGCTCCAAGGGGGCTGCTTGGCCCAATTCTG

GGCATCCCCGGGGTGTGCTAGCTTTGCCCTAGGCTGCTCCCTGGAAGCGAGGTTGACACAACTCCTTC

CCCACACACAGGAGTGGAGCGACTACAAACTGCGCTGGAACCCCACTGATTTTGGCAACATCACATCT

CTCAAGCTCCCTTCTGAGATGATCTGGATCCCCGACATT

The following amino acid sequence <SEQ ID NO.81> is a predicted amino acid sequence derived from the DNA sequence of SEQ ID NO.24:
QEWSDYKLRWNPTDFGNITSLKVPSEMIWIPDI The following DNA sequence Ion 113<SEQ ID NO.25> was identified in *H. sapiens*:
TTATGCCCGGGGGTGATCCGCCGCCACCACGGTGGCGCCACCGACGGACCACGGGAGACTGACGTCAT

CTACTCGCTCATCATCCTCCGGAAGCCGCTCTTCTACGTCATTAACATCATCGTGCCCTGTGTGCTCA

TCTGGGGCCTGGTGCTGCTTGCCTACTTTCTGCCAGCACAGGGTAAGCAGTGGCCCCTAACCTACCCC

CAAACCCGGGCTCGCTCCCGGGAGGCGGGGCCCGCTCTCACT

The following amino acid sequence <SEQ ID NO.82> is a predicted amino acid sequence derived from the DNA sequence of SEQ ID NO.25:
CPGVIRRHHGGATDGPRETDVIYSLIILRKPLFYVINIIVPCVLIWGLVLLAYFLPAQ The following DNA sequence Ion 114 <SEQ ID NO.26> was identified in *H. sapiens*:
CAGGCAGGCGCGGCAGCAGCTCCAGGAGAACCTGGGGCAGGGGCGGGGCTTAAGGGACGAGGTTAGTA

CGAAGCCCCACCCCGAAACCGGGCTGCACCGCCCCCTCCGCGCTTACGTGGCGCAGCCGCGGGGACAT

GGCGTGGGTGGTGGGCGTCCGCTGGGACACGTTGAGCACGATGACGCAATTCATGACAATGAGCGTGG

CGACCACCATGACGAAAATAAGGAACCTGAGGAGCCCGGTAAGGCATGACATCACCGGTCCTCCTTCC

AGCTACCGAAGGCGCCGCGCGCTGACCTCACAAACACGGCTTCTCCTGGTACGGGCTGGTTACGCCCT

CCAGCTGCGCCCCCTACACGACGACAGACGCGTCCCCCAACCCTTCTAACTGTACCTACCACTTGTGG

CGGCCATGAAGGGGACCCCCAGCTCCCTGGA

The following amino acid sequence <SEQ ID NO.83> is a predicted amino acid sequence derived from the DNA sequence of SEQ ID NO.26:
RFLIFVMVVATLIVMNCVIVLNVSQRTPTTHAMSPRLRHVSAE The following DNA sequence Ion 115 <SEQ ID NO.27> was identified in *H. sapiens*:
CTCTGCAACCTGGCTCGTCTTTCCCTAAGGATACAATGCTTACCGTAGTTCTATGACATGAAACATGC

TTTGTGTTGTTTGCTGATGTATTGAGTAATAGAATGTCAGATGGAAGCAAGTAAATTATTTTACAATG

TATTTTAAGCCTTACTTGGAAAAGTAACACCAACAAATACTATTAAGAATTCATTGATGTTTGACCTT

ACATAGAAAGTAAGTCGTCCATAAATATTTGTCAATGGTGAAAGAGTGAATAAATAAGCAATTAAGCA

ATATCTATTCTTTCATTTGGGCTTAATATTTGTCTTTTTTCCACAGCATCCTGACTCCAAATATCATC

TGAAGAAAAGGATCACTTCTCTGTCTTTGCCAATAGTTTCATCTTCCGAGGCCAATAAAGTGCTCACG

AGAGCGCCCATCTTACAATCAACACCTGTCACACCCCCACCACTCTCGCCAGCCTTTGGAGGCACCAG

TAAAATAGACCAGTATTCTCGAATTCTCTTCCCAGTTGCATTTGCAGGATTCAACCTTGTGTACTGGG

GTAGTTTTATCTTTCCAAAGATACAATGGGAAGTGAGTACCAGTGTTGAATAG

The following amino acid sequence <SEQ ID NO.84> is a predicted amino acid sequence derived from the DNA sequence of SEQ ID NO.27:
HPDSKYHLKKRITSLSLPIVSSSEANKVLTRAPILQSTPVTPPPLSPAFGGTSKIDQYSRILFPVA

FAGFNLVYWGSFIFPKIQWEVSTSVE

The following DNA sequence Ion 116 <SEQ ID NO.28> was identified in *H. sapiens*:
GCTCTTTCTCCCAGGAAAGTTTCTGGGCAGCTGCCGCCGGGCGCCAAGACAAGCGAGGGTGGCCTGAG

TCCTGTGCTCACATGGCGTATGCCGCCCAGTAGATGACATTGACGGCCGCAAACGCCGCAGGGAACAC

TABLE 5-continued

AGCGCGGGCGTTAATGTCAATGGTGTCTGCGTCCATGGGCCTGAGCCGGGCACGGATGCCCCCCTGGC

CTCCTGAGCGGGCTGCCCCCTCCTTCTTCGTCTCCCCTGTCTCCACCCCCACCGACCTG

The following amino acid sequence <SEQ ID NO.85> is a predicted amino
acid sequence derived from the DNA sequence of SEQ ID NO.28:
RSVGVETGETKKEGAARSGGQGGIRARLRPMDADTIDINARAVFPAAFAAVNVIYWAAYAM The following DNA sequence Ion 117 <SEQ ID NO.29> was identified in H.
sapiens:
CAACTGTTGTGAAGAGATATACACAGATATAACCTATTCTTTCTACATTATAAGATTGCCGATGTTTT

ACACGATTAATCTGATCATCCCTTGTCTCTTTATTTCATTTCTAACCGTGTTGGTCTTTTACCTTCCT

TCGGACTGTGGTGAAAAAGTGACGCTTTGTATTTCAGTCCTGCTTTCTCTGACTGTGTTTTTGCTGGT

CATCACATAAACCATCCCATCCACATCTCTGGTGGGCCCACTGGTGGGTGAGTACCTGCTGTTCACCA

TGATCTTTGGCACACTGGCCATCGTGGTGACTGTGTTTGAGTTGAACATACACTACCGCACCCCAACC

ACGCACACAATGCCCAGGTGGGTGAAGACAGTTTTCCTGAAGCTGCTGCCCCAGGTCCTGC

The following amino acid sequence <SEQ ID NO.86 > is a predicted amino
acid sequence derived from the DNA sequence of SEQ ID NO.29:
NCCEEIYTDITYSFYIIRLPMFYTINLIIPCLFISFLTVLVFYLPSDCGEKVTLCISVLLSLTVFLLVITT

IPSTSLVGPLVGEYLLFTMIFGTLAIVVTVFELNIHYRTPTTHTMPRWVKTVFLKLLPQVL

The following DNA sequence Ion 118 <SEQ ID NO.30 > was identified in H.
sapiens:
CTCCCCCACGCACGATGAGCACCTCCTGCACGGCGGGCAACCCCCCGAGGGGGACCCCGACTTGGCCA

AAATCCTGGAGGAGGTCCGCTACATTGCCAACCGCTTCCGCTGCCAGGACGAAAGCGAGGCGGTCTGC

AACGAGTGGAAGTTCCCCGCCTGTGTGGTGGACCGCCTGTGCCTCATGGCCTTCTCTGTCTTCACCAT

CATCTGCAC

The following amino acid sequence <SEQ ID NO.87> is a predicted amino
acid sequence derived from the DNA sequence of SEQ ID NO.30:
SPTHDEHLLHGGQPPEGDPDLAKILEEVRYIANRFRCQDESEAVCNEWKFPACVVDRLCLMAFSVFTIIC The following DNA sequence Ion129 <SEQ ID NO.31> was identified in H.
sapiens:
GGATTCAGGTGTGAGCCACTGCACCCGGCCTAGAGCTTCTTTTTTGCTTCCCAAAGAGCCATAGGTCA

AGAGGACAATCAAAGAAGCTGCTGGGATCAGAAGTCAAACAGGGGCCCCTGGACTCACATAAAACATG

ATCTGGTCATATAGGTTGTTGCCCATGGACATCTTTGGGGTGGCCTTGTTGATGCCCAAGAGCTCCCA

CTCCCCCTGGGTTTGGATGACTTTGCGAGACGTGTCTGTGATCTCCCACACCTCCTTGTCCATGCCCA

GCAGCATGCTGTCCACTGGAAGGGAGGCCGGTCAGTTCATTGCAGACGTTTTCCCAAGCCTCCCGCCC

ACGAAATTGGAGTCCTCCCCCACTGAGCTTCTAAACCAAATTTTCCTCTATCCTTTTAAAGCAGGGTA

TCCTGGTTTTCTCAGAAGTGGGTTACCCGACTAGCAATTCATATGTGTGTGGGCAGCGGCATTAATTT

CTTTTGTTGTTGAAAACAAGAGTGAGTCAAGTTCGTTATGGGAATATTGGATATGACTGAAACGTGAG

TCAAGAACTTTTGGAGTCATTCCTATTTTCCTTCTCAGTCCCCCAGTCGTATGGTGGTGTTTTAGTGG

AATCAAGCTTGAATAGCTCAATATTTT

The following amino acid sequence <SEQ ID NO.88> is a predicted amino
acid sequence derived from the DNA sequence of SEQ ID NO.31:
EITDTSRKVIQTQGEWELLGINKATPKMSMGNNLYDQIMFYV The following DNA sequence Ion 130 <SEQ ID NO.32> was identified in H.
sapiens:
CTTCTGCATGACTCAGAATATTCTCCTTGGCATGGATTTCTGCCACAGATTTGTAAAACAGAAACACA

AAAGCTCTATCTAAGAAGGAAACCCCATGTACACACTTCTTTTTACCACCCGCAGTCTTCAACTACAC

AATAGCAATGTGTGTCTCCATATCACTTGTCTTTTGATTTGTCTTGTCTTTTGATTTGTTCAATCATT

GCATGCCTCTATAATATAAATATTATATTACCATGCCTTCTAAGGTCATTGATGAAAGTTATTTTATT

TABLE 5-continued

CATCCTTGCATCTTCTATTCAGGTTTTGGCACATAGTAGGCACTATAAATAAATGTACAATCAATGAA

GCAATGCTGTGCATTTTAAACTAAAGATAGCTAACTAAAGTCAAAGAACCCAAGTAATTCATTTGAGT

ACACACTGTTCAGCTGGAACCCAAACAGAAATCCAAGTCTTTATTCTTCAAATACCACCAGTGCTTTA

GAGTTTGGCACTTGGCCTCTCCTAATCTTGTACTTAAATCCTGACATGTTTATTTTGCATTTTAAAAG

CCAACCGCTTTATAAAATGCTTTGACCTACTTTTTTGTTTTTTATAAGCCTCCATTTTATACCCTATG

AAATGATGATAAAAGCAGTGCCAAACTTACTGAATTATTATGAGAATTAAATAAGATAATACATGTCA

GGCAT

The following amino acid sequence <SEQ ID NO.89> is a predicted amino
acid sequence derived from the DNA sequence of SEQ ID NO.32:
DLSCLLICSIIACLYNINIILPCLLRSLMKVILFILAS The following DNA sequence Ion 131 <SEQ ID NO.33 > was identified in *H.
sapiens*:
CCTATTTTTTCTTTATTCTTCTGGAAGATTTTTCTGTGAGCTCTGAACATGGACTCATCCTTGGGAA

ACACTCATCACGGTCATTCATGCCACGCTTTTGCTCGTTCATTTGCAGGCTGCTTCCTCCCTGTCACT

TTCTTCCTCCTCCCAACTGCGAAACAGCCTTTTCATTTCTTAAACATTTGTGGCTCCAGAAGGCAAAT

CGGTTTCTTCCCTCCTGCCCTTCTGTTTGGTATTTAAAAACACACCCTGAGAGGCATAAATGCAGATT

TTTTTTTTCCTCCAGTGAATTTTCTGTAACCATGGGCCTCGCTTTAAGAAGACTCAACAGATAACAAG

TGTAAATGCCGAAAACATCAACGAAAGGCAGAGGGCCAAAGGGAAGGGTGATGGTTTTACTAAAAGGT

CTTTTTTCTTTATTTTTAAAAATTCAATGTGCATTTCCTTAGTGGTGGTTATCCTTTTGTGCTCATAA

AATGTGAT

The following amino acid sequence <SEQ ID NO.90 > is a predicted amino
acid sequence derived from the DNA sequence of SEQ ID NO.33:
FFILLEDFSVSSEHGLILGKHSSRSFMPRFCSFICRLLPPCHFLPPPNCETAFSFLKHLW The following DNA sequence Ion 132 <SEQ ID NO.34> was identified in *H.
sapiens*:
ATTTCCCTGTTCTCTTCTTTCTTCCTGCTGCTGAGTTAACTGGGTAAACAGAGGTGGTGGTAGAATCT

TAGCTTCATAGGTCATCCATTAGCTGTATCCAAAGGCAACTACAATCCCATGAGACTCCCTGCAGACC

TACGTGGTGTTTGTAGAATGATCTTGGTTATTTATACCACTGAGTATTTGAGACTGATTGTCACATCA

CTATAACCTACTTACACTGTTTGAAACAGACATTGTCAATTCAAAACAAACAATAGAAAACCAAACAA

AAAACAGATCAGGGAAAGAATAAACAACAACAAAGAGAAGATGATTTGCTGGTCAAAACGGGTGGTGA

ATAGAGATTTTCCACTGAATATGAGACACATGAATAAGAAATGAAGGTGAGGGAGATAGCAATGAAAA

TATTTGGGGAAAGACAGTCCAGACTGAGGAAATAGCCTATG

The following amino acid sequence <SEQ ID NO.91> is a predicted amino
acid sequence derived from the DNA sequence of SEQ ID NO.34:
GYFLSLDCLSPNIFIAISLTFISYSCVSYSVENLYSP The following DNA sequence Ion 133 <SEQ ID NO.35 > was identified in *H.
sapiens*:
TTGGTATAAATAAGTTCTATTTTCTCTCCAGTAATATTTTATACCAGTTGCCTAAACTGTGAACTTCT

TGAGGTAGGGTTACCTGATGCACCCCTGGGTTCTCAGTGCACAGGGAGGTAGGCAGGGCAGTGACTGA

AGCACAGGAAGCAGTGACACTCATCAGCCATCATCAAATGGAATAACATAAGCGGCTGATCGAAACTA

GCTGGAAGGAAATTGCAGTCATAATATCTGTAAGCATGTTGGGTTTTTTTTTAATGTTCTGCCCTTT

ACACCTATCATTTTATGAACATTTCTCTATACCAGGGGTTGGCAAACTTTTTCGGTAAAAGGTAAGAT

AATAAATATTTCAAGCTTTGTGGGCTATTTGGTGTGTGTCCCGAATCCTCAATCCCGCCATTGCAATG

AAAAGCAGCCATAAATGAGTGATCATGGCTGTGTTCCAATAAAACTTTATCTAAGAAACAAGTGGCAG

GCTGAAAGTGCTGACCCCTAGTTTACATCATTAGATCTTCTATAAAAATGGCTATAAGATATTCCAGG

CTGTGAATATTTTATGGTATATTTCACAAATTCTC

TABLE 5-continued

The following amino acid sequence <SEQ ID No.92 > is a predicted amino acid sequence derived from the DNA sequence of SEQ ID NO.35:
FLDKVLLEHSHDHSFMAAFHCNGGIEDSGH The following DNA sequence Ion 134<SEQ ID NO.36 > was identified in *H. sapiens*:
GTTACAGGAGGCCTTGGGTGAGACCCAGTTCTGTGCTTGTTTTGGGACTGACCCAGCACAGCTCTAGA

AGCGGTGGCCATAGGCAGTACTTGTGTCACCCCACTGCCAGCTCCAGGTGGCTCAAAACAGTAAAGTA

AAGAGAGACTGTTTAGAAGAAAGTAAGAAGAGAAAACAAGTACTCTTTGCCTTGTAAATCAGAGAATT

CTTCCAGATCTTGTGGAAGACCATCAAGGCAGTACTTCCATGAGTCTGCAAGAAACCACAGCATTAGT

GGGCTTACGGTGCCCCCTAAAGCAGATACAACTTAGATCATAACACCCAAGTCCTTTTGAATATCTGA

AAAGCCTTCCCAAGAAGAATGGGAACAAACAAGCCCAGACTATAAAGACTACAATAAATACCTAATTA

TTCAATGCCTGGGCACAGACAGACATTTACAAGTATCAAGATCATCCAGGAAAACATGACCTCACCAA

ATGAACTAAATAAGGCAACAGAGATCAATCCTGGAGAAACAGAGATATGTGGCCTTTCAGACAGAGAA

TTCAAAATTCAGACAGAGAATTTGAAGAGTATTTTTGCCAGATATACTACTCTAGGATAAAAGGTTTT

TTTTTTTTTTCTTCTTCAGCATGTTAAATATATCATGCCATTCTCTTCTGGCTTATAAGGTTTCCACT

AAA

The following amino acid sequence <SEQ ID NO.93 > is a predicted amino acid sequence derived from the DNA sequence of SEQ ID NO.36:
SPGLISVALFSSFGEVMFSWMILILVNVC The following DNA sequence Ion 135<SEQ ID NO.37 > was identified in *H. sapiens*:
GAAGGGAAATACCAGAGGACAGAGGAACAGGCTAAGCTTCACTGTGAGCATGCAGTTGCAAAAGCCAG

ACTGTGAGAAACTACATGTCAAAGGGCCTGGGTTCCTCAACAGATAAATTGTCAGGAAAAGAAAGGGA

CAGAGGGGAAATCTGTGGATTATGAGTTTAAAAGAAATAAACTTCAAAAATTAGCAAGTCTAAGTTAC

AGTAGCTAGGGATTCTGGTATGTGGAAGCAATATAGGCAATGGAAAGCAAGATATTACTTGCAAGTA

GACACATAATTTCTGCTAACATTCTATTGACCAAAACCAGGTCACATGGCCACATCTGTCCAGCTCCA

GCTGAGGCCTGTGAATGTCTCTAGCTAGGTAGCCAAGTGCCTTGAATAAATGTGAAGGTTTGATTATC

AAAAGAAGAGACAGTAGATAATGGTGAATACTTATTAGTCTCTGCCACTCCCTTAAAAATGGAATACA

CAAACTCGCACTGTGATTTCTAACTTACACTGTACAGCTTCTCTGAATTATTCTGGAACTTAAATTTG

TGCTTGTCTTTACTTGTTATTCAGAAAGTATCTAGAGCCTCTCTTGATTTTCTTTATTTTCTCCCTGA

CAGCATCAGGAAAGTCAGAATCTCAATCAAG

The following amino acid sequence <SEQ ID NO.94 > is a predicted amino acid sequence derived from the DNA sequence of SEQ ID NO.37:
LSKEETVDNGEYLLVSATPLKMEYTNSHCDF The following DNA sequence Ion 136<SEQ ID NO.38> was identified in *H. sapiens*:
TCAATTTTCTAAGCAAAAAATAATTCACCTTTTCCTGTCCACATTATTTAGCATGATATTTATGTAGT

TTTCCAAAATATTCTATTTTTAAATGCACTGACTTTATTTTTATATCATAGATACATTTATATATAAA

GTATTTCAAGATGAATTTGAGACAAATTGAAGTAACAAAGCTTGATTTCCATTCTGCATACAATATTC

TCTATAATTACAATGTAGGTTTTGGCCACTTCTTTTGACTAACATAGCTATGCCATCATTTAAATATC

TGTATGCCTTTGTTTTCTGTAAATTAAAATTCAGACATACAAAGAAATATAAGGAGAGTTAGGAGAAC

AGTGATAAAAGATAAAATGGCACCACAGTAATTCCTAAATAAGGG

The following amino acid sequence <SEQ ID NO.95> is a predicted amino acid sequence derived from the DNA sequence of SEQ ID NO.38:
WCHFIFYHCSPNSPYISL The following DNA sequence Ion137 <SEQ ID NO.39> was identified in *H. sapiens*:

TABLE 5-continued

```
TCAATGAGTACATAGGAACTAATTTATACAGTAATTCCAGTAGTCATAGAGCTCTAAAAATCAACCTC

TCCTCAACACTAAACTCTAATGCTGTTCTCCTGACATGTTCATAGGTAACAAAAGAGAAAGCTCTGTT

TTGTCTTCCAGTTCTATCTGCCGGAATTCCAAAGAGTGCTCCACTTCGTTATATAATGCTGCTACATA

GGTCTCAGAAATCTTTTGGTTTTGAAGAGGGAAAAATTTGAAATTAAATATAGATAAAACTGAACCAT

ATTCAGATCAATATGATCTTAGAACCTATAGATTTTTGCCTGTATTATCTACACTGAGACTGAATAGC

ATACATATTTTGTTCAGTGGGTATTAATGGTTCCATGATTCTAATTTTGCTCATTTTTCTGGCATGTA

TTGGCTACCTGCCCTACTTTTGCAGTTGACCAATTTTGCTTATAAAGACCAGGCTGTAATGTGGCCTT

GGTCCCATCATACCATACCTAACCCCGCTGTATCTGATATTAGGTTCCTAAATAAATAAAAATAAAAC

TTTACTATTTACTCACTAACTCTAAAAATGCCTTCTCTTCTAGTTTACTATACCCACACAGAGAAAAA

CCATAGATATTTTATAATATAGTTTAGATGCTAAGTGGCAATA
```

The following amino acid sequence <SEQ ID NO.96> is a predicted amino acid sequence derived from the DNA sequence of SEQ ID NO.39:
IFNFKFFPLQNQKISETYVAALYNEVEHSLEFRQIELEDKTELS The following DNA sequence Ion 138 <SEQ ID NO.40> was identified in *H. sapiens*:

```
GGTGGTAAGTGATAGATTGTGATATAAAATGTGCTTCTTATGGAGTTGGGGTCCAAAATATTTGAAGG

CCATTGGTGTATGCTGTGGATGCGTCAGTTGGTTTCTTTGCTTCGTCCATGCTACCTTCTCAAGGAAT

CAGTTCTCTCCCACTGATTTTGGCAGTGGCAGCTCAATGTGCTCTATGATCCCAGCTCAACCGAAGAC

ACCTAGATAAGGGTGAACATCTAACCCAAGAGAAAGGAATATATGAACAACCTGAGCCAATCATCCCA

TCCTGAGGAGAGGTCCAAAAGACATCCCCTGAGGTTATGTGCAATTGTGGGCTACAGCTGTAAGAACA

TAAGAAGCACTAGCCAGTCCCCAAGAGATGGAGAGAAGCCCAGTGAAGCTGTTTATGCGCAAAGAGAG

TGATTTTGAGTTCTAAATTTCCAACTCTAGTCCTTATGTGGCCAAGCTCTTATTGCTGACCCGTGGAT

ATGTGAGAGATTGCCTGCAGTGTCTGTGTTTTTATTTGCAATAAATTTCTTAAGCATGCTAGAGTAGG

TTCAGTTCCTTGTTACCAACTGCTCTCTCACCAAGGCAGACTCTTGGGGAGTGATAATATCAACAAGT

AAATATTTATTGTGTAAATATATAATGATAACTATTTGGTGCCTCTGTGTG
```

The following amino acid sequence <SEQ ID NO.97> is a predicted amino acid sequence derived from the DNA sequence of SEQ ID NO.40:
FLCSYSCSPQLHITSGDVFWTSPQDGMIGSGCSYIPFSWVRCS The following DNA sequence Ion 139 <SEQ ID NO.41 > was identified in *H. sapiens*:

```
CCATCTGCACAATTTCAGCAGCCAAGCACACTATGTCACTCCCCAAGTCTCCCCAGTCCTTGTGATGG

TGGCGGCAACCCATCTGGAACAGCTGCTGTGAGGAAACCAGCTGCAGCAAGGGAGGTGTGCCTGGGGC

TGCATGCTCATGGATCCTGCAGGAGCCAGAAATTGGTGATCCCAGCAGGAGCCCCTATGCCCCACCAA

GTTGATGCAGCAGGAGCCCCATGCTCCTGGGCACAGCTGCAGTTGCCCAACTGTGGCTCCAGATCTGG

GCATCTCTGCACTCTTGGGGGCCCAGGAAGTCCCCTGTCCCCACTGGCTCAGAATTGGCTGCTCCTGC

CCTTGGGCAGTGCCTGCTCCAGTGCAGAGCGAAGTTGTGGCCAAGCCCAGGTGCTATCACAGCCTAGC

CAGATGTGCATTCATTTGGGGGTGCTGACACACCAGCCCCCTGCCACCTCAGCCCTCTCTGGACTTT

GGGCAACAACAAGCATGCGAGGGAGGCCAGGGGGCTGAGGCAGCTTGGCACAGGCCTGTGGGCACCCC

TCAGCAT
```

The following amino acid sequence <SEQ ID NO.98 > is a predicted amino acid sequence derived from the DNA sequence of SEQ ID NO.41:
GHSCSCPTVAPDLGISALLGAQEVPCPHWLRIGCSCPWAVPAPVQSEVVAKPRCYHSLAR

CAFIWGVLTHQPPATSALSGLWATTSMRGRPGG

The following DNA sequence lEon 140 <SEQ ID NO.42> was identified in *H. sapiens*:

TABLE 5-continued

CATTGTTCTAATCCCGGCTTATAAATTATGTCACTCAATCCTCATACCCCTTTGAGGCGAAGGTATTA

ATTCTTCCCATGGTCCACATGAGGAAACAGGCACAGGAGAAGCTAAATAACAAGCCCAAGTAGAGGCT

TAGAGCAAGAAAGGCCCTAGCCCATTCCATAGACGTCCACAAAGGAGGAAACCGAGTCCCAGAGACAG

TGGAGCCTCTCCAGATTCAGTGTGACCCGACAGGGCTGTAGGAGTCCAGCCTGGGTGTTCCCAGCTCA

GTCTGGCTCTCTGACCCGGTTCCTACTGAAGATGACTCCTCCAGGAAGTCCACAGGATCCTTAGCCCT

AAAGAACCTGGCTGGGGTGCAGAGGAGGCCAGGGAAGGAGAGCCAGGGGTGGAGCGGAGAGAGGAGCC

CAGGGGAGAGTACCTGCGGCTGGCCCAGAGCCCGCGGGAGAGCTCGGAGCTAGAGCTAGAGGGGAGCA

CATGGGAGAGGACTCGGAGGCAGAGGTCAGGGGCAGAGGCCTGGGAACAGACACACGGGCCGCGCCAC

CCCCGCGCCCCGCCCTTGTACCCCGCCCGGCCCAGCTCCCTTGCCCCGGGATGTACAGCACCTGCCCG

GGCCCGCTGCGCA

The following amino acid sequence <SEQ ID NO.99> is a predicted amino
acid sequence derived from the DNA sequence of SEQ ID NO.42:
YLRLAQSPRESSELELEGSTWERTRRQRSGAEAWEQTHGPRHPRAPPLYPARPSSLA

PGCTAPARAR

The following DNA sequence Ion 141 <SEQ ID NO.43 > was identified in *H.
sapiens*:
CTCTAAACATTGGTTAATATTAGACCTGTCTGCAATGATTTCTCCTAAATATCATTACCAGTGTCATT

TGGTCTCATTCTTACATAAGAATCTTTCTCCATTGTCTACCTGCTGTTTTCCATAAATATTATGCTTC

ATTTATAGTTGTTTACTTCCCTTTTGAGGAAAACAACATGAGTTTTGCATCCCCTCCAAAAACTCATG

TTGAAATTTAGTTGGCATTGGGAATGGTATTAAGAGATGGAGACATTAAAAGGTGAGTAGGCCATGAG

AACACTAACTTCATACATGGATTAATGTTATTGGGGAAGTGGGATTATCATGAGAGTACAATCCGGTA

TAAAAGCGAGCTTGGCCCTTTCTGGCTCTCTTATATGAGGGCTCTCTTGCTCTTCTGCCTTCCACCAT

GGGTAGATGCAGCAAGAAGACCCTCACCACATATGGGCCCCTCACTCTTATGCTTCC

The following amino acid sequence <SEQ ID NO.100 > is a predicted amino
acid sequence derived from the DNA sequence of SEQ ID NO.43:
PAVFHKYYASFIVVYFPFEENNMSFASPPKTH The following DNA sequence Ion 142<SEQ ID NO.44 > was identified in *H.
sapiens*:
AGCAGTCCAGGATGTGTTGAGTAGGGTGAATTGTGGCATATCTGAGGATGGTTCTATCCAGGTACAGG

AATGACAGGAGCAAAGTCCTCTCAAGGAGATCTTGCCTGACATGCTTGAGAAAGAGCAAAGGCAAACT

AGTGATGGTGCCATGAAAGCCTGTCTATTAAGACCACTACTACTCCTTCCTGCTTGACACCTCACCAC

TCACACCCCTTTTTTCTATACCAAGGGTTGACCAGGGCCAGTTCCAGCCTACTACCTGTTTTATTGGA

ACAAAACCATGCTCATTTGTTTACTTGTTGTTTATGGGAGTTCTTATGCTACAACAAGAGTTGAATAT

TACTGCAGAGACTGTATCGCCCTCAAAGAGCCTAAAATATGTACCATCTGGCCCTTAGCAGAAAACGT

TTGCTAACCACTACTTTATATCATGCTCTTTAGTTGATGCGGTTGTCAAATGCGAACATCCCAGAAAA

ATACTGCTTTGGACATCTTTATAATAATGAAATATGCATTTTCCATGTTAAAATCTCGTTACTGATGG

TA

The following amino acid sequence <SEQ ID NO.101 > is a predicted amino
acid sequence derived from the DNA sequence of SEQ ID NO.44:
CTWIEPSSDMPQFTLLNTSW The following DNA sequence Ion 143<SEQ ID NO.45 > was identified in *H.
sapiens*:
GGTCAGCCGTGTTTTGTGCTGGTATTTGCCCCGATTACCAGTCTTAAAGTCTTATTTAATTTCACACT

CTTCAGTGTTAGTTGTGCAAAGTCCCTCTGGCCATGGCAGTGAGCGGTTGGGCTGTGCCGCCAAACTC

TCCGTATCAATCTGGCCTGGGACTCAACCAAGTGATCTCTGACTTTTGGAAAGAGTCTGTCTTCAGAG

TTCACCCAGAAGATGGCTTAATTAGACATCTCCCTGAGCTGTTAGGCCTTAGACGGGTGGGAGTCCTG

TABLE 5-continued

CCCTGCCCAAGCTAGCTCAAGGACGAGGCCCGCCTGGACTCAGCTTGGAGCCACGTGATGGGCGTGAG

TGTGTGAGCTCCTGGTAAGGCGCAGAGGTCAGATGGAGACCTTGCATCCTGCCCGAGAAGTGCCCCAC

CCCCTCCAATATCTGGCTTTTCTCTGCATACAAACCAAGCTGAAAACAGTCCACTACCCACCACCCCT

CATAGCTATGGAACCAAATAACCCAGAAATTAAAAGCTTCACTGTAGCTGTCCTTTTCCCCATTTCCT

AAATGGAATTTAAAAAGCTCTGGCTTGTCAAAAGGGGAAGATTATTTTCTGAATTGGAAGTCTGTAGA

TATATTGAGCAACAGCCACCCTCTCTGGGTCCCTGCAAATGGTACCCATTTTTCCAACCCACAGCTCT

AGCTGCTC

The following amino acid sequence <SEQ ID NO.102 > is a predicted amino
acid sequence derived from the DNA sequence of SEQ ID NO.45:
PGKAQRSDGDLASCPRSAPPPPISGFSLHTNQAENSPLPTTPH The following DNA sequence Ion 144<SEQ ID NO.46> was identified in *H. sapiens*:
TTGCCTTTCTGGATATCATCAACAACCCATTTCTTAATGTGACATAATAATATTTCAAAGTGTTAATT

GAAGTACTACTTACTACCTCCCAGTGTAGCTGCTCACCATCCATCTTTGACACCCAAATGGATGAACA

CGTATTGCAGAAGAGACAGTCCGCAGCTAAGTGTGACATCCTTAGCCTCCAAATGGACAAACAAGTAA

AAAAAATGTTTTCTTCCTGCCCCAAGACTCTACAAAAGATCCTCTGAGCTGCAGATGGACAAAAGAAT

TTAGATTACAAGAGAAAAGACACAGTACCAGGGTGATTTATTCTATCATCTCTCCCTGGAATAAATCC

TATGATGGAGAGGGAAAACTGCCTCACAATGGCTTTTAATTTGGGAACCTGATAATAGAAAGGATTGG

ACCTCTGTCTATTCTGTTTCAAACTATGGTCATTGGTAGTCATATAGAGCTGGGAGTAAGGGGTTAGG

GAAGAGTAATTCTGCAACTCCTGTGGTGCTCCTAAAGATGAGGGACAACAATCAACCCTATAGGAAAG

ACCTGGAAGGACTGAAATTGGGCTGAAAAATCTGAATAAGCCTGGATAAAGGACCTGGTAGGGTGGAG

AATAACCTAAGGACCTGATTATCAAAGCTAGGGCAAAAATCTTGAACATCT

The following amino acid sequence <SEQ ID NO.103> is a predicted
amino acid sequence derived from the DNA sequence of SEQ ID NO.46:
PPYQVLYPGLFRFFSPISVLPGLSYRVDCCPSSLGAPQELQNYSSLTPYSQLYMTTNDHSLKQNRQ The following DNA sequence Ion 145<SEQ ID NO.47> was identified in *H. sapiens*:
GATATGTCACATTTTCTGACCTAGGTACTCGCACTTTAGCAAAAACAAAAACAAAAACAAAACAAAAA

AAACATCAAGGTTCCTGAGCAAGAGAACTTTACACATAGTGGGGACTGGGAAAGAGTAGAGGCAAGGA

CCTGGAAGGAAGCCACTTACAGCAGATGCAGAGGTCCCACTAGGCAGGAATGTAAAGGAGGGGTTGGA

TGAAACACAGTTAACGTATAAAGGTTAAGAGATTACAAATTCAGGCTGGAGGGTAGAAGGAAGAAGTG

AAACTGACTCAGGTTCTCAGAGTGGGAGAATGGTGATACTGTGCTCTAAGACTGAAAATCAGAAAGAA

GAATAAATTTAGGGGAGTGGGAGGGGAGAAGGAAGTGTAAAATTATGAATTTAGTTTTCTATTTGTTG

AGTGTAAGGTACTCATTGAAAATCTAAAAGATGTGTAGAAATCCTAATAGTTGATCCAGAGAGTCCGC

ATAGTGACACAAATTTTAACAATAATGCTAATTTCTACTGAGTGGAGGTCTACCATGTGTCAGGTATG

CTATGTTCAATTTCATTGAGTCCTAACAAGGATCCTATAAAGTAGGTATGATTGCGTCCATTTCACAG

ATGAGGAAGTGGAGGCTCTGAAATGTTACATAACCTGCCCAGGGTCACAGGTATCTGACTCTGGCCAT

TATGCTCTTTCTACTGTGCCCTA

The following amino acid sequence <SEQ ID NO.104> is a predicted
amino acid sequence derived from the DNA sequence of SEQ ID NO.47:
PEQENFTHSGDWERVEARTWKEATYSRC The following DNA sequence Ion 146<SEQ ID NO.48> was identified in *H. sapiens*:
CTCTGTCCCAACTTCCTGGTGGCTTTGTTTACACCATGATGGAAAAACTGCCTACTCCAGTCTCAGTA

ATGGCAAATGTCCCTCCCACCACCAAGCTCGAGCATCCCAGTATTGACTTCAGACTGCTGTGCTGGCA

GCAAGAATTTCAAGCCAGTGGATCTTAGCTTGCTTGGCTCCATTGGGGCAGGATCCACTGAGCTAGAC

TABLE 5-continued

CACTTGGCTCCCTAGCTTCAGCCCCCTTTCCAGGGGAGTGAACGGTTCTGCCTCCCTGGCATTCCAGG

CACCACTGAGGTTTGAAAAAAAAAAAAATCTCCTGCAGCTAGCTCGGCATCTGCCCAAATGGCTGCCC

AGTTTTGTGCTTGAAATCTAGGTCCCTGGTGGTGTAGGCACCTGAGGGAATCTGCTGGTCTGTGGGTT

GTGAAGACCATGGGAAAAGGGTAGTATCTGGGCTGGAATGCACTGTTCCTCATGGCAGAGTCCCTCAG

GGCTTCTTTTGGCTAGGGGAGGGAGTTCCCTGACCCCTTGCCCTTCCCAGGGGACATGGCACTCCACC

CTGCTTCCACTTGCCCTCTGTGGGCTGCACCCAGTGTCTAACCAGTCCCAATGAGATGAGCTGGTTAC

CTCAGTTGGAAATGCAGAAGTCATTCACCTTCTGCATTGATCTTGTTGGGAGCTGCAAAGTGGAGCTG

TT

The following amino acid sequence <SEQ ID NO.105> is a predicted
amino acid sequence derived from the DNA sequence of SEQ ID NO.48:
SAFPTEVTSSSHWDWLDTGCSPQRASGSRVECHVPWEGQGVRELPPLAKRSPEGLCHEEQ

CIPAQILPFSHGLHNPQTSRFPQVPTPPGT

The following DNA sequence Ion147 <SEQ ID NO.49> was identified in *H. sapiens*:
CCTGCCACATCAGCGTTTATCATCTTCCTGAGTCTCTGAGGGAGACAGCACTGGAACTCAGGATTTGG

CTCACCTGTGACAAAGGAAATGCGAGGAGGTAACAAGGCACTGCAAGAAGGAAGCATAGTACAAGGAT

TCTGAATCACTTTGTTCAAAATTGGATATAGAGTAAATAACAGTATTTTAAGATGTTTGCTAAAAATC

AAGTAAATGCAAACAGAATAATTGATGAGATGCCATTATCACTTTCAAAATGGCATCGATTAAAAAAA

TAAGCACTCAGAAGGTTGGTGAGTGGGCAACAGAAGGGACGTGTGCCCACCCCACAGCGGGATGTTGA

GTTAGCCCCTGGCTTTAGAAGGCAGTTGGCAGGGAGCCGCAGAGGAGGCATGTGTGCAGAGCTACGTC

TCGGATCTAGTCTGCGGGCATTACCAGAGATGTGTCCAGAGAGTTCTACAGAGAGCTGTCTGTTACAT

GAGGGAAACTATGATGTGAAGTTTTTAAAAGTCCAAAAATAAGAAGTGGATCAGATAAATAATGGCAC

ATCTGAGTCGTATAAACTATGAAATCACCAAAGTCTTGTTTAATAAAACTAATACCTGGGGGTAAAGC

AACTTATAAGACAATAGGCCT

The following amino acid sequence <SEQ ID NO.106> is a predicted amino
acid sequence derived from the DNA sequence of SEQ ID NO.49:
WHLINYSVCIYLIFSKHLKILLFTLYPILNKVIQNPC The following DNA sequence Ion 148 <SEQ ID NO.50> was identified in *H. sapiens*:
TCTCCCTTCTCCCTCAAACCGGATCCAGCCCTCCTGCACCCCGGCCTGTGTGCAGCCGCAGGGAGAGG

AGTAAGCCAGCCTCTCGCGTGCGGTGCTCTCTGCATAGGTTTAGTGGTGGGGACCAACACGCGAGCTG

GCGCTTTCCGTGCGAGCCCAGCATCAGGCGGAGGCCCAGGGCCAACCGGACTCTGAACAAAGGGAGCC

GACAAATGAGAAAGCAAAGGTACCTCAGAGACTACGAAGCCCTTCAGATGGAAATGGTCATCTCCCAA

CAGCCTCTCTGGACCTCTGCCTGCAAGCCCGGCCCACACATCTTGGACCCAGGCTGGAGACACAGACA

GCCAGGTGGTGATGCCCACGCGCAGCTCCAAGACCCCGGGGAGCCTCCGCCAGGCCGGAACCTGCGCC

AGGCTTCTCTGGAACCTTCTCTCCAGGACGCTCTTCTG

The following amino acid sequence <SEQ ID NO.107> is a predicted amino
acid sequence derived from the DNA sequence of SEQ ID NO.50:
RKAPARVLVPTTKPMQRAPHARGWLTPLPAAAHR The following DNA sequence Ion 149 <SEQ ID NO.51 > was identified in *H. sapiens*:
TAATTCTCCCATTTATCCATTCAATAAGTTGTCACTGACATCTACATAATGACAGGACAGGCGTGGCT

CCAGGGAGCTTAGGGTCAAGTGGGTCTGACCTGAAAATCTACATAAACTCTGTCTTCTACTCCATAAT

ATATTGATGCTTCTTTTAATATAAAATTTTTCTTTCTCCATCCATTTGCAAATAAAATTAGTCCCCCA

GGAAGATAAGTCAGACTTCTCTGTGGCTTCTCAAGTGCCAGCTGGGCATGAGCATCTCAGACTGAGAC

TABLE 5-continued

GCCTGGACAACCTCCTGTTCAAATGTGGCTTTGTCATAGAATTGGAGCACCCTGAGGGCAGGATGACA

CCCATCTGGAGTAAGGGACTCCAGCATGACCACCCACAATGGCAGATGTGCCTACCTGGCAACCACGC

CCATCCCACCCCACACTGCTTCTCTGCCCACACAGCCCCAATCTGTTCAGACAGCCAGTGGAGGTAGG

ACCATCTCCTGCCTCGGGGCATGAATCATTGCTGGGCTGGGGCAGTCAAACAGCCTCACCTGCCCTGG

CTGACTCTGGCCAATGAGATGGAAGGGGAAGTTGGCTTGGGAGCAGGTGGGAATATCCTCTCAAACAA

AGAGCTTTCAGCTCCTCCTCCCTTGC

The following amino acid sequence <SEQ ID NO.108 > is a predicted amino acid sequence derived from the DNA sequence of SEQ ID NO.51:
FVIELEHPEGRMTPIWSKGLQHDHPQWQMCLPGNHAHPTPHCFSAHTAPICSDSQWRDHLLPRGMNHC The following DNA sequence Ion 150 <SEQ ID NO.52> was identified in *H. sapiens*:
TTTATTTTTTCCAGGGCGGGGGAGTTGAAGTAGGAAGAAGAGTAATGAAGAATGTGTTTGCCTTAAAA

GCATAAGCAGACTTATTTTTAATGTAAGTGCCCTCCCCTTTTTGTAATGCCAGGGGCAGAGTATTCTC

CAAATGCCTTATACACTTACTTTCAGCACTAAATGTATTTGTGCAAATCCCATGAATCATCAAGGCTT

TTGAAAATATTTATAGGGAGAGAAACTCAACCCTTTTCATTAGAGTGAGTAAAACTCACACTGGTATC

TTGCTATTGTTTAAGGAGAACAATGGATGGTGGATGAAAGAGAATGTCAGCTGGATCAACAAACAGC

TGTTCCAACAGAAGTCCTGCTATCCTATACAATAAAGCAGTATTAATTGCTGCCTTCCCTGGAGTCTC

TAAAGATACTCGGTAAGTGTACAGTACCCTGATGAACTAAAGCCAAAAGTTAGGGCTGATTTCGGGCT

TCATCACAGTGAACACCTCACCTCCAGAGAGAAAGTTGTAGGCCTTTAAAGCTTTTGATCTCAGAGAA

GACTCCACCGCCTTTCAAGGCAATAAATTCTTGCCTCTTCTCCAAATACTCTAACTGAAACTTCTGCT

GTTGCAGTATAATTCAATGTGTTTTTTTCCAGACTTCAATGAAAGCAAGAATTCTCATTCTGCATGTA

ATTATATCCCTTATAATACCCACAGCC

The following amino acid sequence <SEQ ID NO.109> is a predicted amino acid sequence derived from the DNA sequence of SEQ ID NO.52:
LLFKENNGWVDERECQLDQQTAVPTEVLLSYTIKQY The following DNA sequence Ion 151 <SEQ ID NO.53 > was identified in *H. sapiens*:
TATGAGTGATGCAAATATCACAAATACTGGTGGCACCAAAACGATGATTTTTCTGAAATCTGAAATAA

ACTTGGTAAAATTTCATTTGAAACAAAAGTCTCCTTTCAATTTATTAAGTACAGCGAGTGCTCACCTA

AGGTCTTGGAAATGGCAACTTTAAGTAAAATAATGTATATTAAAACCAATTTTCCCATAAGCTAATTG

ATCTAAACAAGAGTTATGCTTTTATGGCATATTTCTGGTCACAAAAACATCACCAAACTTCTAAAGAA

AGACCAAAATATTTCTGATATTAAACATTTAAAGAAATGTGAGCTATACGTACATTTAAGAAAGGTTA

ATAAAAACAAGTCAGATAATTATTTACCCAATTATTCCAGTTCAGGATACTGGGTAGCCAAAGCTTAT

CTGGGCAGCTTAGGATGCAAGGAAGGAACTCACCTTGAACAGGAAACCAATTCCATCACAGGGCACAT

TCACACACAGACCCACACTCACTTCAGACCAGGAAAATTTAAACACCAATTCACCTACTATGCACATC

TTTGGAATGTGGGATGAAGCCAGCGTACCTGGAGAAAACCCAGGAAGACATGGGGAGAATGGGCAAAC

TCCACACAGACAGAGGCCCTAGTGAAGTATCATTATTATTCT

The following amino acid sequence <SEQ ID NO.110 > is a predicted amino acid sequence derived from the DNA sequence of SEQ ID NO.53:
WNWFPVQGEFLPCILSCPDKLWLPSILNWNNWVNNYLTCFY The following DNA sequence Ion 152<SEQ ID NO.54 > was identified in *H. sapiens*:
CCCAATATGGATGCAAGGGTCACTGATTACTTTAGGGTCCTTATGTTGCAAGGAGTCTAGGAAAAACT

TCAATTTTTTTTTTTTACAGCAACGTGATTCTCTTTGTGGTGTCTACTAAAATAAGAAAGTTACAGTG

AGATTTCTTCAGTGTTCTGATGGCTTTCTGCCTCTCCTCTGACCAGCGTGAGCCACTCCTTCATCTCT

GCCTCTCACTTTCTGCTTGACAGTCAAGGCTCGCCTTGAACCTCCCTCTTCAGAAAGCCTTTCTGACC

TABLE 5-continued

```
TGCCTCCTCAGGAGTGTTTGTTTGTGGTATTTGACCACAATCTGCACTATACTAATTAGCTATGATTT

TTATGGGGCTGGAGGAACTTCTAAGGCAGCAGCCGCGTCGGGTTCTTCTGTCTCCTTCCCAGGGCTTC

CTCAGGGCTTAGTACAGGGCATGTGCTAAGCATTCCCTAGCCCCTTCCTTTGCCCTTGTTTGTTCTTT

CTAATCAGATTCTGTGGGGGAAGTTCATTGTCACAATGTCCAATGTTTAGCATTCAAAGGCTGCATGA

GGTAGATCAGGTAAACATACCTCTCTGGCTGTACCAAAATGGGGGGGTTTGGCATATCCGCCACCTGA

AAGCAGCTGGACCCTGCGTGGATCTGGGTTTGTATGCTGTGAGTAATGCTGTCTGCATCTTCGAATCT

TTCACTGTAAGAAACAAAAGTCTGACAGCCTCTGAATCCCGCCCTCCTTCCTGATACACTGTGACAAT

GTGTTTATAGTACCCTGTTGATGCTGA
```

The following amino acid sequence <SEQ ID NO.111 > is a predicted amino acid sequence derived from the DNA sequence of SEQ ID NO.54:
IQRLHEVDQVNIPLWLYQNGGVWHIRHLKAAGPCVDLGLYAVSNAVCIFESFT The following DNA sequence Ion 153<SEQ ID NO.55 > was identified in *H. sapiens*:
```
AAAAAAAAAAAAAAAAAAGGTGACTGATATTACCAAATAGCCTCCATGATGTACCAATTTACACTGCTT

ATAGGTTTGTCTGTTTTCTTGATATTATACACTCTGTCTTACAGACTCACAGCAACATGTCTTGGAAT

TCCACTTATGTCAATATACATAGATCTACCTTATTAAAAAAAAAAAACATGCCGGGCATAGGGGCTTA

CACCTGTAATCCCAGCACTT
```

The following amino acid sequence <SEQ ID NO.112 > is a predicted amino acid sequence derived from the DNA sequence of SEQ ID NO.55:
YQFTLLIGLSVFLILYTLSYRLTATCLGIPLMSIY The following DNA sequence Ion 154<SEQ ID NO.56> was identified in *H. sapiens*:
```
CACCATCCTCCAGACCCCAGAATGGTAGATCCATCCAAGCTTGCACCCTGCACCTGGGAAAAGCCATA

GGACACTCAACATCAGCCATGAAGGCAGCCCGGAAGGGGGCTATGCCCTGCAAAGCCACAGGGGAGGA

GCTACCCAAGGCCATGGGAGCCCACCTCTTGCATCAGTGTGACCTGGACGTGAAACATGGAGTCCAAG

GAGATCATTTTGGAGCTTTAAGATTTGGCTGCTCCACTGGATTTCAGATTTGCATGGGCCTGTAGCC

TCTTTGTTTTGGCTAATTTCTCCTATTTGGAATGGTTGTATTTCCCCAATGCCTGTACTCCCATTGTA

TCTAGGAAGTATAATAGGTACGTGCTTTTGATTGTAAAGGCTTATAGGCAAAAGGGACTTGCCTTGTC

TCAGATGAGACTTTGAACTCAGACTGTTGAGTTAATGCTGGAATGAGTTAAGATTTT
```

The following amino acid sequence <SEQ ID NO.113> is a predicted amino acid sequence derived from the DNA sequence of SEQ ID NO.56:
IWLLHWISDLHGACSLFVLANFSYLEWLYFPNACTPIVSRKYNRYVLLIVKAYRQKGLALSQ

MRLTQTV

The following DNA sequence Ion 155<SEQ ID NO.57> was identified in *H. sapiens*:
```
CGCTTGGATGGACAGGTTACCACTGGAGTGCTACGGCTCTGATACCTGCAGTTTTGCAGAACCAGCCT

GCAATGGCGAGGCCGGGCCTTTGGTTTAGCACAGAGGTGCGAGTGTGCGGCCCACTCTGAGGGGCAG

CGGTACCTATGTCCTCCCCTTTCCTCCCACTGCAGACTCCCAGGGCCTGGAGATGGTGACTGGAACAA

ATGACACATTTCAGCCACACAAGGAGGCCTCTGTGAGGCCGCTTCTTCCAGCAGAAGCTCCTGTGGAT

GTGCATGTGTCAGAACAAACCCAGCCCAGGACCGAATGGATTTGGGTTATTTGCTTTTCAATTCTGGC

CCCATTCTGTGGGAGGCCATCTGTGATGAGGCAGGGAAAAGCAGACAGAGAAAGGGGATCCATGCTCT

TGCATCCAGCCCTTCCAAGAAAATTCTATGAGAGCAGCACCTGAACCGCAAGGCCCCGTTGGGACAGC

AGATTGTATTTTAGGATTTTAACCACAAATCATCTCTCCTGACTTCTCATTCTCTGCCTCGCAACACT

TCTTTCTCATTTCTTCCACCTAGAATCTCTCTATTTCTACTTGACCTTTGCTTTTGGATGTGGCCACT

CAAACCTTT
```

TABLE 5-continued

The following amino acid sequence <SEQ ID NO.114> is a predicted
amino acid sequence derived from the DNA sequence of SEQ ID NO.57:
CKSMDPLSLSAFPCLITDGLPQNGARIEKQITQIHSVLGWVCSDTCTSTGASAGRSGLTE The following DNA sequence 5HT3C <SEQ ID NO.115> was identified in *H.
sapiens*:
AGCTTTGCTACATTAGCTTCCAGAATTTGCATTCAGGCTCACCCCATCCTCCCGGGCCTCGGAAGAAGAAG

CCCAGCGTCTGGACCCCTCTCGGTGATCCCCTCCCCATTCTTCATCTCATCCCTGGGGACGTATAGCACAG

CAGCAGCAGACAAACCTGGGTTCAGAACAAGTCCGGCTTCTGCCTTTTATTGGCTGTCTGACTGTAGGAAG

TTACTTCCTCTTATTGCACCTTAGTTAGCTCGTTTATTACATGAGGGTAAAGCAGTATCTACCTGATAGGG

GATTGGGAGGATTAAATGAGGTAATCCATTTTTAAAGGGCTTAGAATATACCTGACACACAGCCAGTGCTC

AACAAATGTTAGCTTTCATTTTATCACGGGCGACCCCACGCCCTGCCTTGGGGCCCCTCTCATATAGGGAG

CACAGGGTTGCTCTCCTTCATCTCACACATTCGATGTCCACTACAGGAAGGGGCGTTACTTTCACCATCAA

TTGCTCAGGGTTTGGCCAGCACGGGGCGGATCCCACTGCTGTGAATTCAGTGTTTAATAGAAAGCCCTTCC

GTCCGGTCACCAACATCAGCGTCCCCACCCAAGTCAACATCTCCTTCGCGATGTCTGCCATCCTAGATGTG

AATGAACAGCTGCACCTCTTGTCATCATTCCTGTGGCTGGAAATGGTTTGGGATAACCCATTTATCAGCTG

GAACCCAGAGGAATGTGAGGGCATCACGAAGATGAGTATGGCAGCCAAGAACCTGTGGCTCCCAGACATTT

TCATCATTGAACTCATGGATGTGGATAAGACCCCAAAAGGCCTCACAGCATATGTAAGTAATGAAGGTCGC

ATCAGGTATAAGAAACCCATGAAGGTGGACAGTATCTGTAACCTGGACATCTTCTACTTCCCCTTCGACCA

GCAGAACTGCACACTCACCTTCAGCTCATTCCTCTACACAGTGGACAGCATGTTGCTGGACATGGAGAAAG

AAGTGTGGGAAATAACAGACGCATCCCGGAACATCCTTCAGACCCATGGAGAATGGGAGCTCCTGGGCCTC

AGCAAGGCCACCGCAAAGTTGTCCAGGGGAGGCAACCTGTATGATCAGATCGTGTTCTATGTGGCCATCAG

GCGCAGGCCCAGCCTCTATGTCATAAACCTTCTCGTGCCCAGTGGCTTTCTGGTTGCCATCGATGCCCTCA

GCTTCTACCTGCCAGTGAAAAGTGGGAATCGTGTCCCATTCAAGATAACGCTCCTGCTGGGCTACAACGTC

TTCCTGCTCATGATGACTGACTTGCTCCCCACCAGTGGCACCCCCCTCATCGGTGTCTACTTCGCCCTGTG

CCTGTCCCTGATGGTGGGCAGCCTGCTGGAGACCATCTTCATCACCCACCTGCTGCACGTGGCCACCACCC

AGCCCCCACCCCTGCCTCGGTGGCTCCACTCCCTGCTGCTCCACTGCAACAGCCCGGGGAGATGCTGTCCC

ACTGCGCCCCAGAAGGAAAATAAGGGCCCGGGTCTCACCCCCACCCACCTGCCCGGTGTGAAGGAGCCAGA

GGTATCAGCAGGGCAGATGCCGGGCCCTGCGGAGGCAGAGCTGACAGGGGGCTCAGAATGGACAAGGGCCC

AGCGGGAACACGAGGCCCAGAAGCAGCACTCAGTGGAGCTGTGGTTGCAGTTCAGCCACGCGATGGACGCC

ATGCTCTTCCGCCTCTACCTGCTCTTCATGGCCTCCTCTATCATCACCGTCATATGCCTCTGGAACACCTA

GGCAGGTGCTCACCTGCCAACTTCAGTCTGGAGCTTCTCTTGCCTCCAGGGACTGGCCAGGTCTCCCCCCT

TTCCTGAGTACCAACTATCATATCCCCAAAGATGACTGAGTCTCTGCTGTATTCCATGTATCCCAATCCGG

TCCTGCTGATCAATTCCAATCCCAGACATTTCTCCCTGTTCCTGCATTTTGTTGGCTTCCTTCAGTCCTAC

CATATGGTTCTAGGTCCCTCTTACGTCATCTGCATAGCAGACTATACCTCTTCTGCCCGCTGACTTGCCCA

ATAAATAATTCTGCAGAGAAAAAAAAAAAAAAAAAAAAAAAAAAAAAAAAAAAAAAAAAAAAAAAAAAAAA

A

The following amino acid sequence <SEQ ID NO.116> is a predicted amino
acid sequence derived from the DNA sequence of SEQ ID NO.115:
MLAFILSPATPRPALGPLSYREHRVALLHLTHSMSTTGRGVTFTINCSGFGQHGADPTAV

NSVFNRKPFRPVTNISVPTQVNISFAMSAILDVNEQLHLLSSFLWLEMVWDNPFISWNPE

ECEGITKMSMAAKNLWLPDIFIIELMDVDKTPKGLTAYVSNEGRIRYKKPMKVDSICNLD

IFYFPFDQQNCTLTFSSFLYTVDSMLLDMEKEVWEITDASRNILQTHGEWELLGLSKATA

KLSRGGNLYDQIVFYVAIRRRPSLYVINLLVPSGFLVAIDALSFYLPVKSGNRVPFKITL

TABLE 5-continued

LLGYNVFLLMMSDLLPTSGTPLIGVYFALCLSLMVGSLLETIFITHLLHVATTQPPPLPR

WLHSLLLHCNSPGRCCPTAPQKENKGPGLTPTHLPGVKEPEVSAGQMPGPAEAELTGGSE

WTRAQREHEAQKQHSVELWLQFSHAMDAMLFRLYLLFMASSIITVICLWNT

The following DNA sequence 5HT3D <SEQ ID NO.117> was identified in *H. sapiens*:
ATGTTAGCTTTCATTTTATCACGGGCGACCCCACGCCCTGCCTTGGGGCCCCTCTCATATAGGGAGCACAG

GGTTGCTCTCCTTCATCTCACACATTCGATGTCCACTACAGGAAGGGGCGTTACTTTCACCATCAATTGCT

CAGGGTTTGGCCAGCACGGGGCGGATCCCACTGCTCTGAATTCAGTGTTTAATAGAAAGCCCTTCCGTCCG

GTCACCAACATCAGCGTCCCCACCCAAGTCAACATCTCCTTCGCGATGTCTGCCATCCTAGATGTGAATGA

ACAGCTGCACCTCTTGTCATCATTCCTGTGGCTGGAAATGGTTTGGGATAACCCATTTATCAGCTGGAACC

CAGATGAATGCGGAGGCATCAAGAAGTCCGGCATGGCAACTGAGAACCTATGGCTTTCAGATGTCTTCATC

GAGGAGTCTGTGGATCAGACACCTGCAGGTCTCATGGCTAGTATGTCAATAGTGAAGGCCACATCAAACAC

AATAAGCCAATGTGGGTGGTCAGCATCTGCAAACTGGACACCTTCTATTTCCCCTTCCATGGACAGAGGTG

AACGCTCTCCTTCAGCCCTTTCACCTACACAGGTAACCCGGGCATGGAGAAGGATGTCCAGGAGCTTTCAA

ATACATCACAGAACCTCATTCAGAACAAGGAGGGAGTGGGTACTGCTGGGTATCCAAAAAAGAACAATAAA

GGTGACCGTGGCCACTAACCAGTATGAACAAGCCATCTTCCATGTGGCCATCAGGCGCAGGTGCAGGCCCA

GCCCCTACGTGGTAAACTTTCTGGTGCCCAGTGGCATTCTGATTGCCATCGATGCCCTCAGTTTCTACCTG

CCACTGGAAAGTGGGAATTGTGCCCCATTCAAGATGACTGTTCTGCTGGGCTACAGCGTCTTCCTGCTCAT

GATGAATGACTTGCTCCCAGCCACTAGCACTTCATCACATGCTTCACTAGTACGTGTCTACTTCGCCCTGT

GCCTGTCCCTGATGGTGGGCAGCCTGCTGGAGACCATCTTCATCACCCACCTGCTGCACGTGGCCACCACC

CAGCCCCTACCTCTGCCTCGGTGGCTCCACTCCCTGCTGCTGCACTGCACCGGCCAAGGGAGATGCTGTCC

CACTGCGCCCCAGAAGGGAAATAAGGGCCCGGGTCTCACCCCCACCCACCTGCCCGGTGTGAAGGAGCCAG

AGGTATCAGCAGGGCAGATGCCAGGCCCTGGGGAGGCAGAGCTGACAGGGGGCTCAGAATGGACAAGGGCC

CAGCGGGAACACGAGGCCCAGAAGCAGCACTCGGTGGAGCTGTGGGTGCAGTTCAGCCACGCGATGGACGC

CCTGCTCTTCCGCCTCTACCTGCTCTTCATGGCCTCCTCCATCATCACCGTCATATGCCTCTGGAACACCT

AGGCAGGTGCTCACCTGCAAACTTCAGTCTGGACTTCTTTTTGCC

The following amino acid sequence <SEQ ID NO.118> is a predicted amino acid sequence derived from the DNA sequence of SEQ ID NO.117:
WNPDECGGIKKSGMATENLWLSDVFIEESVDQTPAGLMASMSIVKATSNTISQCGWSASANWTPSISPSMD

RGERSPSALSPTQVTRAWRRMSRSFQIHHRTSFRTRREWVLLGIQKRTIKVTVATNQYEQAIFHVAIRRRC

RPSPYVVNFLVPSGILIAIDALSFYLPLESGNCAPFKMTVLLGYSVFLLMMNDLLPATSTSSHASLVRVYF

ALCLSLMVGSLLETIFITHLLHVATTQPLPLPRWLHSLLLHCTGQGRCCPTAPQKGNKGPGLTPTHLPGVK

EPEVSAGQMPGPGEAELTGGSEWTRAQREHEAQKQHSVELWVQFSHAMDALLFRLYLLFMASSIITVICLW

NT

The following DNA sequence 5HT3D-genomic <SEQ ID NO.119> was identified in *H. sapiens*:
gtatcatcaaatatacaaactaggcatgatcaaagagcaatgttttcaattctgtctatttgtcaaattt cctccatctactaaagtactaaagcatctaagaatataaagtctcacagaggaaactgttgaagaacggct gctctcgagagaataaacacgacagagttgaaagaccttgagcaagatcacggaattgccgagctagaagg tttcttcacacctacgtaaacagcatccaggagctgtgctgtgcaagaatctccaggctgtaaaattaga aacactcaggtttaagtcgggcgcggtggctcacgcctgtaatcccagcactttgagaggccgaggcaggc agatcatgaagtcaggagttcgagaccagtctggccaacagggtgaaactcgtctctactaaaaatacaaa TABLE 5-continued

```
aaattagccaggcgtggtagcacatgcctctaatcacagctacttgggatgctgagacaggaaaatagctt
gaacctgggagacagaggtggcaatgagccgagattgcgccactggactccagcctgggtgataaagcgag
actccgtctcagaaagaaaaagaaacacttaggtttaattcgcagttctgacacttttgggcaagtaaac
caaatcaagatttggtttccgctgtgcgcagtggctcacgcctgtaatcccagcactttgggaggctgagg
cgggtggattgcctgaggttaggagtccgagaccagcctggctaacatggtgaagccctgtctctactaaa
aatacaaaaattagctgggtgtggtggcgcacgcctgtagttccagctacttgagaggctgaggcaggaga
atcgcttgaacccgggaggcggaggttgcagtgagctgagatcatgccaccacactctagcctgggtgaca
gaacaagactccgtctcaaaaaaaaaaatatatatatatatacacacacacacgtatatatacatata
tatacacgtatatatgtatatgtgtatatatagtgtatatatgtatatgtgtatatatgtatatgtgta
tatatgtatatacgtgtatatgtgtatatatgtatatatgtgtatatgtatatatacacgtatatat
gtatatatacgtgtatatatgtgtataataatgcagccgggtgtggtgactcatgcctataatcccagt
actttgggaggccaaggcgggcagatcacttgaggtcaggagttcgagaccagcctggccaaatatggtga
aaccttgtctctactaaaaatacaaaaattagccggacttagtggcgggcacctgtaatcccagctactcg
ggaggctgaggcacaagaattgcttgaatcgaggaggcggaggttgcagtgagcagagatggcaccactgc
actctagcctgggcaatatagcgagactatctcaaaaaaaataaataaataaaaataaatttaaaaatata
ataatgcatgaagaatacctagcacagtccctggtacatgctaagtgcctaataaattgcaactactaata
ataatcaataaatattccttcgcctggttcatggtcagcacaccttacccagtccttcccttttgtcagctg
actgagccctggctgtcccctgaggatgctcctgcagcctctgaatggagggtgcttgtttcctgtgccag
ttcagttctgatcagaaagggcacgctcactcactcaaatggagcaatgaggagagtttcagaacagagaa
cacagaagccaatgcatgtggctcaagaagggagggactgggaagaataagtgctctaaactcattttcc
cttatgctccgatctcttgtttgtggctgtaattggctgagcccagctaggagccagagagcaagagagcc
cattgatgtagtccataaaggtcagcctcctggccgggcgcggtggctcacacctgtaatcccagcacttt
gggaggccgaggcgagtggatcacctgaggtcaggagttgaagaccagcctgaccaatatggtgaaaccct
gcctctactaaaaatacaaaaattaggccaggcacagtggctcacgcctataatcccaacactttgggagg
ctgaggcaggcggatcacaaagtaaagagatcgagaccatcctggctaacatggtgaaacccatctctac
taaaaatacaaaaattagctaggtgtggtggcgtgtgcctgtaatcccagctactcaggaggctgaggcag
gaggatcacttgaacccaggaggcagaggttgcagtgagctgagatcgtgccactgcactctagcctggcg
acagagcaagactctgtctcaaaaaaataataaaatacaaaattaaaaaaccagaaaataacaagtgttgg
tgataatgtggagaaattggaacccttgtgcactgcttgtgaggatgtaaaattgtgtagccactgtggaa
aaacagtatggcttttttctcaaaatattaaaaatagaattaccatacaaccaaataattatacttctggat
aaaatacccgaaaaagtgaaaacggggtatttgtacacttatgttcatagcagaattactcacaatagtta
aaactcagaagcagtctaagtgtctattgacagatgaatggacagattaaatgtggtatgtacttacaatg
gaatactatgcagccttcaaatggaacaaaattctaacacatgccacaatgtggataagctgtgaggccat
tatgctaagtgaaataagtcagtcacaaaagacaaatagtgtatttgtctaattttatagagacagaaag
tagaatagctgttgccaggggttggagagagggtgaaataggaattactgtttaacgggtgtagagtttc
cattttgcaagaagaaaagagctctggtgatggagggtggtggctggacaacagtgtgaatgtgtttaacg
ccacggaactgtacacttaaaatggttaagagagtacattttatgttatatatttttcacaataaaata
ttgaaaaaattattttagcctgggcaacatggcgaaacccatctctaccaaaaatacaaaagttagct
gggcgtggtggtgtgtgcctctaatcccagctgctcgggaggctgaggcaggaggcaggagaatcacctga
acctgggaggcagaggttgcagtgagccgaaatggcgccactgcactccagcctgggcgacagagcaagat
```

TABLE 5-continued

```
tctgtctcaaaaaaaagaaaaaatgatttttaaaagtgtttaaaaaattagaggtgcattcggcggggtg
aggagtagaaaggcatgataagaaatgctgtaatgacattactgcaggtaaaatctgttcttttggaata
cttgtcaaaacatattcccaatggaccttcatactgtgtttttcatttacattttccatgtaccttgaatt
gttttgatctacatcattttttcagtggcttagatcaaaaatcattattgccacatggaccagccttggaag
tgaacaaggagaggtggtggcatgggacctgccttcctggagttaatcatctagatgaaagctgctattc
caggattcacaccttcaactggtgacatcgttcctgtggctaaatatggtatgacagactcagtttcccct
ttcctctactctggtgcctctcttttttccactcctaggtccagctttgcagattatattggttaaagctg
agaatatccataaattagacaagttcaaatagaccaataatgaaaatacaaaactttctgattattctgct
ggtttaggagggcagaaaatgggcacagggagaaggtggtatacactaaggccatgggagtcaatacttat
gtggctccatcccagagaatcctgagccaagctcaagctcaagtctgtcttgagaaaactgaggtaagca
agtgttagtgtgatggctgccaccagagaggtggcaggagagtgaagaaatgggcgaaaaaggaaaggga
aggtgcagaagacagagcaaaactaaaactagttccttcccctgtttctctcatgccatggtttcctaca
gacctagcacaatcaattctttttttttttttttgagagagtctcactctgtcgcccaggctcaagggcag
tggtgcgatctcagcccactgcaacctccacctcctgggttcaagcgattttcctgcctcctgcctcagcc
tcctgagtatctgggattacaggggcccaccaccacacccagctaattttttgtatttttagtagagatggg
gtttcaccatgttagctaggctggtcctgaactcctgaccttcagtgatcccccgcctcagccttccaaa
gtgctgggattacagacagaagccaccatgcccggccttggcacaatcaatttgtgcagtggaacccagat
gaatgcggaggcatcaagaagtccggcatggcaactgagaacctatggctttcagatgtcttcatcgagga
gtcgtgagtctcaggccaaaaaagcagaatggaaaccacgtctacagggaaggacacaatgttaccgataa
ggccacacaaagactcaacttagaaaagagcagagtctgaattgaagagcttacaaaccccagaatatga
ttataggtagaagagagcagtcatctgagtggggctggagctcgagaatgggatgacctgacagagaaaga
aggccaagtctgatggggaaacccacagcacctacctccctgtccttctcccacacagcatcagtgtggat
cagacacctgcaggtctcatggctagtatgtcaatagtgaaggccacatcaaacacaataagccaatgtgg
gtggtcagcatctgcaaactggacaccttctatttccccttccatggacagaggtgaacgctctccttcag
cccttcacctacacaggtaagtggggctcactaaagtagactgttgagaggcagagaaagggctttgagt
gagaagaggacagaaagctgggaacagtgagggaatcttgctgaaaaggggcctggaagctaagcagtgagg
gatccaacagtctgggcaagggacttgggcgcatttggggaggctgagtcttctgggcctgctttgcagtg
gagaacacgagcccgggcatggagaaggatgtccaggagctttcaaatacatcacagaacctcattcagaa
caaggagggagtgggtactgctgggtatccaaaaaagaacaataaaggtgaccgtggccactaaccagtat
gaacaagccatcttccatgtgagctcaggggccaagacaaggtttcaccatgttggccaggctggtcttga
actcctggcttcaggtgatccgcccgcctcggcctcccaaagtgctgggattacgggcgtgaaccacgaag
cccggcctttgtcactcttttttttttttttaaatttgagatagagttttgttcttgtcgctcaggctggag
tgcaatgacgtgatctcagctcactgcaacttccacctcctgggttcaagtgattctcctgcttcagcctc
ctgagtagctgggattacaagggcccgccaccatgcccggctaattttttgtattttagtagagatggggt
ttcaccacgttcaccaggccggtctcaaagtcctgaactcaggtatctgcctgcctcggcctcccaaagtt
ctgggattacaggtatgagccaccgtgcccagccttttgtcacttttttcactgataaaccttcagtacta
aaacaatacctggtactcagtaaatagttactaaataaagcatcccttgaggaagaaacaaaggctctatg
ccagtgattcatggtgagggtgagcccgccttccccaatggctgtcagaactttttggaaggcaggaatt
tttgtttattttaaaaagatatggtagaaagagttaggaaacactgccttagggatatgatgattccaaa
```

TABLE 5-continued

```
tcctgataaccccaaaatatctgatactgtctgctttccctcccactggtctcaaatgttccctgcaaag
tcactagagattagaccttgacgagaaaagcaattagaaatgaaaagataaaacacacgcgacacctaagt
cggtggttccacagtcttgctaagagcacgtcggtaggaataaaaatttaagtggagaaagttgacacctt
gggccaaaaggaatgagatacatttcagaggtaagcagcatgggagactctaaccttgtgagacgcctttg
gatgaaaagaccggatgctgaaagggacgggaggtaatatttccttactagacagtttggcctgggacaaa
tcccagttcttactcttacctgtcttgacagcctcccagcctacttctcacttgcccctccttctcctccc
caccaggtggccatcaggcgcaggtgcaggcccagccctacgtggtaaactttctggtgcccagtggcat
tctgattgccatcgatgccctcagtttctacctgccactggaaagtgggaattgtgccccattcaagatga
ctgttctgctgggctacagcgtcttcctgctcatgatgaatgacttgctcccagccactagcacttcatca
catgcttcactagtacgtcctcatccatcaagagaccaaaagcgaggtgtgtgttggatggggagaggat
gggcagaaccaggcgaagtgaaaagggatcctggaaaaagatcctctgggaaagaaacaagaaattctagg
tggcgcctctggccctcatgcagacccccttgcctgcaggtgtctacttcgccctgtgcctgtccctgatg
gtgggcagcctgctggagaccatcttcatcacccacctgctgcacgtggccaccacccagcccctacctct
gcctcggtggctccactccctgctgctgcactgcaccggccaagggagatgctgtcccactgcgcccaga
agggaaataagggcccgggtctcacccccacccacctgcccggtgagggaagtcatacttcctcttccccc
acctccacttctctgctcctgcctccttccctgtctccctccctccacaggtgacatttgcagcccatggc
tgagtctctgtctttctgtaggtgtgaaggagccagaggtatcagcagggcagatgccaggccctggggag
gcagagctgacaggggctcagaatggacaagggcccagcgggaacacgaggcccagaagcagcactcggt
ggagctgtgggtgcagttcagccacgcgatggacgccctgctcttccgcctctacctgctcttcatggcct
cctccatcatcaccgtcatatgcctctggaacacctaggcaggtgctcacctgcaaacttcagtctggact
tcttttgccagagaactccagaaaccagtcaggctctcagtcagccttgtggccctgtcaaccgcctcat
ttttaacccagtcctctgtgtagtttcagaccagacctgaatagtctcctatgccctccaaaagtcgggtc
cttgctcctgcatgccatcagccccactcagccctcccatacctccctggctcctcaggattcaggttcct
agggtacgtccttgattaaatcacccaatatgccctttgcagaaagtattggcttttccctgaatt
```

EXAMPLES

Example 1

Identification of Ion Channel Sequences in GenBank/EMBL

A brief description of the searching mechanism follows. The BLAST algorithm, Basic Local Alignment Search Tool, is suitable for determining sequence similarity (Altschul et al., *J. Mol. Biol.*, 1990, 215, 403–410, which is incorporated herein by reference in its entirety). Software for performing BLAST analyses is publicly available through the National Center for Biotechnology Information (www.ncbi.nlm.nih.gov/). This algorithm involves first identifying high scoring sequence pair (HSPs) by identifying short words of length "W" in the query sequence that either match or satisfy some positive valued threshold score "T" when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T and X determine the sensitivity and speed of the alignment. The BLAST program uses as defaults a word length (W) of 11, the BLOSUM62 scoring matrix (see Henikoff et al., *Proc. Natl. Acad. Sci. USA*, 1992, 89,10915–19, which is incorporated herein by reference in its entirety) alignments (B) of 50, expectation (E) of 10, M=5, N=4, and a comparison of both strands.

The BLAST algorithm (Karlin et al., *Proc. Natl. Acad. Sci. USA*, 1993, 90, 5873–5787, which is incorporated herein by reference in its entirety) and Gapped BLAST (Altschul et al., *Nuc. Acids Res.*, 1997, 25, 3389–3402, which is incorporated herein by reference in its entirety) perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to an ion channel gene or cDNA if the smallest sum probability in comparison of the test nucleic acid to an ion channel nucleic acid is less than about 1, preferably less than about 0.1, more preferably less than about 0.01, and most preferably less than about 0.001.

The Celera database was searched with the NCBI program BLAST (Altschul et al., *Nuc. Acids Res.*, 1997, 25, 3389, which is incorporated herein by reference in its entirety), using the known protein sequences of ion channels from the SWISSPROT database as query sequences to find patterns suggestive of novel ion channels. Specifically, one of the BLAST programs TBLASTN was used to compare protein sequences to the DNA database dynamically translated in six reading frames. Alternatively, a second search strategy was developed using a hidden Markov model (HMM)(Krogh et al., J Mol Biol 1994, 235;1501–1531) to query that nucleotide database translated in six reading frames. HMMs, as used herein, describe the probability distribution of conserved sequence when compared to a related protein family. Because of this different search algorithm, the use of HMMs may yield different and possibly more relevant results than are generated by the BLAST search. Positive hits were further analyzed with the program BLASTX against the non-redundant protein and nucleotide databases maintained at NCBI to determine which hits were most likely to encode novel ion channels, using the standard (default) parameters. This search strategy, together with the insight of the inventors, identified SEQ ID NO:1 to SEQ ID NO:57, SEQ ID NO:115, SEQ ID NO:117, and SEQ ID NO:119 as candidate sequences.

5HT-3C

Ion1, ion 52, and ion110 were combined to provide an almost full-length gene, named ion-5HT-3C (nucleotide sequence—SEQ ID NO:115, amino acid sequence—SEQ ID NO:116).

5HT-3D

All available genomic databases were searched with the fragments identified in Celera database previously and with the 5HT3A and ion-5HT-3C (SEQ ID NO:116) protein sequences. The search was performed using either the blastn or tblastn algorithm with default parameters. Two high scoring genomic sequences were identified, retrieved and compared using the Sequencher program (GeneCodes). Since the sequences were very similar they were assembled into one contig. Several gene prediction programs were used to predict exons. The output of these programs was formatted and put into the genome browser program Artemis (Sanger Centre). Intron-exon boundaries were adjusted manually. Ion-5HT-3D appears to have 8 exons. Using a FORTRAN computer program called "tmtrest.all" [Parodi et al., Comput. Appl. Biosci. 5:527–535 (1994)], ion-5HT-3D was shown to contain four transmembrane-spanning domains.

SEQ ID NO:118 sets forth the predicted full-length protein structure of 5HT-3D, while SEQ ID NO:119 sets forth the genomic sequence of 5HT-3D.

Example 2

Detection of Open Reading Frames and Prediction of the Primary Transcript for Ion Channels The predictions of the primary transcript and mature mRNA were made manually. Consensus sequences found in textbooks (i.e., Lodish et al. *Molecular Cell Biology,* 1997, ISBN: 0-7167-2380-8) and regions of similarity to known ion channels were used to discover the primary transcripts of the ion channel polypeptides.

Through sequence alignment, both 5HT-3C and 5HT-3D appear to have homology to 5HT-3A; e.g. 5HT-3C and 5HT-3D are serotonin receptors.

Example 3

Cloning of Ion Channel cDNA

To isolate cDNA clones encoding full length ion channel proteins, DNA fragments corresponding to a portion of SEQ ID NO:1 to SEQ ID NO:57, SEQ ID NO:115, SEQ ID NO:117, and SEQ ID NO:119, or complementary nucleotide sequence thereof, can be used as probes for hybridization screening of a phage, phagemid, or plasmid cDNA library. The DNA fragments are amplified by PCR. The PCR reaction mixture of 50 µl contains polymerase mixture (0.2 mM dNTPs, 1×PCR Buffer and 0.75 µl Expand High Fidelity Polymerase (Roche Biochemicals)), 100 ng to 1 µg of human cDNA, and 50 pmoles of forward primer and 50 pmoles of reverse primer. Primers may be readily designed by those of skill in the art based on the nucleotide sequences provided herein. Amplification is performed in an Applied Biosystems PE2400 thermocycler using for example, the following program: 95° C. for 15 seconds, 52° C. for 30 seconds and 72° C. for 90 seconds; repeated for 25 cycles. The actual PCR conditions will depend, for example on the physical characteristics of the oligonucleotide primers and the length of the PCR product. The amplified product can be separated from the plasmid by agarose gel electrophoresis, and purified by Qiaquick™ gel extraction kit (Qiagen).

A lambda phage library containing cDNAs cloned into lambda ZAPII phage-vector is plated with *E. coli* XL-1 blue host, on 15 cm LB-agar plates at a density of 50,000 pfu per plate, and grown overnight at 37° C.; (plated as described by Sambrook et al., supra). Phage plaques are transferred to nylon membranes (Amersham Hybond N.J.), denatured for 2 minutes in denaturation solution (0.5 M NaOH, 1.5 M NaCl), renatured for 5 minutes in renaturation solution (1 M Tris pH 7.5, 1.5 M NaCl), and washed briefly in 2×SSC (20×SSC: 3 M NaCl, 0.3 M Na-citrate). Filter membranes are dried and incubated at 80° C. for 120 minutes to cross-link the phage DNA to the membranes.

The membranes are hybridized with a DNA probe prepared as described above. A DNA fragment (25 ng) is labeled with α-$^{32}$P-dCTP (NEN) using Rediprime™ random priming (Amersham Pharmacia Biotech), according to manufacturers instructions. Labeled DNA is separated from unincorporated nucleotides by S200 spin columns (Amersham Pharmacia Biotech), denatured at 95° C. for 5 minutes and kept on ice. The DNA-containing membranes (above) are pre-hybridized in 50 ml ExpressHyb™ (Clontech) solution at 68° C. for 90 minutes. Subsequently, the labeled DNA probe is added to the hybridization solution, and the probe is left to hybridize to the membranes at 68° C. for 70 minutes. The membranes are washed five times in 2×SSC, 0.1% SDS at 42° C. for 5 minutes each, and finally washed 30 minutes in 0.1×SSC, 0.2% SDS. Filters are exposed to Kodak XAR film (Eastman Kodak Company, Rochester, N.Y., USA) with an intensifying screen at −80° C. for 16 hours. One positive colony is isolated from the plates, and re-plated with about 1000 pfu on a 15 cm LB plate. Plating, plaque lift to filters, and hybridization are performed as described above. About four positive phage plaques may be isolated form this secondary screening.

cDNA containing plasmids (pBluescript SK-) are rescued from the isolated phages by in vivo excision by culturing XL-1 blue cells co-infected with the isolated phages and with the Excision helper phage, as described by the manufacturer (Stratagene). XL-blue cells containing the plasmids are plated on LB plates and grown at 37° C. for 16 hours. Colonies (18) from each plate are re-plated on LB plates and grown. One colony from each plate is stricken onto a nylon filter in an ordered array, and the filter is placed on a LB plate to raise the colonies. The filter is hybridized with a labeled probe as described above. About three positive colonies are selected and grown up in LB medium. Plasmid DNA is isolated from the three clones by Qiagen Midi Kit (Qiagen) according to the manufacturer's instructions. The size of the insert is determined by digesting the plasmid with the restriction enzymes NotI and SalI, which establishes an insert size.

The clones are sequenced directly using an ABI377 fluorescence-based sequencer (Perkin-Elmer/Applied Biosystems Division, PE/ABD, Foster City, Calif.) and the ABI PRISM™ Ready Dye-Deoxy Terminator kit with Taq FSTM polymerase. Each ABI cycle sequencing reaction contains about 0.5 µg of plasmid DNA. Cycle-sequencing is performed using an initial denaturation at 98° C. for 1 minute, followed by 50 cycles using the following parameters: 98° C. for 30 seconds, annealing at 50° C. for 30 seconds, and extension at 60° C. for 4 minutes. Temperature cycles and times are controlled by a Perkin-Elmer 9600 thermocycler. Extension products are purified using Centriflex™ gel filtration cartridges (Advanced Genetic Technologies Corp., Gaithersburg, Md.). Each reaction product is loaded by pipette onto the column, which is centrifuged in a swinging bucket centrifuge (Sorvall model RT6000B tabletop centrifuge) at 1500×g for 4 minutes at room temperature. Column-purified samples are dried under vacuum for about 40 minutes and dissolved in 5 µl of DNA loading solution (83% deionized formamide, 8.3 mM EDTA, and 1.6 mg/ml Blue Dextran). The samples are heated to 90° C. for three minutes and loaded into the gel sample wells for sequence analysis using the ABI377 sequencer. Sequence analysis is performed by importing ABI377 files into the Sequencer program (Gene Codes, Ann Arbor, Mich.). Generally, sequence reads of up to about 700 bp are obtained. Potential sequencing errors are minimized by obtaining sequence information from both DNA strands and by re-sequencing difficult areas using primers annealing at different locations until all sequencing ambiguities are removed.

Example 4

Northern Blot Analysis

Ion channel expression patterns can be determined through northern blot analysis of mRNA from different cell and tissue types. Typically, "blots" of isolated mRNA from such cells or tissues are prepared by standard methods or purchased, from commercial suppliers, and are subsequently probed with nucleotide probes representing a fragment of the polynucleotide encoding the ion channel polypeptide.

Those skilled in the art are familiar with standard PCR protocols for the generation of suitable probes using pairs of sense and antisense orientation oligonucleotide primers derived from SEQ ID NO:1 to SEQ ID NO:57, SEQ ID NO:115, SEQ ID NO:117, and SEQ ID NO:119. During the PCR process, the probe is labeled radioactively with the use of $\alpha^{32}P$-dCTP by Rediprime™ DNA labeling system (Amersham Pharmacia) so as to permit detection during analysis. The probe is further purified on a Nick Column (Amersham Pharmacia).

A multiple human tissue northern blot from Clontech (Human II # 7767-1) is used in hybridization reactions with the probe to determine which tissues express ion channels. Pre-hybridization is carried out at 42° C. for 4 hours in 5×SSC, 1× Denhardt's reagent, 0.1% SDS, 50% formamide, 250 µg/ml salmon sperm DNA. Hybridization is performed overnight at 42° C. in the same mixture with the addition of about $1.5 \times 10^6$ cpm/ml of labeled probe. The filters are washed several times at 42° C. in 0.2×SSC, 0.1% SDS. Filters were exposed to Kodak XAR film (Eastman Kodak Company, Rochester, N.Y., USA) with an intensifying screen at −80° C., allowing analysis of mRNA expression.

Example 5

Expression of Ion Channel Polypeptides in Mammalian Cells

1. Expression of Ion Channel Polypeptides in HEK-293 Cells

For expression of ion channel polypeptides in mammalian cells HEK-293 (transformed human, primary embryonic kidney cells), a plasmid bearing the relevant ion channel coding sequence is prepared, using vector pcDNA6 (Invitrogen). Vector pcDNA6 contains the CMV promoter and a blasticidin resistant gene for selection of stable transfectants. Many other vectors can be used containing, for example, different promoters, epitope tags for detection and/or purification of the protein, and resistance genes. The forward primer for amplification of this ion channel polypeptide encoding cDNA is determined by procedures as well known in the art and preferably contains a 5' extension of nucleotides to introduce a restriction cloning site not present in the ion channel cDNA sequence, for example, a HindIII restriction site and nucleotides matching the ion channel nucleotide sequence. The reverse primer is also determined by procedures known in the art and preferably contains a 5' extension of nucleotides to introduce a restriction cloning site not present in the ion channel cDNA sequence, for example, an XhoI restriction site, and nucleotides corresponding to the reverse complement of the ion channel nucleotide sequence. The PCR conditions are determined by the physical properties of the oligonucleotide primer and the length of the ion channel gene. The PCR product is gel purified and cloned into the HindIII-XhoI sites of the vector.

The plasmid DNA is purified using a Qiagen plasmid mini-prep kit and transfected into, for example, HEK-293 cells using DOTAP transfection media (Boehringer Mannhein, Indianapolis, Ind.). Transiently transfected cells are tested for ion channel activity and expression after 24–48 hours by established techniques of electrophysiology Electrophysiology, A Practical Approach, Wallis, ed., IRL Press at Oxford University Press, (1993), and Voltage and patch Clamping with Microelectrodes, Smith et al., eds., Waverly Press, Inc for the American Physiology Society (1985). This provides one means by which ion channel activity can be characterized.

DNA is purified using Qiagen chromatography columns and transfected into HBEK-293 cells using DOTAP transfection media (Boehringer Mannheim, Indianapolis, Ind.). Transiently transfected cells are tested for expression after 24 hours of transfection, using Western blots probed with anti-His and anti-ion channel peptide antibodies. Permanently transfected cells are selected with Zeocin and propagated. Production of the recombinant protein is detected from both cells and media by western blots probed with anti-His, anti-Myc or anti-ion channel peptide antibodies.

2. Expression of Ion Channel Polypeptides in COS Cells

For expression of ion channel polypeptides in COS7 cells, a polynucleotide molecule having a nucleotide of SEQ ID NO:1 to SEQ ID NO:57, SEQ ID NO:115, SEQ ID NO:117, and SEQ ID NO:119, or complementary nucleotide sequences thereof, can be cloned into vector p3-CI. This vector is a pUC18-derived plasmid that contains the HCMV (human cytomegalovirus) intron located upstream from the bGH (bovine growth hormone) polyadenylation sequence and a multiple cloning site. In addition, the plasmid contains the dhrf (dihydrofolate reductase) gene which provides selection in the presence of the drug methotrexane (MTX) for selection of stable transformants. Many other vectors can be used containing, for example, different promoters, epitope tags for detection and/or purification of the protein, and resistance genes.

The forward primer is determined by procedures known in the art and preferably contains a 5' extension which introduces an XbaI restriction site for cloning, followed by nucleotides which correspond to a nucleotide sequence given in SEQ ID NO:1 to SEQ ID NO:57, SEQ ID NO:115, SEQ ID NO:117, and SEQ ID NO:119, or portion thereof. The reverse primer is also determined by methods well known in the art and preferably contains a 5' extension of nucleotides which introduces a SalI cloning site followed by nucleotides which correspond to the reverse complement of a nucleotide sequence given in SEQ ID NO:1 to SEQ ID NO:57, SEQ ID NO:115, SEQ ID NO:117, and SEQ ID NO:119, or portion thereof.

The PCR consists of an initial denaturation step of 5 min at 95° C., 30 cycles of 30 sec denaturation at 95° C., 30 sec annealing at 58° C. and 30 sec extension at 72° C., followed by 5 min extension at 72° C. The PCR product is gel purified and ligated into the XbaI and SalI sites of vector p3-CI. This construct is transformed into $E.$ $coli$ cells for amplification and DNA purification. The DNA is purified with Qiagen chromatography columns and transfected into COS 7 cells using Lipofectamine™ reagent (Gibco/BRL), following the manufacturer's protocols. Forty-eight and 72 hours after transfection, the media and the cells are tested for recombinant protein expression.

Ion channel polypeptides expressed in cultured COS cells can be purified by disrupting cells via homogenization and purifying membranes by centrifugation, solubilizing the protein using a suitable detergent, and purifying the protein by, for example, chromatography. Purified ion channel is concentrated to 0.5 mg/ml in an Amicon concentrator fitted with a YM-10 membrane and stored at −80° C.

Example 6

Expression of Ion Channel Polypeptides in Insect Cells

For expression of ion channel polypeptides in a baculovirus system, a polynucleotide molecule having a sequence selected from the group consisting of SEQ ID NO:1 to SEQ ID NO:57, SEQ ID NO:115, SEQ ID NO:117, and SEQ ID NO:119, or a portion thereof, or complement thereof, is amplified by PCR. The forward primer is determined by methods known in the art and preferably constitutes a 5' extension adding a NdeI cloning site, followed by nucleotides which corresponding to a nucleotide sequence provided in SEQ ID NO:1 to SEQ ID NO:57, SEQ ID NO:115, SEQ ID NO:117, and SEQ ID NO:119, or a portion thereof. The reverse primer is also determined by methods known in the art and preferably constitutes a 5' extension which introduces a KpnI cloning site, followed by nucleotides which correspond to the reverse complement of a nucleotide sequence provided in SEQ ID NO:1 to SEQ ID NO:57, SEQ ID NO:115, SEQ ID NO:117, and SEQ ID NO:119, or a portion thereof.

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the $Autographa$ $californica$ nuclear polyhedrosis virus (AcMNPV), and a 10XHis tag upstream from the multiple cloning site. A protein kinase site for phosphorylation and a thrombin site for excision of the recombinant protein preceding the multiple cloning site is also present. Of course, many other baculovirus vectors can be used in place of pAcHTL-A, such as pAc373, pVL941 and pAcIM1. Other suitable vectors for the expression of ion channel polypeptides can be used, provided that such vector constructs include appropriately located signals for transcription, translation, and trafficking, such as an in-frame AUG and a signal peptide, as required. Such vectors are described in Luckow et al., $Virology,$ 1989, 170, 31–39, among others.

The virus is grown and isolated using standard baculovirus expression methods, such as those described in Summers et al., $A$ $Manual$ $of$ $Methods$ $for$ $Baculovirus$ $Vectors$ $and$ $Insect$ $Cell$ $Culture$ $Procedures,$ Texas Agricultural Experimental Station Bulletin No. 1555 (1987).

In a preferred embodiment, pAcHLT-A containing the gene encoding the ion channel polypeptides is introduced into baculovirus using the "BaculoGold" transfection kit (Pharmingen, San Diego, Calif.) using methods provided by the manufacturer. Individual virus isolates are analyzed for protein production by radiolabeling infected cells with $^{35}S$-methionine at 24 hours post infection. Infected cells are harvested at 48 hours post infection, and the labeled proteins are visualized by SDS-PAGE autoradiography. Viruses exhibiting high expression levels can be isolated and used for scaled up expression.

For expression of the ion channel polypeptides in Sf9 insect cells, a polynucleotide molecule having a sequence of SEQ ID NO:1 to SEQ ID NO:57, SEQ ID NO:115, SEQ ID NO:117, and SEQ ID NO:119, or a portion thereof, is amplified by PCR using the primers and methods described above for baculovirus expression. The ion channel polypeptide encoding cDNA insert is cloned into vector pAcHLT-A (Pharmingen), between the NdeI and KpnI sites (after elimination of an internal NdeI site). DNA is purified using Qiagen chromatography columns. Preliminary Western blot experiments from non-purified plaques are tested for the presence of the recombinant protein of the expected size which reacts with the poly-His tag antibody. Because ion channel polypeptides are integral membrane proteins, preparation of the protein sample is facilitated using detergent extraction. Results are confirmed after further purification and expression optimization in HiG5 insect cells.

Example 7

Interaction Trap/Two-Hybrid System

In order to assay for ion channel polypeptide-interacting proteins, the interaction trap/two-hybrid library screening method can be used. This assay was first described in Fields, et al., *Nature*, 1989, 340, 245, which is incorporated herein by reference in its entirety. A protocol is published in *Current Protocols in Molecular Biology* 1999, John Wiley & Sons, NY, and Ausubel, F. M. et al. 1992, *Short Protocols in Molecular Biology*, 4$^{th}$ ed., Greene and Wiley-Interscience, NY, both of which are incorporated herein by reference in their entirety. Kits are available from Clontech, Palo Alto, Calif. (Matchmaker Two Hybrid System 3).

A fusion of the nucleotide sequences encoding all or a partial ion channel polypeptide and the yeast transcription factor GAL4 DNA-binding domain (DNA-BD) is constructed in an appropriate plasmid (i.e., pGBKT7), using standard subcloning techniques. Similarly, a GAL4 active domain (AD) fusion library is constructed in a second plasmid (i.e., pGADT7) from cDNA of potential ion channel polypeptide-binding proteins (for protocols on forming cDNA libraries, see Sambrook et al., supra. The DNA-BD/ion channel fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. 105 transformants/mg DNA) with both the ion channel and library fusion plasmids according to standard procedure (Ausubel et al., supra). In vivo binding of DNA-BD/ion channel with AD/library proteins results in transcription of specific yeast plasmid reporter genes (i.e., lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-β-D-galactoside) supplemented media (filter assay for β-galactosidase activity is described in Breeden et al., *Cold Spring Harb. Symp. Quant. Biol.*, 1985, 50, 643, which is incorporated herein by reference in its entirety). Positive AD-library plasmids are rescued from transformants and reintroduced into the original yeast strain as well as other strains containing unrelated DNA-BD fusion proteins to confirm specific ion channel polypeptide/library protein interactions. Insert DNA is sequenced to verify the presence of an open reading frame fused to GAL4 AD and to determine the identity of the ion channel polypeptide-binding protein.

Example 8

FRET Analysis of Protein-Protein Interactions Involving Ion Channel Polypeptides In order to assay for ion channel polypeptide-interacting proteins, fluorescence resonance energy transfer (FRET) methods can be used. An example of this type of assay is described in Mahajan et al., *Nature Biotechnology*, 1998, 16, 547, which is incorporated herein by reference in its entirety. This assay is based on the fact that when two fluorescent moieties having the appropriate excitation/emission properties are brought into close proximity, the donor fluorophore, when excited, can transfer its energy to the acceptor fluorophore whose emission is measured. The emission spectrum of the donor must overlap with the absorption spectrum of the acceptor while overlaps between the two absorption spectra and between the two emission spectra, respectively, should be minimized. An example of a useful donor/acceptor pair is Cyan Fluorescent Protein (CFP)/Yellow Fluorescent Protein (YFP) (Tsien (1998), Annual Rev Biochem 67, 509–544, which is incorporated by reference in its entirety).

A fusion of the nucleotide sequences encoding whole or partial ion channel polypeptides and CFP is constructed in an appropriate plasmid, using standard subcloning techniques. Similarly, a nucleotide encoding a YFP fusion of the possibly interacting target protein is constructed in a second plasmid. The CFP/ion channel polypeptide fusion construct is verified by sequencing. Similar controls are performed with the YFP/target protein construct. The expression of each protein can be monitored using fluorescence techniques (e.g., fluorescence microscopy or fluorescence spectroscopy). Host cells are transformed with both the CFP/ion channel polypeptide and YFP/target protein fusion plasmids according to standard procedure. In situ interactions between CFP/ion channel polypeptide and the YFP/target protein are detected by monitoring the YFP fluorescence after exciting the CFP fluorophore. The fluorescence is monitored using fluorescence microscopy or fluorescence spectroscopy. In addition, changes in the interaction due to e.g., external stimuli are measured using time-resolved fluorescence techniques.

Alternatively, a YFP fusion library may be constructed from cDNA of potential ion channel polypeptide-binding proteins (for protocols on forming cDNA libraries, see Sambrook et al., supra). Host cells are transformed with both the CFP/ion channel polypeptide and YFP fusion library plasmids. Clones exhibiting FRET are then isolated and the protein interacting with an ion channel polypeptide is identified by rescuing and sequencing the DNA encoding the YFP/target fusion protein.

Example 9

Assays to Identify Modulators of Ion Channel Activity

Set forth below are several nonlimiting assays for identifying modulators (agonists and antagonists) of ion channel activity. Although the following assays typically measure calcium flux, it is contemplated that measurement of other ions may be made. Among the modulators that can be identified by these assays are natural ligand compounds of the ion channel; synthetic analogs and derivatives of natural ligands; antibodies, antibody fragments, and/or antibody-like compounds derived from natural antibodies or from antibody-like combinatorial libraries; and/or synthetic compounds identified by high-throughput screening of libraries; and the like. All modulators that bind ion channel are useful for identifying such ion channels in tissue samples (e.g., for diagnostic purposes, pathological purposes, and the like). Agonist and antagonist modulators are useful for up-regulating and down-regulating ion channel activity, respectively, to treat disease states characterized by abnormal levels of ion channels. The assays may be performed using single putative modulators, and/or may be performed using a known agonist in combination with candidate antagonists (or visa versa).

A. Aequorin Assays

In one assay, cells (e.g., CHO cells) are transiently co-transfected with both an ion channel expression construct and a construct that encodes the photoprotein apoaequorin. In the presence of the cofactor coelenterazine, apoaequorin will emit a measurable luminescence that is proportional to the amount of intracellular (cytoplasmic) free calcium. (See generally, Cobbold et al. "Aequorin measurements of cytoplasmic free calcium," In: McCormack J. G. and Cobbold P. H., eds., *Cellular Calcium: A Practical Approach*. Oxford: IRL Press (1991); Stables et al., Analytical Biochemistry 252: 115–26 (1997); and Haugland, Handbook of Fluorescent Probes and Research Chemicals. Sixth edition. Eugene Oreg.: Molecular Probes (1996).), each of which is incorporated by reference in its entirety.

In one exemplary assay, ion channel nucleic acid is subcloned into the commercial expression vector pzeoSV2 (Invitrogen) and transiently co-transfected along with a construct that encodes the photoprotein apoaquorin (Molecular Probes, Eugene, Oreg.) into CHO cells using the transfection reagent FuGENE 6 (Boehringer-Mannheim) and the transfection protocol provided in the product insert.

The cells are cultured for 24 hours at 37° C. in MEM (Gibco/BRL, Gaithersburg, Md.) supplemented with 10% fetal bovine serum, 2 mM glutamine, 10 U/ml penicillin and 10 µg/ml streptomycin, at which time the medium is changed to serum-free MEM containing 5 µM coelenterazine (Molecular Probes, Eugene, Oreg.). Culturing is then continued for two additional hours at 37° C. Subsequently, cells are detached from the plate using VERSENE (Gibco/BRL), washed, and resuspended at 200,000 cells/ml in serum-free MEM.

Dilutions of candidate ion channel modulator compounds are prepared in serum-free MEM and dispensed into wells of an opaque 96-well assay plate at 50 µl/well. Plates are then loaded onto an MLX microtiter plate luminometer (Dynex Technologies, Inc., Chantilly, Va.). The instrument is programmed to dispense 50 µl cell suspensions into each well, one well at a time, and immediately read luminescence for 15 seconds. Dose-response curves for the candidate modulators are constructed using the area under the curve for each light signal peak. Data are analyzed with SlideWrite, using the equation for a one-site ligand, and $EC_{50}$ values are obtained. Changes in luminescence caused by the compounds are considered indicative of modulatory activity.

B. Intracellular Calcium Measurement Using FLIPR

Changes in intracellular calcium levels are another recognized indicator of ion channel activity, and such assays can be employed to screen for modulators of ion channel activity. For example, CHO cells stably transfected with an ion channel expression vector are plated at a density of $4 \times 10^4$ cells/well in Packard black-walled, 96-well plates specially designed to discriminate fluorescence signals emanating from the various wells on the plate. The cells are incubated for 60 minutes at 37° C. in modified Dulbecco's PBS (D-PBS) containing 36 mg/L pyruvate and 1 g/L glucose with the addition of 1% fetal bovine serum and one of four calcium indicator dyes (Fluo-3™ AM, Fluo-4™ AM, Calcium Green™-1 AM, or Oregon Green™ 488 BAPTA-1 AM), each at a concentration of 4 µM. Plates are washed once with modified D-PBS without 1% fetal bovine serum and incubated for 10 minutes at 37° C. to remove residual dye from the cellular membrane. In addition, a series of washes with modified D-PBS without 1% fetal bovine serum is performed immediately prior to activation of the calcium response.

A calcium response is initiated by the addition of one or more candidate receptor agonist compounds, calcium ionophore A23187 (10 µM; positive control), or ATP (4 µM; positive control). Fluorescence is measured by Molecular Device's FLIPR with an argon laser (excitation at 488 nm). (See, e.g., Kuntzweiler et al., Drug Development Research, 44(1): 14–20 (1998)). The F-stop for the detector camera was set at 2.5 and the length of exposure was 0.4 milliseconds. Basal fluorescence of cells was measured for 20 seconds prior to addition of candidate agonist, ATP, or A23187, and the basal fluorescence level was subtracted from the response signal. The calcium signal is measured for approximately 200 seconds, taking readings every two seconds. Calcium ionophore A23187 and ATP increase the calcium signal 200% above baseline levels.

C. Extracellular Acidification Rate

In yet another assay, the effects of candidate modulators of ion channel activity are assayed by monitoring extracellular changes in pH induced by the test compounds. (See, e.g., Dunlop et al., Journal of Pharmacological and Toxicological Methods 40(1):47–55 (1998).) In one embodiment, CHO cells transfected with an ion channel expression vector are seeded into 12 mm capsule cups (Molecular Devices Corp.) at $4 \times 10^5$ cells/cup in MEM supplemented with 10% fetal bovine serum, 2 mM L-glutamine, 10 U/ml penicillin, and 10 µg/ml streptomycin. The cells are incubated in this medium at 37° C. in 5% $CO_2$ for 24 hours.

Extracellular acidification rates are measured using a Cytosensor microphysiometer (Molecular Devices Corp.). The capsule cups are loaded into the sensor chambers of the microphysiometer and the chambers are perfused with running buffer (bicarbonate-free MEM supplemented with 4 mM L-glutamine, 10 units/ml penicillin, 10 µg/ml streptomycin, 26 mM NaCl) at a flow rate of 100%/minute. Candidate agonists or other agents are diluted into the running buffer and perfused through a second fluid path. During each 60-second pump cycle, the pump is run for 38 seconds and is off for the remaining 22 seconds. The pH of the running buffer in the sensor chamber is recorded during the cycle from 43–58 seconds, and the pump is re-started at 60 seconds to start the next cycle. The rate of acidification of the running buffer during the recording time is calculated by the Cytosoft program. Changes in the rate of acidification are calculated by subtracting the baseline value (the average of 4 rate measurements immediately before addition of a modulator candidate) from the highest rate measurement obtained after addition of a modulator candidate. The selected instrument detects 61 mV/pH unit. Modulators that act as agonists of the ion channel result in an increase in the rate of extracellular acidification compared to the rate in the absence of agonist. This response is blocked by modulators which act as antagonists of the ion channel.

Example 10

High Throughput Screening for Modulators of Ion Channels Using FLIPR

One method to identify compounds that modulate the activity of an ion channel polypeptide is through the use of the FLIPR system. Changes in plasma membrane potential correlate with the modulation of ion channels as ions move into or out of the cell. The FLIPR system measures such changes in membrane potential. This is accomplished by loading cells expressing an ion channel gene with a cell-membrane permeant fluorescent indicator dye suitable for measuring changes in membrane potential such as diBAC (bis-(1,3-dibutylbarbituric acid)pentamethine oxonol, Molecular Probes). Thus the modulation of ion channel activity is assessed with FLIPR and detected as changes in the emission spectrum of the diBAC dye.

As an example, COS cells that have been transfected with an ion channel gene of interest are bathed in diBAC. Due to the presence of both endogenous potassium channels in the cells as well as the transfected channel, the addition of 30 mM extracellular potassium causes membrane depolarization which results in an increase in diBAC uptake by the cell, and thus an overall increase in fluorescence. When cells are treated with a potassium channel opener, such as chromakalim, the membrane is hyper-polarized, causing a net outflow of diBAC, and thus a reduction in fluorescence. In this manner the effect of unknown test compounds on membrane potential can be assessed using this assay.

Example 11

Chimeric Receptors

A chimeric receptor can be used to measure the activity of ligand binding when the ligand's native receptor activity is not amenable to easy measurement. Such chimera may consist of a ligand-binding domain of one receptor fused to the pore-forming domain of another receptor. A useful example of such a chimera can be found in WO 00/73431 A2.

The transmembrane domain of ion-5HT-3D (SEQ ID NO:118) can be fused, for example, with the extracellular domain of the alpha7 nicotinic acetylcholine receptor to form a chimeric receptor that binds alpha7 receptor ligands but passes current like that of ion-5HT-3D. To generate this chimera, PCR primers are designed to amplify the 5' region of the alpha7 receptor (GenBank accession number U62436) with a region of overlap with ion-5HT-3D on the 3'-most primer.

PCR is performed using the appropriate cDNA clone as a template using Platinum Taq polymerase (Life Technologies, Gaithersburg, Md.) according to the manufacturer's instructions. The PCR products from these two reactions are then diluted 1:1000 and pooled in a second PCR mixture with appropriately designed primers to generate the final chimeric cDNA by splice-overlap PCR. These primers also add an EcoRI restriction site to the 5' end and a NotI site to the 3' end to facilitate subcloning into pcDNA3.1 (Invitrogen). The PCR product is ligated into pcDNA3.1 and transformed into competent *E. coli* (Life Technologies, Gaithersburg, Md.). Isolated *E. coli* colonies selected on ampicillin-containing medium are isolated and expanded. The DNA from the plasmid in *E. coli* is isolated and sequenced to verify that the expected sequences are obtained. The DNA is then transformed into mammalian cells such as SH-EP1 cells using cationic lipid transfection reagent. Cells that are stably transformed are selected in the presence of 800 μg/ml geneticin. These cells are then assayed as described supra for changes in intracellular calcium or changes in membrane potential in response to ligands, e.g. nicotine.

Example 12

Tissue Expression Profiling

Tissue specific expression of the cDNA encoding ion-x can be detected using a PCR-based method. Multiple Choice™ first strand cDNAs (OriGene Technologies, Rockville, Md.) from 12 human tissues is serially diluted over a 3-log range and arrayed into a multi-well PCR plate. This array is used to generate a comprehensive expression profile of the putative ion channel in human tissues. Human tissues arrayed may include: brain, heart, kidney, peripheral blood leukocytes, liver, lung, muscle, ovary, prostate, small intestine, spleen and testis.

PCR primers are designed based on the sequences of ion-x provided herein. The primer set primes the synthesis of a known sized fragment in the presence of the appropriate cDNA. PCR reactions are assembled using the components of the Expand Hi-Fi PCR System™ (Roche Molecular Biochemicals, Indianapolis, Ind.). Twenty-five microliters of the PCR reaction mixture are added to each well of the RapidScan PCR plate. The plate is placed in a GeneAmp 9700 PCR thermocycler (Perkin Elmer Applied Biosystems). The following cycling program is executed: Pre-soak at (94° C. for 3 min.) followed by 35 cycles of [(94° C. for 45 sec.)(52.5° C. for 2 min.)(72° C. for 45 sec.)]. PCR reaction products are then separated and analyzed by electrophoresis on a 2.0% agarose gel stained with ethidium bromide.

5HT-3C

Multi-Tissue Northern Blot Analysis

A multi-tissue human mRNA Northern blot and a multi-tissue brain mRNA blot were purchased from Clontech Laboratories. A 767 base pair portion (bases 1284–2050) of ion-5HT-3C was amplified by PCR using primers 5HT3For:

(5'-GCTCATGATAGTGACTTGCTCC (SEQ ID NO:120)), and 5HT3Rev:

(5'-CAGCGGGCAGAAGAGGTATAG (SEQ ID NO:121)). This product was labeled with [α32P]-dCTP using a Stratagene Prime-It Random Primer Labeling Kit (Stratagene, La Jolla, Calif.). Labeled DNA was separated from unincorporated nucleotides using ProbeQuant™ G-50 Micro Columns (Amersham Pharmacia Biotech Inc, Piscataway, N.J.). The blots were pre-hybridized in ExpressHyb (Clontech) for 1.5 hour at 68° C., then hybridized in denatured probe/ExpressHyb for 2 hours at 68° C. After hybridization the membranes were washed in several rinses then 4×10 min washes in 2×SSC, 0.05% SDS at room temp. Finally, the membranes were washed 2 times for 40 min each in 0.1×SSC, 0.1% SDS at 50° C. Membranes were exposed to film at −70° C. for 48 hours.

The sequence of the probe used to detect 5HT-3C was as follows:

```
                                          (SEQ ID NO:122)
TTAAGATTTGCGCTTTGCCAACTGTACACCCAACCTCGGTTTATTGTCGA

ACCTCCCGCTTGTGCCGCCATCTGCATATAGATCCCGGTCAGTCCGTCAC

ATTCTGCCAATTGAGTATCCTCGAAGTCTTATTCCACGTGCTCAAAGCAA

GGGTATCGTACAGTGATAACCGCCTCGTGCAGATCCAAATTCTCGATTAA

CACTCAAGTACTGATTTTTATCATCAGGTAACTAAAAACTCACAATTTGA

AGCACCAGCGAGAATCGTTCTATTCTCTAGCTTCGCAACATCGACAGTTG

TAATGGCATAACTTCGGCATTCATAGTGGCTGAGTTTAGCGGACTAAGCG

AAAAACTGGTCGTTAGATCTTCCTCACCATGATTTTACAAGAAAGGTGAA

CTCAATTTGACGGCGGTAAAGTTAGATGGCTACGCGCGACAAGTCTCCGT

ATCGTCATGAAATTAGCGAAGAGGTAATGGCAAAGCTTGGCTACGAATAC

AGGAGCGCGCTGTGATTACAGTAGGGTTAGGATAGCGAAAACGTTCAACG

TGGATAGACTCTTATCGGCACACGATCATATGCTTCCAAGGTTCCCAAGG

CGAATTACTAGGGTGCACAGAGCTACGAGTACGCTGTCCGGCTTGATTCG

CTCGTACATCCACTGTTCAAAAAGCTCCGATACCGACGATCACTCTCGAT

CTCTGTGTGGGACGCACTTATTGTGGAATCAGTCAACCAGTGAAGCATTC

ACATGTACGTGGTACGGCACGCCGTGGTATGTTAGCGTTCCCTGCGCCGC
```

-continued

AAGTAAACCCTTCAGCTGTCACCTCCTATAGTAACACGCTCGCATGCAGA

GCCTAGCACCTTAGCTCTGAGTTGCCTGCCGGAAGGATATATTCTGTATG

TGATTAAAGCGAAGTCAAAGTAAACCCCCCACATGCAGACCTGGGTAAAT

TCTCACTCAGTTGAAACGTAGGGGCCAATACGTGTGTCCTTGATACTACT

Ion-5HT-3C was found to be expressed in many tissues, including but not limited to small intestine, colon, placenta, and peripheral blood leukocytes.

5HT-3D

Using the commercially available kit TaqMan™ (Applied Biosystems) according to the manufacturer's instructions, the 5HT-3D was localized to several different tissues. Primers were derived from exon 4 of ion-5HT-3D and were:

CAATGTGGGTGGTCAGCATCT (SEQ ID NO:123), and

GGACAGAGGTGAACGCTCTCC (SEQ ID NO:124).

Forty cycles were run, and cycle thresholds were determined by the Applied Biosystems software running the TaqMan hardware, the ABI Prism 7700.

The probe used to localize 5HT-3D was:

CAAACTGGACACCTTCTATTTCCCCTTCCA (SEQ ID NO:125). Ion-5HT-3D was expressed in fetal brain, whole brain, and testis.

Example 13

Chromosomal Localization

Procedures

Localization of the novel ion channel gene sequences identified herein may be achieved by insertion into the sequence manipulation software package, Sequencher™ (version 4.0.5, Gene Codes Corp.) to visualize the amino acid sequence along with the nucleic acid sequence. This will aid in demarcating which regions of the genomic sequence most likely represent exons, as recognized by regions of conserved amino acids, and which most likely may be selected using the PrimerSelect portion of the DNASTAR software package (version 3.01a, DNASTAR Inc.) under the criteria that the PCR product size should optimally be 100–500 bp and that the product should span an intron-exon boundary.

PCR may be carried out using 3 Units/100 µl of Amplitaq Gold DNA Polymerase (Perkin-Elmer), 1.5 mM $MgCl_2$, 0.2 mM dNTPs mix, 0.5 µM of each primer, and 50 ng of Stanford G3 Radiation Hybrid Panel genomic DNA per 25 µl reaction. The Stanford G3 Radiation Hybrid Panel can be purchased from Research Genetics, Inc. and iss used to perform medium resolution radiation hybrid mapping (RHM). RHM is a PCR based method for determining the cytogenetic location of a unique sequence in the human genome. Each primer set is used to PCR the complete panel twice, on separate days, unless another "Ion" novel sequence is grouped with it (due to sequence overlap), or had already been subject to RHM and generated the same profile. Data profiles consisting of the presence or absence of the appropriate size PCR product across the panel of radiation hybrid clones may be submitted to the Stanford Radiation Hybrid Mapping server at the web site "www-shgc.stanford.edu/RH/rhserverformew.html". The data is subjected to two-point statistical analysis with all assayed G3 or TNG radiation hybrid panel markers to determine which markers are most closely linked to the PCR amplified region. The server automatically and anonymously sends back the nearest markers and their associated LOD scores.

The Stanford RHM server may be used to obtain further marker location information as well as the GeneMap pages at the National Center for Biotechnology Information (NCBI) site: "www.ncbi.nlm.nih.gov/genemap/page.cgi?F=Home.html". Ion159 was localized to chromosomal region 20q12-q13.13.

As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:

1. An isolated polypeptide that comprises SEQ ID NO: 116.

* * * * *

SEQUENCE LISTING

<160> NUMBER OF SEQ ID NOS: 125

<210> SEQ ID NO 1
<211> LENGTH: 443
<212> TYPE: DNA
<213> ORGANISM: Homo sapiens

<400> SEQUENCE: 1

```
ttcctgccta gtgttctggc tgctctcgag gcctcctgct tgactgttag cctggggctt      60
accttctttc ctctcctgct ttccgaatcg catgtttccc tctttcttga tttattcgct     120
tattttggtg gaacacatct ccagtatctt cctaggaaaa ggaacatggt agatcaattt     180
ttcaaattct tgcatgtctg atttattctc tcttcatact tgattggtag ttttgatacc     240
aaattctagg ttgaaaataa ttttcacttg gaatttaaa ggcatttatt cctccattgt      300
cttctaggtt ccagcattgc tattgaggac tctgatgaca ttttcttttt cttttttct      360
```

| | |
|---|---|
| ttaggctctg gaaactttta ggatcttctc cttaataaca gtgtcctgaa tttcacactg | 420 |
| atgtgcctta ggacgggtct ttt | 443 |

<210> SEQ ID NO 2
<211> LENGTH: 509
<212> TYPE: DNA
<213> ORGANISM: Homo sapiens

<400> SEQUENCE: 2

| | |
|---|---|
| ctttgtagct gtcatctgca gtgtgggaca gctgcacaag gcccagcat gtctgtgtgt | 60 |
| ttacccaggg gactgccgca tggctcatgc tgagcagaag ctgatggacg accttctgaa | 120 |
| caaaacccgt tacaacaacc tgatctgccc agccaccagc tcctcacagc tcatctccat | 180 |
| cgagacagag ctctccctgg cgcagtgcat cagtgtggta agtgcagagg gcacctgtgg | 240 |
| ctcaggctca gatgaagagg cagctcatgc ccaagcctca agcaatcaat gtccagagga | 300 |
| atgaaatgac cagagttgac ttagactcac caatacgtgg cggggaggct ggaggaaggt | 360 |
| ccctgaggtt tataggtgtc caatatttaa tgaggtcatg gttttcttaa caagaagaa | 420 |
| atgagggtgg gagcgggatc accactggct aggcagccaa tgggcctgca tagactctgc | 480 |
| tcagctgagt ctccagcacg actataagc | 509 |

<210> SEQ ID NO 3
<211> LENGTH: 534
<212> TYPE: DNA
<213> ORGANISM: Homo sapiens

<400> SEQUENCE: 3

| | |
|---|---|
| gaaaaggaat gttattgatg aattttgaga taattttgt atatagcata gggtaaggaa | 60 |
| aagagaggtg taaggatta gagatcagtc ttagaatgta cctggtggac acaactctcc | 120 |
| caaagggcta tgttcccatt gctgtgtgcc aattgattga tcatgaagtt tgatggttgc | 180 |
| agctgagcta ggtacgacct gtggggacaa agcagggact ggcatgagtg gcttccagat | 240 |
| ctcacccatt acaagatcaa tctcacattc cattccccca agcctccaaa attagacaga | 300 |
| acttgcatct ttctcccagt tctaaaactc aaccatttgt ttgtgctcat ctttgtctct | 360 |
| ttgtccccat gcccccagcc tgtggcaact accattctac tgtctgtttc tatgaattta | 420 |
| actactctac atacttcata taaatggaga catacagtat tttatggttt tcttgaggct | 480 |
| ggcatatttc aattagcata aaatcatcac gatccatcca ttcggtacca tgca | 534 |

<210> SEQ ID NO 4
<211> LENGTH: 595
<212> TYPE: DNA
<213> ORGANISM: Homo sapiens

<400> SEQUENCE: 4

| | |
|---|---|
| aaggggatct gtgctgagac cgggagtctg aagttcaggt tcctgccctg ccactaacca | 60 |
| accattggag ggacacttct gggcctcagt ttcctcatct gtaaagccct ggtgattctc | 120 |
| gagagttctt cacacttctt tgtagacaga cgccggggct caggcaagaa agcctacgct | 180 |
| aataagcagc cccaggggaa gccagcagca ggggcccttc cctcctggct aagaaaactg | 240 |
| ccactgggga gaagaggagg agagcccagg cctagctctg aacgtacctg atgtcacttc | 300 |
| ccctccctgg tccacagttc cagcagattc actccagcat tttaggattc tgcgagattt | 360 |
| gtctgagggg cctgatttat aggagagagg aggccagact tgcccctccc ttaccccgact | 420 |
| taggatggta aagcaacttg ggaaaagcat ttactctcag ctcccggaat taccccttcac | 480 |

| | |
|---|---:|
| tttcctggca gataaatggg gcaaaacaga agatgcagtt acatttaaat ggagcgaggc | 540 |
| aggtggaagt ttataagatt tgaatacact ttttggctgc ttttgaatat tcatt | 595 |

<210> SEQ ID NO 5
<211> LENGTH: 341
<212> TYPE: DNA
<213> ORGANISM: Homo sapiens

<400> SEQUENCE: 5

| | |
|---|---:|
| cttcttcctg taggaaaatg cacatcattt tttaggtgct gagacagagg actaagaaat | 60 |
| caatgacata aaaatgcata ctttaatatt ttttctttaa aactattatc ctaaggtgtc | 120 |
| ctacatacta taatttataa gtatctggaa gagtgaaaac aatttttattg aggccttgta | 180 |
| aaatatggca ggtgcctagg acctcatgga actcaggtat cttcagtagg atgtgaaaca | 240 |
| tcacatcatg gggcgtggtg cagtgtaagc aggtaaagaa aagccagttc ttccacatgt | 300 |
| aaactacttg aactccattt catcttttttt cataccatct c | 341 |

<210> SEQ ID NO 6
<211> LENGTH: 241
<212> TYPE: DNA
<213> ORGANISM: Homo sapiens

<400> SEQUENCE: 6

| | |
|---|---:|
| cagacgggga gtcagtactt gagaagaccc ggaaggcggg gagcacttgg actccagacg | 60 |
| gggagtcagt actgagagac ccggaaggct gggagcactg gactccagac ggggagtcag | 120 |
| tactgagaga cccggaaggc tgggagcact ggactccaga cggggagtca gtacttgaga | 180 |
| gacccagaag gcggggagca cccgaagact ccacaccggg gagtcagtac tgagagaccc | 240 |
| g | 241 |

<210> SEQ ID NO 7
<211> LENGTH: 521
<212> TYPE: DNA
<213> ORGANISM: Homo sapiens

<400> SEQUENCE: 7

| | |
|---|---:|
| ggacacctgg cacggggcct gtgcgtgcgg gaaagagggg agccctgtgg gcagtccagg | 60 |
| ccacctgagt tatctcctag cccccagtcg cctgaaggag gggctggccc cccagcgggc | 120 |
| ccttgccacg agccacgatg tctgtgccgc caggaagccc tactgcacca cgtagccacc | 180 |
| attgccaata ccttccgcag ccaccgagct gcccagcgct gccatgagga ctggaagcgc | 240 |
| ctggcccgtg tgatggaccg cttcttcctg gccatcttct tctccatggc cctggtcatg | 300 |
| agcctcctgg tgctggtgca ggccctgtga gggctggac taagtcacag ggatctgctg | 360 |
| cagccacagc tcctccagaa agggacagcc acggccaagt ggttgctggt ctttgggcca | 420 |
| gccagtctct ccccactgct cctaagatcc tgagacactt gacttcacaa tccacaaggg | 480 |
| agcactcatt gtctacacac cctaactaaa ggaagtccag a | 521 |

<210> SEQ ID NO 8
<211> LENGTH: 624
<212> TYPE: DNA
<213> ORGANISM: Homo sapiens

<400> SEQUENCE: 8

| | |
|---|---:|
| ttttgttccg ttacacttcc aattttggac ttctttgtgt agttttacaa gagggatatc | 60 |
| tcttttaaaa aaaaaaagca caacaaattc cacacacaaa atataagtac aaatcagctc | 120 |

```
tctgcatgag tgggtctcca tctcttgctt aaccaacagc tgatggaaaa tattccgggg      180
ggcagtgggg agagctgaca atgcaaaaat aaaataata taaataaaaa ccaatatagt      240
ataacaacta ttcgcatagc attacactgt attatgtata taagtaatct aaagatgatt      300
tcaagtatac gggagcatgc gcatactttc tcattttata taaggaactt gagcatcact      360
ttttggtatt gggggtaggt cctagaacct attccccct gtttccaagg caagactttg       420
tataaattgc gtgacatatt aaatgtaatt ttaaaaacct ggtaacattt tccgagttcc      480
acaatggcag cattttcagg attttagcct aaccttttaac ctaacaaaat actatgatac     540
ttcttggagg tagttttatt tttaaataat ttccttttc catttggtaa gaaacatctt      600
ggtgtttatg aataaactta atgc                                             624

<210> SEQ ID NO 9
<211> LENGTH: 443
<212> TYPE: DNA
<213> ORGANISM: Homo sapiens

<400> SEQUENCE: 9
cctctaggcc agggccccaa gtgctgagct gggcagggaa caggactcag ccctggatag      60
tgctggggtc tcctgctgcg ttctttcaac acagcgctca ccctgaggtg atgcattgcc     120
cttcccccag gacatcctgc gatacacaat gtcctccatg ctgctgctta ggctggtgag     180
ctcctatgcc tggggaggtg ggatgggaaa gcccagctga gtccagctca gaactaccag     240
ccttcatcaa catgctgagc ttaggggcat ggatatgtgg agagcaggag cctcagtggt     300
gcccttgtgt ccccagtcct ggctggacac tcgcctggcc tggaacacta gtgcacaccc    360
gcggcacgcc atcacgctgc cctgggagtc tctctggaca ccaaggctca ccatcctgga     420
ggcgtaagtg agacagttcc tgc                                              443

<210> SEQ ID NO 10
<211> LENGTH: 563
<212> TYPE: DNA
<213> ORGANISM: Homo sapiens

<400> SEQUENCE: 10
aattgaagga ttagaaaata atgttagaga aaacctacc agaacaacaa aaagaaatg        60 aaacatagga gagaaatatc agaaaactag aggatcaatg cacaaaggcc gacagtggat     120
tggaatatta agagttccaa aaagagaaca gaggaaaaga tgaggaagaa attaaggatg     180
aactaaccgt aagaaaattt gccaaaacag agaatgagtc ttcaatgcta aaaggttgac     240
tgagttccca aaaaagaccc gtcctaaggc acatcagtgt gaaattcagg acactgttat    300
taaggagaag atcctaaaag tttccagagc ctaaagaaaa aagaaaaag aaatgtcat       360 cagagtcctc aatagcaatg ctggaaccta aagacaatg gaggaataaa tgcctttaaa      420
attccaagtg aaaattattt tcaacctaga atttggtatc aaaactacca atcaagtatg     480
aagagagaat aaatcagaca tgcaagaatt tgaaaaattg atctaccatg ttccttttcc     540
taggaagata ctggagatgt gtt                                              563

<210> SEQ ID NO 11
<211> LENGTH: 485
<212> TYPE: DNA
<213> ORGANISM: Homo sapiens
```

<400> SEQUENCE: 11

| | |
|---|---|
| ctggaaaggt ccatcgcgtg gctgaactgc aaccacagct ccactgagtg ctgcttctgg | 60 |
| gcctcgtgtt cccgctgggc ccttgtccat tctgagcccc ctgtcagctc tgcctccgca | 120 |
| gggcccggca tctgccctgc tgatacctct ggctccttca cacctacaga aagacagaga | 180 |
| ctcagccatg ggctgcaaat gtcacctgtg gagggaggga gacagggaag gaggcaggag | 240 |
| cagagaagtg gaggtggggg aagaggaatg tgacttccct caccgggcag gtgggtgggg | 300 |
| ggtgagaccc gggcccttat tttccttctg gggcgcagtg ggacagcatc tccccgggct | 360 |
| gttgcagtgg agcagcaggg agtggagcca ccgaggcagg ggtgggggct gggtggtggc | 420 |
| cacgtgcagc aggtgggtga tgaagatggt ctccagcagg ctgcccacca tcagggacag | 480 |
| gcaca | 485 |

<210> SEQ ID NO 12
<211> LENGTH: 527
<212> TYPE: DNA
<213> ORGANISM: Homo sapiens

<400> SEQUENCE: 12

| | |
|---|---|
| tagatgataa ttacggcttt ttttttttgt ggttttattt tgaaaactcg tatgatctat | 60 |
| aaccttcgcc gggagtgatc tgccgccact agggcgcagc agatagctca ggggagactg | 120 |
| acgtcatcta cttactcatc atctgccgga atcacaaaac atcatggttc cctgcgtgct | 180 |
| catctcaggc ttggtgctgc tagcctactt cctgccggct gcctcaccag agcctgggca | 240 |
| ctgccgcccc ggagatacgc tgctgtgggg atgccgtgaa cttcgtggcc aagaacatga | 300 |
| gagggcagga cacgagaggc caggacgcca tcggcgaggt tggacaggag ccagaggcgg | 360 |
| atggagcgcg gcagaggcgc ccccactgtc tcccgtgcca ctggctcctg cagctgcccc | 420 |
| tttaaggact gttttgtgccg acccttcccc aggaagtgac ggcatctgct tctgggtcgc | 480 |
| tcgggtgctc ttcagcctgg gctccaacct tatctcatcg tggccta | 527 |

<210> SEQ ID NO 13
<211> LENGTH: 451
<212> TYPE: DNA
<213> ORGANISM: Homo sapiens

<400> SEQUENCE: 13

| | |
|---|---|
| atgacagtac caaagcgcgg cctcagaaat atgagcaact tctccatata gaggacaacg | 60 |
| atttcgcaat gagacctgga tttggaggtg agtattatcc tctcaaaatt catttcaaaa | 120 |
| cccattgcac tgtcaaaatg gaggtgaaaa tttaaaacaa gaccaaaatg caagtaaagt | 180 |
| ccatcagttt aaaacaaaaa aagaaggctt ttacaatcac cttctcttta atgaaacaa | 240 |
| ttgatgagtt atccatttta aattgaccaa aaaaactcat tttcctacta tgcacactgt | 300 |
| agtaaatagt atgtgttcca taaatacgag aatggatata tgttgcctat acaccaactt | 360 |
| attttctaac taaaaatcct taaattggat acatggttat ttataaaatc ttattgaata | 420 |
| ttcttatgag ctagaaatgc catgctttgg g | 451 |

<210> SEQ ID NO 14
<211> LENGTH: 524
<212> TYPE: DNA
<213> ORGANISM: Homo sapiens

```
<400> SEQUENCE: 14
cccacaaggg tctgttgtcc accccgcgtg gaccgcccag gccgtggga gtcaaaaaag        60 ggggaggggc gggggatctt ccactttctc acccgagtt tctttgcttg cttgccccga       120
gtatctgtca agaggcagcc ctctcccta aaggcccctt catcctgaac gtgcatgatg       180
cccctgcagt gacaaataca gaatcttagg gggcctggat tcgaggccga gctaatcact       240 ggttgctgc gggtgggtag gttatttaaa ccacctggaa atcagtttct ctgggttatg       300
gggattgtac ctggctcact ggatttgagg agtaaccaga ttttaggaca gactcttttct      360 ctgtccgtcc tactcagatc ccagtaggaa acttacccct tccctgcgcc acggagtgca       420
aagaaaacag cccaaagact tctttaacga ctctggatcc ctcagccaga tcacggatat       480
ggaaaaagct taaattagaa agaggaggtc gtgaagggac ctcc                       524

<210> SEQ ID NO 15
<211> LENGTH: 501
<212> TYPE: DNA
<213> ORGANISM: Homo sapiens

<400> SEQUENCE: 15
agactcagct gagcagagtc tctgcaggcc cattggctgc ctagccagtg gtgatctcgc        60
tcccaccctc atttcttctt tgttaacaaa accatgacct cattaaatac tggacaccta       120
taaacctcat ggaccctcct ccagcctccc caccgtgtac cggtgagtct aagtcaactc       180
tagtcatttc attcctctgg acattgactg cttagggctt gggcatgagc tgcctcttca       240
cctgagcctg agccacaggt accctctgca cctaccacgc tgatgcactg ggccagggag       300
agcgccgtct ggatggagat gagctgtgag gagctggtgg ctgggcggat caggttgttg       360
taacaggttt tgttcaaaag gtcgtccatc aatttctgct cggcatgggc catgcggcag       420 tccctgggt aaacacacag acatgctggg cccttgtgca gctggctccc actgcagctg       480
acagctatga agcaggagct g                                                501

<210> SEQ ID NO 16
<211> LENGTH: 664
<212> TYPE: DNA
<213> ORGANISM: Homo sapiens

<400> SEQUENCE: 16
gtgggcaggg cgggggaggc agggacatgg ctgtagccgt ggagatggga ggacagacag        60
gacttggtgg ccacttgggt gaaccaaggg agggtcagg aagagacacc cagttttgta       120
tcagatgtgt agagcgtggg atgctgttca ttgattgagg gaggaggagg aggaagaggt       180
atggcatggg aggaggtagc tgagctctgt catgaatgtc atttgaagtc cccagggaga       240
gccaggccgg ccagccccctt cactgcttta gccagctctc agggtgtctg tgctccctgg       300
ccctctcagc tcctgcttca tagctgtcaa ctgcagtggg ggacagctgc acaaggacca       360
agcaggtctg tgtgtttacg cagggttctg ccgcatggcc ctgccgagca gaagctgatg       420 gacgacctc tgaacaaaac ccgttaccac aacctgatcc gcccagccgc cagctcctca       480
cagctcatct ccatcgagat ggagctctcc ctggcccagt gcatcagtgt ggtaggtgca       540
gagggcacct gtggctcagg ctcaggcgaa gaggcagctc atgcccaagc ccaaagcaat       600
caatgtccag aggaatgaaa tgactagagt tgacttagac tcaccaatac attggcgggg       660
aggc                                                                   664
```

<210> SEQ ID NO 17
<211> LENGTH: 628
<212> TYPE: DNA
<213> ORGANISM: Homo sapiens

<400> SEQUENCE: 17

| | | | | | |
|---|---|---|---|---|---|
| gtcctgcgcc | tacacctggg | cctctgtacc | cgtcagttcc | cccagtctgg | ttcttattcc | 60 |
| ctgcaaagag | tagggagcct | gtaaggtcac | ctgttgagca | agctggggga | gaaaagtagg | 120 |
| gtggggatgg | gaggatcagg | atgagaagct | catggtcgtg | ctggagactc | agctgagcag | 180 |
| agtctctgca | ggcccattgg | ctgcctagcc | agtggtgatc | tcgctcccac | cctcatttct | 240 |
| tctttgttaa | caaaaccatg | acctcattaa | atactggaca | cctataaacc | tcatggaccc | 300 |
| tcctccagcc | tccccaccgt | gtaccggtga | gtctaagtca | actctagtca | tttcattcct | 360 |
| ctggacattg | actgcttagg | gcttgggcat | gagctgcctc | ttcacctgag | cctgagccac | 420 |
| aggtaccctc | tgcacctacc | acgctgatgc | actgggccag | ggagagcgcc | gtctggatgg | 480 |
| agatgagctg | tgaggagctg | gtggctgggc | ggatcaggtt | gttgtaacag | gttttgttca | 540 |
| gaaggtcgtc | catcagtttt | ctgctcggca | tgggccatgc | ggcagttccc | ctgggtaaac | 600 |
| acacagacat | gctgggccct | tgtgcagc | | | | 628 |

<210> SEQ ID NO 18
<211> LENGTH: 348
<212> TYPE: DNA
<213> ORGANISM: Homo sapiens

<400> SEQUENCE: 18

| | | | | | |
|---|---|---|---|---|---|
| ggctgcatcc | atatttatcc | aaagggaaac | ccaggacaaa | attactataa | gcaggcttgg | 60 |
| gatgtacatc | tggatcaaat | aatatcccat | ttggcgttcc | agatgaaact | tgacctcaat | 120 |
| gcaggtaaac | tttcctagaa | ggaggagggg | gtcatttaaa | gtccagcctg | aatttatatt | 180 |
| tccaattcca | ttatcccacg | ttgttttaaaa | aaaaaaaaa | aaagactact | gcagatggat | 240 |
| ttggaagatt | gcacaaaatg | ttcaccctac | gtaaccaatt | caactcttct | ccaactgaac | 300 |
| cagtaataga | aataattact | ggggaataat | agtgataata | atagtgtg | | 348 |

<210> SEQ ID NO 19
<211> LENGTH: 569
<212> TYPE: DNA
<213> ORGANISM: Homo sapiens

<400> SEQUENCE: 19

| | | | | | |
|---|---|---|---|---|---|
| attgcctatc | tagtccttgc | agccctgggg | tgggtcttgg | tttgtgggga | ggcggagtag | 60 |
| ggaggaagga | gtccaaagga | gaaaggcagt | gggccgctcc | ctagttgtac | tcaccaagcg | 120 |
| ttggcgcctc | tgccttcttc | gaagtcgtat | gaattcttta | tgctgacgag | aaacaaaatt | 180 |
| tatggcagca | tactccagca | aggcagcgaa | cacaaagagc | agacacacag | ccatccagat | 240 |
| gtcgattgcc | ttcacgtagg | acacctacaa | catccagcga | cagaacgatc | aaccttcttg | 300 |
| aagtccttcc | gtggcctact | gagtggattt | tcaaccccta | tcgattgcct | gctctttttg | 360 |
| agctttatcc | tgaatttctt | ctggtgttta | agaagccctt | ccatgacata | tcccattgtc | 420 |
| tgaaagccca | gatggaaaag | atcggactgc | ccatcatact | ccacctcttc | gcactctcca | 480 |
| ccctctactt | ctacaagttt | ttccttccta | caattctttc | cctttctttc | tttattcttc | 540 |
| ttgtacttct | gcttctgctt | tttattatt | | | | 569 |

-continued

```
<210> SEQ ID NO 20
<211> LENGTH: 534
<212> TYPE: DNA
<213> ORGANISM: Homo sapiens

<400> SEQUENCE: 20
catttttata ggcatcttca atgtcttaat tcaagagagg taaaggtgga actacttcag      60
gcactgtgag agggacata cgtttgggca gagaagatgt cgctcaaatc gccccccaaa     120
acagcacaaa cacatttgtg cgtaaggctg atgccttccc gttccccagc cccatggaac    180
agccagatca gcaaataacg tggggatgaa aaacacactg gctagggt tagggacccc      240 tggtttctag tctcatctgt gccaagaatt ggctgggtgt gcttgagtaa gttcctccca    300
actctgagtg gccctttttcc tgtctgtgat gtcatgaggt cgggttaact ggctgttatt   360
ccaggctctc tgtgactcta tatagacact tacagctctc aagctgcatc gtgcaggtct    420
ggatgtccat ggggaagttc ttgaggtcca tcaggcagga caaaatgagg gtcagcctag    480
tggggacagt aagaaagaag tgacatcggc ttactggggc ccatcacagt gcaa          534

<210> SEQ ID NO 21
<211> LENGTH: 439
<212> TYPE: DNA
<213> ORGANISM: Homo sapiens

<400> SEQUENCE: 21
gttgaacaaa tgttgatgga gtgccaggcc caactaaatg gagatgagtt tgtcaaattc      60
cgtgtcccca agagcttgga gtctaaagaa gcaggtcatt tcactaagtg cagtgtttct    120
aaggggaagc ttgctctaat gaaaactttg gcttttttcc acaggttggt acaataggct    180
tttcatcaac tttgtgctaa ggaggcatgt tttcttcttt gtgctgcaaa cctatttccc    240
agccatattg atggtgatgc tttcatgggt ttcattttgg attgaccgaa gagctgttcc    300
tgcaagagtt tccctgggta aatctttccc catctttata aaatgttaac aatgggagaa    360
agttcaaggg aggtaaataa aatgggtcat acatggagag gaaagagag tggtggttta    420 gtagggatag tcagagatg                                                 439

<210> SEQ ID NO 22
<211> LENGTH: 622
<212> TYPE: DNA
<213> ORGANISM: Homo sapiens

<400> SEQUENCE: 22
tacctgtctt gacagcctcc cagcctactt gctcacttgc ccctccttct cctccccacc      60
aggtggccat caggcacagg tgcaggccca gccctacgt ggtaaacttt ctggtgccca     120
gtggcattct gattgccatc gatgccctca gtttctacct gccactggaa agtgggaatt    180
gtgccccatt caagatgact gttctgctgg gctacacgct cttcctgctc atgatgaatg    240
acttgctccc agccactagc acttcatcac atgcttcact agtacgtcct catccatcaa    300
gagaccaaaa gcgaggtgtg tgttggatgg ggagagggat gggcagaacc aggcgaagtg    360
aaaagggatc ctggaaaaag atcctctggg aaagaaacaa gaaattctag gtggcgcctc    420
tggccctcat gcagaccccc ttgcctgcag gtgtctactt cgccctgtgc ctgtccctga    480
tggtgggcag cctgctggag accatcttca tcacccacct gcttgcacgt ggccaccacc    540
cagcccctac ctctgcctcg gtggctccac tccctgctgc tgcactgcac cggccaaggg    600
agatgctgtc ccactgcgcc cc                                             622
```

<210> SEQ ID NO 23
<211> LENGTH: 584
<212> TYPE: DNA
<213> ORGANISM: Homo sapiens

<400> SEQUENCE: 23

| | | |
|---|---|---|
| cccagcactt tgggaggcca aggtgggtgg atcacttcag ttcaggagtt tgagaccagc | 60 |
| ctgggcaaca tggtgaaacc tcatctctta aaaaaaaaaa aaaaaaaaaa attagccagg | 120 |
| cctggtggtg cgcctgtagt cccagctact tgggaggctg aggctgagac aggaggatca | 180 |
| tttgagccca ggacatggaa gttgcagtga gctgagagca tgccactcta ctccagcctg | 240 |
| ggtgacagag caagatcctg tctcaaaaaa aaaaaaaaaa aaaaggaga gagagaaact | 300 |
| gcggcccctg cctcttgcgt tatctctcct ccagcatgga tgtggataaa accccaaaag | 360 |
| gcctcacagc atatgtaagt aatgaaggtc gcatcaggta taaaaaccc atgaagggg | 420 |
| acagtatctg taacctggac atcttctact tccccttcga ccagcaaaac tgcacactca | 480 |
| ccttcagctc attcctctac acaggtaagt tgcagtgagg tctcagggat ggggtgaatg | 540 |
| agagcaacca acaaatttaa agaaactatg agtaaatggt gacc | 584 |

<210> SEQ ID NO 24
<211> LENGTH: 243
<212> TYPE: DNA
<213> ORGANISM: Homo sapiens

<400> SEQUENCE: 24

| | | |
|---|---|---|
| tccctacact attctgggct gggtggggag ccctggctgc tccaaggggg ctgcttggcc | 60 |
| caattctggg catccccggg gtgtgctagc tttgccctag gctgctccct ggaagcgagg | 120 |
| ttgacacaac tccttcccca cacacaggag tggagcgact acaaactgcg ctggaacccc | 180 |
| actgattttg gcaacatcac atctctcaag gtcccttctg agatgatctg gatccccgac | 240 |
| att | 243 |

<210> SEQ ID NO 25
<211> LENGTH: 246
<212> TYPE: DNA
<213> ORGANISM: Homo sapiens

<400> SEQUENCE: 25

| | | |
|---|---|---|
| ttatgcccgg gggtgatccg ccgccaccac ggtggcgcca ccgacggacc acgggagact | 60 |
| gacgtcatct actcgctcat catcctccgg aagccgctct tctacgtcat taacatcatc | 120 |
| gtgccctgtg tgctcatctg gggcctggtg ctgcttgcct actttctgcc agcacagggt | 180 |
| aagcagtggc ccctaaccta cccccaaacc cgggctcgct cccgggaggc ggggcccgct | 240 |
| ctcact | 246 |

<210> SEQ ID NO 26
<211> LENGTH: 439
<212> TYPE: DNA
<213> ORGANISM: Homo sapiens

<400> SEQUENCE: 26

| | | |
|---|---|---|
| caggcaggcg cggcagcagc tccaggagaa cctggggcag gggcggggct aagggacga | 60 |
| ggttagtacg aagccccacc ccgaaaccgg gctgcaccgc cccctccgcg cttacgtggc | 120 |
| gcagccgcgg ggacatggcg tgggtggtgg gcgtccgctg ggacacgttg agcacgatga | 180 |
| cgcaattcat gacaatgagc gtggcgacca ccatgacgaa aataaggaac ctgaggagcc | 240 |

```
cggtaaggca tgacatcacc ggtcctcctt ccagctaccg aaggcgccgc gcgctgacct      300
cacaaacacg gcttctcctg gtacgggctg gttacgccct ccagctgcgc ccctacacg       360 acgacagacg cgtcccccaa cccttctaac tgtacctacc acttgtggcg gccatgaagg      420 ggaccccag ctccctgga                                                    439
```

<210> SEQ ID NO 27
<211> LENGTH: 597
<212> TYPE: DNA
<213> ORGANISM: Homo sapiens

<400> SEQUENCE: 27

```
ctctgcaacc tggctcgtct ttccctaagg atacaatgct taccgtagtt ctatgacatg       60
aaacatgctt tgtgttgttt gctgatgtat tgagtaatag aatgtcagat ggaagcaagt      120
aaattatttt acaatgtatt ttaagcctta cttggaaaag taacaccaac aaatactatt      180
aagaattcat tgatgtttga ccttacatag aaagtaagtc gtccataaat atttgtcaat      240
ggtgaaagag tgaataaata agcaattaag caatatctat tctttcattt gggcttaata      300
tttgtctttt ttccacagca tcctgactcc aaatatcatc tgaagaaaag gatcacttct      360
ctgtctttgc caatagtttc atcttccgag gccaataaag tgctcacgag agcgcccatc      420
ttacaatcaa cacctgtcac accccacca ctctcgccag cctttggagg caccagtaaa      480
atagaccagt attctcgaat tctcttccca gttgcatttg caggattcaa ccttgtgtac      540
tggggtagtt ttatctttcc aaagatacaa tgggaagtga gtaccagtgt tgaatag         597
```

<210> SEQ ID NO 28
<211> LENGTH: 263
<212> TYPE: DNA
<213> ORGANISM: Homo sapiens

<400> SEQUENCE: 28

```
gctctttctc ccaggaaagt ttctgggcag ctgccgccgg gcgccaagac aagcgagggt       60
ggcctgagtc ctgtgctcac atggcgtatg ccgcccagta gatgacattg acggccgcaa      120
acgccgcagg gaacacagcg cgggcgttaa tgtcaatggt gtctgcgtcc atgggcctga      180
gccgggcacg gatgccccc tggcctcctg agcgggctgc cccctccttc ttcgtctccc       240
ctgtctccac ccccaccgac ctg                                              263
```

<210> SEQ ID NO 29
<211> LENGTH: 401
<212> TYPE: DNA
<213> ORGANISM: Homo sapiens

<400> SEQUENCE: 29

```
caactgttgt gaagagatat acacagatat aacctattct ttctacatta taagattgcc       60
gatgttttac acgattaatc tgatcatccc ttgtctcttt atttcatttc taaccgtgtt      120
ggtcttttac cttccttcgg actgtggtga aaaagtgacg cttttgtattt cagtcctgct     180 ttctctgact gtgttttttgc tggtcatcac ataaaccatc ccatccacat ctctggtggg     240
cccactggtg ggtgagtacc tgctgttcac catgatcttt ggcacactgg ccatcgtggt     300
gactgtgttt gagttgaaca tacactaccg caccccaacc acgcacacaa tgcccaggtg     360
ggtgaagaca gttttcctga agctgctgcc ccaggtcctg c                          401
```

<210> SEQ ID NO 30
<211> LENGTH: 213
<212> TYPE: DNA
<213> ORGANISM: Homo sapiens

<400> SEQUENCE: 30

| | |
|---|---|
| ctcccccacg cacgatgagc acctcctgca cggcgggcaa ccccccgagg gggacccgga | 60 |
| cttggccaaa atcctggagg aggtccgcta cattgccaac cgcttccgct gccaggacga | 120 |
| aagcgaggcg gtctgcaacg agtggaagtt ccccgcctgt gtggtggacc gcctgtgcct | 180 |
| catggccttc tctgtcttca ccatcatctg cac | 213 |

<210> SEQ ID NO 31
<211> LENGTH: 639
<212> TYPE: DNA
<213> ORGANISM: Homo sapiens

<400> SEQUENCE: 31

| | |
|---|---|
| ggattcaggt gtgagccact gcacccggcc tagagcttct ttttgcttc ccaaagagcc | 60 |
| ataggtcaag aggacaatca agaagctgc tgggatcaga agtcaaacag ggcccctgg | 120 |
| actcacataa aacatgatct ggtcatatag gttgttgccc atggacatct ttggggtggc | 180 |
| cttgttgatg cccaagagct cccactcccc ctgggtttgg atgactttgc gagacgtgtc | 240 |
| tgtgatctcc cacacctcct tgtccatgcc cagcagcatg ctgtccactg aagggaggc | 300 |
| cggtcagttc attgcagacg ttttcccaag cctcccgccc acgaaattgg agtcctcccc | 360 |
| cactgagctt ctaaaccaaa ttttcctcta ccttttaaa gcagggtatc ctggttttct | 420 |
| cagaagtggg ttacccgact agcaattcat atgtgtgtgg gcagcggcat taatttcttt | 480 |
| tgttgttgaa acaagagtg agtcaagttc gttatgggaa tattggatat gactgaaacg | 540 |
| tgagtcaaga acttttggag tcattcctat tttccttctc agtcccccag tcgtatggtg | 600 |
| gtgttttagt ggaatcaagc ttgaatagct caatatttt | 639 |

<210> SEQ ID NO 32
<211> LENGTH: 685
<212> TYPE: DNA
<213> ORGANISM: Homo sapiens

<400> SEQUENCE: 32

| | |
|---|---|
| cttctgcatg actcagaata ttctccttgg catggatttc tgccacagat ttgtaaaaca | 60 |
| gaaacacaaa agctctatct aagaaggaaa ccccatgtac acacttcttt ttaccacccg | 120 |
| cagtcttcaa ctacacaata gcaatgtgtg tctccatatc acttgtcttt tgatttgtct | 180 |
| tgtcttttga tttgttcaat cattgcatgc ctctataata taaatattat attaccatgc | 240 |
| cttctaaggt cattgatgaa agttatttta ttcatccttg catcttctat tcaggttttg | 300 |
| gcacatagta ggcactataa ataaatgtac aatcaatgaa gcaatgctgt gcattttaaa | 360 |
| ctaaagatag ctaactaaag tcaagaaccc caagtaattc atttgagtac acactgttca | 420 |
| gctggaaccc aaacagaaat ccaagtcttt attcttcaaa taccaccagt gctttagagt | 480 |
| ttggcacttg gcctctccta atcttgtact taaatcctga catgtttatt ttgcatttta | 540 |
| aaagccaacc gctttataaa atgctttgac ctactttttt gttttttata agcctccatt | 600 |
| ttataccctg tgaaatgatg ataaaagcag tgccaaactt actgaattat tatgagaatt | 660 |
| aaataagata atacatgtca ggcat | 685 |

<210> SEQ ID NO 33
<211> LENGTH: 484
<212> TYPE: DNA
<213> ORGANISM: Homo sapiens

<400> SEQUENCE: 33

| | | | | | |
|---|---|---|---|---|---|
| cctattttt | tctttattct | tctggaagat | ttttctgtga | gctctgaaca | tggactcatc | 60 |
| cttgggaaac | actcatcacg | gtcattcatg | ccacgctttt | gctcgttcat | ttgcaggctg | 120 |
| cttcctccct | gtcactttct | tcctcctccc | aactgcgaaa | cagccttttc | atttcttaaa | 180 |
| catttgtggc | tccagaaggc | aaatcggttt | cttccctcct | gcccttctgt | ttggtattta | 240 |
| aaaacacacc | ctgagaggca | taaatgcaga | ttttttttt | cctccagtga | attttctgta | 300 |
| accatgggcc | tcgctttaag | aagactcaac | agataacaag | tgtaaatgcc | gaaaacatca | 360 |
| acgaaaggca | gagggccaaa | gggaagggtg | atggttttac | taaaaggtct | tttttcttta | 420 |
| tttttaaaaa | ttcaatgtgc | atttccttag | tggtggttat | ccttttgtgc | tcataaaatg | 480 |
| tgat | | | | | 484 |

<210> SEQ ID NO 34
<211> LENGTH: 449
<212> TYPE: DNA
<213> ORGANISM: Homo sapiens

<400> SEQUENCE: 34

| | | | | | |
|---|---|---|---|---|---|
| atttccctgt | tctcttcttt | cttcctgctg | ctgagttaac | tgggtaaaca | gaggtggtgg | 60 |
| tagaatctta | gcttcatagg | tcatccatta | gctgtatcca | aggcaacta | caatcccatg | 120 |
| agactccctg | cagacctacg | tggtgtttgt | agaatgatct | tggttattta | taccactgag | 180 |
| tatttgagac | tgattgtcac | atcactataa | cctacttaca | ctgtttgaaa | cagacattgt | 240 |
| caattcaaaa | caaacaatag | aaaaccaaac | aaaaaacaga | tcagggaaag | aataaacaac | 300 |
| aacaaagaga | agatgatttg | ctggtcaaaa | cgggtggtga | atagagattt | tccactgaat | 360 |
| atgagacaca | tgaataagaa | atgaaggtga | gggagatagc | aatgaaaata | tttggggaaa | 420 |
| gacagtccag | actgaggaaa | tagcctatg | | | 449 |

<210> SEQ ID NO 35
<211> LENGTH: 579
<212> TYPE: DNA
<213> ORGANISM: Homo sapiens

<400> SEQUENCE: 35

| | | | | | |
|---|---|---|---|---|---|
| ttggtataaa | taagttctat | tttctctcca | gtaatatttt | ataccagttg | cctaaactgt | 60 |
| gaacttcttg | aggtagggtt | acctgatgca | cccctgggtt | gtcagtgcac | agggaggtag | 120 |
| gcagggcagt | gactgaagca | caggaagcag | tgacactcat | cagccatcat | caaatggaat | 180 |
| aacataagcg | gctgatcgaa | actagctgga | aggaaattgc | agtcataata | tctgtaagca | 240 |
| tgttgggttt | ttttttttaat | gttctgccct | ttacacctat | cattttatga | acatttctct | 300 |
| ataccagggg | ttggcaaact | ttttcggtaa | aaggtaagat | aataaatatt | tcaagctttg | 360 |
| tgggctattt | ggtgtgtgtc | ccgaatcctc | aatcccgcca | ttgcaatgaa | agcagccat | 420 |
| aaatgagtga | tcatggctgt | gttccaataa | aactttatct | aagaaacaag | tggcaggctg | 480 |
| aaagtgctga | cccctagttt | acatcattag | atcttctata | aaaatggcta | taagatattc | 540 |
| caggctgtga | atattttatg | gtatatttca | caaattctc | | 579 |

-continued

<210> SEQ ID NO 36
<211> LENGTH: 683
<212> TYPE: DNA
<213> ORGANISM: Homo sapiens

<400> SEQUENCE: 36

```
gttacaggag gccttgggtg agacccagtt ctgtgcttgt tttgggactg acccagcaca      60
gctctagaag cggtggccat aggcagtact tgtgtcaccc cactgccagc tccaggtggc     120
tcaaaacagt aaagtaaaga gagactgttt agaagaaagt aagaagagaa acaagtact     180
ctttgccttg taaatcagag aattcttcca gatcttgtgg aagaccatca aggcagtact     240
tccatgagtc tgcaagaaac cacagcatta gtgggcttag ggtgcccct aaagcagata     300
caacttagat cataacaccc aagtcctttt gaatatctga aaagccttcc caagaagaat     360
gggaacaaac aagcccagac tataaagact acaataaata cctaattatt caatgcctgg     420
gcacagacag acatttacaa gtatcaagat catccaggaa acatgaccct caccaaatga     480
actaaataag gcaacagaga tcaatcctgg agaaacagag atatgtggcc tttcagacag     540
agaattcaaa attcagacag agaatttgaa gagtatttt gccagatata ctactctagg      600
ataaaaggtt tttttttttt tccttcttca gcatgttaaa tatatcatgc cattctcttc     660
tggcttataa ggtttccact aaa                                             683
```

<210> SEQ ID NO 37
<211> LENGTH: 643
<212> TYPE: DNA
<213> ORGANISM: Homo sapiens

<400> SEQUENCE: 37

```
gaagggaaat accagaggac agaggaacag gctaagcttc actgtgagca tgcagttgca      60
aaagccagac tgtgagaaac tacatgtcaa agggcctggg ttcctcaaca gataaattgt     120
caggaaaaga aagggacaga ggggaaatct gtggattatg agtttaaaag aaataaactt     180
caaaaattag caagtctaag ttacagtagc tagggattct ggtatgtggg aagcaatata     240
ggcaatggaa agcaagatat tacttgcaag tagacacata atttctgcta acattctatt     300
gaccaaaacc aggtcacatg gccacatctg tccagctcca gctgaggcct gtgaatgtct     360
ctagctaggt agccaagtgc cttgaataaa tgtgaaggtt tgattatcaa agaagagac      420
agtagataat ggtgaatact tattagtctc tgccactccc ttaaaaatgg aatacacaaa     480
ctcgcactgt gatttctaac ttacactgta cagcttctct gaattattct ggaacttaaa     540
tttgtgcttg tctttacttg ttattcagaa agtatctaga gcctctcttg attttcttta     600
ttttctccct gacagcatca ggaaagtcag aatctcaatc aag                        643
```

<210> SEQ ID NO 38
<211> LENGTH: 385
<212> TYPE: DNA
<213> ORGANISM: Homo sapiens

<400> SEQUENCE: 38

```
tcaattttct aagcaaaaaa taattcacct tttcctgtcc acattattta gcatgatatt      60
tatgtagttt tccaaaatat tctattttta aatgcactga ctttattttt atatcataga     120
tacatttata tataaagtat ttcaagatga atttgagaca aattgaagta acaaagcttg     180
atttccattc tgcatacaat attctctata attacaatgt aggttttggc cacttgtttt     240
gactaacata gctatgccat catttaaata tctgtatgcc tttgttttct gtaaattaaa     300
```

| | |
|---|---|
| attcagacat acaaagaaat ataaggagag ttaggagaac agtgataaaa gataaaatgg | 360 |
| caccacagta attcctaaat aaggg | 385 |

<210> SEQ ID NO 39
<211> LENGTH: 655
<212> TYPE: DNA
<213> ORGANISM: Homo sapiens

<400> SEQUENCE: 39

| | |
|---|---|
| tcaatgagta cataggaact aatttataca gtaattccag tagtcataga gctctaaaaa | 60 |
| tcaacctctc ctcaacacta aactctaatg ctgttctcct gacatgttca taggtaacaa | 120 |
| aagagaaagc tctgttttgt cttccagttc tatctgccgg aattccaaag agtgctccac | 180 |
| ttcgttatat aatgctgcta cataggtctc agaaatcttt tggttttgaa gagggaaaaa | 240 |
| tttgaaatta aatatagata aaactgaacc atattcagat caatatgatc ttagaaccta | 300 |
| tagattttg cctgtattat ctacactgag actgaatagc atacatattt tgttcagtgg | 360 |
| gtattaatgg ttccatgatt ctaattttgc tcatttttct ggcatgtatt ggctacctgc | 420 |
| cctacttttg cagttgacca attttgctta taaagaccag gctgtaatgt ggccttggtc | 480 |
| ccatcatacc atacctaacc ccgctgtatc tgatattagg ttcctaaata aataaaaata | 540 |
| aaactttact atttactcac taactctaaa aatgccttct cttctagttt actatacccca | 600 |
| cacagagaaa aaccatagat attttataat atagtttaga tgctaagtgg caata | 655 |

<210> SEQ ID NO 40
<211> LENGTH: 663
<212> TYPE: DNA
<213> ORGANISM: Homo sapiens

<400> SEQUENCE: 40

| | |
|---|---|
| ggtggtaagt gatagattgt gatataaaat gtgcttctta tggagttggg gtccaaaata | 60 |
| tttgaaggcc attggtgtat gctgtggatg cgtcagttgg tttctttgct tcgtccatgc | 120 |
| taccttctca aggaatcagt tctctcccac tgattttggc agtggcagct caatgtgctc | 180 |
| tatgatccca gctcaaccga agacacctag ataagggtga acatctaacc caagagaaag | 240 |
| gaatatatga acaacctgag ccaatcatcc catcctgagg agaggtccaa aagacatccc | 300 |
| ctgaggttat gtgcaattgt gggctacagc tgtaagaaca taagaagcac tagccagtcc | 360 |
| ccaagagatg gagagaagcc cagtgaagct gtttatgcgc aaagagagtg attttgagtt | 420 |
| ctaaatttcc aactctagtc cttatgtggc caagctctta ttgctgaccc gtggatatgt | 480 |
| gagagattgc ctgcagtgtc tgtgttttta tttgcaataa atttcttaag catgctagag | 540 |
| taggttcagt tccttgttac caactgctct ctcaccaagg cagactcttg gggagtgata | 600 |
| atatcaacaa gtaaatattt attgtgtaaa tatataatga taactatttg gtgcctctgt | 660 |
| gtg | 663 |

<210> SEQ ID NO 41
<211> LENGTH: 551
<212> TYPE: DNA
<213> ORGANISM: Homo sapiens

<400> SEQUENCE: 41

| | |
|---|---|
| ccatctgcac aatttcagca gccaagcaca ctatgtcact ccccaagtct ccccagtcct | 60 |
| tgtgatggtg gcggcaaccc atctggaaca gctgctgtga ggaaaccagc tgcagcaagg | 120 |
| gaggtgtgcc tggggctgca tgctcatgga tcctgcagga gccagaaatt ggtgatccca | 180 |

```
gcaggagccc ctatgcccca ccaagttgat gcagcaggag ccccatgctc ctgggcacag      240
ctgcagttgc ccaactgtgg ctccagatct gggcatctct gcactcttgg gggcccagga      300
agtcccctgt ccccactggc tcagaattgg ctgctcctgc ccttgggcag tgcctgctcc      360
agtgcagagc gaagttgtgg ccaagcccag gtgctatcac agcctagcca gatgtgcatt      420 catttgggg gtgctgacac accagccccc tgccacctca gccctctctg gactttgggc      480
aacaacaagc atgcgaggga ggccagggg ctgaggcagc ttggcacagg cctgtgggca      540
cccctcagca t                                                            551

<210> SEQ ID NO 42
<211> LENGTH: 625
<212> TYPE: DNA
<213> ORGANISM: Homo sapiens

<400> SEQUENCE: 42
cattgttcta atcccggctt ataaattatg tcactcaatc ctcatacccc tttgaggcga       60
aggtattaat tcttcccatg gtccacatga ggaaacaggc acaggagaag ctaaataaca      120
agcccaagta gaggcttaga gcaagaaagg ccctagccca ttccatagac gtccacaaag      180
gaggaaaccg agtcccagag acagtggagc ctctccagat tcagtgtgac ccgacagggc      240
tgtaggagtc cagcctgggt gttcccagct cagtctggct ctctgacccg gttcctactg      300
aagatgactc ctccaggaag tccacaggat ccttagccct aaagaacctg gctggggtgc      360
agaggaggcc agggaaggag agccagggt ggagcggaga gaggagccca ggggagagta      420
cctgcggctg gcccagagcc cgcgggagag ctcggagcta gagctagagg ggagcacatg      480
ggagaggact cggaggcaga ggtcagggc agaggcctgg gaacagacac acgggccgcg      540 ccaccccgc gccccgccct tgtaccccgc ccggcccagc tcccttgccc cgggatgtac      600
agcacctgcc cgggcccgct gcgca                                             625

<210> SEQ ID NO 43
<211> LENGTH: 465
<212> TYPE: DNA
<213> ORGANISM: Homo sapiens

<400> SEQUENCE: 43
ctctaaacat tggttaatat tagacctgtc tgcaatgatt tctcctaaat atcattacca       60
gtgtcatttg gtctcattct tacataagaa tctttctcca ttgtctacct gctgtttttcc     120 ataaatatta tgcttcattt atagttgttt acttcccttt tgaggaaaac aacatgagtt      180
ttgcatcccc tccaaaaact catgttgaaa tttagttggc attgggaatg gtattaagag      240
atggagacat taaaggtga gtaggccatg agaaactaa cttcatacat ggattaatgt        300
tattggggaa gtgggattat catgagagta caatccggta taaaagcgag cttggcccctt     360 tctggctctc ttatatgagg gctctcttgc tcttctgcct tccaccatgg gtagatgcag      420
caagaagacc ctcaccacat atgggcccct cactcttatg cttcc                      465

<210> SEQ ID NO 44
<211> LENGTH: 546
<212> TYPE: DNA
<213> ORGANISM: Homo sapiens

<400> SEQUENCE: 44
agcagtccag gatgtgttga gtagggtgaa ttgtggcata tctgaggatg gttctatcca       60
ggtacaggaa tgacaggagc aaagtcctct caaggagatc ttgcctgaca tgcttgagaa      120
```

```
agagcaaagg caaactagtg atggtgccat gaaagcctgt ctattaagac cactactact      180
ccttcctgct tgacacctca ccactcacac cccttttttc tataccaagg gttgaccagg      240
gccagttcca gcctactacc tgttttattg gaacaaaacc atgctcattt gtttacttgt      300
tgtttatggg agttcttatg ctacaacaag agttgaatat tactgcagag actgtatcgc      360
cctcaaagag cctaaaatat gtaccatctg gcccttagca gaaaacgttt gctaaccact      420
actttatatc atgctcttta gttgatgcgg ttgtcaaatg cgaacatccc agaaaaatac      480
tgctttggac atctttataa taatgaaata tgcattttcc atgttaaaat ctcgttactg      540
atggta                                                                 546

<210> SEQ ID NO 45
<211> LENGTH: 688
<212> TYPE: DNA
<213> ORGANISM: Homo sapiens

<400> SEQUENCE: 45
ggtcagccgt gttttgtgct ggtatttgcc ccgattacca gtcttaaagt cttatttaat       60
ttcacactct tcagtgttag ttgtgcaaag tccctctggc catggcagtg agcggttggg      120
ctgtgccgcc aaactctccg tatcaatctg gcctgggact caaccaagtg atctctgact      180
tttggaaaga gtctgtcttc agagttcacc cagaagatgg cttaattaga catctccctg      240
agctgttagg ccttagacgg gtgggagtcc tgccctgccc aagctagctc aaggacgagg      300
cccgcctgga ctcagcttgg agccacgtga tgggcgtgag tgtgtgagct cctggtaagg      360
cgcagaggtc agatggagac cttgcatcct gcccgagaag tgccccaccc cctccaatat      420
ctggcttttc tctgcataca aaccaagctg aaaacagtcc actacccacc accccctcata     480 gctatggaac caaataaccc agaaattaaa agcttcactg tagctgtcct tttcccatt      540 tcctaaatgg aatttaaaaa gctctggctt gtcaaaaggg gaagattatt ttctgaattg      600
gaagtctgta gatatattga gcaacagcca ccctctctgg gtccctgcaa atggtaccca      660
tttttccaac ccacagctct agctgctc                                         688

<210> SEQ ID NO 46
<211> LENGTH: 663
<212> TYPE: DNA
<213> ORGANISM: Homo sapiens

<400> SEQUENCE: 46
ttgcctttct ggatatcatc aacaacccat tcttaatgt gacataataa tatttcaaag        60
tgttaattga agtactactt actacctccc agtgtagctg ctcaccatcc atctttgaca      120
cccaaatgga tgaacacgta ttgcagaaga gacagtccgc agctaagtgt gacatcctta      180
gcctccaaat ggacaaacaa gtaaaaaaaa tgttttcttc ctgccccaag actctacaaa      240
agatcctctg agctgcagat ggacaaaaga atttagatta caagagaaaa gacacagtac      300
cagggtgatt tattctatca tctctccctg gaataaatcc tatgatggag agggaaaact      360
gcctcacaat ggcttttaat ttgggaacct gataatagaa aggattggac ctctgtctat      420
tctgtttcaa actatggtca ttggtagtca tatagagctg ggagtaaggg gttagggaag      480
agtaattctg caactcctgt ggtgctccta agatgaggg acaacaatca ccctataggg       540
aaagacctgg aaggactgaa attgggctga aaaatctgaa taagcctgga taaaggacct      600
ggtagggtgg agaataaccct aaggacctga ttatcaaagc tagggcaaaa atcttgaaca     660
tct                                                                    663
```

<210> SEQ ID NO 47
<211> LENGTH: 703
<212> TYPE: DNA
<213> ORGANISM: Homo sapiens

<400> SEQUENCE: 47

| | | | | | |
|---|---|---|---|---|---|
| gatatgtcac | attttctgac | ctaggtactc | gcactttagc | aaaaacaaaa | acaaaaacaa | 60 |
| aacaaaaaaa | acatcaaggt | tcctgagcaa | gagaacttta | cacatagtgg | ggactgggaa | 120 |
| agagtagagg | caaggacctg | gaaggaagcc | acttacagca | gatgcagagg | tcccactagg | 180 |
| caggaatgta | aaggagggt | tggatgaaac | acagttaacg | tataaaggtt | aagagattac | 240 |
| aaattcaggc | tggagggtag | aaggaagaag | tgaaactgac | tcaggttctc | agagtgggag | 300 |
| aatggtgata | ctgtgctcta | agactgaaaa | tcagaaagaa | gaataaattt | agggagtgg | 360 |
| gaggggagaa | ggaagtgtaa | aattatgaat | ttagttttct | atttgttgag | tgtaaggtac | 420 |
| tcattgaaaa | tctaaaagat | gtgtagaaat | cctaatagtt | gatccagaga | gtccgcatag | 480 |
| tgacacaaat | tttaacaata | atgctaattt | ctactgagtg | gaggtctacc | atgtgtcagg | 540 |
| tatgctatgt | tcaatttcat | tgagtcctaa | caaggatcct | ataaagtagg | tatgattgcg | 600 |
| tccatttcac | agatgaggaa | gtggaggctc | tgaaatgtta | cataacctgc | ccagggtcac | 660 |
| aggtatctga | ctctggccat | tatgctcttt | ctactgtgcc | cta | | 703 |

<210> SEQ ID NO 48
<211> LENGTH: 682
<212> TYPE: DNA
<213> ORGANISM: Homo sapiens

<400> SEQUENCE: 48

| | | | | | |
|---|---|---|---|---|---|
| ctctgtccca | acttcctggt | ggctttgttt | acaccatgat | ggaaaactg | cctactccag | 60 |
| tctcagtaat | ggcaaatgtc | cctcccacca | ccaagctcga | gcatcccagt | attgacttca | 120 |
| gactgctgtg | ctggcagcaa | gaatttcaag | ccagtggatc | ttagcttgct | tggctccatt | 180 |
| ggggcaggat | ccactgagct | agaccacttg | gctccctagc | ttcagccccc | tttccagggg | 240 |
| agtgaacggt | tctgcctccc | tggcattcca | ggcaccactg | aggtttgaaa | aaaaaaaaaa | 300 |
| tctcctgcag | ctagctcggc | atctgcccaa | atggctgccc | agttttgtgc | ttgaaatcta | 360 |
| ggtccctggt | ggtgtaggca | cctgagggaa | tctgctggtc | tgtgggttgt | gaagaccatg | 420 |
| ggaaaagggt | agtatctggg | ctggaatgca | ctgttcctca | tggcagagtc | cctcagggct | 480 |
| tcttttggct | aggggaggga | gttccctgac | cccttgccct | tcccagggga | catggcactc | 540 |
| caccctgctt | ccacttgccc | tctgtgggct | gcacccagtg | tctaaccagt | cccaatgaga | 600 |
| tgagctggtt | acctcagttg | gaaatgcaga | agtcattcac | cttctgcatt | gatcttgttg | 660 |
| ggagctgcaa | agtggagctg | tt | | | | 682 |

<210> SEQ ID NO 49
<211> LENGTH: 633
<212> TYPE: DNA
<213> ORGANISM: Homo sapiens

<400> SEQUENCE: 49

| | | | | | |
|---|---|---|---|---|---|
| cctgccacat | cagcgtttat | catcttcctg | agtctctgag | ggagacagca | ctggaactca | 60 |
| ggatttggct | cacctgtgac | aaaggaaatg | cgaggaggta | acaaggcact | gcaagaagga | 120 |
| agcatagtac | aaggattctg | aatcactttg | ttcaaaattg | gatatagagt | aaataacagt | 180 |
| attttaagat | gtttgctaaa | aatcaagtaa | atgcaaacag | aataattgat | gagatgccat | 240 |

```
tatcactttc aaaatggcat cgattaaaaa aataagcact cagaaggttg gtgagtgggc      300
aacagaaggg acgtgtgccc accccacagc gggatgttga gttagcccct ggctttagaa      360
ggcagttggc agggagccgc agaggaggca tgtgtgcaga gctacgtctc ggatctagtc      420
tgcgggcatt accagagatg tgtccagaga gttctacaga gagctgtctg ttacatgagg      480
gaaactatga tgtgaagttt ttaaaagtcc aaaaataaga agtggatcag ataaataatg      540
gcacatctga gtcgtataaa ctatgaaatc accaaagtct tgtttaataa aactaatacc      600
tgggggtaaa gcaacttata agacaatagg cct                                   633
```

```
<210> SEQ ID NO 50
<211> LENGTH: 446
<212> TYPE: DNA
<213> ORGANISM: Homo sapiens

<400> SEQUENCE: 50
tctcccttct ccctcaaacc ggatccagcc ctcctgcacc ccggcctgtg tgcagccgca       60
gggagaggag taagccagcc tctcgcgtgc ggtgctctct gcataggttt agtggtgggg      120
accaacacgc gagctggcgc tttccgtgcg agcccagcat caggcggagg cccagggcca      180
accggactct gaacaaaggg agccgacaaa tgagaaagca aggtacctc agagactacg       240 aagcccttca gatggaaatg gtcatctccc aacagcctct ctggacctct gcctgcaagc      300
ccggcccaca catcttggac ccaggctgga gacacagaca gccaggtggt gatgcccacg      360
cgcagctcca agaccccggg gagcctccgc caggccggaa cctgcgccag gcttctctgg      420
aaccttctct ccaggacgct cttctg                                           446
```

```
<210> SEQ ID NO 51
<211> LENGTH: 638
<212> TYPE: DNA
<213> ORGANISM: Homo sapiens

<400> SEQUENCE: 51
taattctccc atttatccat tcaataagtt gtcactgaca tctacataat gacaggacag       60
gcgtggctcc agggagctta gggtcaagtg gtctgacct gaaaatctac ataaactctg       120
tcttctactc cataatatat tgatgcttct tttaatataa aattttctt tctccatcca       180 tttgcaaata aaattagtcc cccaggaaga taagtcagac ttctctgtgg cttctcaagt      240
gccagctggg catgagcatc tcagactgag acgcctggac aacctcctgt tcaaatgtgg      300
ctttgtcata gaattggagc accctgaggg caggatgaca cccatctgga gtaagggact      360
ccagcatgac cacccacaat ggcagatgtg cctacctggc aaccacgccc atcccacccc      420
acactgcttc tctgcccaca cagccccaat ctgttcagac agccagtgga ggtaggacca      480
tctcctgcct cggggcatga atcattgctg ggctgggca gtcaaacagc ctcacctgcc       540
ctggctgact ctggccaatg agatggaagg ggaagttggc ttgggagcag gtgggaatat      600
cctctcaaac aaagagcttt cagctcctcc tcccttgc                              638
```

```
<210> SEQ ID NO 52
<211> LENGTH: 707
<212> TYPE: DNA
<213> ORGANISM: Homo sapiens

<400> SEQUENCE: 52
tttatttttt ccagggcggg ggagttgaag taggaagaag agtaatgaag aatgtgtttg       60
ccttaaaagc ataagcagag ttatttttaa tgtaagtgcc ctcccctttt tgtaatgcca      120
```

| | |
|---|---|
| gggcagagt attctccaaa tgccttatac acttactttc agcactaaat gtatttgtgc | 180 |
| aaatcccatg aatcatcaag cttttgaaa atatttatag ggagagaaac tcaacccttt | 240 |
| tcattagagt gagtaaaact cacactggta tcttgctatt gtttaaggag aacaatggat | 300 |
| gggtggatga agagaatgt cagctggatc aacaaacagc tgttccaaca gaagtcctgc | 360 |
| tatcctatac aataaagcag tattaattgc tgccttccct ggagtctcta aagatactcg | 420 |
| gtaagtgtac agtaccctga tgaactaaag ccaaaagtta gggctgattt cgggcttcat | 480 |
| cacagtgaac acctcacctc cagagagaaa gttgtaggcc tttaaagctt ttgatctcag | 540 |
| agaagactcc accgcctttc aaggcaataa attcttgcct cttctccaaa tactctaact | 600 |
| gaaacttctg ctgttgcagt ataattcaat gtgttttttt ccagacttca atgaaagcaa | 660 |
| gaattctcat tctgcatgta attatatccc ttataatacc cacagcc | 707 |

<210> SEQ ID NO 53
<211> LENGTH: 654
<212> TYPE: DNA
<213> ORGANISM: Homo sapiens

<400> SEQUENCE: 53

| | |
|---|---|
| tatgagtgat gcaaatatca caaatactgg tggcaccaaa acgatgattt ttctgaaatc | 60 |
| tgaaataaac ttggtaaaat ttcatttgaa acaaaagtct cctttcaatt tattaagtac | 120 |
| agcgagtgct cacctaaggt cttggaaatg gcaactttaa gtaaaataat gtatattaaa | 180 |
| accaattttc cctaaagcta attgatctaa acaagagtta tgcttttatg gcatatttct | 240 |
| ggtcacaaaa acatcaccaa acttctaaag aaagaccaaa atatttctga tattaaacat | 300 |
| ttaaagaaat gtgagctata cgtacattta agaaaggtta ataaaaacaa gtcagataat | 360 |
| tatttaccca attattccag ttcaggatac tgggtagcca aagcttatct gggcagctta | 420 |
| ggatgcaagg aaggaactca ccttgaacag gaaaccaatt ccatcacagg gcacattcac | 480 |
| acacagaccc acactcactt cagaccagga aaatttaaac accaattcac ctactatgca | 540 |
| catctttgga atgtgggatg aagccagcgt acctggagaa aacccaggaa gacatgggga | 600 |
| gaatgggcaa actccacaca gacagaggcc ctagtgaagt atcattatta ttct | 654 |

<210> SEQ ID NO 54
<211> LENGTH: 775
<212> TYPE: DNA
<213> ORGANISM: Homo sapiens

<400> SEQUENCE: 54

| | |
|---|---|
| cccaatatgg atgcaagggt cactgattac tttagggtcc ttatgttgca aggagtctag | 60 |
| gaaaaacttc aatttttttt tttttacagca acgtgattct ctttgtggtg tctactaaaa | 120 |
| taagaaagtt acagtgagat ttcttcagtg ttctgatggc tttctgcctc tcctctgacc | 180 |
| agcgtgagcc actccttcat ctctgcctct cactttctgc ttgacagtca aggctcgcct | 240 |
| tgaacctccc tcttcagaaa gccttctga cctgcctcct caggagtgtt tgtttgtggt | 300 |
| atttgaccac aatctgcact atactaatta gctatgattt tatgggggct ggaggaactt | 360 |
| ctaaggcagc agccgcgtcg ggttcttctg tctccttccc agggcttcct cagggcttag | 420 |
| tacagggcat gtgctaagca ttccctagcc ccttcctttg cccttgtttg ttctttctaa | 480 |
| tcagattctg tgggggaagt tcattgtcac aatgtccaat gtttagcatt caaaggctgc | 540 |
| atgaggtaga tcaggtaaac atacctctct ggctgtacca aaatgggggg gtttggcata | 600 |
| tccgccacct gaaagcagct ggaccctgcg tggatctggg tttgtatgct gtgagtaatg | 660 |

```
ctgtctgcat cttcgaatct ttcactgtaa gaaacaaaag tctgacagcc tctgaatccc      720
gccctccttc ctgatacact gtgacaatgt gtttatagta ccctgttgat gctga           775
```

<210> SEQ ID NO 55
<211> LENGTH: 224
<212> TYPE: DNA
<213> ORGANISM: Homo sapiens

<400> SEQUENCE: 55

```
aaaaaaaaaa aaaaaaaggt gactgatatt accaaatagc ctccatgatg taccaattta       60
cactgcttat aggtttgtct gttttcttga tattatacac tctgtcttac agactcacag      120
caacatgtct tggaattcca cttatgtcaa tatacataga tctaccttat taaaaaaaaa      180
aaacatgccg ggcatagggg cttacacctg taatcccagc actt                       224
```

<210> SEQ ID NO 56
<211> LENGTH: 465
<212> TYPE: DNA
<213> ORGANISM: Homo sapiens

<400> SEQUENCE: 56

```
caccatcctc cagacccag aatggtagat ccatccaagc ttgcaccctg cacctgggaa        60 aagcctatagg acactcaaca tcagccatga aggcagcccg aagggggct atgccctgca      120 aagccacagg ggaggagcta cccaaggcca tgggagccca cctcttgcat cagtgtgacc      180
tggacgtgaa acatggagtc caaggagatc attttggagc tttaagattt ggctgctcca      240
ctggatttca gatttgcatg gggcctgtag cctctttgtt ttggctaatt tctcctattt      300
ggaatggttg tatttcccca atgcctgtac tcccattgta tctaggaagt ataataggta      360
cgtgcttttg attgtaaagg cttataggca aagggactt gccttgtctc agatgagact      420
ttgaactcag actgttgagt taatgctgga atgagttaag atttt                      465
```

<210> SEQ ID NO 57
<211> LENGTH: 621
<212> TYPE: DNA
<213> ORGANISM: Homo sapiens

<400> SEQUENCE: 57

```
cgcttggatg gacaggttac cactggagtg ctacggctct gatacctgca gttttgcaga       60
accagcctgc aatggcgagg ccggggcctt tggtttagca cagaggtgcg agtgtgcggc      120
ccactctgag gggcagcggt acctatgtcc tccccttttcc tcccactgca gactcccagg      180
gcctggagat ggtgactgga acaaatgaca catttcagcc acacaaggag gcctctgtga      240
ggccgcttct tccagcagaa gctcctgtgg atgtgcatgt gtcagaacaa acccagccca      300
ggaccgaatg gatttgggtt atttgctttt caattctggc cccattctgt gggaggccat      360
ctgtgatgag gcagggaaaa gcagacagag aaagggatc catgctcttg catccagccc      420
ttccaagaaa attctatgag agcagcacct gaaccgcaag gccccgttgg gacagcagat      480
tgtattttag gattttaacc acaaatcatc tctcctgact tctcattctc tgcctcgcaa      540
cacttctttc tcatttcttc cacctagaat ctctctattt ctacttgacc tttgcttttg      600
gatgtggcca ctcaaaacctt t                                                621
```

<210> SEQ ID NO 58
<211> LENGTH: 24
<212> TYPE: PRT
<213> ORGANISM: Homo sapiens

```
<400> SEQUENCE: 58

Trp Asn Leu Glu Asp Asn Gly Gly Ile Asn Ala Phe Lys Ile Pro Ser
1               5                   10                  15

Glu Asn Tyr Phe Gln Pro Arg Ile
            20

<210> SEQ ID NO 59
<211> LENGTH: 27
<212> TYPE: PRT
<213> ORGANISM: Homo sapiens

<400> SEQUENCE: 59

Pro Ala Thr Ser Ser Gln Leu Ile Ser Ile Glu Thr Glu Leu Ser
1               5                   10                  15

Leu Ala Gln Cys Ile Ser Val Val Ser Ala Glu
            20                  25

<210> SEQ ID NO 60
<211> LENGTH: 63
<212> TYPE: PRT
<213> ORGANISM: Homo sapiens

<400> SEQUENCE: 60

Thr Cys Ile Phe Leu Pro Val Leu Lys Leu Asn His Leu Phe Val Leu
1               5                   10                  15

Ile Phe Val Ser Leu Ser Pro Cys Pro Gln Pro Val Ala Thr Thr Ile
            20                  25                  30

Leu Leu Ser Val Ser Met Asn Leu Thr Thr Leu His Thr Ser Tyr Lys
        35                  40                  45

Trp Arg His Thr Val Phe Tyr Gly Phe Leu Glu Ala Gly Ile Phe
    50                  55                  60

<210> SEQ ID NO 61
<211> LENGTH: 64
<212> TYPE: PRT
<213> ORGANISM: Homo sapiens

<400> SEQUENCE: 61

Thr Ile Gly Gly Thr Leu Leu Gly Leu Ser Phe Leu Ile Cys Lys Ala
1               5                   10                  15

Leu Val Ile Leu Glu Ser Ser Ser His Phe Val Asp Arg Arg Arg
            20                  25                  30

Gly Ser Gly Lys Lys Ala Tyr Ala Asn Lys Gln Pro Gln Gly Lys Pro
        35                  40                  45

Ala Ala Gly Ala Leu Pro Ser Trp Leu Arg Lys Leu Pro Leu Gly Arg
    50                  55                  60

<210> SEQ ID NO 62
<211> LENGTH: 50
<212> TYPE: PRT
<213> ORGANISM: Homo sapiens

<400> SEQUENCE: 62

Trp Lys Asn Trp Leu Phe Phe Thr Cys Leu His Cys Thr Thr Pro His
1               5                   10                  15

Asp Val Met Phe His Ile Leu Leu Lys Ile Pro Glu Phe His Glu Val
            20                  25                  30
```

```
Leu Gly Thr Cys His Ile Leu Gln Gly Leu Asn Lys Ile Val Phe Thr
        35                  40                  45
Leu Pro
    50

<210> SEQ ID NO 63
<211> LENGTH: 36
<212> TYPE: PRT
<213> ORGANISM: Homo sapiens

<400> SEQUENCE: 63

Thr Trp Thr Pro Asp Gly Glu Ser Val Leu Arg Asp Pro Glu Gly Trp
1               5                   10                  15

Glu His Trp Thr Pro Asp Gly Glu Ser Val Leu Arg Asp Pro Glu Gly
            20                  25                  30

Trp Glu His Trp
        35

<210> SEQ ID NO 64
<211> LENGTH: 45
<212> TYPE: PRT
<213> ORGANISM: Homo sapiens

<400> SEQUENCE: 64

Arg Gln Glu Ala Leu Leu His His Val Ala Thr Ile Ala Asn Thr Phe
1               5                   10                  15

Arg Ser His Arg Ala Ala Gln Arg Cys His Glu Asp Trp Lys Arg Leu
            20                  25                  30

Ala Arg Val Met Asp Arg Phe Phe Leu Ala Ile Phe Phe
        35                  40                  45

<210> SEQ ID NO 65
<211> LENGTH: 24
<212> TYPE: PRT
<213> ORGANISM: Homo sapiens

<400> SEQUENCE: 65

His Cys Gln Leu Ser Pro Leu Pro Pro Gly Ile Phe Ser Ile Ser Cys
1               5                   10                  15

Trp Leu Ser Lys Arg Trp Arg Pro
            20

<210> SEQ ID NO 66
<211> LENGTH: 36
<212> TYPE: PRT
<213> ORGANISM: Homo sapiens

<400> SEQUENCE: 66

Gln Ser Trp Leu Asp Thr Arg Leu Ala Trp Asn Thr Ser Ala His Pro
1               5                   10                  15

Arg His Ala Ile Thr Leu Pro Trp Glu Ser Leu Trp Thr Pro Arg Leu
            20                  25                  30

Thr Ile Leu Glu
        35

<210> SEQ ID NO 67
<211> LENGTH: 24
<212> TYPE: PRT
<213> ORGANISM: Homo sapiens
```

```
<400> SEQUENCE: 67

Trp Asn Leu Glu Asp Asn Gly Gly Ile Asn Ala Phe Lys Ile Pro Ser
1               5                   10                  15

Glu Asn Tyr Phe Gln Pro Arg Ile
            20

<210> SEQ ID NO 68
<211> LENGTH: 38
<212> TYPE: PRT
<213> ORGANISM: Homo sapiens

<400> SEQUENCE: 68

Cys Leu Ser Leu Met Val Gly Ser Leu Leu Glu Thr Ile Phe Ile Thr
1               5                   10                  15

His Leu Leu His Val Ala Thr Thr Gln Pro Pro Leu Pro Arg Trp
            20                  25                  30

Leu His Ser Leu Leu Leu
            35

<210> SEQ ID NO 69
<211> LENGTH: 89
<212> TYPE: PRT
<213> ORGANISM: Homo sapiens

<400> SEQUENCE: 69

Gly Glu Thr Asp Val Ile Tyr Leu Leu Ile Ile Cys Arg Lys Ile Thr
1               5                   10                  15

Asn Ile Met Val Pro Cys Val Leu Ile Ser Gly Leu Val Leu Leu Ala
            20                  25                  30

Tyr Phe Leu Pro Ala Gln Ser Leu Gly Thr Ala Ala Pro Glu Ile Arg
        35                  40                  45

Cys Cys Gly Asp Ala Val Asn Phe Val Ala Lys Asn Met Arg Gly Gln
    50                  55                  60

Asp Thr Arg Gly Gln Asp Asp Gly Ile Cys Phe Trp Val Ala Arg Val
65                  70                  75                  80

Leu Phe Ser Leu Gly Ser Asn Leu Ile
            85

<210> SEQ ID NO 70
<211> LENGTH: 29
<212> TYPE: PRT
<213> ORGANISM: Homo sapiens

<400> SEQUENCE: 70

Asp Ser Thr Lys Ala Arg Pro Gln Lys Tyr Glu Gln Leu Leu His Ile
1               5                   10                  15

Glu Asp Asn Asp Phe Ala Met Arg Pro Gly Phe Gly Gly
            20                  25

<210> SEQ ID NO 71
<211> LENGTH: 40
<212> TYPE: PRT
<213> ORGANISM: Homo sapiens

<400> SEQUENCE: 71

Pro Asp Phe Arg Thr Asp Ser Phe Ser Val Arg Pro Thr Gln Ile Pro
1               5                   10                  15
```

```
Val Gly Asn Leu Pro Phe Pro Cys Ala Thr Glu Cys Lys Glu Asn Ser
            20                  25                  30

Pro Lys Thr Ser Leu Thr Thr Leu
            35                  40

<210> SEQ ID NO 72
<211> LENGTH: 50
<212> TYPE: PRT
<213> ORGANISM: Homo sapiens

<400> SEQUENCE: 72

Gly Asp Cys Arg Met Ala His Ala Glu Gln Lys Leu Met Asp Asp Leu
 1               5                  10                  15

Leu Asn Lys Thr Cys Tyr Asn Asn Leu Ile Arg Pro Ala Thr Ser Ser
            20                  25                  30

Ser Gln Leu Ile Ser Ile Gln Thr Ala Leu Ser Leu Ala Gln Cys Ile
            35                  40                  45

Ser Val
    50

<210> SEQ ID NO 73
<211> LENGTH: 43
<212> TYPE: PRT
<213> ORGANISM: Homo sapiens

<400> SEQUENCE: 73

Ala Glu Gln Lys Leu Met Asp Asp Leu Leu Asn Lys Thr Arg Tyr His
 1               5                  10                  15

Asn Leu Ile Arg Pro Ala Ala Ser Ser Ser Gln Leu Ile Ser Ile Glu
            20                  25                  30

Met Glu Leu Ser Leu Ala Gln Cys Ile Ser Val
            35                  40

<210> SEQ ID NO 74
<211> LENGTH: 51
<212> TYPE: PRT
<213> ORGANISM: Homo sapiens

<400> SEQUENCE: 74

Arg Gly Thr Ala Ala Trp Pro Met Pro Ser Arg Lys Leu Met Asp Asp
 1               5                  10                  15

Leu Leu Asn Lys Thr Cys Tyr Asn Asn Leu Ile Arg Pro Ala Thr Ser
            20                  25                  30

Ser Ser Gln Leu Ile Ser Ile Gln Thr Ala Leu Ser Leu Ala Gln Cys
            35                  40                  45

Ile Ser Val
    50

<210> SEQ ID NO 75
<211> LENGTH: 45
<212> TYPE: PRT
<213> ORGANISM: Homo sapiens

<400> SEQUENCE: 75

Gly Lys Phe Thr Cys Ile Glu Val Lys Phe His Leu Glu Arg Gln Met
 1               5                  10                  15

Gly Tyr Tyr Leu Ile Gln Met Tyr Ile Pro Ser Leu Leu Ile Val Ile
            20                  25                  30

Leu Ser Trp Val Ser Leu Trp Ile Asn Met Asp Ala Ala
            35                  40                  45
```

```
<210> SEQ ID NO 76
<211> LENGTH: 50
<212> TYPE: PRT
<213> ORGANISM: Homo sapiens

<400> SEQUENCE: 76

Val Ser Tyr Val Lys Ala Ile Asp Ile Trp Met Ala Val Cys Leu Leu
1               5                   10                  15

Phe Val Phe Ala Ala Leu Leu Glu Tyr Ala Ala Ile Asn Phe Val Ser
            20                  25                  30

Arg Gln His Lys Glu Phe Ile Arg Leu Arg Arg Gln Arg Arg Gln
        35                  40                  45

Arg Leu
    50

<210> SEQ ID NO 77
<211> LENGTH: 28
<212> TYPE: PRT
<213> ORGANISM: Homo sapiens

<400> SEQUENCE: 77

Arg Leu Thr Leu Ile Leu Ser Cys Leu Met Asp Leu Lys Asn Phe Pro
1               5                   10                  15

Met Asp Ile Gln Thr Cys Thr Met Gln Leu Glu Ser
            20                  25

<210> SEQ ID NO 78
<211> LENGTH: 72
<212> TYPE: PRT
<213> ORGANISM: Homo sapiens

<400> SEQUENCE: 78

Ile Ser Leu Ser Ala Val Phe Leu Arg Gly Ser Leu Leu Lys Leu Trp
1               5                   10                  15

Leu Phe Ser Thr Gly Trp Tyr Asn Arg Leu Phe Ile Asn Phe Val Leu
            20                  25                  30

Arg Arg His Val Phe Phe Phe Val Leu Gln Thr Tyr Phe Pro Ala Ile
        35                  40                  45

Leu Met Val Met Leu Ser Trp Val Ser Phe Trp Ile Asp Arg Arg Ala
    50                  55                  60

Val Pro Ala Arg Val Ser Leu Gly
65                  70

<210> SEQ ID NO 79
<211> LENGTH: 159
<212> TYPE: PRT
<213> ORGANISM: Homo sapiens

<400> SEQUENCE: 79

Arg Cys Arg Pro Ser Pro Tyr Val Asn Phe Leu Val Pro Ser Gly
1               5                   10                  15

Ile Leu Ile Ala Ile Asp Ala Leu Ser Phe Tyr Leu Pro Leu Glu Ser
            20                  25                  30

Gly Asn Cys Ala Pro Phe Lys Met Thr Val Leu Leu Gly Tyr Ser Val
        35                  40                  45

Phe Leu Leu Met Met Asn Asp Leu Leu Pro Ala Thr Ser Thr Ser Ser
    50                  55                  60

His Ala Ser Leu Val Arg Pro His Pro Ser Arg Asp Gln Lys Arg Gly
65                  70                  75                  80
```

```
Val Cys Trp Met Gly Arg Gly Met Gly Arg Thr Arg Arg Ser Glu Lys
                 85                  90                  95

Gly Ser Trp Lys Lys Ile Leu Trp Glu Arg Asn Lys Lys Phe Val Ala
            100                 105                 110

Pro Leu Ala Leu Met Gln Thr Pro Leu Pro Ala Gly Val Tyr Phe Ala
        115                 120                 125

Leu Cys Leu Ser Leu Met Val Gly Ser Leu Leu Glu Thr Ile Phe Ile
    130                 135                 140

Thr His Leu Leu Ala Arg Gly His His Pro Ala Pro Thr Ser Ala
145                 150                 155

<210> SEQ ID NO 80
<211> LENGTH: 60
<212> TYPE: PRT
<213> ORGANISM: Homo sapiens

<400> SEQUENCE: 80

Leu Ser Ser Ser Met Asp Val Asp Lys Thr Pro Lys Gly Leu Thr Ala
1               5                  10                  15

Tyr Val Ser Asn Glu Gly Arg Ile Arg Tyr Lys Lys Pro Met Lys Gly
            20                  25                  30

Asp Ser Ile Cys Asn Leu Asp Ile Phe Tyr Phe Pro Phe Asp Gln Gln
        35                  40                  45

Asn Cys Thr Leu Thr Phe Ser Ser Phe Leu Tyr Thr
    50                  55                  60

<210> SEQ ID NO 81
<211> LENGTH: 33
<212> TYPE: PRT
<213> ORGANISM: Homo sapiens

<400> SEQUENCE: 81

Gln Glu Trp Ser Asp Tyr Lys Leu Arg Trp Asn Pro Thr Asp Phe Gly
1               5                  10                  15

Asn Ile Thr Ser Leu Lys Val Pro Ser Glu Met Ile Trp Ile Pro Asp
            20                  25                  30

Ile

<210> SEQ ID NO 82
<211> LENGTH: 58
<212> TYPE: PRT
<213> ORGANISM: Homo sapiens

<400> SEQUENCE: 82

Cys Pro Gly Val Ile Arg Arg His His Gly Gly Ala Thr Asp Gly Pro
1               5                  10                  15

Arg Glu Thr Asp Val Ile Tyr Ser Leu Ile Ile Leu Arg Lys Pro Leu
            20                  25                  30

Phe Tyr Val Ile Asn Ile Ile Val Pro Cys Val Leu Ile Trp Gly Leu
        35                  40                  45

Val Leu Leu Ala Tyr Phe Leu Pro Ala Gln
    50                  55

<210> SEQ ID NO 83
<211> LENGTH: 43
<212> TYPE: PRT
<213> ORGANISM: Homo sapiens
```

```
<400> SEQUENCE: 83

Arg Phe Leu Ile Phe Val Met Val Ala Thr Leu Ile Val Met Asn
1               5                   10                  15

Cys Val Ile Val Leu Asn Val Ser Gln Arg Thr Pro Thr Thr His Ala
            20                  25                  30

Met Ser Pro Arg Leu Arg His Val Ser Ala Glu
        35                  40

<210> SEQ ID NO 84
<211> LENGTH: 92
<212> TYPE: PRT
<213> ORGANISM: Homo sapiens

<400> SEQUENCE: 84

His Pro Asp Ser Lys Tyr His Leu Lys Lys Arg Ile Thr Ser Leu Ser
1               5                   10                  15

Leu Pro Ile Val Ser Ser Glu Ala Asn Lys Val Leu Thr Arg Ala
            20                  25                  30

Pro Ile Leu Gln Ser Thr Pro Val Thr Pro Pro Leu Ser Pro Ala
        35                  40                  45

Phe Gly Gly Thr Ser Lys Ile Asp Gln Tyr Ser Arg Ile Leu Phe Pro
50                  55                  60

Val Ala Phe Ala Gly Phe Asn Leu Val Tyr Trp Gly Ser Phe Ile Phe
65                  70                  75                  80

Pro Lys Ile Gln Trp Glu Val Ser Thr Ser Val Glu
                85                  90

<210> SEQ ID NO 85
<211> LENGTH: 61
<212> TYPE: PRT
<213> ORGANISM: Homo sapiens

<400> SEQUENCE: 85

Arg Ser Val Gly Val Glu Thr Gly Glu Thr Lys Lys Glu Gly Ala Ala
1               5                   10                  15

Arg Ser Gly Gly Gln Gly Gly Ile Arg Ala Arg Leu Arg Pro Met Asp
            20                  25                  30

Ala Asp Thr Ile Asp Ile Asn Ala Arg Ala Val Phe Pro Ala Ala Phe
        35                  40                  45

Ala Ala Val Asn Val Ile Tyr Trp Ala Ala Tyr Ala Met
50                  55                  60

<210> SEQ ID NO 86
<211> LENGTH: 132
<212> TYPE: PRT
<213> ORGANISM: Homo sapiens

<400> SEQUENCE: 86

Asn Cys Cys Glu Glu Ile Tyr Thr Asp Ile Thr Tyr Ser Phe Tyr Ile
1               5                   10                  15

Ile Arg Leu Pro Met Phe Tyr Thr Ile Asn Leu Ile Ile Pro Cys Leu
            20                  25                  30

Phe Ile Ser Phe Leu Thr Val Leu Val Phe Tyr Leu Pro Ser Asp Cys
        35                  40                  45

Gly Glu Lys Val Thr Leu Cys Ile Ser Val Leu Leu Ser Leu Thr Val
    50                  55                  60

Phe Leu Leu Val Ile Thr Thr Ile Pro Ser Thr Ser Leu Val Gly Pro
65                  70                  75                  80
```

Leu Val Gly Glu Tyr Leu Leu Phe Thr Met Ile Phe Gly Thr Leu Ala
                85                  90                  95

Ile Val Val Thr Val Phe Glu Leu Asn Ile His Tyr Arg Thr Pro Thr
            100                 105                 110

Thr His Thr Met Pro Arg Trp Val Lys Thr Val Phe Leu Lys Leu Leu
        115                 120                 125

Pro Gln Val Leu
    130

<210> SEQ ID NO 87
<211> LENGTH: 70
<212> TYPE: PRT
<213> ORGANISM: Homo sapiens

<400> SEQUENCE: 87

Ser Pro Thr His Asp Glu His Leu Leu His Gly Gly Gln Pro Pro Glu
1               5                   10                  15

Gly Asp Pro Asp Leu Ala Lys Ile Leu Glu Glu Val Arg Tyr Ile Ala
            20                  25                  30

Asn Arg Phe Arg Cys Gln Asp Glu Ser Glu Ala Val Cys Asn Glu Trp
        35                  40                  45

Lys Phe Pro Ala Cys Val Val Asp Arg Leu Cys Leu Met Ala Phe Ser
    50                  55                  60

Val Phe Thr Ile Ile Cys
65                  70

<210> SEQ ID NO 88
<211> LENGTH: 42
<212> TYPE: PRT
<213> ORGANISM: Homo sapiens

<400> SEQUENCE: 88

Glu Ile Thr Asp Thr Ser Arg Lys Val Ile Gln Thr Gln Gly Glu Trp
1               5                   10                  15

Glu Leu Leu Gly Ile Asn Lys Ala Thr Pro Lys Met Ser Met Gly Asn
            20                  25                  30

Asn Leu Tyr Asp Gln Ile Met Phe Tyr Val
        35                  40

<210> SEQ ID NO 89
<211> LENGTH: 38
<212> TYPE: PRT
<213> ORGANISM: Homo sapiens

<400> SEQUENCE: 89

Asp Leu Ser Cys Leu Leu Ile Cys Ser Ile Ala Cys Leu Tyr Asn
1               5                   10                  15

Ile Asn Ile Ile Leu Pro Cys Leu Leu Arg Ser Leu Met Lys Val Ile
            20                  25                  30

Leu Phe Ile Leu Ala Ser
        35

<210> SEQ ID NO 90
<211> LENGTH: 60
<212> TYPE: PRT
<213> ORGANISM: Homo sapiens

<400> SEQUENCE: 90

Phe Phe Ile Leu Leu Glu Asp Phe Ser Val Ser Ser Glu His Gly Leu
1               5                   10                  15

```
Ile Leu Gly Lys His Ser Ser Arg Ser Phe Met Pro Arg Phe Cys Ser
            20                  25                  30

Phe Ile Cys Arg Leu Leu Pro Pro Cys His Phe Leu Pro Pro Pro Asn
        35                  40                  45

Cys Glu Thr Ala Phe Ser Phe Leu Lys His Leu Trp
    50                  55                  60

<210> SEQ ID NO 91
<211> LENGTH: 37
<212> TYPE: PRT
<213> ORGANISM: Homo sapiens

<400> SEQUENCE: 91

Gly Tyr Phe Leu Ser Leu Asp Cys Leu Ser Pro Asn Ile Phe Ile Ala
1               5                   10                  15

Ile Ser Leu Thr Phe Ile Ser Tyr Ser Cys Val Ser Tyr Ser Val Glu
            20                  25                  30

Asn Leu Tyr Ser Pro
        35

<210> SEQ ID NO 92
<211> LENGTH: 30
<212> TYPE: PRT
<213> ORGANISM: Homo sapiens

<400> SEQUENCE: 92

Phe Leu Asp Lys Val Leu Leu Glu His Ser His Asp His Ser Phe Met
1               5                   10                  15

Ala Ala Phe His Cys Asn Gly Gly Ile Glu Asp Ser Gly His
            20                  25                  30

<210> SEQ ID NO 93
<211> LENGTH: 29
<212> TYPE: PRT
<213> ORGANISM: Homo sapiens

<400> SEQUENCE: 93

Ser Pro Gly Leu Ile Ser Val Ala Leu Phe Ser Ser Phe Gly Glu Val
1               5                   10                  15

Met Phe Ser Trp Met Ile Leu Ile Leu Val Asn Val Cys
            20                  25

<210> SEQ ID NO 94
<211> LENGTH: 31
<212> TYPE: PRT
<213> ORGANISM: Homo sapiens

<400> SEQUENCE: 94

Leu Ser Lys Glu Glu Thr Val Asp Asn Gly Glu Tyr Leu Leu Val Ser
1               5                   10                  15

Ala Thr Pro Leu Lys Met Glu Tyr Thr Asn Ser His Cys Asp Phe
            20                  25                  30

<210> SEQ ID NO 95
<211> LENGTH: 18
<212> TYPE: PRT
<213> ORGANISM: Homo sapiens
```

```
<400> SEQUENCE: 95

Trp Cys His Phe Ile Phe Tyr His Cys Ser Pro Asn Ser Pro Tyr Ile
1               5                   10                  15

Ser Leu

<210> SEQ ID NO 96
<211> LENGTH: 44
<212> TYPE: PRT
<213> ORGANISM: Homo sapiens

<400> SEQUENCE: 96

Ile Phe Asn Phe Lys Phe Pro Leu Gln Asn Gln Lys Ile Ser Glu
1               5                   10                  15

Thr Tyr Val Ala Ala Leu Tyr Asn Glu Val Glu His Ser Leu Glu Phe
            20                  25                  30

Arg Gln Ile Glu Leu Glu Asp Lys Thr Glu Leu Ser
        35                  40

<210> SEQ ID NO 97
<211> LENGTH: 43
<212> TYPE: PRT
<213> ORGANISM: Homo sapiens

<400> SEQUENCE: 97

Phe Leu Cys Ser Tyr Ser Cys Ser Pro Gln Leu His Ile Thr Ser Gly
1               5                   10                  15

Asp Val Phe Trp Thr Ser Pro Gln Asp Gly Met Ile Gly Ser Gly Cys
            20                  25                  30

Ser Tyr Ile Pro Phe Ser Trp Val Arg Cys Ser
        35                  40

<210> SEQ ID NO 98
<211> LENGTH: 93
<212> TYPE: PRT
<213> ORGANISM: Homo sapiens

<400> SEQUENCE: 98

Gly His Ser Cys Ser Cys Pro Thr Val Ala Pro Asp Leu Gly Ile Ser
1               5                   10                  15

Ala Leu Leu Gly Ala Gln Glu Val Pro Cys Pro His Trp Leu Arg Ile
            20                  25                  30

Gly Cys Ser Cys Pro Trp Ala Val Pro Ala Pro Val Gln Ser Glu Val
        35                  40                  45

Val Ala Lys Pro Arg Cys Tyr His Ser Leu Ala Arg Cys Ala Phe Ile
    50                  55                  60

Trp Gly Val Leu Thr His Gln Pro Pro Ala Thr Ser Ala Leu Ser Gly
65                  70                  75                  80

Leu Trp Ala Thr Thr Ser Met Arg Gly Arg Pro Gly Gly
                85                  90

<210> SEQ ID NO 99
<211> LENGTH: 67
<212> TYPE: PRT
<213> ORGANISM: Homo sapiens

<400> SEQUENCE: 99

Tyr Leu Arg Leu Ala Gln Ser Pro Arg Glu Ser Ser Glu Leu Glu Leu
1               5                   10                  15
```

```
Glu Gly Ser Thr Trp Glu Arg Thr Arg Arg Gln Arg Ser Gly Ala Glu
         20                  25                  30

Ala Trp Glu Gln Thr His Gly Pro Arg His Pro Arg Ala Pro Pro Leu
 35                      40                  45

Tyr Pro Ala Arg Pro Ser Ser Leu Ala Pro Gly Cys Thr Ala Pro Ala
 50                  55                  60

Arg Ala Arg
 65

<210> SEQ ID NO 100
<211> LENGTH: 32
<212> TYPE: PRT
<213> ORGANISM: Homo sapiens

<400> SEQUENCE: 100

Pro Ala Val Phe His Lys Tyr Tyr Ala Ser Phe Ile Val Val Tyr Phe
 1               5                  10                  15

Pro Phe Glu Glu Asn Asn Met Ser Phe Ala Ser Pro Pro Lys Thr His
         20                  25                  30

<210> SEQ ID NO 101
<211> LENGTH: 20
<212> TYPE: PRT
<213> ORGANISM: Homo sapiens

<400> SEQUENCE: 101

Cys Thr Trp Ile Glu Pro Ser Ser Asp Met Pro Gln Phe Thr Leu Leu
 1               5                  10                  15

Asn Thr Ser Trp
         20

<210> SEQ ID NO 102
<211> LENGTH: 43
<212> TYPE: PRT
<213> ORGANISM: Homo sapiens

<400> SEQUENCE: 102

Pro Gly Lys Ala Gln Arg Ser Asp Gly Asp Leu Ala Ser Cys Pro Arg
 1               5                  10                  15

Ser Ala Pro Pro Pro Ile Ser Gly Phe Ser Leu His Thr Asn Gln
         20                  25                  30

Ala Glu Asn Ser Pro Leu Pro Thr Thr Pro His
         35                  40

<210> SEQ ID NO 103
<211> LENGTH: 66
<212> TYPE: PRT
<213> ORGANISM: Homo sapiens

<400> SEQUENCE: 103

Pro Pro Tyr Gln Val Leu Tyr Pro Gly Leu Phe Arg Phe Phe Ser Pro
 1               5                  10                  15

Ile Ser Val Leu Pro Gly Leu Ser Tyr Arg Val Asp Cys Cys Pro Ser
         20                  25                  30

Ser Leu Gly Ala Pro Gln Glu Leu Gln Asn Tyr Ser Ser Leu Thr Pro
         35                  40                  45

Tyr Ser Gln Leu Tyr Met Thr Thr Asn Asp His Ser Leu Lys Gln Asn
 50                      55                  60

Arg Gln
 65
```

-continued

<210> SEQ ID NO 104
<211> LENGTH: 28
<212> TYPE: PRT
<213> ORGANISM: Homo sapiens

<400> SEQUENCE: 104

Pro Glu Gln Glu Asn Phe Thr His Ser Gly Asp Trp Glu Arg Val Glu
1               5                   10                  15

Ala Arg Thr Trp Lys Glu Ala Thr Tyr Ser Arg Cys
            20                  25

<210> SEQ ID NO 105
<211> LENGTH: 90
<212> TYPE: PRT
<213> ORGANISM: Homo sapiens

<400> SEQUENCE: 105

Ser Ala Phe Pro Thr Glu Val Thr Ser Ser His Trp Asp Trp Leu
1               5                   10                  15

Asp Thr Gly Cys Ser Pro Gln Arg Ala Ser Gly Ser Arg Val Glu Cys
            20                  25                  30

His Val Pro Trp Glu Gly Gln Gly Val Arg Glu Leu Pro Pro Leu Ala
        35                  40                  45

Lys Arg Ser Pro Glu Gly Leu Cys His Glu Gln Cys Ile Pro Ala
    50                  55                  60

Gln Ile Leu Pro Phe Ser His Gly Leu His Asn Pro Gln Thr Ser Arg
65                  70                  75                  80

Phe Pro Gln Val Pro Thr Pro Pro Gly Thr
                85                  90

<210> SEQ ID NO 106
<211> LENGTH: 37
<212> TYPE: PRT
<213> ORGANISM: Homo sapiens

<400> SEQUENCE: 106

Trp His Leu Ile Asn Tyr Ser Val Cys Ile Tyr Leu Ile Phe Ser Lys
1               5                   10                  15

His Leu Lys Ile Leu Leu Phe Thr Leu Tyr Pro Ile Leu Asn Lys Val
            20                  25                  30

Ile Gln Asn Pro Cys
        35

<210> SEQ ID NO 107
<211> LENGTH: 34
<212> TYPE: PRT
<213> ORGANISM: Homo sapiens

<400> SEQUENCE: 107

Arg Lys Ala Pro Ala Arg Val Leu Val Pro Thr Thr Lys Pro Met Gln
1               5                   10                  15

Arg Ala Pro His Ala Arg Gly Trp Leu Thr Pro Leu Pro Ala Ala Ala
            20                  25                  30

His Arg

<210> SEQ ID NO 108
<211> LENGTH: 68
<212> TYPE: PRT
<213> ORGANISM: Homo sapiens -continued

```
<400> SEQUENCE: 108

Phe Val Ile Glu Leu Glu His Pro Glu Gly Arg Met Thr Pro Ile Trp
1               5                   10                  15

Ser Lys Gly Leu Gln His Asp His Pro Gln Trp Gln Met Cys Leu Pro
            20                  25                  30

Gly Asn His Ala His Pro Thr Pro His Cys Phe Ser Ala His Thr Ala
        35                  40                  45

Pro Ile Cys Ser Asp Ser Gln Trp Arg Asp His Leu Leu Pro Arg Gly
50                  55                  60

Met Asn His Cys
65

<210> SEQ ID NO 109
<211> LENGTH: 36
<212> TYPE: PRT
<213> ORGANISM: Homo sapiens

<400> SEQUENCE: 109

Leu Leu Phe Lys Glu Asn Asn Gly Trp Val Asp Glu Arg Glu Cys Gln
1               5                   10                  15

Leu Asp Gln Gln Thr Ala Val Pro Thr Glu Val Leu Leu Ser Tyr Thr
            20                  25                  30

Ile Lys Gln Tyr
        35

<210> SEQ ID NO 110
<211> LENGTH: 41
<212> TYPE: PRT
<213> ORGANISM: Homo sapiens

<400> SEQUENCE: 110

Trp Asn Trp Phe Pro Val Gln Gly Glu Phe Leu Pro Cys Ile Leu Ser
1               5                   10                  15

Cys Pro Asp Lys Leu Trp Leu Pro Ser Ile Leu Asn Trp Asn Asn Trp
            20                  25                  30

Val Asn Asn Tyr Leu Thr Cys Phe Tyr
        35                  40

<210> SEQ ID NO 111
<211> LENGTH: 53
<212> TYPE: PRT
<213> ORGANISM: Homo sapiens

<400> SEQUENCE: 111

Ile Gln Arg Leu His Glu Val Asp Gln Val Asn Ile Pro Leu Trp Leu
1               5                   10                  15

Tyr Gln Asn Gly Gly Val Trp His Ile Arg His Leu Lys Ala Ala Gly
            20                  25                  30

Pro Cys Val Asp Leu Gly Leu Tyr Ala Val Ser Asn Ala Val Cys Ile
        35                  40                  45

Phe Glu Ser Phe Thr
50

<210> SEQ ID NO 112
<211> LENGTH: 35
<212> TYPE: PRT
<213> ORGANISM: Homo sapiens
```

```
-continued

<400> SEQUENCE: 112

Tyr Gln Phe Thr Leu Leu Ile Gly Leu Ser Val Phe Leu Ile Leu Tyr
1               5                   10                  15

Thr Leu Ser Tyr Arg Leu Thr Ala Thr Cys Leu Gly Ile Pro Leu Met
            20                  25                  30

Ser Ile Tyr
        35

<210> SEQ ID NO 113
<211> LENGTH: 69
<212> TYPE: PRT
<213> ORGANISM: Homo sapiens

<400> SEQUENCE: 113

Ile Trp Leu Leu His Trp Ile Ser Asp Leu His Gly Ala Cys Ser Leu
1               5                   10                  15

Phe Val Leu Ala Asn Phe Ser Tyr Leu Glu Trp Leu Tyr Phe Pro Asn
            20                  25                  30

Ala Cys Thr Pro Ile Val Ser Arg Lys Tyr Asn Arg Tyr Val Leu Leu
        35                  40                  45

Ile Val Lys Ala Tyr Arg Gln Lys Gly Leu Ala Leu Ser Gln Met Arg
    50                  55                  60

Leu Thr Gln Thr Val
65

<210> SEQ ID NO 114
<211> LENGTH: 60
<212> TYPE: PRT
<213> ORGANISM: Homo sapiens

<400> SEQUENCE: 114

Cys Lys Ser Met Asp Pro Leu Ser Leu Ser Ala Phe Pro Cys Leu Ile
1               5                   10                  15

Thr Asp Gly Leu Pro Gln Asn Gly Ala Arg Ile Glu Lys Gln Ile Thr
            20                  25                  30

Gln Ile His Ser Val Leu Gly Trp Val Cys Ser Asp Thr Cys Thr Ser
        35                  40                  45

Thr Gly Ala Ser Ala Gly Arg Ser Gly Leu Thr Glu
    50                  55                  60

<210> SEQ ID NO 115
<211> LENGTH: 2131
<212> TYPE: DNA
<213> ORGANISM: Homo sapiens

<400> SEQUENCE: 115
agctttgcta cattagcttc cagaatttgc attcaggctc accccatcct cccgggcctc      60
ggaagaagaa gcccagcgtc tggacccctc tcggtgatcc cctccccatt cttcatctca     120
tccctgggga cgtatagcac agcagcagca gacaaacctg ggttcagaac aagtccggct     180
tctgcctttt attggctgtc tgactgtagg aagttacttc ctcttattgc accttagtta     240
gctcgtttat tacatgaggg taaagcagta tctacctgat aggggattgg gaggattaaa     300
tgaggtaatc cattttaaa  gggcttagaa tatacctgac acacagccag tgctcaacaa     360
atgttagctt tcattttatc acgggcgacc ccacgccctg ccttgggcc  cctctcatat     420
agggagcaca gggttgctct ccttcatctc acacattcga tgtccactac aggaagggc      480
gttactttca ccatcaattg ctcagggttt ggccagcacg gggcggatcc cactgctgtg     540
```

```
aattcagtgt ttaatagaaa gcccttccgt ccggtcacca acatcagcgt ccccacccaa    600
gtcaacatct ccttcgcgat gtctgccatc ctagatgtga atgaacagct gcacctcttg    660
tcatcattcc tgtggctgga aatggtttgg gataacccat ttatcagctg aacccagag     720
gaatgtgagg gcatcacgaa gatgagtatg gcagccaaga acctgtggct cccagacatt    780
ttcatcattg aactcatgga tgtggataag accccaaaag gcctcacagc atatgtaagt    840
aatgaaggtc gcatcaggta taagaaaccc atgaaggtgg acagtatctg taacctggac    900
atcttctact tccccttcga ccagcagaac tgcacactca ccttcagctc attcctctac    960
acagtggaca gcatgttgct ggacatggag aagaagtgt gggaaataac agacgcatcc    1020
cggaacatcc ttcagaccca tggagaatgg gagctcctgg gcctcagcaa ggccaccgca    1080
aagttgtcca ggggaggcaa cctgtatgat cagatcgtgt ctatgtggc catcaggcgc    1140
aggcccagcc tctatgtcat aaaccttctc gtgcccagtg ctttctggt tgccatcgat    1200
gccctcagct ctacctgcc agtgaaaagt gggaatcgtg tcccattcaa gataacgctc    1260
ctgctgggct acaacgtctt cctgctcatg atgagtgact tgctccccac cagtggcacc    1320
cccctcatcg tgtctactt cgccctgtgc ctgtccctga tggtgggcag cctgctggag    1380
accatcttca tcacccacct gctgcacgtg ccaccaccc agccccacc cctgcctcgg    1440
tggctccact ccctgctgct ccactgcaac agccggggga gatgctgtcc cactgcgccc    1500
cagaaggaaa ataagggccc gggtctcacc cccacccacc tgcccggtgt aaggagcca    1560
gaggtatcag cagggcagat gccgggccct gcggaggcag agctgacagg gggctcagaa    1620
tggacaaggg cccagcggga acacgaggcc agaagcagc actcagtgga gctgtggttg    1680
cagttcagcc acgcgatgga cgccatgctc ttccgcctct acctgctctt catggcctcc    1740
tctatcatca ccgtcatatg cctctggaac acctaggcag gtgctcacct gccaacttca    1800
gtctggagct tctcttgcct ccagggactg gccaggtctc ccccttttcc tgagtaccaa    1860
ctatcatatc cccaaagatg actgagtctc tgctgtattc catgtatccc aatccggtcc    1920
tgctgatcaa ttccaatccc agacatttct ccctgttcct gcattttgtt ggcttccttc    1980
agtcctacca tatggttcta ggtccctctt acgtcatctg catagcagac tatacctctt    2040
ctgcccgctg acttgcccaa taataattc tgcagagaaa aaaaaaaaaa aaaaaaaaa     2100
aaaaaaaaa aaaaaaaaa aaaaaaaaa a                                     2131
```

<210> SEQ ID NO 116
<211> LENGTH: 471
<212> TYPE: PRT
<213> ORGANISM: Homo sapiens

<400> SEQUENCE: 116

```
Met Leu Ala Phe Ile Leu Ser Arg Ala Thr Pro Arg Pro Ala Leu Gly
1               5                   10                  15

Pro Leu Ser Tyr Arg Glu His Arg Val Ala Leu Leu His Leu Thr His
            20                  25                  30

Ser Met Ser Thr Thr Gly Arg Gly Val Thr Phe Thr Ile Asn Cys Ser
        35                  40                  45

Gly Phe Gly Gln His Gly Ala Asp Pro Thr Ala Val Asn Ser Val Phe
    50                  55                  60

Asn Arg Lys Pro Phe Arg Pro Val Thr Asn Ile Ser Val Pro Thr Gln
65                  70                  75                  80

Val Asn Ile Ser Phe Ala Met Ser Ala Ile Leu Asp Val Asn Glu Gln
                85                  90                  95
```

```
Leu His Leu Leu Ser Ser Phe Leu Trp Leu Glu Met Val Trp Asp Asn
            100                 105                 110

Pro Phe Ile Ser Trp Asn Pro Glu Glu Cys Glu Gly Ile Thr Lys Met
            115                 120                 125

Ser Met Ala Ala Lys Asn Leu Trp Leu Pro Asp Ile Phe Ile Ile Glu
    130                 135                 140

Leu Met Asp Val Asp Lys Thr Pro Lys Gly Leu Thr Ala Tyr Val Ser
145                 150                 155                 160

Asn Glu Gly Arg Ile Arg Tyr Lys Lys Pro Met Lys Val Asp Ser Ile
                165                 170                 175

Cys Asn Leu Asp Ile Phe Tyr Phe Pro Phe Asp Gln Gln Asn Cys Thr
            180                 185                 190

Leu Thr Phe Ser Ser Phe Leu Tyr Thr Val Asp Ser Met Leu Leu Asp
            195                 200                 205

Met Glu Lys Glu Val Trp Glu Ile Thr Asp Ala Ser Arg Asn Ile Leu
    210                 215                 220

Gln Thr His Gly Glu Trp Glu Leu Leu Gly Leu Ser Lys Ala Thr Ala
225                 230                 235                 240

Lys Leu Ser Arg Gly Gly Asn Leu Tyr Asp Gln Ile Val Phe Tyr Val
                245                 250                 255

Ala Ile Arg Arg Arg Pro Ser Leu Tyr Val Ile Asn Leu Leu Val Pro
            260                 265                 270

Ser Gly Phe Leu Val Ala Ile Asp Ala Leu Ser Phe Tyr Leu Pro Val
            275                 280                 285

Lys Ser Gly Asn Arg Val Pro Phe Lys Ile Thr Leu Leu Leu Gly Tyr
    290                 295                 300

Asn Val Phe Leu Leu Met Met Ser Asp Leu Leu Pro Thr Ser Gly Thr
305                 310                 315                 320

Pro Leu Ile Gly Val Tyr Phe Ala Leu Cys Leu Ser Leu Met Val Gly
                325                 330                 335

Ser Leu Leu Glu Thr Ile Phe Ile Thr His Leu Leu His Val Ala Thr
            340                 345                 350

Thr Gln Pro Pro Leu Pro Arg Trp Leu His Ser Leu Leu Leu His
            355                 360                 365

Cys Asn Ser Pro Gly Arg Cys Cys Pro Thr Ala Pro Gln Lys Glu Asn
    370                 375                 380

Lys Gly Pro Gly Leu Thr Pro Thr His Leu Pro Gly Val Lys Glu Pro
385                 390                 395                 400

Glu Val Ser Ala Gly Gln Met Pro Gly Pro Ala Glu Ala Glu Leu Thr
                405                 410                 415

Gly Gly Ser Glu Trp Thr Arg Ala Gln Arg Glu His Glu Ala Gln Lys
            420                 425                 430

Gln His Ser Val Glu Leu Trp Leu Gln Phe Ser His Ala Met Asp Ala
            435                 440                 445

Met Leu Phe Arg Leu Tyr Leu Leu Phe Met Ala Ser Ser Ile Ile Thr
    450                 455                 460

Val Ile Cys Leu Trp Asn Thr
465                 470

<210> SEQ ID NO 117
<211> LENGTH: 1465
<212> TYPE: DNA
<213> ORGANISM: Homo sapiens
```

```
<400> SEQUENCE: 117
atgttagctt tcattttatc acgggcgacc ccacgccctg ccttgggcc cctctcatat      60 agggagcaca gggttgctct ccttcatctc acacattcga tgtccactac aggaaggggc    120
gttactttca ccatcaattg ctcagggttt ggccagcacg gggcggatcc cactgctctg    180
aattcagtgt ttaatagaaa gcccttccgt ccggtcacca acatcagcgt ccccacccaa    240
gtcaacatct ccttcgcgat gtctgccatc ctagatgtga atgaacagct gcacctcttg    300
tcatcattcc tgtggctgga atggtttggg gataacccat ttatcagctg aacccagat    360 gaatgcggag gcatcaagaa gtccggcatg gcaactgaga acctatggct ttcagatgtc    420
ttcatcgagg agtctgtgga tcagacacct gcaggtctca tggctagtat gtcaatagtg    480
aaggccacat caaacacaat aagccaatgt gggtggtcag catctgcaaa ctggacacct    540
tctatttccc cttccatgga cagaggtgaa cgctctcctt cagcccttc acctacacag    600 gtaacccggg catggagaag gatgtccagg agctttcaaa tacatcacag aacctcattc    660
agaacaagga gggagtgggt actgctgggt atccaaaaaa gaacaataaa ggtgaccgtg    720
gccactaacc agtatgaaca agccatcttc catgtggcca tcaggcgcag gtgcaggccc    780
agcccctacg tggtaaactt tctggtgccc agtggcattc tgattgccat cgatgccctc    840
agtttctacc tgccactgga aagtgggaat tgtgccccat tcaagatgac tgttctgctg    900
ggctacagcg tcttcctgct catgatgaat gacttgctcc cagccactag cacttcatca    960
catgcttcac tagtacgtgt ctacttcgcc ctgtgcctgt ccctgatggt gggcagcctg   1020
ctggagacca tcttcatcac ccacctgctg cacgtggcca ccacccagcc cctacctctg   1080
cctcggtggc tccactccct gctgctgcac tgcaccggcc aagggagatg ctgtcccact   1140
gcgccccaga agggaaataa gggcccgggt ctcaccccca cccacctgcc cggtgtgaag   1200
gagccagagg tatcagcagg gcagatgcca ggccctgggg aggcagagct gacaggggc    1260 tcagaatgga caagggccca gcgggaacac gaggcccaga gcagcactc ggtggagctg     1320 tgggtgcagt tcagccacgc gatggacgcc ctgctcttcc gcctctacct gctcttcatg    1380
gcctcctcca tcatcaccgt catatgcctc tggaacacct aggcaggtgc tcacctgcaa    1440
acttcagtct ggacttcttt ttgcc                                         1465

<210> SEQ ID NO 118
<211> LENGTH: 357
<212> TYPE: PRT
<213> ORGANISM: Homo sapiens

<400> SEQUENCE: 118

Trp Asn Pro Asp Glu Cys Gly Gly Ile Lys Lys Ser Gly Met Ala Thr
1               5                   10                  15

Glu Asn Leu Trp Leu Ser Asp Val Phe Ile Glu Glu Ser Val Asp Gln
            20                  25                  30

Thr Pro Ala Gly Leu Met Ala Ser Met Ser Ile Val Lys Ala Thr Ser
        35                  40                  45

Asn Thr Ile Ser Gln Cys Gly Trp Ser Ala Ser Ala Asn Trp Thr Pro
    50                  55                  60

Ser Ile Ser Pro Ser Met Asp Arg Gly Glu Arg Ser Pro Ser Ala Leu
65                  70                  75                  80

Ser Pro Thr Gln Val Thr Arg Ala Trp Arg Arg Met Ser Arg Ser Phe
                85                  90                  95
```

```
Gln Ile His His Arg Thr Ser Phe Arg Thr Arg Arg Glu Trp Val Leu
            100                 105                 110

Leu Gly Ile Gln Lys Arg Thr Ile Lys Val Thr Val Ala Thr Asn Gln
        115                 120                 125

Tyr Glu Gln Ala Ile Phe His Val Ala Ile Arg Arg Cys Arg Pro
    130                 135                 140

Ser Pro Tyr Val Val Asn Phe Leu Val Pro Ser Gly Ile Leu Ile Ala
145                 150                 155                 160

Ile Asp Ala Leu Ser Phe Tyr Leu Pro Leu Glu Ser Gly Asn Cys Ala
                165                 170                 175

Pro Phe Lys Met Thr Val Leu Leu Gly Tyr Ser Val Phe Leu Leu Met
            180                 185                 190

Met Asn Asp Leu Leu Pro Ala Thr Ser Thr Ser Ser His Ala Ser Leu
            195                 200                 205

Val Arg Val Tyr Phe Ala Leu Cys Leu Ser Leu Met Val Gly Ser Leu
    210                 215                 220

Leu Glu Thr Ile Phe Ile Thr His Leu Leu His Val Ala Thr Thr Gln
225                 230                 235                 240

Pro Leu Pro Leu Pro Arg Trp Leu His Ser Leu Leu His Cys Thr
                245                 250                 255

Gly Gln Gly Arg Cys Cys Pro Thr Ala Pro Gln Lys Gly Asn Lys Gly
            260                 265                 270

Pro Gly Leu Thr Pro Thr His Leu Pro Gly Val Lys Glu Pro Glu Val
        275                 280                 285

Ser Ala Gly Gln Met Pro Gly Pro Glu Ala Glu Leu Thr Gly Gly
    290                 295                 300

Ser Glu Trp Thr Arg Ala Gln Arg Glu His Glu Ala Gln Lys Gln His
305                 310                 315                 320

Ser Val Glu Leu Trp Val Gln Phe Ser His Ala Met Asp Ala Leu Leu
                325                 330                 335

Phe Arg Leu Tyr Leu Leu Phe Met Ala Ser Ser Ile Ile Thr Val Ile
            340                 345                 350

Cys Leu Trp Asn Thr
        355

<210> SEQ ID NO 119
<211> LENGTH: 7736
<212> TYPE: DNA
<213> ORGANISM: Homo sapiens

<400> SEQUENCE: 119
gtatcatcaa atatacaaac taggcatgat caaagagcaa tgttttttcaa ttctgtctat    60 ttgtcaaatt tcctccatct actaaagtac taaagcatct aagaatataa agtctcacag   120
aggaaactgt tgaagaacgg ctgctctcga gagaataaac acgacagagt tgaaagacct   180
tgagcaagat cacggaattg ccgagctaga aggtttcttt cacacctacg taaacagcat   240
ccaggagctg tgctgtgcaa gaatctccag gctgtaaaat tagaaacact caggtttaag   300
tcgggcgcgg tggctcacgc ctgtaatccc agcactttga gaggccgagg caggcagatc   360
atgaagtcag gagttcgaga ccagtctggc caacagggtg aaactcgtct ctactaaaaa   420
tacaaaaaat tagccaggcg tggtagcaca tgcctctaat cacagctact gggatgctg    480 agacaggaaa atagcttgaa cctgggagac agaggtggca atgagccgag attgcgccac   540
tggactccag cctgggtgat aaagcgagac tccgtctcag aaagaaaaaa gaaacactta   600
```

-continued

```
ggtttaattc gcagttctga cacttttggg caagtaaacc aaatcaagat ttggtttccg    660
ctgtgcgcag tggctcacgc ctgtaatccc agcactttgg gaggctgagg cggtggatt    720
gcctgaggtt aggagtccga gaccagcctg gctaacatgg tgaagccctg tctctactaa    780
aaatacaaaa attagctggg tgtggtggcg cacgcctgta gttccagcta cttgagaggc    840
tgaggcagga gaatcgcttg aacccgggag gcggaggttg cagtgagctg agatcatgcc    900
accacactct agcctgggtg acagaacaag actccgtctc aaaaaaaaaa aatatatata    960
tatatacaca cacacacacg tatatataca tatatataca cgtatatata tgtatatgtg   1020
tatatatagt gtatatatgt atatgtgtat atatgtatat gtgtatatat gtatatatac   1080
gtgtatatgt gtatatatgt atatatatgt gtatatgtat atatacacgt atatatgtat   1140
atatatacgt gtatatatat gtataataat gcagccgggt gtggtgactc atgcctataa   1200
tcccagtact ttgggaggcc aaggcgggca gatcacttga ggtcaggagt tcgagaccag   1260
cctggccaaa tatggtgaaa ccttgtctct actaaaaata caaaaattag ccggacttag   1320
tggcgggcac ctgtaatccc agctactcgg gaggctgagg cacaagaatt gcttgaatcg   1380
aggaggcgga ggttgcagtg agcagagatg gcaccactgc actctagcct gggcaatata   1440
gcgagactat ctcaaaaaaa ataaataaat aaaataaat ttaaaatat aataatgcat    1500
gaagaatacc tagcacagtc cctggtacat gctaagtgcc taataaattg caactactaa   1560
taataatcaa taaatattcc ttcgcctggt tcatggtcag cacaccttac ccagtccttc   1620
cctttgtcag ctgactgagc cctggctgtc ccctgaggat gctcctgcag cctctgaatg   1680
gagggtgctt gtttcctgtg ccagttcagt tctgatcaga aagggcacgc tcactcactc   1740
aaatggagca atgaggagag tttcagaaca gagaacacag aagccaatgc atgtggctca   1800
agaagggagg gactgggaag aataagtgct ctaaactcat ttttccctta tgctccgatc   1860
tcttgtttgt ggctgtaatt ggctgagccc agctaggagc cagagagcaa gagagcccat   1920
tgatgtagtc cataaaggtc agcctcctgg ccgggcgcgg tggctcacac ctgtaatccc   1980
agcactttgg gaggccgagg cgagtggatc acctgaggtc aggagttgaa gaccagcctg   2040
accaatatgg tgaaaccctg cctctactaa aaatacaaaa attaggccag cacagtggc    2100
tcacgcctat aatcccaaca ctttgggagg ctgaggcagg cggatcacaa agtaaagaga   2160
tcgagaccat cctggctaac atggtgaaac cccatctcta ctaaaaatac aaaaattagc   2220
taggtgtggt ggcgtgtgcc tgtaatccca gctactcagg aggctgaggc aggaggatca   2280
cttgaaccca ggaggcagag gttgcagtga gctgagatcg tgccactgca ctctagcctg   2340
gcgacagagc aagactctgt ctcaaaaaaa taataaaata caaaattaaa aaaccagaaa   2400
ataacaagtg ttggtgataa tgtggagaaa ttggaaccct tgtgcactgc ttgtgaggat   2460
gtaaaattgt gtagccactg tggaaaaaca gtatggcttt ttctcaaaat attaaaaata   2520
gaattaccat acaaccaaat aattatactt ctggataaat acccgaaaaa agtgaaaacg   2580
gggtatttgt acacttatgt tcatagcaga attactcaca atagttaaaa ctcagaagca   2640
gtctaagtgt ctattgacag atgaatggac agattaaatg tggtatgtac ttacaatgga   2700
atactatgca gccttcaaat ggaacaaaat tctaacacat gccacaatgt ggataagctg   2760
tgaggccatt atgctaagtg aaataagtca gtcacaaaaa gacaaatagt gtatttgtct   2820
aatttttatag agacagaaag tagaatagct gttgccaggg gttggagaga gggtgaaata   2880
gggaattact gtttaacggg tgtagagttt ccattttgca agaagaaaag agctctggtg   2940
atggagggtg gtggctggac aacagtgtga atgtgtttaa cgccacggaa ctgtacactt   3000
```

```
                                      -continued
aaaatggtta agagagtaca ttttatgtta tatattttta tcacaataaa atattgaaaa    3060
aattattttt agcctgggca acatggcgaa accccatctc taccaaaaat acaaaaagtt    3120
agctgggcgt ggtggtgtgt gcctctaatc ccagctgctc gggaggctga ggcaggaggc    3180
aggagaatca cctgaacctg ggaggcagag gttgcagtga gccgaatggc gccactgca    3240 ctccagcctg ggcgacagag caagattctg tctcaaaaaa aagaaaaaat gattttttaaa   3300 agtgtttaaa aaattagagg tgcattcggc ggggtgagg agtagaaagg catgataaga    3360
aatgctgtaa tgacattact gcaggtaaaa tctgttcttt ttggaatact tgtcaaaaca    3420
tattcccaat ggaccttcat actgtgtttt tcatttacat tttccatgta ccttgaattg    3480
ttttgatcta catcatttt cagtggctta gatcaaaaat cattattgcc acatggacca    3540
gccttggaag tgaacaagga gagggtggtg gcatgggacc tgccttcctg gagttaatca    3600
tctagatgaa agctgctatt ccaggattca caccttcaac tggtgacatc gttcctgtgg    3660
ctaaatatgg tatgacagac tcagtttccc ctttcctcta ctctggtgcc tctctttttt    3720
ccactcctag gtccagcttt gcagattata ttggttaaag ctgagaatat ccataaatta    3780
gacaagttca aatagaccaa taatgaaaat acaaaacttt ctgattattc tgctggttta    3840
ggagggcaga aaatgggcac agggagaagg tggtatacac taaggccatg ggagtcaata    3900
cttatgtggc tccatcccag agaatcctga gccaagctca agctcaagct ctgtcttgag    3960
aaaactgagg taagcaagtg ttagtgtgat ggctgccacc agagaggtgg caggagagtg    4020
aagaaatggg cgaaaaaagg aaagggaagg tgcagaagac agagcaaaac taaaactagt    4080
tccttccccc tgtttctctc atgccatggt ttcctacaga cctagcacaa tcaattcttt    4140 ttttttttt ttgagagagt ctcactctgt cgcccaggct caagggcagt ggtgcgatct    4200
cagcccactg caacctccac ctcctgggtt caagcgattt tcctgcctcc tgcctcagcc    4260
tcctgagtat ctgggattac aggggcccac caccacaccc agctaatttt tgtatttta    4320 gtagagatgg ggtttcacca tgttagctag gctggtcctg aactcctgac cttcagtgat    4380
ccccccgcct cagccttcca aagtgctggg attacagaca gaagccacca tgcccggcct    4440
tggcacaatc aatttgtgca gtggaaccca gatgaatgcg gaggcatcaa gaagtccggc    4500
atggcaactg agaacctatg gctttcagat gtcttcatcg aggagtcgtg agtctcaggc    4560
caaaaaagca gaatggaaac cacgtctaca gggaaggaca caatgttacc gataaggcca    4620
cacaaagact caacttagaa aagagcagag tctgaattga agagcttaca aaccccccaga   4680 atatgattat aggtagaaga gagcagtcat ctgagtgggg ctggagctcg agaatgggat    4740
gacctgacag agaaagaagg ccaagtctga tggggaaacc cacagcacct acctccctgt    4800
ccttctccca cacagcatca gtgtggatca gacacctgca ggtctcatgg ctagtatgtc    4860
aatagtgaag gccacatcaa acacaataag ccaatgtggg tggtcagcat ctgcaaactg    4920
gacaccttct atttcccctt ccatggacag aggtgaacgc tctccttcag ccctttcacc    4980
tacacaggta agtggggctc actaaagtag actgttgaga ggcagagaaa gggctttgag    5040
tgagaagagc acagaaagct gggaacagtg agggaatctt gctgaaaagg gcctggaagc    5100
taagcagtga gggatccaac agtctgggca agggacttgg gcgcatttgg ggaggctgag    5160
tcttctgggc ctgctttgca gtggagaaca cgagcccggg catggagaag gatgtccagg    5220
agctttcaaa tacatcacag aacctcattc agaacaagga gggagtgggt actgctggt    5280 atccaaaaaa gaacaataaa ggtgaccgtg gccactaacc agtatgaaca agccatcttc    5340
catgtgagct caggggccaa gacaaggttt caccatgttg gccaggctgg tcttgaactc    5400
```

-continued

```
ctggcttcag gtgatccgcc cgcctcggcc tcccaaagtg ctgggattac gggcgtgaac    5460
cacgaagccc ggcctttgtc actcttttt tttttttaaa tttgagatag agttttgttc    5520
ttgtcgctca ggctggagtg caatgacgtg atctcagctc actgcaactt ccacctcctg    5580
ggttcaagtg attctcctgc ttcagcctcc tgagtagctg ggattacaag ggcccgccac    5640
catgcccggc taattttgt attttagta gagatgggt ttcaccacgt tcaccaggcc    5700
ggtctcaaag tcctgaactc aggtatctgc ctgcctcggc ctcccaaagt tctgggatta    5760
caggtatgag ccaccgtgcc cagccttttg tcactttttt cactgataaa ccttcagtac    5820
taaaacaata cctggtactc agtaaatagt tactaaataa agcatccctt gaggaagaaa    5880
caaaggctct atgccagtga ttcatggtga gggtgagccc cgccttcccc aatggctgtc    5940
agaactttt ggaaggcagg aatttttgtt tatttttaaa aagatatggt agaaagagtt    6000
aggaaacact gccttaggga tatgatgatt ccaaatcctg ataaccccaa aatatctgat    6060
actgtctgct ttccctccca ctggtctcaa atgttcccct gcaaagtcac tagagattag    6120
accttgacga gaaagcaat tagaaatgaa aagataaaac acacgcgaca cctaagtcgg    6180
tggttccaca gtcttgctaa gagcacgtcg gtaggaataa aaatttaagt ggagaaagtt    6240
gacaccttgg gccaaaagga atgagataca tttcagaggt aagcagcatg ggagactcta    6300
accttgtgag acgcctttgg atgaaaagac cggatgctga aagggacggg aggtaatatt    6360
tccttactag acagtttggc ctgggacaaa tcccagttct tactcttacc tgtcttgaca    6420
gcctcccagc ctacttctca cttgcccctc cttctcctcc ccaccaggtg gccatcaggc    6480
gcaggtgcag gcccagcccc tacgtggtaa actttctggt gcccagtggc attctgattg    6540
ccatcgatgc cctcagtttc tacctgccac tggaaagtgg gaattgtgcc ccattcaaga    6600
tgactgttct gctgggctac agcgtcttcc tgctcatgat gaatgacttg ctcccagcca    6660
ctagcacttc atcacatgct tcactagtac gtcctcatcc atcaagagac caaaagcgag    6720
gtgtgtgttg gatggggaga gggatgggca gaaccaggcg aagtgaaaag ggatcctgga    6780
aaaagatcct ctgggaaaga aacaagaaat tctaggtggc gcctctggcc tcatgcaga    6840
cccccttgcc tgcaggtgtc tacttcgccc tgtgcctgtc cctgatggtg ggcagcctgc    6900
tggagaccat cttcatcacc cacctgctgc acgtggccac cacccagccc ctacctctgc    6960
ctcggtggct ccactccctg ctgctgcact gcaccggcca agggagatgc tgtcccactg    7020
cgccccagaa gggaaataag ggcccgggtc tcaccccac ccacctgccc ggtgagggaa    7080
gtcatacttc ctcttccccc acctccactt ctctgctcct gcctcctcc ctgtctccct    7140
ccctccacag gtgacatttg cagcccatgg ctgagtctct gtctttctgt aggtgtgaag    7200
gagccagagg tatcagcagg gcagatgcca ggccctgggg aggcagagct gcagggggc    7260
tcagaatgga caagggccca gcgggaacac gaggcccaga agcagcactc ggtggagctg    7320
tgggtgcagt tcagccacgc gatggacgcc ctgctcttcc gcctctacct gctcttcatg    7380
gcctcctcca tcatcaccgt catatgcctc tggaacacct aggcaggtgc tcacctgcaa    7440
acttcagtct ggacttctt ttgccagaga actccagaaa ccagtcaggc tctcagtcag    7500
ccttgtggcc ctgtcaaccg cctcatttt aacccagtcc tctgtgtagt ttcagaccag    7560
acctgaatag tctcctatgc cctccaaaag tcgggtcctt gctcctgcat gccatcagcc    7620
ccactcagcc ctcccatacc tccctggctc ctcaggattc aggttcctag ggtacgtcct    7680
tgattaaatc accccaatat gccccttgc agaaagtatt ggcttttccc tgaatt    7736
```

<210> SEQ ID NO 120
<211> LENGTH: 22
<212> TYPE: DNA
<213> ORGANISM: Artificial Sequence
<220> FEATURE:
<221> NAME/KEY: misc_feature
<223> OTHER INFORMATION: Primer

<400> SEQUENCE: 120
gctcatgata gtgacttgct cc                                              22

<210> SEQ ID NO 121
<211> LENGTH: 21
<212> TYPE: DNA
<213> ORGANISM: Artificial Sequence
<220> FEATURE:
<221> NAME/KEY: misc_feature
<223> OTHER INFORMATION: Primer

<400> SEQUENCE: 121
cagcgggcag aagaggtata g                                               21

<210> SEQ ID NO 122
<211> LENGTH: 1000
<212> TYPE: DNA
<213> ORGANISM: Artificial Sequence
<220> FEATURE:
<221> NAME/KEY: misc_feature
<223> OTHER INFORMATION: Primer/Probe

<400> SEQUENCE: 122
ttaagatttg cgctttgcca actgtacacc caacctcggt ttattgtcga acctcccgct     60
tgtgccgcca tctgcatata gatcccggtc agtccgtcac attctgccaa ttgagtatcc    120
tcgaagtctt attccacgtg ctcaaagcaa gggtatcgta cagtgataac cgcctcgtgc    180
agatccaaat tctcgattaa cactcaagta ctgatttta tcatcaggta actaaaaact     240
cacaatttga agcaccagcg agaatcgttc tattctctag cttcgcaaca tcgacagttg    300
taatggcata acttcggcat tcatagtggc tgagtttagc ggactaagcg aaaaactggt    360
cgttagatct tcctcaccat gattttacaa gaaaggtgaa ctcaatttga cggcggtaaa    420
gttagatggc tacgcgcgac aagtctccgt atcgtcatga aattagcgaa gaggtaatgg    480
caaagcttgg ctacgaatac aggagcgcgc tgtgattaca gtagggttag gatagcgaaa    540
acgttcaacg tggatagact cttatcggca cacgatcata tgcttccaag gttcccaagg    600
cgaattacta gggtgcacag agctacgagt acgctgtccg gcttgattcg ctcgtacatc    660
cactgttcaa aaagctccga taccgacgat cactctcgat ctctgtgtgg gacgcactta    720
ttgtggaatc agtcaaccag tgaagcattc acatgtacgt ggtacggcac gccgtggtat    780
gttagcgttc cctgcgccgc aagtaaaccc ttcagctgtc acctcctata gtaacacgct    840
cgcatgcaga gcctagcacc ttagctctga gttgcctgcc ggaaggatat attctgtatg    900
tgattaaagc gaagtcaaag taaaccccc acatgcagac ctgggtaaat tctcactcag    960
ttgaaacgta ggggccaata cgtgtgtcct tgatactact                         1000

<210> SEQ ID NO 123
<211> LENGTH: 21
<212> TYPE: DNA
<213> ORGANISM: Artificial Sequence
<220> FEATURE:
<221> NAME/KEY: misc_feature
<223> OTHER INFORMATION: Primer -continued

```
<400> SEQUENCE: 123
caatgtgggt ggtcagcatc t                                              21

<210> SEQ ID NO 124
<211> LENGTH: 21
<212> TYPE: DNA
<213> ORGANISM: Artificial Sequence
<220> FEATURE:
<221> NAME/KEY: misc_feature
<223> OTHER INFORMATION: Primer

<400> SEQUENCE: 124
ggacagaggt gaacgctctc c                                              21

<210> SEQ ID NO 125
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 125
caaactggac accttctatt tccccttcca                                     30
```